US008178668B2

(12) United States Patent
Steinig et al.

(10) Patent No.: US 8,178,668 B2
(45) Date of Patent: May 15, 2012

(54) 2-AMINOPYRIDINE KINASE INHIBITORS

(75) Inventors: Arno G. Steinig, East Northport, NY (US); Mark J. Mulvihill, East Northport, NY (US); Jing Wang, Syosset, NY (US); Douglas S. Werner, Holtsville, NY (US); Qinghua Weng, West Islip, NY (US); Heather Coate, San Diego, CA (US); Xin Chen, Commack, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 491 days.

(21) Appl. No.: 12/365,325

(22) Filed: Feb. 4, 2009

(65) Prior Publication Data

US 2009/0197862 A1 Aug. 6, 2009

Related U.S. Application Data

(60) Provisional application No. 61/063,539, filed on Feb. 4, 2008.

(51) Int. Cl.
*C07D 401/14* (2006.01)
*C07D 405/14* (2006.01)
*C07D 413/14* (2006.01)
*C07D 417/14* (2006.01)
*C07D 451/02* (2006.01)
*C07D 471/04* (2006.01)
*C07D 487/04* (2006.01)

(52) U.S. Cl. ........ 544/128; 544/350; 544/363; 546/121; 546/126; 546/144; 546/148; 546/194; 546/271.7

(58) Field of Classification Search .................. None
See application file for complete search history.

(56) References Cited

U.S. PATENT DOCUMENTS

| 7,230,098 | B2 | 6/2007 | Cui |
| 7,259,154 | B2 | 8/2007 | Cox |
| 2006/0046991 | A1 | 3/2006 | Cui |
| 2006/0128724 | A1 | 6/2006 | Cui |
| 2006/0178374 | A1 | 8/2006 | Cui |
| 2007/0072874 | A1 | 3/2007 | Cui |
| 2008/0032972 | A1 | 2/2008 | Dorsey |
| 2008/0167338 | A1 | 7/2008 | Spevak |
| 2008/0221148 | A1 | 9/2008 | Ibrahim |
| 2008/0293769 | A1 | 11/2008 | Cui |
| 2009/0005356 | A1 | 1/2009 | Blaney |
| 2009/0005378 | A1 | 1/2009 | Arnold |
| 2009/0118305 | A1 | 5/2009 | Barlaam |

FOREIGN PATENT DOCUMENTS

| WO | 03059913 A1 | 7/2003 |
| WO | 03093297 A2 | 11/2003 |
| WO | 2004069160 A2 | 8/2004 |
| WO | 2004076412 A2 | 9/2004 |
| WO | 2006021881 A2 | 3/2006 |
| WO | 2007027855 A2 | 3/2007 |
| WO | 2007111904 A2 | 10/2007 |
| WO | 2007124181 A2 | 11/2007 |
| WO | 2008074997 A1 | 6/2008 |
| WO | 2008124849 A2 | 10/2008 |
| WO | 2009053737 A2 | 4/2009 |
| WO | 2009070294 A2 | 6/2009 |
| WO | 2009139576 A2 | 11/2009 |
| WO | 2009140549 A1 | 11/2009 |

OTHER PUBLICATIONS

Cho et al, Discovery of Aminopyridine Substituted with Benzoxazole as Orally Active c-Met Kinase Inhibitors, 20 Bioorg. & Med. Chem. Letts. 4223-4227 (2010).*
Arteaga, C.L. (2007) Nature Medicine 13(6): 675-677.
Brabletz, T. et al. Nature Reviews Cancer 5:745-749, Sep. 2005.
Camp, E.R. et al. (2007) American Cancer Society pp. 1030-1039 Published online Feb. 20, 2007 in Wiley Interscience (www.interscience.wiley.com).
Christofori, G. (2006) Nature 441:444-450.
Duyster, J. et al. (2001) Oncogene 20: 5623-5637.
Engelman, J.A. et al. (2007) Science 316: 1039-1043.
Grotegut,S. et al. (2006) The EMBO Journal 25: 3534-3545.
Gupta, G.P. et al. (2006) Cell 127:679-695.
International Search Report and Written Opinion in the International Searching Authority in PCT/US2009/032791, Apr. 23, 2009.
Jarvis, L.M. (2007) Chemical and Engineering News 85 (34): 15-23.
Kutok, J.L. et al. (2002) Journal of Clinical Oncology 20(17): 3691-3702.
Maggiora, P. et al. (1997) Journal of Cellular Physiology 173:183-186.
Maulik, G. et al. (2002) Cytokine and Growth Factor Reviews 13:41-59.

(Continued)

*Primary Examiner* — Janet Andres
*Assistant Examiner* — Timothy R Rozof

(57) ABSTRACT

2-Aminopyridine compounds having the structure of Formula I, and pharmaceutically acceptable salts of these compounds. Compounds of Formula I inhibit the activity of tyrosine kinase enzymes in animals, including humans, and are useful in the treatment and/or prevention of various diseases and conditions. In particular, compounds disclosed herein are inhibitors of kinases, in particular, but not limited to, KDR, Tie-2, Flt3, FGFR3, Ab1, Aurora A, c-Src, IGF-1R, ALK, c-MET, RON, PAK1, PAK2, and TAK1, and can be used in the treatment of proliferative diseases, such as, but not limited to, cancer. The present invention is also directed to a pharmaceutical composition comprising a therapeutically effective amount of a compound of Formula I, or a pharmaceutically acceptable salt thereof, and a pharmaceutically acceptable carrier. The present invention is further directed to a method of treating a patient having a condition which is mediated by protein kinase activity by administering to the patient a therapeutically effective amount of the above-mentioned pharmaceutical composition.

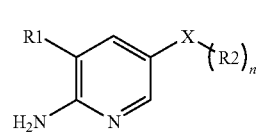

9 Claims, No Drawings

OTHER PUBLICATIONS

Oft, M. et al. (1996) Genes and Development 10:2462-2477.
Perl, A. et al. (1998) Nature 392:190-193.
Powers, C. et al. (2002) The Journal of Biological Chemistry 277(16): 14153-14158.
Schlessinger, J. and Ullrich, A. (1992) Neuron 9: 383-391.
Thiery, J.P. (2002) Nature 2:442-454.
Turturro, F. et al. (2002) Clinical Cancer Research 8: 240-245.
Ullrich, A and Schlessinger, J. (1990) Cell 61: 203-212.
Wang, D. (2004) Oncogene 23: 1668-1680.
Yarden, Y. et al. (1988) Ann. Rev. Biochem. 57:443-478.
Zou, H.Y. et at (2007) Cancer Res 67(9):4408-4417.

* cited by examiner

2-AMINOPYRIDINE KINASE INHIBITORS

BACKGROUND OF THE INVENTION

The present invention is directed to novel 2-aminopyridine compounds, their salts, and compositions comprising them. In particular, the present invention is directed to novel 2-aminopyridine compounds that inhibit the activity of tyrosine kinase enzymes in animals, including humans, for the treatment and/or prevention of various diseases and conditions such as cancer.

Protein tyrosine kinases (PTKs) are enzymes that catalyze the phosphorylation of specific tyrosine residues in various cellular proteins involved in regulation of cell proliferation, activation, or differentiation (Schlessinger and Ullrich, 1992, Neuron 9:383-391). Aberrant, excessive, or uncontrolled PTK activity has been shown to result in uncontrolled cell growth and has been observed in diseases such as benign and malignant proliferative disorders, as well as having been observed in diseases resulting from an inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas). Other kinases that are believed to be important mediators of tumor angiogenesis include FGFR3, Tie-2, and Flt3. For example, FGFR3 mutations are often seen in bladder cancer cells. Tie-2 is a protein receptor found on cells lining blood vessels. When activated by growth factors secreted by tumor cells, Tie2 triggers vessel cell walls to part and grow new capillaries. Flt3, also known as "vascular endothelial cell growth factor receptor 3" or VEGFR-3, is believed to assist in vascular development important to angiogenesis. Thus, it is desirable to identify inhibitors of FGFR3, Tie-2, and/or Flt3.

Tyrosine kinases can be of the receptor-type (having extracellular, transmembrane and intracellular domains) or the non-receptor type (being wholly intracellular). The Receptor Tyrosine Kinases (RTKs) comprise a large family of transmembrane receptors with at least nineteen distinct RTK subfamilies having diverse biological activities. The RTK family includes receptors that are crucial for the growth and differentiation of a variety of cell types (Yarden and Ullrich, Ann. Rev. Biochem. 57:433-478, 1988; Ullrich and Schlessinger, Cell 61:243-254, 1990). The intrinsic function of RTKs is activated upon ligand binding, which results in phosphorylation of the receptor and multiple cellular substrates, and subsequently results in a variety of cellular responses (Ullrich & Schlessinger, Cell 61:203-212, 1990). Thus, RTK mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate a corresponding cellular response such as cell division, differentiation, metabolic effects, and changes in the extracellular microenvironment (Schlessinger and Ullrich, Neuron 9:1-20, 1992).

In appropriately high protein kinase activity has been implicated in many diseases resulting from abnormal cellular function. This might arise either directly or indirectly by a failure of the proper control mechanisms for the kinase, related to mutation, over-expression or inappropriate activation of the enzyme; or by an over- or underproduction of cytokines or growth factors participating in the transduction of signals upstream or downstream of the kinase. In all of these instances, selective inhibition of the action of the kinase might be expected to have a beneficial effect.

Many of the tyrosine kinases, whether an RTK or non-receptor tyrosine kinase, have been found to be involved in cellular signaling pathways involved in numerous disorders, including cancer, psoriasis, fibrosis, atherosclerosis, restenosis, auto-immune disease, allergy, asthma, transplantation rejection, inflammation, thrombosis, nervous system diseases, and other hyperproliferative disorders or hyper-immune responses. It is desirable to provide novel inhibitors of kinases involved in mediating or maintaining disease states to treat such diseases.

Cells may migrate and divide inappropriately if the signals for division or motility cannot be stopped. This might occur if the complex system of control proteins and messengers, which signal changes in the actin system, goes awry. One such control factor is the proto-oncogene protein Ab1, a tyrosine kinase. It is implicated in cancer, including leukemia. Accordingly, it is desirable to identify inhibitors of Ab1.

The Aurora kinase family is one regulator of chromosome segregation—regulating the structure and function of centrosomes and mitotic spindle. One member, the Aurora-A kinase, has been shown to play a role in tumorigenesis—being located at a chromosomal hot-spot, 20q13, frequently amplified in a variety of human cancers such as those of colon, ovary, breast and pancreas. It appears that overexpression of Aurora-A kinase alone is sufficient to cause aneupoidy in normal diploid epithelial cells. Over-expression of Aurora-A kinase in NIH3T3 cells results in centrosome aneupoidy. Thus, it is desirable to identify inhibitors of Aurora-A.

The cytoplasmic tyrosine kinase c-Src is involved in the signal transduction pathway and is elevated in breast cancer cell lines. Similarly, Src is involved in the regulation of cell growth and transformation. Thus over-expression of c-Src can lead to excess proliferation. Thus, it is desirable to identify inhibitors of c-Src.

IGF-1R (type 1 insulin-like growth factor receptor) performs important roles in cell division, development, and metabolism, and in its activated state, plays a role in oncogenesis and suppression of apoptosis. IGF-1R is known to be overexpressed in a number of cancer cell lines (IGF-1R overexpression is linked to acromegaly and to cancer of the prostate). By contrast, down-regulation of IGF-1R expression has been shown to result in the inhibition of tumorigenesis and an increased apoptosis of tumor cells. Thus, it is desirable to identify compounds that inhibit IGF-1R.

ALK (Anaplastic Lymphoma Kinase) is a receptor tyrosine kinase that belongs to the insulin receptor subfamily. It is implicated in the progression of certain tumors such as anaplastic large cell lymphomas (ALCL; Kutok J. L. & Aster J. C., J. Clin Oncol., 20:3691-3702, 2002; Duyster J. et al., Oncogene, 20:5623-5637, 2001), inflammatory myofibroblastic tumors (IMT; Duyster J. et al.), and glioblastomas (Powers C. et al, J. Biol Chem., 276:16772-16779, 2001). It has been demonstrated that inhibition of ALK can impair the growth and induce apoptosis of lymphoma cells containing ALK (Turturro F. et al., Clin. Cancer Res., 8:240-245, 2002). Thus, it is desirable to identify compounds that inhibit ALK.

RON (recepteur d' origine nantais) is a receptor tyrosine kinase that is part of the MET proto-oncogene family. It is activated by binding to its natural ligand MSP and signals via the PI3K and MAPK pathways. RON can be deregulated in cancer by mechanisms such as over-expression of the receptor and/or the presence of constitutively active splice variants. Inhibition of RON has been shown to lead to a decrease in proliferation, induction of apoptosis and affects cell metastasis. RON overexpression is observed in a variety of human cancers and exhibit increased expression with progression of the disease.

MET is a receptor tyrosine kinase that is a heterodimeric protein comprising of a 50 kDa α-subunit and a 145kDa β-subunit (Maggiora et al, *J. Cell Physiol*, 173:183-186, 1997). It is activated by binding to its natural ligand HGF (hepatocyte growth factor, also known as scatter factor) and signals via the PI3K and MAPK pathways. MET can be deregulated in cancer by mechanisms such as autocrine/paracrine HGF activation, over-expression of the receptor, and/or the presence of activating mutations. Significant expression of MET has been observed in a variety of human tumors, such as colon, lung, prostate (including bone metastases), gastric, renal, HCC, ovarian, breast, ESCC, and melanoma (Maulik et al, *Cytokine & Growth Factor Reviews* 13:41-59, 2002). MET is also implicated in atherosclerosis and lung fibrosis. Inhibition of MET can cause a decrease in cell motility, proliferation and metastasis, as reviewed in, e.g., *Chemical & Engineering News* 2007, 85 (34), 15-23.

As human cancers progress to a more invasive, metastatic state, multiple signaling programs regulating cell survival and migration programs are observed depending on cell and tissue contexts (Gupta and Massague, 2006). Recent data highlight the transdifferentiation of epithelial cancer cells to a more mesenchymal-like state, a process resembling epithelial-mesenchymal transition (EMT; (Oft et al., 1996; Perl et al., 1998), to facilitate cell invasion and metastasis (Brabletz et al., 2005; Christofori, 2006). Through EMT-like transitions mesenchymal-like tumor cells are thought to gain migratory capacity at the expense of proliferative potential. A mesenchymal-epithelial transition (MET) has been postulated to regenerate a more proliferative state and allow macrometastases resembling the primary tumor to form at distant sites (Thiery, 2002). MET and RON kinases have been shown to play a role in the EMT process (Camp et al., 2007; Grotegut et al., 2006; Wang et al., 2004).

Thus, it is desirable to identify inhibitors of RON and/or it related family MET for use in proliferative diseases, such as, but not limited to, cancer.

It has been documented in vitro that RON and MET can form heterodimers and signal via such RON-MET dimers. Since co-expression of RON and MET in cancer has been observed, such "cross-talk" may contribute to tumor growth. It is therefore especially desirable to identify compounds that inhibit both RON and MET.

In view of the importance of PTKs to the control, regulation, and modulation of cell proliferation and the diseases and disorders associated with abnormal cell proliferation, many attempts have been made to identify small molecule tyrosine kinase inhibitors. International Patent Publications Nos. WO 2006/021881 and WO 2004/076412 describe 3-alkoxysubstituted 2-aminopyridines and 2-aminopyrazines as kinases inhibitors. International Patent Publication No. WO 2004/069160 describes benzimidazolyl-pyridines as SGK-1 inhibitors. International Patent Publication No. WO 2007/111904 describes tetrazolyl substituted pyridinamines or pyrazinamines as c-Met protein kinase inhibitors.

Although the anticancer compounds described above have made contribution to the art, there is a continuing need to improve anticancer pharmaceuticals with better selectivity or potency, reduced toxicity, or fewer side effects.

It has been found that compounds of this invention, and pharmaceutically acceptable compositions thereof, are effective as inhibitors of kinases. In particular, the compounds are effective as inhibitors of at least one of the KDR, Tie-2, Flt3, FGFR3, Ab1, Aurora A, c-Src, IGF-1R, ALK, c-MET, RON, PAK1, PAK2, and TAK1 kinases.

SUMMARY OF THE INVENTION

The present invention is directed to a novel class of 2-aminopyridine compounds having the structure of Formula I, and pharmaceutically acceptable salts of these compounds. The compounds of Formula I inhibit the activity of tyrosine kinase enzymes in animals, including humans, and they are useful in the treatment and/or prevention of various diseases and conditions. In particular, compounds disclosed herein are inhibitors of kinases, in particular, but not limited to, KDR, Tie-2, Flt3, FGFR3, Ab1, Aurora A, c-Src, IGF-1R, ALK, c-MET, RON, PAK1, PAK2, and TAK1, and can be used in the treatment of proliferative diseases, such as, but not limited to, cancer. Compounds disclosed herein are also useful in the treatment and/or prevention of various diseases and conditions in which EMT is involved, for example, the treatment of conditions characterized by a disregulation of EMT. The present invention is also directed to a pharmaceutical composition comprising a therapeutically effective amount of a compound of Formula I, or a pharmaceutically acceptable salt thereof, and a pharmaceutically acceptable carrier. The present invention is further directed to a method of treating a patient having a condition which is mediated by protein kinase activity by administering to the patient a therapeutically effective amount of the above-mentioned pharmaceutical composition.

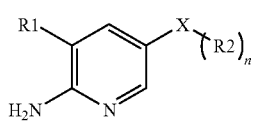

I

DETAILED DESCRIPTION OF THE INVENTION

The present invention relates to a compound of Formula I:

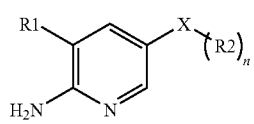

I or a pharmaceutically acceptable salt thereof, wherein:

R1 is isoquinolin-3-yl, benzothiazol-2-yl, 1,2,3,4-tetrahydroisoquinolin-3-yl, 4,5,6,7-tetrahydrobenzothiazol-2-yl, benzofuran-2-yl, benzoxazol-2-yl, benzothiophen-2-yl, 5,6,7,8-tetrahydro-4H-cycloheptathiazol-2-yl, 3,3-disubstituted 3H-indol-2-yl, imidazo[1,2-a]pyridine-2-yl, thiazolo[4,5-c]pyridin-2-yl, oxazolo[4,5-c]pyridin-2-yl, imidazo[1,2-a]pyrazin-2-yl, furo[2,3-c]pyridin-2-yl, thieno[2,3-c]pyridin-2-yl, or 2-naphthyl, any of which is optionally further substituted with one to four independent R3 groups;

X is pyrazol, phenyl, pyridyl, thiazolyl, imidazolyl, furyl, thienyl, pyrrolyl, indolyl, indazolyl, or tetrahydropyridyl;

R2 is H, halogen, CN, alkyl, cycloalkyl, bicycloalkyl, hydroxy, hydroxyalkyl, alkoxy, aryloxy, amino, aminoalkyl, alkylamino, alkylsulfonyl, C(=O)R4, C(=O)OR4, C(=O)NR5R6, NR7C(=O)R4, NR7C(=O)OR4, NR7C(=O)NR5R6, NR7S(=O)$_2$R4, NR7S(=O)R4, aryl, heterocyclyl, heterobicycloalkyl, heterospiroalkyl, heteroaryl, -alkyl-C(=O)R4, -alkyl-C(=O)OR4, -alkyl-C(=O)NR5R6, -alkyl-NR7C(=O)R4, -alkyl-NR7C(=O)OR4, -alkyl-NR7C(=O)NR5R6, -alkyl-NR7SO$_2$R4, -alkyl-NR7SOR4, aryl-alkyl, heterocyclyl-alkyl, or heteroaryl-alkyl, any of which is NR7SO$_2$R4, -alkyl-NR7SOR4, aryl-alkyl, heterocyclyl-alkyl, or heteroaryl-alkyl, any of which is optionally substituted by one or more independent R3 groups;

R3 is H, halogen, CN, alkyl, cycloalkyl, alkenyl, alkynyl, hydroxy, hydroxyalkyl, alkoxy, aryloxy, amino, aminoalkyl, alkylamino, alkylsulfonyl, C(=O), C(=S), C(=O)R4, C(=O)OR4, C(=O)NR5R6, NR7C(=O)OR4, NR7C(=O)OR4, NR7C(=O)NR5R6, NR7SO$_2$R4, NR7SOR4, aryl, heterocyclyl, heteroaryl, -alkyl-C(=O)R4, -alkyl-C(=O)OR4, -alkyl-C(=O)NR5R6, -alkyl-NR7C(=O)R4, -alkyl-NR7C(=O)OR4, -alkyl-NR7C(=O)NR5R6, -alkyl-NR7SO$_2$R4, -alkyl-NR7SOR4, aryl-alkyl, heterocyclyl-alkyl, or heteroaryl-alkyl, any of which is optionally further substituted by one or more independent R7 groups;

R4 is alkyl, cycloalkyl, alkenyl, alkynyl, hydroxy, hydroxyalkyl, alkoxy, aryloxy, amino, aminoalkyl, alkylamino, dialkylamino, alkylsulfonyl, aryl, heterocyclyl, heteroaryl, aryl-alkyl, heterocyclyl-alkyl, or heteroaryl-alkyl, any of which is optionally further substituted by one or more independent R7 groups;

R5 and R6 are each independently H, alkyl, cycloalkyl, or alkoxyalkyl, any of which is optionally substituted by one or more independent R7 groups; or R5 and R6 taken together with the atom that they are attached to form a 4-7 membered saturated or unsaturated heterocycle; wherein said heterocycle is optionally further substituted by one or more independent R7 groups;

R7 is H, halogen, alkyl, trifluoroalkyl, alkoxy, CN, cycloalkyl, alkoxyalkyl, aryl, hetaryl, or heterocyclyl;

n is 0, 1 or 2.

In one embodiment of the invention, R1 is isoquinolin-3-yl, benzothiazol-2-yl, 1,2,3,4-tetrahydroisoquinolin-3-yl, 4,5,6,7-tetrahydrobenzothiazol-2-yl, benzofuran-2-yl, benzoxazol-2-yl, benzothiophen-2-yl, 3,3-disubstituted 3H-indol-2-yl, imidazo[1,2-a]pyridine-2-yl, thiazolo[4,5-c]pyridin-2-yl, oxazolo[4,5-c]pyridin-2-yl, imidazo[1,2-a]pyrazin-2-yl, furo[2,3-c]pyridin-2-yl, or thieno[2,3-c]pyridin-2-yl, any of which is optionally further substituted by one to four independent R3 groups as defined in Formula I.

In another embodiment of the invention, R1 is isoquinolin-3-yl, benzothiazol-2-yl, 1,2,3,4-tetrahydroisoquinolin-3-yl, 4,5,6,7-tetrahydrobenzothiazol-2-yl, benzoxazol-2-yl, 3,3-disubstituted 3H-indol-2-yl, or imidazo[1,2-a]pyridine-2-yl, any of which is optionally further substituted by one to four independent R3 groups as defined in Formula I.

In another embodiment of the invention, R1 is isoquinolin-3-yl, benzothiazol-2-yl, benzoxazol-2-yl, or imidazo[1,2-a]pyridine-2-yl, any of which is optionally further substituted by one to four independent R3 groups as defined in Formula I.

In another embodiment of the invention, R1 is isoquinolin-3-yl or benzothiazol-2-yl, any of which is optionally further substituted by one to four independent R3 groups as defined in Formula I.

In another embodiment of the invention, R1 is thiazolo[4,5-c]pyridin-2-yl, oxazolo[4,5-c]pyridin-2-yl, imidazo[1,2-a]pyrazin-2-yl, furo[2,3-c]pyridin-2-yl, or thieno[2,3-c]pyridin-2-yl, any of which is optionally further substituted by one to four independent R3 groups as defined in Formula I.

In another embodiment of the invention, the compound of Formula I has the Formula Ia wherein X is pyrazolyl and n is 1, and all other variables are as defined in Formula I.

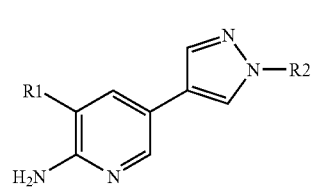

Ia

In another embodiment of the invention, the compound of Formula Ia has the Formula Iaa wherein Raa is H, alkoxy, or alkyl wherein alkoxy or alkyl is optionally further substituted with halogen; Rab is H or F; and all other variables are as defined in Formula I.

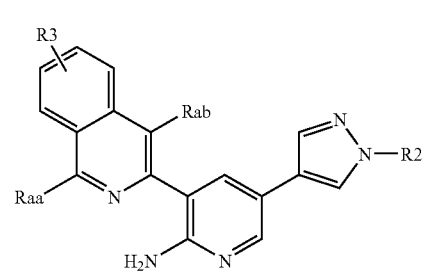

Iaa

In another embodiment of the invention, the compound of Formula Ia has the formula Iab wherein all variables are as defined in Formula I.

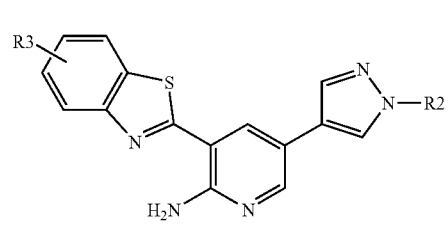

Iab

In another embodiment of the invention, the compound of Formula Ia has the Formula Iac wherein Rc is H or alkyl wherein alkyl is optionally further substituted with halogen; and all other variables are as defined in Formula I.

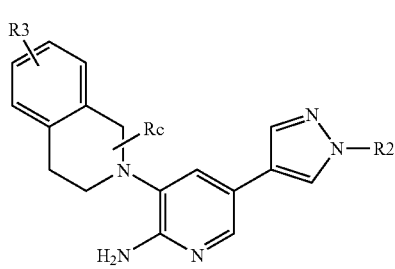

Iac

In another embodiment of the invention, the compound of Formula Ia has the Formula Iad wherein all variables are as defined in Formula I.

Iad

In another embodiment of the invention, the compound of Formula Ia has the Formula Iae wherein Y is O or S; and all other variables are as defined in Formula I.

Iae

In another embodiment of the invention, the compound of Formula Ia has the Formula Iaf wherein all variables are as defined in Formula I.

Iaf

In another embodiment of the invention, the compound of Formula Ia has the Formula Iag wherein Rga and Rgb are independently alkyl, alkoxy or alkylthio wherein said alkyl group is optionally further substituted with halogen; or Rga and Rgb, together with the carbon atom that both are attached to, form a 3-7-membered saturated or unsaturated ring containing zero to two O, N, or S atoms; and all other variables are as defined in Formula I.

Iag

In another embodiment of the invention, the compound of Formula Ia has the Formula Iah wherein all variables are as defined in Formula I.

Iah

In another embodiment of the invention, the compound of Formula Ia has the Formula Iai wherein W is CR3 or N; and all other variables are as defined in Formula I.

Iai

In another embodiment of the invention, the compound of Formula Ia has the Formula Iaj wherein W is CR3 or N; and all other variables are as defined in Formula I.

Iaj

In another embodiment of the invention, the compound of Formula Ia has the Formula Iak wherein W is CR3 or N; and all other variables are as defined in Formula I.

Iak

In another embodiment of the invention, the compound of Formula Ia has the Formula Ial wherein Y is O or S, W is CR3 or N; and all other variables are as defined in Formula I.

Ial

In another embodiment of the invention, the compound of Formula Ia has the Formula Iam wherein all variables are as defined in Formula I.

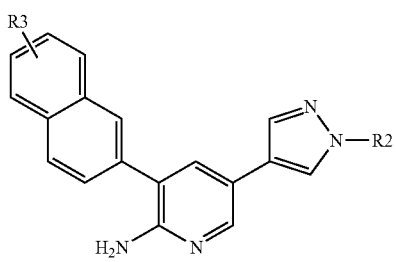

Iam

In another embodiment of compounds of formula Ia, R2 is H, alkyl, cycloalkyl, bicycloalkyl, alkylsulfonyl, C(=O)NR5R6, aryl, heterocyclyl, heterobicycloalkyl, heterospiroalkyl, heteroaryl, -alkyl-C(=O)R4, -alkyl-C(=O)OR4, -alkyl-C(=O)NR5R6, -alkyl-NR7C(=O)R4, -alkyl-NR7C(=O)OR4, -alkyl-NR7C(=O)NR5R6, -alkyl-NR7SO$_2$R4, -alkyl-NR7SOR4, aryl-alkyl, heterocyclyl-alkyl, or heteroaryl-alkyl, any of which is optionally further substituted by one or more independent R3 groups.

In another embodiment of compounds of formula Ia, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Ia, R2 is heterocyclyl or heterobicycloalkyl, any of which is optionally further substituted by one or more independent R3 groups.

In another embodiment of compounds of formula Iaa, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iab, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iac, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iad, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iae, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iaf, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iag, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iah, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iai, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iaj, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iak, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Ial, R2 is H, alkyl, aryl, heterocyclyl, heterobicycloalkyl, heterospiroalkyl, or heteroaryl, any of which is optionally further substituted by one or more independent R3 groups.

In another embodiment of compounds of formula Iam, R2 is H, alkyl, aryl, heterocyclyl, heterobicycloalkyl, heterospiroalkyl, or heteroaryl, any of which is optionally further substituted by one or more independent R3 groups.

The compounds of Formula I inhibit the activity of tyrosine kinase enzymes in animals, including humans, and they are useful in the treatment and/or prevention of various diseases and conditions. In particular, compounds disclosed herein are inhibitors of kinases, in particular, but not limited to, KDR, Tie-2, Flt3, FGFR3, Ab1, Aurora A, c-Src, IGF-1R, ALK, c-MET, RON, PAK1, PAK2, and TAK1, and can be used in the treatment of proliferative diseases, such as, but not limited to, cancer. Since MET and RON kinases have been shown to play a role in the EMT process, the compounds of Formula I are useful in the treatment and/or prevention of various diseases and conditions in which EMT is involved, for example, the treatment of conditions characterized by a disregulation of EMT.

Specifically, the compounds of Formula I of the present invention are useful in the treatment of a variety of cancers, including, but not limited to, solid tumor, sarcoma, fibrosarcoma, osteoma, melanoma, retinoblastoma, rhabdomyosarcoma, glioblastoma, neuroblastoma, teratocarcinoma, hematopoietic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, and a glioblastoma.

In another embodiment, the present invention is directed to a pharmaceutical composition comprising a therapeutically effective amount of a compound of Formula I, or a pharmaceutically acceptable salt thereof, and a pharmaceutically acceptable carrier.

The present invention is also directed to a method of treating a patient having a condition which is mediated by protein kinase activity by administering to the patient a therapeutically effective amount of the above-mentioned pharmaceutical composition.

Unless otherwise stated, the connections of compound name moieties are at the rightmost recited moiety. That is, the substituent name starts with a terminal moiety, continues with any bridging moieties, and ends with the connecting moiety. For example, hetarylthioC$_{1-4}$alkyl has a heteroaryl group connected through a thio sulfur to a C$_{1-4}$ alkyl that connects to the chemical species bearing the substituent.

As used herein, for example, "C$_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group. Further, C$_0$alkyl includes being a substituted bond—that is, for example, —X—Y—Z is —C(O)—C$_{2-4}$alkyl when X is C$_0$alkyl, Y is C$_0$alkyl, and Z is —C(O)—C$_{2-4}$alkyl.

In all embodiments of this invention, the term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl, and the like.

The term "halo" refers to fluoro, chloro, bromo, or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, and the like.

The term "acyl" refers to the structure —C(=O)—R, in which R is a general substituent variable such as, for example $R^1$ described above. Examples include, but are not limited to, (bi)(cyclo)alkylketo, (cyclo)alkenylketo, alkynylketo, arylketo, hetarylketo, heterocyclylketo, heterobicycloalkylketo, spiroalkylketo.

Unless otherwise specified, the term "cycloalkyl" refers to a 3-8 carbon cyclic aliphatic ring structure, optionally substituted with for example, alkyl, hydroxy, oxo, and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like.

The term "bicycloalkyl" refers to a structure consisting of two cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" refers to a structure consisting of two cycloalkyl moieties that have exactly one atom in common. Examples include, but are not limited to, spiro[4.5]decyl, spiro[2.3]hexyl, and the like.

The term "heterobicycloalkyl" refers to a bicycloalkyl structure in which at least one carbon atom is replaced with a heteroatom independently selected from oxygen, nitrogen, and sulfur.

The term "heterospiroalkyl" refers to a spiroalkyl structure in which at least one carbon atom is replaced with a heteroatom independently selected from oxygen, nitrogen, and sulfur.

The term "alkylcarbonyloxyalkyl" refers to an ester moiety, for example acetoxymethyl, n-butyryloxyethyl, and the like.

The term "alkynylcarbonyl" refers to an alkynylketo functionality, for example propynoyl and the like.

The term "hydroxyalkyl" refers to an alkyl group substituted with one or more hydroxy groups, for example hydroxymethyl, 2,3-dihydroxybutyl, and the like.

The term "alkylsulfonylalkyl" refers to an alkyl group substituted with an alkylsulfonyl moiety, for example mesylmethyl, isopropylsulfonylethyl, and the like.

The term "alkylsulfonyl" refers to a sulfonyl moiety substituted with an alkyl group, for example mesyl, n-propylsulfonyl, and the like.

The term "acetylaminoalkyl" refers to an alkyl group substituted with an amide moiety, for example acetylaminomethyl and the like.

The term "acetylaminoalkenyl" refers to an alkenyl group substituted with an amide moiety, for example 2-(acetylamino)vinyl and the like.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl, and the like.

The term "haloalkenyl" refers to an alkenyl group substituted with one or more halo groups.

Unless otherwise specified, the term "cycloalkenyl" refers to a cyclic aliphatic 3 to 8 ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl, and the like.

The term "alkynyl" refers to an unsaturated hydrocarbon group, straight or branched, having at least one acetylenic bond, for example ethynyl, propargyl, and the like.

The term, "haloalkynyl" refers to an alkynyl group substituted with one or more independent halo groups.

The term "alkylcarbonyl" refers to an alkylketo functionality, for example acetyl, n-butyryl, and the like.

The term "alkenylcarbonyl" refers to an alkenylketo functionality, for example, propenoyl and the like.

The term "aryl" refers to phenyl or naphthyl which may be optionally substituted. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl.

The terms "heteroaryl" or "hetaryl" or "heteroar-" or "hetar-" refer to substituted or unsubstituted 5- or 6-membered heteroaryl rings containing 1-4 heteroatoms chosen from oxygen, sulfur, and nitrogen in which oxygen and sulfur are not next to each other. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" or "hetaryl" or "heteroar-" or "hetar-" also include hetaryl rings with fused carbocyclic ring systems that are partially or fully unsaturated, such as a benzene ring, to form a benzofused hetaryl. For example, benzimidazole, benzoxazole, benzothiazole, benzofuran, quinoline, isoquinoline, quinoxaline, and the like. Furthermore, the terms "heteroaryl" or "hetaryl" or "heteroar-" or "hetar-" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]traizinyl, and the like. Hetaryl groups may be attached to other groups through their carbon atoms or the heteroatom(s), if applicable. For example, pyrrole may be connected at the nitrogen atom or at any of the carbon atoms.

The terms "aryl-alkyl" or "arylalkyl" or "aralkyl" are used to describe a group wherein the alkyl chain can be branched or straight chain forming a bridging portion with the terminal aryl, as defined above, of the aryl-alkyl moiety. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)

butyl, 4-(2-methylphenyl)butyl, 4-(2,4-dichlorophenyl) butyl, 4-(2-methoxphenyl)butyl, and 10-phenyldecyl.

The terms "aryl-cycloalkyl" or "arylcycloalkyl" are used to describe a group wherein the terminal aryl group is attached to a cycloalkyl group, for example phenylcyclopentyl and the like.

The terms "aryl-alkenyl" or "arylalkenyl" or "aralkenyl" are used to describe a group wherein the alkenyl chain can be branched or straight chain forming a bridging portion of the aralkenyl moiety with the terminal aryl portion, as defined above, for example styryl (2-phenylvinyl), phenpropenyl, and the like.

The terms "aryl-alkynyl" or "arylalkynyl" or "aralkynyl" are used to describe a group wherein the alkynyl chain can be branched or straight chain forming a bridging portion of the aryl-alkynyl moiety with the terminal aryl portion, as defined above, for example 3-phenyl-1-propynyl, and the like.

The terms "aryl-oxy" or "aryloxy" or "aroxy" are used to describe a terminal aryl group attached to a bridging oxygen atom. Typical aryl-oxy groups include phenoxy, 3,4-dichlorophenoxy, and the like.

The terms "aryl-oxyalkyl" or "aryloxyalkyl" or "aroxyalkyl" are used to describe a group wherein an alkyl group is substituted with a terminal aryl-oxy group, for example pentafluorophenoxymethyl and the like.

The term "heterocycloalkenyl" refers to a cycloalkenyl structure in which at least one carbon atom is replaced with a heteroatom selected from oxygen, nitrogen, and sulfur.

The terms "hetaryl-oxy" or "heteroaryl-oxy" or "hetaryloxy" or "heteroaryloxy" or "hetaroxy" or "heteroaroxy" are used to describe a terminal hetaryl group attached to a bridging oxygen atom. Typical hetaryl-oxy groups include 4,6-dimethoxypyrimidin-2-yloxy and the like.

The terms "hetarylalkyl" or "heteroarylalkyl" or "hetarylalkyl" or "heteroaryl-alkyl" or "hetaralkyl" or "heteroaralkyl" are used to describe a group wherein the alkyl chain can be branched or straight chain forming a bridging portion of the heteroaralkyl moiety with the terminal heteroaryl portion, as defined above, for example 3-furylmethyl, thenyl, furfuryl, and the like.

The terms "hetarylalkenyl" or "heteroarylalkenyl" or "hetaryl-alkenyl" or "heteroaryl-alkenyl" or "hetaralkenyl" or heteroaralkenyl" are used to describe a group wherein the alkenyl chain can be branched or straight chain forming a bridging portion of the heteroaralkenyl moiety with the terminal heteroaryl portion, as defined above, for example 3-(4-pyridyl)-1-propenyl.

The terms "hetarylalkynyl" or "heteroarylalkynyl" or "hetaryl-alkynyl" or "heteroaryl-alkynyl" or "hetaralkynyl" or "heteroaralkynyl" are used to describe a group wherein the alkynyl chain can be branched or straight chain forming a bridging portion of the heteroaralkynyl moiety with the heteroaryl portion, as defined above, for example 4-(2-thienyl)-1-butynyl.

Unless otherwise stated, the terms "heterocyclic ring", "heterocyclyl" and "heterocycle" are equivalent, and include 4-10-membered, e.g. 5-membered, saturated or partially saturated rings containing 1-4 heteroatoms chosen from oxygen, sulfur, and nitrogen. The sulfur and oxygen heteroatoms are not directly attached to one another. Any nitrogen heteroatoms in the ring may optionally be substituted with $C_{1-4}$alkyl. Examples of heterocyclic rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocyclic rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocyclic rings. The term "heterocyclic" also includes fused ring systems and can include a carbocyclic ring that is partially or fully unsaturated, such as a benzene ring, to form benzofused heterocycles. For example, 3,4-dihydro-1,4-benzodioxine, tetrahydroquinoline, tetrahydroisoquinoline and the like.

The terms "heterocyclylalkyl" or "heterocyclyl-alkyl" or "hetcyclylalkyl" or "hetcyclyl-alkyl" are used to describe a group wherein the alkyl chain can be branched or straight chain forming a bridging portion of the heterocyclylalkyl moiety with the terminal heterocyclyl portion, as defined above, for example 3-piperidinylmethyl and the like.

The terms "heterocyclylalkenyl" or "heterocyclyl-alkenyl" or "hetcyclylalkenyl" or "hetcyclyl-alkenyl" are used to describe a group wherein the alkenyl chain can be branched or straight chain forming a bridging portion of the heterocyclylalkenyl moiety with the terminal heterocyclyl portion, as defined above, for example 2-morpholinyl-1-propenyl and the like.

The terms "heterocyclylalkynyl" or "heterocyclyl-alkynyl" or "hetcyclylalkynyl" or "hetcyclyl-alkynyl" are used to describe a group wherein the alkynyl chain can be branched or straight chain forming a bridging portion of the heterocyclylalkynyl moiety with the terminal heterocyclyl portion, as defined above, for example 2-pyrrolidinyl-1-butynyl and the like.

The term "carboxylalkyl" refers to a terminal carboxyl (—COOH) group attached to branched or straight chain alkyl groups as defined above.

The term "carboxylalkenyl" refers to a terminal carboxyl (—COOH) group attached to branched or straight chain alkenyl groups as defined above.

The term "carboxylalkynyl" refers to a terminal carboxyl (—COOH) group attached to branched or straight chain alkynyl groups as defined above.

The term "carboxylcycloalkyl" refers to a terminal carboxyl (—COOH) group attached to a cyclic aliphatic ring structure as defined above.

The term "carboxylcycloalkenyl" refers to a terminal carboxyl (—COOH) group attached to a cyclic aliphatic ring structure having ethylenic bonds as defined above.

The terms "cycloalkylalkyl" or "cycloalkyl-alkyl" refer to a terminal cycloalkyl group as defined above attached to an alkyl group, for example cyclopropylmethyl, cyclohexylethyl, and the like.

The terms "cycloalkylalkenyl" or "cycloalkyl-alkenyl" refer to a terminal cycloalkyl group as defined above attached to an alkenyl group, for example cyclohexylvinyl, cycloheptylallyl, and the like.

The terms "cycloalkylalkynyl" or "cycloalkyl-alkynyl" refer to a terminal cycloalkyl group as defined above attached to an alkynyl group, for example cyclopropylpropargyl, 4-cyclopentyl-2-butynyl, and the like.

The terms "cycloalkenylalkyl" or "cycloalkenyl-alkyl" refer to a terminal cycloalkenyl group as defined above attached to an alkyl group, for example 2-(cyclopenten-1-yl) ethyl and the like.

The terms "cycloalkenylalkenyl" or "cycloalkenyl-alkenyl" refer to terminal a cycloalkenyl group as defined above attached to an alkenyl group, for example 1-(cyclohexen-3-yl)allyl and the like.

The terms "cycloalkenylalkynyl" or "cycloalkenyl-alkynyl" refer to terminal a cycloalkenyl group as defined above attached to an alkynyl group, for example 1-(cyclohexen-3-yl)propargyl and the like.

The term "carboxylcycloalkylalkyl" refers to a terminal carboxyl (—COOH) group attached to the cycloalkyl ring portion of a cycloalkylalkyl group as defined above.

The term "carboxylcycloalkylalkenyl" refers to a terminal carboxyl (—COOH) group attached to the cycloalkyl ring portion of a cycloalkylalkenyl group as defined above.

The term "carboxylcycloalkylalkynyl" refers to a terminal carboxyl (—COOH) group attached to the cycloalkyl ring portion of a cycloalkylalkynyl group as defined above.

The term "carboxylcycloalkenylalkyl" refers to a terminal carboxyl (—COOH) group attached to the cycloalkenyl ring portion of a cycloalkenylalkyl group as defined above.

The term "carboxylcycloalkenylalkenyl" refers to a terminal carboxyl (—COOH) group attached to the cycloalkenyl ring portion of a cycloalkenylalkenyl group as defined above.

The term "carboxylcycloalkenylalkynyl" refers to a terminal carboxyl (—COOH) group attached to the cycloalkenyl ring portion of a cycloalkenylalkynyl group as defined above.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

The term "haloalkoxy" refers to an alkoxy group substituted with one or more halo groups, for example chloromethoxy, trifluoromethoxy, difluoromethoxy, perfluoroisobutoxy, and the like.

The term "alkoxyalkoxyalkyl" refers to an alkyl group substituted with an alkoxy moiety which is in turn is substituted with a second alkoxy moiety, for example methoxymethoxymethyl, isopropoxymethoxyethyl, and the like.

The term "alkylthio" includes both branched and straight chain alkyl groups attached to a bridging sulfur atom, for example methylthio and the like.

The term "haloalkylthio" refers to an alkylthio group substituted with one or more halo groups, for example trifluoromethylthio and the like.

The term "alkoxyalkyl" refers to an alkyl group substituted with an alkoxy group, for example isopropoxymethyl and the like.

The term "alkoxyalkenyl" refers to an alkenyl group substituted with an alkoxy group, for example 3-methoxyallyl and the like.

The term "alkoxyalkynyl" refers to an alkynyl group substituted with an alkoxy group, for example 3-methoxypropargyl.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkoxycarbonylalkenyl" refers to a straight chain or branched alkenyl as defined above substituted with an alkoxycarbonyl, for example 4-(ethoxycarbonyl)-2-butenyl and the like.

The term "alkoxycarbonylalkynyl" refers to a straight chain or branched alkynyl as defined above substituted with an alkoxycarbonyl, for example 4-(ethoxycarbonyl)-2-butynyl and the like.

The term "haloalkoxyalkyl" refers to a straight chain or branched alkyl as defined above substituted with a haloalkoxy, for example 2-chloroethoxymethyl, trifluoromethoxymethyl and the like.

The term "haloalkoxyalkenyl" refers to a straight chain or branched alkenyl as defined above substituted with a haloalkoxy, for example 4-(chloromethoxy)-2-butenyl and the like.

The term "haloalkoxyalkynyl" refers to a straight chain or branched alkynyl as defined above substituted with a haloalkoxy, for example 4-(2-fluoroethoxy)-2-butynyl and the like.

The term "alkylthioalkyl" refers to a straight chain or branched alkyl as defined above substituted with an alkylthio group, for example methylthiomethyl, 3-(isobutylthio)heptyl, and the like.

The term "alkylthioalkenyl" refers to a straight chain or branched alkenyl as defined above substituted with an alkylthio group, for example 4-(methylthio)-2-butenyl and the like.

The term "alkylthioalkynyl" refers to a straight chain or branched alkynyl as defined above substituted with an alkylthio group, for example 4-(ethylthio)-2-butynyl and the like.

The term "haloalkylthioalkyl" refers to a straight chain or branched alkyl as defined above substituted with an haloalkylthio group, for example 2-chloroethylthiomethyl, trifluoromethylthiomethyl and the like.

The term "haloalkylthioalkenyl" refers to a straight chain or branched alkenyl as defined above substituted with an haloalkylthio group, for example 4-(chloromethylthio)-2-butenyl and the like.

The term "haloalkylthioalkynyl" refers to a straight chain or branched alkynyl as defined above substituted with a haloalkylthio group, for example 4-(2-fluoroethylthio)-2-butynyl and the like.

One in the art understands that an "oxo" requires a second bond from the atom to which the oxo is attached. Accordingly, it is understood that oxo cannot be subststituted onto an aryl or heteroaryl ring.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula (I) exists, the present invention includes any possible tautomers and pharmaceutically acceptable salts thereof, and mixtures thereof, except where specifically stated otherwise.

When the compound of Formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid.

Since the compounds of Formula (I) are intended for pharmaceutical use they are preferably provided in substantially pure form, for example at least 60% pure, more suitably at least 75% pure especially at least 98% pure (% are on a weight for weight basis).

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or a pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Biological Assays

The efficacy of the Examples of the invention, compounds of Formula I, as inhibitors of protein tyrosine kinases were demonstrated and confirmed by a number of pharmacological in vitro assays. The following assays and their respective methods can be carried out with the compounds according to the present invention. Activity possessed by compounds of Formula I may be demonstrated in vivo.

Person skilled in the art will appreciate that a variety of assay formats may be used to determine the activity of the compounds of this invention. For example, AlphaScreen (Amplified Luminescent Proximity Homogeneous Assay) technology was used with the kinases described below. Assay ATP concentrations for individual kinases are included in the text.

KDR (human)—100 μM ATP: 9 μL of the reaction mix containing ATP at the desired concentration, biotinylated poly(Glu,Tyr) (84 ng/mL) and 0.334 mM vanadate in assay buffer (50 mM HEPES (pH=7.4), 12.5 mM $MgCl_2$ and 1% glycerol) are added to a well of a 384 well plate along with 1 μl of compound (or vehicle control, usually DMSO). DMSO concentration is controlled at a concentration of 1%. KDR is diluted to the optimized concentration (optimized on a lot-by-lot basis) in an enzyme diluent buffer (50 mM HEPES pH=7.4, 12.5 mM $MgCl_2$ and 1% glycerol, 0.03% Brij35 and 0.3 mM EGTA). 5 μL of this solution are then added to the well, and the complete reaction mixture is incubated for 60 min at RT. In subdued light, 5 μL of PT66 donor and acceptor beads (diluted 1:200 from manufacturers provision in a 25 mM Tris HCl (pH=7.5), 200 mM NaCl, 100 mM EDTA, 0.3% BSA buffer) are added to the wells. The plates are then incubated for 4 h and read on an AlphaQuest plate reader.

IGF-1R (human)—100 μM ATP: To a well of a 384 well plate are added 9 μL of the reaction mix containing ATP at the desired concentration, biotinylated poly(Glu,Tyr) (84 ng/mL) and 0.334 mM vanadate in assay buffer (50 mM HEPES (pH=7.4), 12.5 mM $MgCl_2$ and 1% glycerol) along with 1 μL of compound (or vehicle control, usually DMSO). DMSO concentration is controlled at a concentration of 1%. IGF-1R is diluted to the optimized concentration (optimized on a lot-by-lot basis) in an enzyme diluent buffer (50 mM HEPES pH=7.4, 12.5 mM $MgCl_2$ and 1% glycerol, 0.03% Brij35, 0.3 mM EGTA, 6 mM DTT, and 0.003% BSA). 5 μL of this solution are then added to the well, and the complete reaction mixture is incubated for 60 min at RT. In subdued light, 5 μL of PT66 donor and acceptor beads (diluted 1:200 from manufacturer's provision in a 25 mM Tris HCl (pH=7.5), 200 mM NaCl, 100 mM EDTA, 0.3% BSA buffer) are added to the wells. The plates are then incubated for 4 h and read on an AlphaQuest plate reader.

RON (human)—$K_m$ of ATP: RON assay is performed in a 384 well assay containing 200 ng/μL biotinylated poly(Glu,Tyr), 0.334 mM vanadate, desired concentration of ATP optimized for the enzyme in assay buffer (50 mM HEPES (pH=7.4), 12.5 mM $MgCl_2$ and 1% glycerol). Desired compound is added in a final concentration of 1% DMSO with control being vehicle of DMSO alone. RON is diluted to the optimized (on a lot-by-lot basis) concentration in an enzyme diluent buffer (50 mM HEPES pH=7.4, 12.5 mM $MgCl_2$ and 1% glycerol, 0.03% Brij35, 0.3 mM EGTA, 1mM DTT, and 0.003% BSA). Enzyme is added to initiate the reaction and incubated for 30 min at RT. In subdued light, appropriate amount of PT66 donor and acceptor beads (diluted 1:260 from manufacturer's provision in a 25 mM Tris HCl (pH=7.5), 200 mM NaCl, 100 mM EDTA, 0.3% BSA buffer) are added to the wells. The plates, incubated for 1 h, are read on an AlphaQuest plate reader.

MET (human)—Km of ATP: MET assay is performed in a 384 well assay containing 200 ng/μL biotinylated poly(Glu, Tyr), 0.334 mM vanadate, desired concentration of ATP optimized for the enzyme in assay buffer (50 mM HEPES (pH=7.4), 5 mM $MgCl_2$, 5 mM $MnCl_2$, and 1% glycerol). Desired compound is added in a final concentration of 1% DMSO with control being vehicle of DMSO alone. MET is diluted to the optimized concentration (optimized on a lot-by-lot basis) in an enzyme diluent buffer (50 mM Tris pH=7.4, 1% glycerol, 0.03% Brij35, 0.24 mM EGTA, 1 mM DTT, and 0.003% BSA). Enzyme is added to initiate the reaction and incubated for 60 min at RT. In subdued light, appropriate amount of PT66 donor and acceptor beads (diluted 1:260 from manufacturer's provision in a 25 mM Tris HCl (pH=7.5), 400 mM NaCl, 100 mM EDTA, 0.3% BSA buffer) are added to the wells. The plates, incubated for 1 h, are read on an AlphaQuest plate reader The activities of compounds of the present invention against the kinases for which assays are not described above were determined at Invitrogen using the SelectScreen™ Kinase Profiling Service.

The examples of this invention were tested for inhibition of various kinases according to the procedures described herein. Activities of exemplary compounds of the present invention are shown in Table I. The $IC_{50}$ values determined against RON and MET in at least duplicate experiments are abbreviated as follows and are shown in Table 1: A, $IC_{50} \leq 0.1$ μM; B, $0.1$ μM $< IC_{50} \leq 1$ μM; C, $1$ μM $< IC_{50} \leq 20$ μM; D, $IC_{50} > 20$ μM; ND, not determined. The Example # of Table I corresponds to the compound example number as illustrated under the following working examples section.

TABLE 1

$IC_{50}$ values of examples against RON and MET

| Example | RON $IC_{50}$ | MET $IC_{50}$ | Example | RON $IC_{50}$ | MET $IC_{50}$ |
|---|---|---|---|---|---|
| 1 | C | C | 2 | D | C |
| 3 | A | A | 4 | C | B |
| 5 | B | B | 6 | B | B |
| 7 | B | A | 8 | C | C |
| 9 | B | A | 10 | C | B |
| 11 | B | A | 12 | C | B |
| 13 | C | B | 14 | C | C |
| 15 | B | A | 16 | B | B |
| 17 | B | B | 18 | B | B |
| 19 | B | B | 20 | B | B |
| 21 | C | B | 22 | C | B |
| 23 | B | B | 24 | B | B |
| 25 | B | B | 26 | B | B |
| 27 | B | B | 28 | C | B |
| 29 | B | B | 30 | C | B |
| 31 | C | C | 32 | B | B |
| 33 | B | B | 34 | C | B |
| 35 | C | C | 36 | B | B |
| 37 | B | B | 38 | B | A |
| 39 | B | A | 40 | B | B |
| 41 | C | B | 42 | B | B |
| 43 | B | B | 44 | C | C |
| 45 | C | B | 46 | C | B |
| 47 | B | B | 48 | B | B |
| 49 | B | A | 50 | B | B |
| 51 | A | A | 52 | A | A |
| 53 | B | B | 54 | C | B |
| 55 | C | B | 56 | B | B |
| 57 | C | B | 58 | B | B |
| 59 | B | B | 60 | C | C |
| 61 | D | D | 62 | B | B |
| 63 | B | B | 64 | B | B |
| 65 | C | C | 66 | C | C |
| 67 | B | B | 68 | B | B |
| 69 | C | C | 70 | C | B |
| 71 | B | A | 72 | B | A |
| 73 | B | B | 74 | C | C |
| 75 | ND | ND | 76 | D | D |
| 77 | D | D | 78 | C | C |
| 79 | C | C | 80 | C | C |
| 81 | C | C | 82 | D | C |
| 83 | C | C | 84 | C | C |
| 85 | D | C | 86 | D | C |
| 87 | C | C | 88 | C | C |
| 89 | C | C | 90 | B | B |
| 91 | D | D | 92 | C | B |
| 93 | B | B | 94 | C | B |
| 95 | C | C | 96 | C | C |
| 97 | C | B | 98 | C | B |
| 99 | B | B | 100 | B | B |
| 101 | C | C | 102 | C | B |
| 103 | C | B | 104 | B | A |
| 105 | C | C | 106 | B | A |
| 107 | A | A | 108 | A | A |
| 109 | A | A | 110 | B | B |
| 111 | B | B | 112 | C | C |
| 113 | C | B | 114 | B | B |
| 115 | C | C | 116 | B | B |
| 117 | B | B | 118 | B | B |
| 119 | C | C | 120 | C | C |
| 121 | B | B | 122 | B | B |
| 123 | B | B | 124 | C | D |
| 125 | D | C | 126 | D | C |
| 127 | C | C | 128 | C | C |
| 129 | C | C | 130 | C | B |
| 131 | C | C | 132 | C | C |
| 133 | C | C | 134 | C | C |
| 135 | C | C | 136 | C | C |
| 137 | D | D | 138 | C | C |
| 139 | C | C | 140 | C | C |
| 141 | C | C | 142 | C | C |
| 143 | C | C | 144 | C | C |
| 145 | C | B | 146 | C | C |
| 147 | C | C | 148 | C | C |
| 149 | C | C | 150 | B | B |
| 151 | B | B | 152 | C | C |
| 153 | D | B | 154 | B | A |
| 155 | B | A | 156 | A | A |
| 157 | A | A | 158 | A | A |
| 159 | A | A | 160 | B | A |
| 161 | B | A | 162 | B | A |
| 163 | B | B | 164 | B | B |
| 165 | B | B | 166 | B | A |
| 167 | B | A | 168 | B | B |
| 169 | B | A | 170 | B | A |
| 171 | B | A | 172 | B | B |
| 173 | B | B | 174 | C | A |
| 175 | B | B | 176 | B | B |
| 177 | B | A | 178 | B | B |
| 179 | B | A | 180 | B | A |
| 181 | B | A | 182 | C | B |
| 183 | C | C | 184 | C | C |
| 185 | C | B | 186 | D | C |
| 187 | C | C | 188 | C | C |
| 189 | C | C | 190 | D | C |
| 191 | D | D | 192 | C | C |
| 193 | C | C | 194 | D | D |
| 195 | D | D | 196 | C | C |
| 197 | C | C | 198 | D | C |
| 199 | C | C | 200 | ND | ND |
| 201 | C | C | 202 | C | B |
| 203 | C | B | 204 | D | C |
| 205 | C | C | 206 | D | C |
| 207 | C | C | 208 | C | B |
| 209 | C | C | 210 | C | B |
| 211 | C | C | 212 | D | C |
| 213 | C | C | 214 | D | C |
| 215 | C | C | 216 | D | D |

TABLE 1-continued

IC$_{50}$ values of examples against RON and MET

| Example | RON IC$_{50}$ | MET IC$_{50}$ | Example | RON IC$_{50}$ | MET IC$_{50}$ |
|---|---|---|---|---|---|
| 217 | C | B | 218 | C | B |
| 219 | D | B | 220 | C | B |
| 221 | C | C | 222 | C | C |
| 223 | C | C | 224 | C | B |
| 225 | C | C | 226 | C | B |
| 227 | C | C | 228 | C | B |
| 229 | C | C | 230 | C | C |
| 231 | C | C | 232 | C | B |
| 233 | D | C | 234 | D | C |
| 235 | C | C | 236 | C | C |
| 237 | C | B | 238 | C | C |
| 239 | C | C | 240 | C | C |
| 241 | D | C | 242 | C | C |
| 243 | D | C | 244 | D | C |
| 245 | D | C | 246 | C | B |
| 247 | B | A | 248 | B | B |
| 249 | B | A | 250 | B | A |
| 251 | B | B | 252 | B | B |
| 253 | B | B | 254 | B | B |
| 255 | B | B | 256 | B | A |
| 257 | B | B | 258 | B | A |
| 259 | A | A | 260 | B | B |
| 261 | B | B | 262 | B | B |
| 263 | A | A | 264 | B | A |
| 265 | B | A | 266 | C | C |
| 267 | A | A | 268 | B | B |
| 269 | B | B | 270 | B | B |
| 271 | B | B | 272 | B | B |
| 273 | A | A | 274 | B | A |
| 275 | B | B | 276 | B | B |
| 277 | B | B | 278 | B | A |
| 279 | B | B | 280 | B | B |
| 281 | B | B | 282 | B | B |
| 283 | A | A | 284 | B | B |
| 285 | C | B | 286 | B | B |
| 287 | B | C | 288 | D | B |
| 289 | C | B | 290 | C | B |
| 291 | D | C | 292 | D | C |
| 293 | C | B | 294 | C | C |
| 295 | C | B | 296 | C | C |
| 297 | C | B | 298 | A | A |
| 299 | B | B | 300 | C | B |
| 301 | C | C | 302 | B | B |
| 303 | B | B | 304 | C | B |

General Synthetic Schemes

The compounds of the formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-VI (published by Wiley-Interscience)). Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed hereinbelow. Unless otherwise indicated, the substituents in the Schemes are defined as above. Isolation and purification of the products is accomplished by standard procedures, which are known to a chemist of ordinary skill.

Scheme I illustrates a method for the preparation of compounds of Formula I.

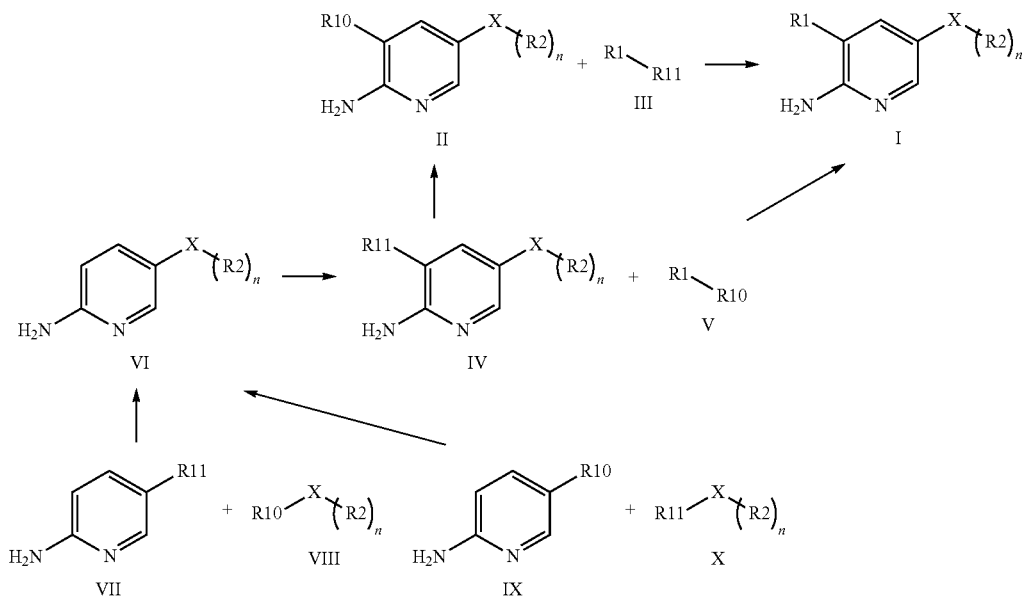

Compounds of formula II wherein R10=boronic acid/ester or trialkyltin can be reacted under catalysis by metals such as palladium or nickel with compounds of formula III wherein R11=Cl, Br, I, triflate to give compounds of formula I. Alternatively, compounds IV and V in which R10 and R11 are switched can also be coupled under substantially similar conditions to give compounds of formula I. Such coupling reactions are known to someone skilled in the art. Compounds of formula IV wherein R11=Cl, Br, or I can be prepared from compounds of formula VI by reaction with a halogenating agent. Typical halogenating agents include, but are not limited to, $Cl_2$, $Br_2$, $I_2$, NCS, NBS, NIS, ICl. Compounds of formula VI may be prepared under similar coupling conditions from compounds of formulas VII and VIII, or from compounds of formulas IX and X. Many compounds of formulas VII-X are commercially available, have been described in the literature, or can be prepared according to the literature.

In the alternate route shown in Scheme 2, the X—$(R2)_n$ moiety of compounds of formula I can be introduced on the last step.

of formulas XIV-XV are commercially available, have been described in the literature, or can be prepared according to the literature.

While the above descriptions for Schemes 1 and 2 mention coupling reactions of boronic esters/acids or organotin compounds with halides or triflates, commonly referred to as Suzuki and Stille couplings, respectively, someone skilled in the art will recognize that further types of coupling can be applied here if deemed advantageous, such as, but not limited to, Negishi couplings (with organozinc reagents), Hiyama couplings (with organosilicon reagents), or couplings that involve C—H activation.

Scheme 3 shows two routes used for the preparation of building blocks III. Building blocks III are compounds R1-R11 shown in the above Schemes 1 and 2 wherein R1 is isoquinolin-3-yl optionally substituted with 1-4 R3 group and R11 is triflate. In the first route, benzylamines are first converted into their dimethoxyacetamides. This can be accomplished conveniently by reacting the amine neat with methyl dimethoxyacetate, or the amine hydrochloride with methyl dimethoxyacetate in the presence of a base in a solvent such

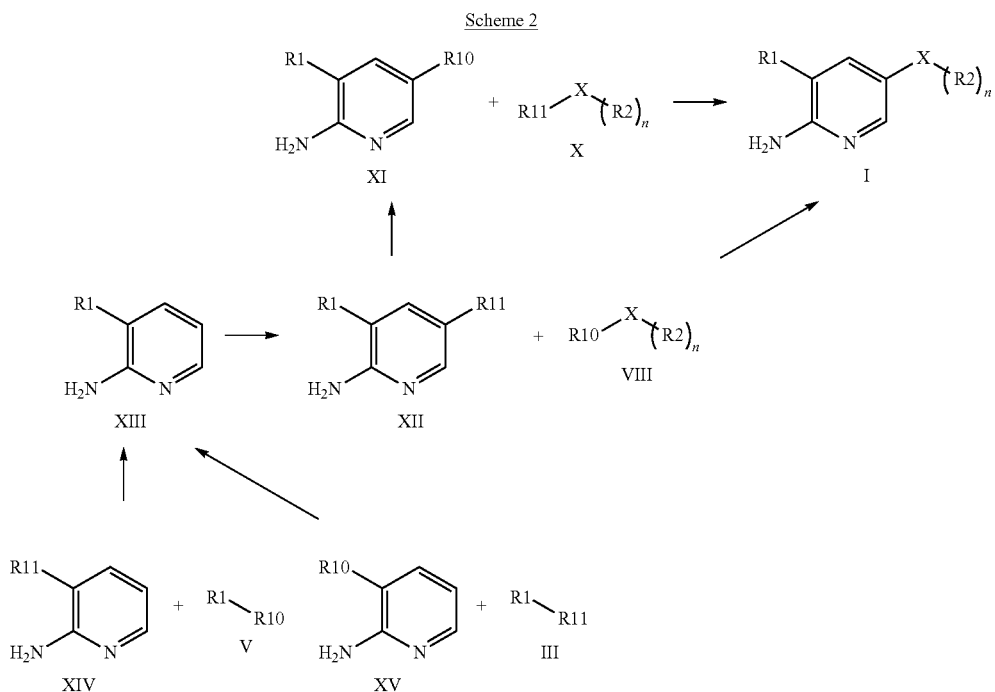

Scheme 2

Compounds of formula XI wherein R10=boronic acid/ester or trialkyltin can be reacted under catalysis by metals such as palladium or nickel with compounds of formula X wherein R11=Cl, Br, I, triflate to give compounds of formula I. Alternatively, compounds XII and VIII in which R10 and R11 are switched can also be coupled under substantially similar conditions to give compounds of formula I. Such coupling reactions are known to someone skilled in the art. Compounds of formula XII wherein R11=Cl, Br, or I can be prepared from compounds of formula XIII by reaction with a halogenating agent. Typical halogenating agents include, but are not limited to, $Cl_2$, $Br_2$, $I_2$, NCS, NBS, NIS, ICl. Compounds of formula XIII may be prepared under similar coupling conditions from compounds of formulas XIV and V, or from compounds of formulas XV and III. Many compounds as methanol. Those amides can be cyclized to yield 3-hydroxyisoquinolines by treatment with strong acids, such as, but not limited to, concentrated sulfuric acid. In the second route, a phenylacetyl chloride is reacted with formamide in the presence of a base, such as pyridine, to give an N-formylphenylacetamide that can be cyclized to yield 3-hydroxyisoquinolines by treatment with strong acids, such as, but not limited to, concentrated sulfuric acid. Many of the needed starting materials are commercially available, have been described in the literature, or can be prepared according to the literature. The conversion of the resulting 3-hydroxyisoquinolines to the corresponding trifluoromethanesulfonate esters (triflates) III can be accomplished by reacting the hydroxy compounds with triflating agents such as, but not limited to, trifluoromethanesulfonic anhydride or N-phenyl-bis(trifluoromethanesulfonimide).

Scheme 3

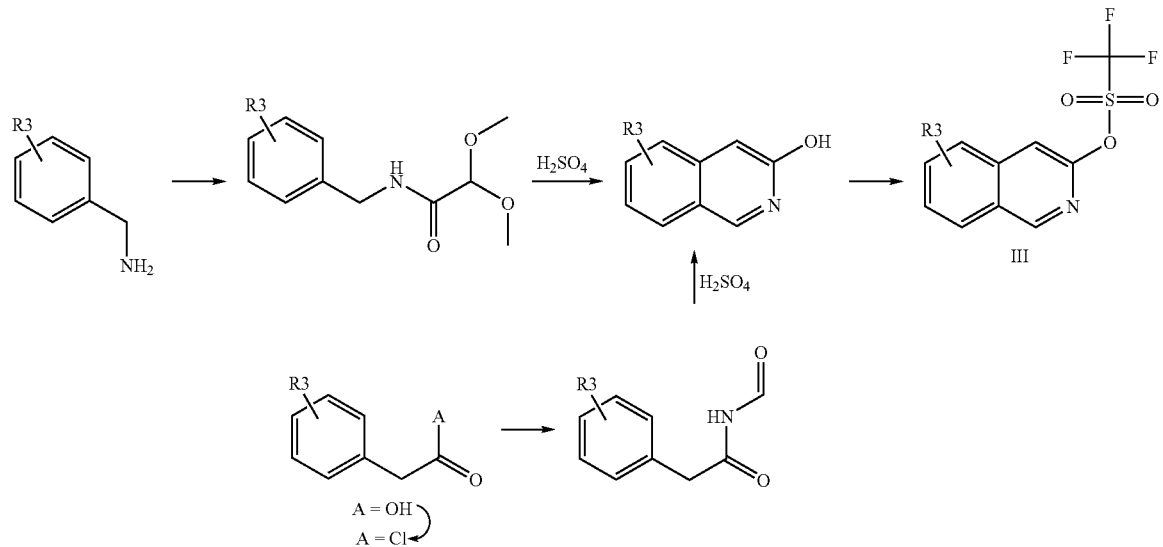

Scheme 4 illustrates three routes used for the preparation of building blocks III. Building blocks III are compounds R1-R11 shown in the above Schemes 1 and 2 wherein R1 is benzothiazol-2-yl optionally substituted with 1-4 R3 group and R11 is Cl, Br or I. In Route 1, anilines wherein LG is F, Cl, or Br are reacted with potassium ethyl xanthogenate to give 2-mercaptobenzothiazoles. These compounds may be converted by reaction with sulfuryl chloride to 2-chlorobenzothiazoles. Alternatively, in Route 2, the 2-mercaptobenzothiazoles are reacted with a methyl halide or sulfate, such as methyl iodide, and a base to give 2-methylsulfanylbenzothiazoles. Longer-chain alkyl halides or sulfates may alternatively be used. Such compounds can be converted by various oxidizing agents to the corresponding 2-methylsulfonylbenzothiazoles. Nucleophilic displacement of the methylsulfonyl group with ammonia yields 2-aminobenzothiazoles. Someone skilled in the art will recognize that the 2-amino group in these compounds can be converted to halogen such as Cl, Br, or I by the Sandmeyer reaction resulting in compounds III. In Route 3, anilines are first converted into thioureas, a conversion well known in the literature, and then reacted with an oxidizing agent such as bromine to give 2-aminobenzothiazoles. This conversion may also be accomplished directly by reacting the aniline, ammonium or sodium or potassium thiocyanate, and bromine in a one-pot procedure. The resulting 2-aminobenzothiazoles are converted to compounds III as described for Route 2. Many of the needed starting materials are commercially available, have been described in the literature, or can be prepared according to the literature.

Scheme 4

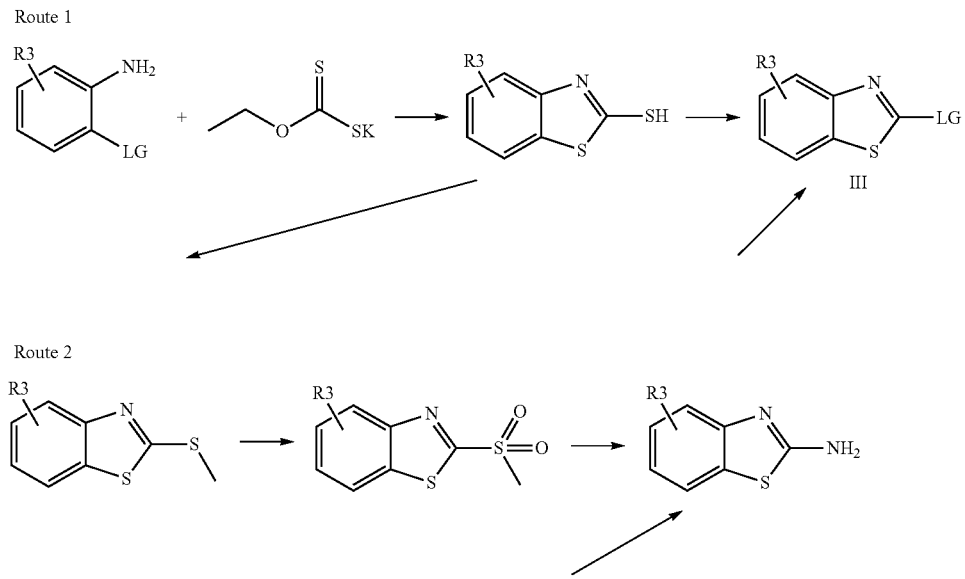

Route 3

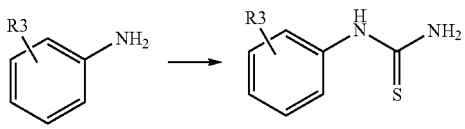

Person skilled in the art will realize that further functionalization of the above-described R1 moieties in Schemes 3 and 4 may be possible at various stages during their synthesis, or at the stage of the compounds of Formula I. Compounds or intermediates wherein substituents R3 (shown in Schemes 3 and 4) is Cl, Br, I, or triflate may be reacted under transition metal catalysis with (het)arylboronic acids or -trialkyltin reagents or alkylzinc reagents to introduce R3 as (het)aryl or alkyl, respectively, or with a cyanide source to introduce R3 as CN (which itself may be reacted further), or with KOH to introduce R3 as OH. In compounds or intermediates wherein R3 is F, the fluorine may be displaced with alkoxides to introduce R3 as alkoxy. In compounds or intermediates wherein R3 is alkoxy, these ethers may be cleaved to introduce R3 as OH. The intermediate 3-hydroxyisoquinolines wherein C4 is unsubstituted may be reacted with electrophiles to introduce substitution at C4. These examples are not meant in any way to be limiting.

WORKING EXAMPLES

The following illustrate the synthesis of various compounds of the present invention. Additional compounds within the scope of this invention may be prepared using the methods illustrated in these Examples, either alone or in combination with techniques generally known in the art.

The following abbreviations are used:

| | |
|---|---|
| NMR | Nuclear magnetic resonance |
| MDPS | Mass-directed HPLC purification system |
| MDP | Mass-directed HPLC purification |
| LC/MS | Liquid chromatography mass spectrometry |
| LDA | Lithium diisopropylamide |
| DCM | Dichloromethane |
| THF | Tetrahydrofuran |
| EtOAc | Ethyl acetate |
| MeCN | Acetonitrile |
| DMSO | Dimethylsulfoxide |
| Boc | t-Butyloxycarbonyl |
| DMF | N,N-Dimethylformamide |
| PS-DIEA | Polymer-supported diisopropylethylamine |
| PS-PPh$_3$-Pd | Polymer-supported Pd(PPh$_3$)$_4$ |
| EDCI or EDC | 1-(3-Dimethylaminopropyl)-3-ethylcarbodiimide |
| HOBt | 1-Hydroxybenzotriazole |
| DMAP | 4-Dimethylaminopyridine |
| TFA | Trifluoroacetic acid |
| TLC | Thin layer chromatography |
| Min | Minute(s) |
| h | Hour(s) |
| d | Day(s) |
| RT or rt | Room temperature |
| $t_R$ | Retention time |

Unless otherwise noted, all materials/reagents were obtained from commercial suppliers and used without further purification. $^1$H NMR (400 MHz or 300 MHz) and $^{13}$C NMR (100.6 MHz) spectra were recorded on Bruker or Varian instruments at ambient temperature with TMS or the residual solvent peak as the internal standard. The line positions or multiples are given in ppm (δ) and the coupling constants (J) are given as absolute values in Hertz (Hz). The multiplicities in $^1$H NMR spectra are abbreviated as follows: s (singlet), d (doublet), t (triplet), q (quartet), quint (quintet), m (multiplet), m$_c$ (centered multiplet), br or broad (broadened), AA'BB'. The signal multiplicities in $^{13}$C NMR spectra were determined using the DEPT135 pulse sequence and are abbreviated as follows: +(CH or CH$_3$), —(CH$_2$), C$_{quart}$ (C). Reactions were monitored by thin layer chromatography (TLC) on silica gel 60 F$_{254}$ (0.2 mm) precoated aluminum foil and visualized using UV light. Flash chromatography was performed with silica gel (400-230 mesh). Preparatory TLC was performed on Whatman LK6F Silica Gel 60 Å size 20×20 cm plates with a thickness of 1000 μm. Hydromatrix (=diatomaceous earth) was purchased from Varian. Mass-directed HPLC purification of compounds was performed on a Waters system composed of the following: 2767 Sample Manager, 2525 Binary Gradient Module, 600 Controller, 2487 Dual λ Absorbance Detector, Micromass ZQ2000 for ionization, Phenomenex Luna 5μ C18(2) 100 Å 150×21.2 mm 5μ column with mobile phases of 0.01% Formic Acid Acetonitrile (A) and 0.01% Formic Acid in HPLC water (B), a flow rate of 20 mL/min, and a run time of 13 min. LC-MS data was collected on ZQ2, ZQ3, or UPLC-ACQUITY. ZQ2 is an Agilent 1100 HPLC equipped with a Gilson 215 Liquid Handler, Gilson 819 Injection Module, and Waters Micromass ZQ2000 for ionization. ZQ3 is an Agilent 1100 HPLC equipped with an HP Series 1100 auto injector and Waters Micromass ZQ2000 for ionization. Both systems use the Xterra MS C18, 5μ particle size, 4.6×50 mm with a mobile phase of Acetonitrile (A) and 0.01% Formic Acid in HPLC water (B). The flow rate is 1.3 mL/min, the run time is 5 min, and the gradient profiles are 0.00 min 5% A, 3.00 min 90% A, 3.50 min 90% A, 4.00 min 5% A, 5.00 min 5% A for polar_5 min and 0.00 min 25% A, 3.00 min 99% A, 3.50 min 99% A, 4.00 min 25% A, 5.00 min 25% A for nonpolar_5 min. All Waters Micromass ZQ2000 instruments utilized electrospray ionization in positive (ES+) or negative (ES−) mode. The Waters Micromass ZQ2000 instruments from ZQ2 and ZQ3 can also utilize atmospheric pressure chemical ionization in positive (AP+) or negative (AP−) mode. The Waters UPLC-ACQUITY system consists of an ACQUITY sample manager attached to ACQUITY SQ MS and ACQUITY PDA detectors. It uses an ACQUITY UPLC BEH® C18 2.1×50 mm 1.7 μm column with a mobile phase of 0.1% formic acid in water (A) and 0.1% formic acid in acetonitrile (B). The flow rate is 1.0 mL/min, run time is 2 min, and the gradient profile is 0.00 min 95% A, 1.50 min 1% A, 1.85 min 1% A, 2.0 min 95% A for analytical UV detection is at 254 nm, and the MS utilizes electrospray ionization in positive mode (ES+). HPLC purification of compounds was performed on a Gilson system consisting of a 215 Liquid Handler, 819 Injection Module, a 322 Pump, and a 155 U/VIS dual wavelength detector set to 254 and 210 nm. This system uses Phenomenex Luna C18(2), 5μ particle size, 50×21.2 mm or 60×21.2 mm columns with a mobile phase of Acetonitrile and 0.1% Formic Acid in HPLC water. The flow rate is 15 mL/min and the run time is 25 min. All melting points were determined with a Mel-Temp II apparatus and are uncorrected. Elemental analyses were obtained by Atlantic Microlab, Inc., Norcross, Ga.

Scheme 5: Synthesis of key building blocks BB1, BB2, and BB3

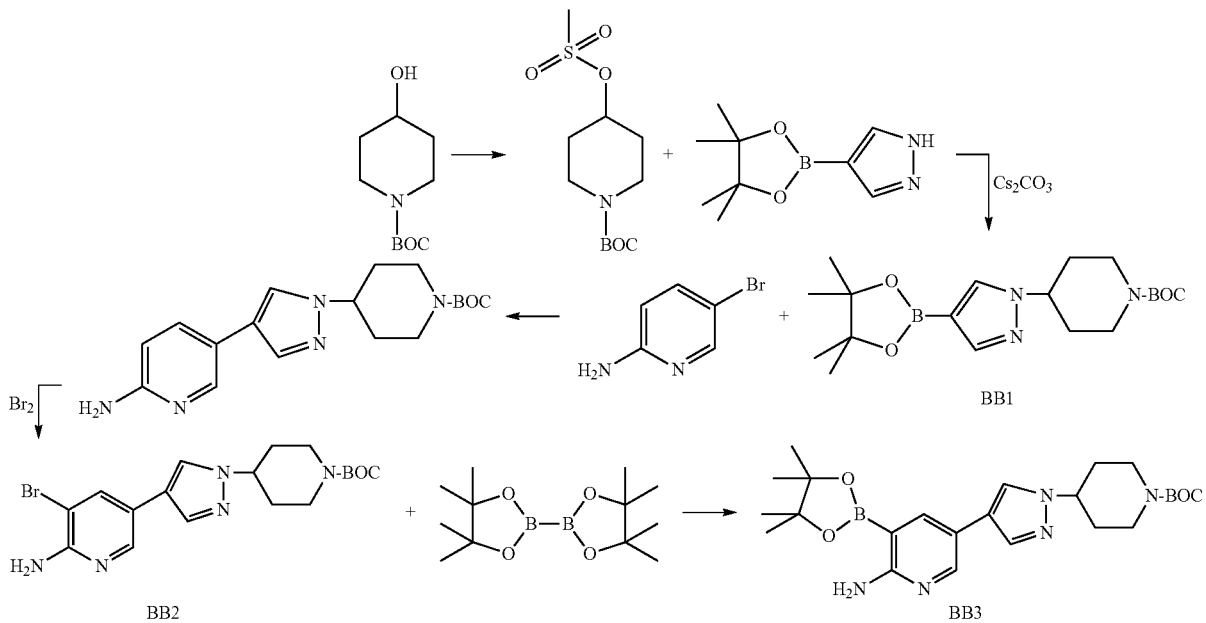

BB3: 4-{4-[6-Amino-5-(4,4,5,5-tetramethyl-[1,3,2] dioxaborolan-2-yl)-pyridin-3-yl]-pyrazol-1-yl}-piperidine-1-carboxylic acid tert-butyl ester Into a solution of $Pd_2(dba)_3$ (627 mg, 0.686 mmol) and tricyclohexylphosphine (768 mg, 2.74 mmol) in dioxane (200 mL), nitrogen was bubbled for 15 min at ambient temperature. Bispinacolatodiborane (11.32 g, 44.6 mmol), potassium acetate (5.37 g, 54.8 mmol), and 4-[4-(6-amino-5-bromopyridin-3-yl)-pyrazol-1-yl]-piperidine-1-carboxylic acid tert-butyl ester (14.5 g, 34.3 mmol) were added to the stirred solution and $N_2$ gas bubbling was continued for another 10 min. The reaction mixture was then heated at 100° C. for 8 h. The reaction mixture was cooled to ambient temperature and filtered. The filtrate was evaporated under reduced pressure. The residue was stirred with diisopropyl ether (100 mL) for 10 min at ambient temperature. The white precipitate that formed was filtered off and dried in vacuo. The filtrate was evaporated under reduced pressure, and the residue was stirred with diethyl ether (50 mL) for 10 min. The off-white precipitate that formed was filtered off, combined with the first precipitate, and dried in vacuo to give the title compound as white solid. $^1$H NMR (300 MHz, $CDCl_3$): δ=1.27 (s, 12H), 1.48 (s, 9H), 1.92-1.96 (m, 2H), 2.13-2.17 (m, 2H), 2.89 (m, 2H), 4.23-4.28 (m, 3H), 5.48 (s, broad, 2H), 7.59 (s, 1H), 7.70 (s, 1H), 7.90 (d, 1H, J=2.1 Hz), 8.25 (d, 1H, J=2.1 Hz).

BB2: 4-[4-(6-Amino-5-bromopyridin-3-yl)-pyrazol-1-yl]-piperidine-1-carboxylic acid tert-butyl ester To a well stirred solution of 4-[4-(6-aminopyridin-3-yl)-pyrazol-1-yl]-piperidine-1-carboxylic acid tert-butyl ester (24.4 g, 71.1 mmol) in DCM (800 mL) was added solid $Na_2CO_3$ (11.2 g, 107 mmol), and the mixture was cooled to 0° C. A solution of bromine (3.6 mL, 71 mmol) in DCM (200 mL) was added dropwise during 30 min, and the reaction mixture was stirred for further 5 h at ambient temperature. The reaction mixture was then cooled to 10° C., and a cold solution of 10% sodium thiosulfate in water (100 mL) followed by saturated sodium bicarbonate solution (100 mL) was added. After stirring for 10 min, the organic layer was separated, washed with brine, dried over $Na_2SO_4$, filtered, and concentrated under reduced pressure to yield a brown solid. It was triturated twice with tert-butyl methyl ether (100 mL) at 40-45° C., filtered, and dried in vacuo to yield the title compound as white solid. $^1$H NMR (300 MHz, $CDCl_3$): δ=1.48 (s, 9H), 1.92-1.96 (m, 2H), 2.13-2.17 (m, 2H), 2.89 (m, 2H), 4.23-4.28 (m, 3H), 4.86 (s, broad, 2H), 7.56 (s, 1H), 7.66 (s, 1H), 7.75 (d, 1H, J=2.1 Hz), 8.15 (d, 1H, J=2.1 Hz).

4-[4-(6-Aminopyridin-3-yl)-pyrazol-1-yl]-piperidine-1-carboxylic acid tert-butyl ester Into a well stirred suspension of 2-amino-5-bromopyridine (14.6 g, 84.8 mmol), 4-[4-(4,4,5,5-tetramethyl[1,3,2]dioxaborolan-2-yl)-1H-pyrazol-1-yl]-piperidine-1-carboxylic acid tert-butylester (40.0 g, 106 mmol) and $Cs_2CO_3$ (55.1 g, 170 mmol) in dioxane (700 mL)/water (140 mL) was bubbled $N_2$ gas for 15 min at ambient temperature. $Pd(PPh_3)_4$ (4.8 g, 4.2 mmol) was then added to the solution followed by $N_2$ gas bubbling for another 10 min. The reaction mixture was then heated at 100° C. for 3 h. The cooled reaction mixture was concentrated under reduced pressure to yield an off-white residue. It was stirred with water/DCM (100 mL each) for 5 min, and the organic layer was separated. The aqueous layer was extracted with DCM (3×100 mL). The combined organic layers were washed with water (50 mL) followed by brine (50 mL), dried over sodium sulfate, filtered, and concentrated under reduced pressure to yield a light yellowish residue. It was triturated with 1:1 EtOAc:Hexane (100 mL) with ice cooling for 10 min. Off-white crystals separated out which were filtered and dried in vacuo to give the title compound as white solid. $^1$H NMR (300 MHz, $CDCl_3$): δ=1.49 (s, 9H), 1.89-2.03 (m, 2H), 2.12-2.22 (m, 2H), 2.91 (m, 2H), 4.23-4.28 (m, 3H), 4.48 (s, broad, 2H), 6.53 (d, J=8.4 Hz, 1H), 7.24-7.33 (d, J=8.4 Hz, 1H), 7.67 (s, 1H), 7.90 (d, 1H, J=2.1 Hz), 8.25 (d, 1H, J=2.1 Hz).

BB1: 4-[4-(4,4,5,5-Tetramethyl[1,3,2]dioxaborolan-2-yl)-1H-pyrazol-1-yl]-piperidine-1-carboxylic acid tert-butylester A mixture of 4-(4,4,5,5-tetramethyl[1,3,2]dioxaborolan-2-yl)-1H-pyrazole (30.0 g, 154 mmol), 4-methanesulfonyloxypiperidine-1-carboxylic acid tert-butylester (52.5 g, 200 mmol) and cesium carbonate (80.1 g, 246 mmol) in anhydrous DMF (400 mL) was heated to 100° C. for 24 h. DMF was removed under high vacuum. The residue was then diluted with water (200 mL) and extracted with EtOAc (3×200 mL). The combined organic phases were washed with water (3×50 mL) and brine (100 mL), dried over anhydrous sodium sulfate, filtered and concentrated under reduced pressure. To the orange-brown oily residue was added diisopropyl ether (300 mL), and the mixture was stirred at 0° C. for 2 h. Colorless crystals separated out that were filtered off and dried in vacuo to give a $1^{st}$ crop of the title compound. The filtrate was then concentrated in vacuo, the residue was mixed with diisopropyl ether (100 mL), a small amount of the $1^{st}$ crop was added as a seed, and the mixture was stirred overnight. The resulting white precipitate was filtered and dried in vacuo as $2^{nd}$ crop of the title compound. $^1$H NMR (300 MHz, CDCl$_3$): δ=1.33 (s, 12H), 1.48 (s, 9H), 1.85-1.93 (m, 2H), 2.15-2.18 (m, 2H), 2.83-2.92 (m, 2H), 4.23-4.39 (m, 3H), 7.76 (s, 1H), 7.84 (s, 1H).

4-Methanesulfonyloxypiperidine-1-carboxylic acid tert-butyl ester

To a solution of 1-Boc-4-hydroxypiperidine (32.2 g, 0.160 mol) in DCM (400 mL) were added triethylamine (26.8 mL, 0.192 mol), methanesulfonyl chloride (13.6 mL, 0.176 mol) and 4-dimethylaminopyridine (0.20 g, 0.0016 mol) at 0° C. under nitrogen atmosphere. The resulting mixture was slowly warmed to rt and stirred at rt overnight. The mixture was washed with sat. aq. NaHCO$_3$ (3×80 mL), brine (2×80 mL), and dried over anhydrous sodium sulfate. The filtrate was concentrated to give the title compound as a white solid. It was used in the next step without further purification. $^1$H NMR (CDCl$_3$): δ=1.47 (s, 9H), 1.80-1.85 (m, 2H), 1.95-1.99 (m, 2H), 3.05 (s, 3H), 3.28-3.34 (m, 2H), 3.68-3.74 (m, 2H), 4.89 (m$_c$, 1H).

Example 1

3-(1-Methylisoquinolin-3-yl)-5-(1-piperidin-4-yl-1H-pyrazol-4-yl)-pyridin-2-ylamine trihydrochloride To a solution of 4-{4-[6-Amino-5-(1-methylisoquinolin-3-yl)-pyridin-3-yl]-pyrazol-1-yl}-piperidine-1-carboxylic acid tert-butyl ester (36.8 mg, 0.0759 mmol) in 1,4-dioxane (1.0 mL, 13 mmol) was added 4.0 M of HCl in 1,4-dioxane (1.0 mL, 4.0 mmol), and the mixture was stirred at ambient temperature for 1.5 h. Almost immediately a pale yellow solid precipitated. The solid was filtered off, washed with MTBE, and dried in vacuo, giving the title compound as pale yellow solid. $^1$H NMR (400 MHz, DMSO-d$_6$): δ=14.7 (very brs, 1H), 9.33-9.23 (brm, 1H), 9.21-9.08 (brm, 1H), 8.82 (d, J=1.8 Hz, 1H), 8.8 (very brs, 2H), 8.59 (s, 1H), 8.50 (s, 1H), 8.48 (d, J=1.8 Hz, 1H), 8.38 (d, J=8.4 Hz, 1H), 8.14 (s, 1H), 8.13 (d, J=8.0 Hz, 1H), 7.95 (dd, J=7.2, 7.2 Hz, 1H), 7.84 (dd, J=7.8, 7.8 Hz, 1H), 4.58-4.49 (m$_c$, 1H), 3.39 (brd, J=12.6 Hz, 1H), 3.11 (brq, J=11.4 Hz, 2H), 3.07 (s, 3H), 2.30-2.13 (m, 4H). MS(ES+): m/z=385.15 (53) [MH$^+$], 302.12 (100) [MH$^+$-piperidine]. HPLC: t$_R$=1.88 min (polar_5 min, ZQ3).

4-{4-[6-Amino-5-(1-methylisoquinolin-3-yl)-pyridin-3-yl]-pyrazol-1-yl}-piperidine-1-carboxylic acid tert-butyl ester To a solution of 4-{4-[6-Amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (97.5 mg, 0.208 mmol), trifluoromethanesulfonic acid 1-methylisoquinolin-3-yl ester (62.3 mg, 0.214 mmol), and Pd(PPh$_3$)$_4$ (15 mg, 0.013 mmol) in 1,4-dioxane (3.2 mL, 41 mmol) in a sealable microwave tube was added a solution of Cs$_2$CO$_3$ (135 mg, 0.413 mmol) in H$_2$O (0.95 mL, 53 mmol). The tube was sealed, evacuated and refilled with nitrogen (3×), and heated in the microwave reactor to 100° C. for 30 minutes. The reaction mixture was diluted with EtOAc, washed with water and brine, and dried over MgSO$_4$. The EtOAc extract was diluted with DCM (to give DCM:EtOAc≈1:1) and filtered through a plug of silica gel. The silica gel was then washed with DCM:EtOAc 1:2, DCM:EtOAc 1:5, and EtOAc until no more product eluted. Filtrate/washings that contained product were concentrated in vacuo. The crude material was chromatographed on silica gel [10 g/70 mL prepacked cartridge, eluting with DCM→DCM:EtOAc 2:1→DCM:EtOAc 1:1→DCM:EtOAc 1:2→EtOAc]. Mixed fractions were combined, concentrated in vacuo, and purified by prep. TLC [20×20 cm plates, 500 µm, eluting with 2% MeOH/DCM (1×) and 4% MeOH/DCM (3×)]. Clean material from prep. TLC was combined with pure fractions from the column chromatography and dried in vacuo, yielding the title compound as viscous, yellow oil. $^1$H NMR (400 MHz, CDCl$_3$): δ=8.26 (d, J=2.0 Hz, 1H), 8.15 (dd, J=0.8, 8.4 Hz, 1H), 7.94 (d, J=2.0 Hz, 1H), 7.89 (d, J=8.0 Hz, 1H), 7.88 (s, 1H), 7.77 (d, J=0.4 Hz, 1H), 7.72 (ddd, J=1.2, 7.2, 8.2 Hz, 1H), 7.66 (d, J=0.4 Hz, 1H), 7.62 (ddd, J=1.2, 6.8, 8.2 Hz, 1H), 6.49 (brs, 2H), 4.38-4.20 (m, 3H), 3.03 (s, 3H), 2.92 (brt, J=12.0 Hz, 2H), 2.19 (brd, J=12.0 Hz, 2H), 1.98 (dq, J=4.4, 12.2 Hz, 2H), 1.49 (s, 9H). MS(ES+): m/z=485.18 (100) [MH$^+$], 429.06 (39) [MH$^+$-isobutene]. HPLC: t$_R$=2.76 min (polar_5 min, ZQ3).

Trifluoromethanesulfonic acid 1-methylisoquinolin-3-yl ester

To a suspension of 1-methylisoquinolin-3-ol (0.242 g, 1.52 mmol) and triethylamine (0.40 mL, 2.9 mmol) in DCM (10 mL, 160 mmol), cooled in an ice bath, was added dropwise trifluoromethanesulfonic anhydride (0.31 mL, 1.8 mmol). The solid dissolved, and the solution was stirred at 0° C. for 75 min. More trifluoromethanesulfonic anhydride (0.15 mL, 0.89 mmol) and triethylamine (0.15 mL, 1.1 mmol) were added, and stirring at 0° C. was continued for 1 h. The reaction solution was then diluted with more DCM to a total volume of 40 mL, washed with water, NaHCO$_3$ solution, and brine, and dried over MgSO4. The extract was filtered through a plug of silica gel (≈1" high in a 60 mL fritted funnel), which was rinsed with DCM until no further product eluted. The combined fractions containing product were concentrated and dried in vacuo to give the title compound as a brown oil. It was used in the next reaction without further purification. $^1$H NMR (400 MHz, CDCl$_3$): δ=8.17 (dd, J=1.2, 8.4 Hz, 1H), 7.88 (d, J=8.4 Hz, 1H), 7.76 (ddd, J=1.2, 6.8, 8.4 Hz, 1H), 7.67 (ddd, J=1.2, 6.8, 8.4 Hz, 1H), 7.42 (s, 1H), 2.97 (s, 3H). MS(ES+): m/z=291.98 (100) [MH$^+$], 159.08 (90) [MH$^+$—SO$_2$CF$_3$]. HPLC: t$_R$=3.95 min (polar_5 min, ZQ3).

1-Methylisoquinolin-3-ol

Concentrated sulfuric acid (18 M; 6.0 mL) was added to 2,2-dimethoxy-N-(1-phenylethyl)-acetamide (2.49 g, 11.2 mmol), and the resulting solution was stirred at 60° C. for 105 min. The reaction mixture was added to ≈100 mL of ice, and the yellow precipitate was filtered off. The pH of the filtrate was adjusted to 7-8 with NaHCO$_3$ solution, the initial yellow solid was added, and the yellow precipitate was filtered off, washed with water, and dried in vacuo, giving the title compound as yellow solid. $^1$H NMR (400 MHz, DMSO-d$_6$): δ=10.68 (brs, 1H), 8.00 (dd, J=1.0, 8.6 Hz, 1H), 7.64 (d, J=8.4 Hz, 1H), 7.53 (dt, J=1.0, 8.0 Hz, 1H), 7.28 (dt, J=0.8, 8.0 Hz, 1H), 6.69 (s, 1H), 2.78 (s, 3H). MS(ES+): m/z=160.10 (100) [MH$^+$]. HPLC: t$_R$=2.13 min (polar_5 min, ZQ3).

2,2-Dimethoxy-N-(1-phenylethyl)-acetamide

A mixture of methyl dimethoxyacetate (2.10 g, 15.6 mmol) and α-methylbenzylamine (1.90 g, 15.7 mmol) was stirred at ambient temperature for 5 d and at 40° C. for 4 d. To the reaction mixture was added hexane (5 mL), and the mixture was sonicated. Two layers formed, but no solid precipitated, even upon cooling, and the hexane layer was withdrawn with a pipette. This was repeated twice. The residue was dissolved in EtOAc (≈100 mL), and the solution was washed with aqueous solutions of NH$_4$Cl, NaHCO$_3$, and brine, and dried over MgSO$_4$. The solution was filtered and dried in vacuo overnight to give the title compound as pale yellow oil. $^1$H NMR (CDCl$_3$, 400 MHz): δ=7.38-7.30 (m, 4H), 7.29-7.24 (m, 1H), 6.80 (brs, 1H), 5.16 (dq, J=8.0, 6.8 Hz, 1H), 4.70 (s, 1H), 3.42 (s, 3H), 3.36 (s, 3H), 1.52 (d, J=6.8 Hz, 3H). MS(ES+): m/z=246.07 (64) [MNa$^+$], 224.11 (78) [MH$^+$], 192.11 (52) [MH$^+$-MeOH], 160.10 (60) [MH$^+$-2 MeOH]. HPLC: t$_R$=2.76 min (polar_5 min, ZQ3).

Example 2

3-(4-Methylisoquinolin-3-yl)-5-(1-piperidin-4-yl-1H-pyrazol-4-yl)-pyridin-2-ylamine trihydrochloride To a solution of 4-{4-[6-amino-5-(4-methylisoquinolin-3-yl)-pyridin-3-yl]-pyrazol-1-yl}-piperidine-1-carboxylic acid tert-butyl ester (79.1 mg, 0.163 mmol) in 1,4-dioxane (2.0 mL, 26 mmol) was added 4.0 M of HCl in 1,4-dioxane (2.0 mL), and the mixture was stirred at ambient temperature for 3 h. Almost immediately an off-white solid precipitated. The solid was filtered off, washed with MTBE, and dried in vacuo overnight to give the title compound as an off-white solid. It appeared to be slightly hygroscopic during the filtration; however, after the washing and initial drying it appeared to be non-hygroscopic. $^1$H NMR (400 MHz, DMSO-d$_6$): δ=14.6 (very brs, 1H), 9.68 (s, 1H), 9.37-9.24 (brm, 1H), 9.24-9.10 (brm, 1H), 8.55 (d, J=2.0 Hz, 1H), 8.47 (d, J=7.6 Hz, 1H), 8.46 (d, J=2.0 Hz, 1H), 8.39 (s, 1H), 8.38 (d, J=7.6 Hz, 1H), 8.14 (t, J=7.2 Hz, 1H), 8.05 (s, 1H), 7.98 (t, J=7.6 Hz, 1H), 7.81 (brs, 2H), 4.54-4.45 (m$_c$, 1H), 3.35 (brd, J=12.6 Hz, 2H), 3.07 (brq, J=11.2 Hz, 2H), 2.59 (s, 3H), 2.26-2.09 (m, 4H). MS(ES+): m/z=385.17 (96) [MH$^+$], 302.1 (100) [MH$^+$-piperidine]. HPLC: t$_R$=0.65 & 1.72 min (peak splitting; polar_5 min, ZQ3).

4-{4-[6-Amino-5-(4-methylisoquinolin-3-yl)-pyridin-3-yl]-pyrazol-1-yl}-piperidine-1-carboxylic acid tert-butyl ester To a solution of 4-{4-[6-Amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (86.3 mg, 0.184 mmol), trifluoromethanesulfonic acid 4-methylisoquinolin-3-yl ester (54.8 mg, 0.188 mmol), and Pd(PPh$_3$)$_4$ (14 mg, 0.012 mmol) in 1,4-dioxane (2.8 mL, 36 mmol) in a sealable microwave tube was added a solution of Cs$_2$CO$_3$ (118 mg, 0.361 mmol) in H$_2$O (0.80 mL, 44 mmol). The tube was sealed, evacuated and refilled with nitrogen (3×), and heated in the microwave reactor to 100° C. for 30 min. The reaction mixture was diluted with DCM, washed with water and brine, and dried over MgSO$_4$. The crude material was chromatographed on silica gel [20 g/70 mL prepacked cartridge, eluting with DCM→1% MeOH in DCM→2% MeOH in DCM→2.5% MeOH in DCM→3% MeOH in DCM→3.5% MeOH in DCM→4% MeOH in DCM]. Fractions containing the title compound were combined and dried in vacuo, giving the title compound as a glassy solid. $^1$H NMR (400 MHz, CDCl$_3$): δ=9.22 (s, 1H), 8.30 (d, J=2.4 Hz, 1H), 8.08 (dd, J=0.8, 8.6 Hz, 1H), 8.03 (d, J=8.0 Hz, 1H), 7.81 (ddd, J=1.2, 6.8, 8.3 Hz, 1H), 7.71 (d, J=0.8 Hz, 1H), 7.68 (ddd, J=0.8, 7.0, 8.0 Hz, 1H), 7.62 (s, 1H), 7.57 (d, J=2.4 Hz, 1H), 4.85 (brs, 2H), 4.42-4.13 (m, 3H), 2.90 (brt, J=11.2 Hz, 2H), 2.62 (s, 3H), 2.15 (brdd, J=2.0, 12.4 Hz, 2H), 1.95 (dq, J=4.0, 12.0 Hz, 2H), 1.48 (s, 9H). MS(ES+): m/z=485.14 (100) [MH$^+$], 429.12 (66) [MH$^+$-isobutene]. HPLC: t$_R$=2.62 min (polar_5 min, ZQ3).

Trifluoromethanesulfonic acid 4-methylisoquinolin-3-yl ester

To a suspension of 4-methylisoquinolin-3-ol (0.243 g, 1.53 mmol) and triethylamine (0.40 mL, 2.9 mmol) in DCM (10 mL, 160 mmol), cooled in an ice bath, was added dropwise trifluoromethanesulfonic anhydride (0.31 mL, 1.8 mmol) at 15:20. The solid dissolved, and the solution was stirred at 0° C. for 1 h. More trifluoromethanesulfonic anhydride (0.10 mL, 0.59 mmol) was added (the yellow color of the reaction solution faded to a very pale yellow), and stirring at 0° C. was continued for 30 min. The reaction solution was diluted with more DCM to a total volume of ≈40 mL, washed with water, NaHCO$_3$ solution, and brine, and dried over MgSO$_4$. The extract was filtered through a plug of silica gel (≈1" high in a 60 mL fritted funnel), which was rinsed with DCM until no further product eluted. The combined fractions containing product were concentrated and dried in vacuo, giving the title compound as a pale yellow solid. It was used for the next reaction without further purification. $^1$H NMR (400 MHz, CDCl$_3$): δ=8.93 (s, 1H), 8.08-8.03 (m, 2H), 7.83 (ddd, J=1.4, 6.8, 8.4 Hz, 1H), 7.69 (ddd, J=1.2, 7.0, 8.0 Hz, 1H), 2.68 (d, J=0.4 Hz, 3H). MS(ES+): m/z=292.00 (95) [MH$^+$], 159.08 (100) [MH$^+$—SO$_2$CF$_3$]. HPLC: t$_R$=3.96 min (polar_5 min, ZQ3).

4-Methylisoquinolin-3-ol

Concentrated sulfuric acid (18 M; 6.0 mL) was added to N-benzyl-2,2-dimethoxypropionamide (1.38 g, 6.18 mmol) at ambient temperature, and the solution was stirred at ambient temperature for 30 min and at 55° C. overnight. The reaction mixture was added to ≈100 mL of ice, and the pH of the yellow solution was adjusted to 7-8 with NaHCO$_3$ solution. Small amounts of a brown solid that precipitated very soon during the addition (pH was still <2) were filtered off, and neutralization was continued. The yellow precipitate was filtered off, washed with water, and dried in vacuo, giving the title compound as yellow solid. It was used in the next step without further purification. $^1$H NMR (400 MHz, DMSO-d$_6$): δ=10.6 (very brs, 1H), 8.74 (s, 1H), 7.91 (d, J=8.4 Hz, 1H), 7.83 (dd, J=0.8, 8.6 Hz, 1H), 7.61 (ddd, J=1.6, 6.4, 8.4 Hz, 1H), 7.31 (ddd, J=0.8, 6.4, 8.0 Hz, 1H), 2.37 (d, J=0.4 Hz, 3H). MS(ES+): m/z=160.10 (100) [MH+]. HPLC: $t_R$=2.3 min (polar_5 min, ZQ3).

N-Benzyl-2,2-dimethoxypropionamide

A mixture of methyl 2,2-dimethoxypropionate (2.33 g, 15.7 mmol) and benzylamine (1.68 g, 15.7 mmol) in a 20 mL screw-capped vial was stirred at 55° C. for 12 d. To the reaction mixture, which mostly solidified upon cooling to ambient temperature was added hexane (5 mL), and the mixture was sonicated and stirred vigorously. The solid was filtered off, washed with hexanes, and dried in vacuo to give the title compound as off-white solid. $^1$H NMR (400 MHz, CDCl$_3$): δ=7.38-7.25 (m, 5H), 7.08 (brs, 1H), 4.49 (d, J=5.6 Hz, 2H), 3.25 (s, 6H), 1.52 (s, 3H). MS(ES+): m/z=246.07 (58) [MNa+], 224.11 (58) [MH+], 192.12 (100) [MH+-MeOH], 160.11 (33) [MH+-2 MeOH]. HPLC: $t_R$=2.78 min (polar_5 min, ZQ3).

Example 3

3-(8-Chloroisoquinolin-3-yl)-5-(1-piperidin-4-yl-1H-pyrazol-4-yl)-pyridin-2-ylamine trihydrochloride To a solution of 4-{4-[6-amino-5-(8-chloroisoquinolin-3-yl)-pyridin-3-yl]-pyrazol-1-yl}-piperidine-1-carboxylic acid tert-butyl ester (64.2 mg, 0.127 mmol) in 1,4-dioxane (1.5 mL, 19 mmol) was added HCl (4.0 M in 1,4-dioxane; 1.2 mL, 4.8 mmol), and the mixture was stirred at ambient temperature for 70 min. Almost immediately an off-white solid precipitated. The solid was filtered off, washed with MTBE, and dried in vacuo overnight to give the title compound as yellow solid. It appeared to be slightly hygroscopic during the filtration; however, after the washing and initial drying it appeared to be non-hygroscopic. $^1$H NMR (400 MHz, DMSO-d$_6$): δ=14.7 (very brs, 1H), 9.68 (s, 1H), 9.23-9.14 (brm, 1H), 9.12-8.99 (brm, 1H), 8.89 (d, J=2.0 Hz, 1H), 8.82 (s, 1H), 8.76 (brs, 2H), 8.52 (s, 1H), 8.49 (d, J=2.0 Hz, 1H), 8.16 (s, 1H), 8.12 (d, J=8.0 Hz, 1H), 7.95 (dd, J=1.2, 7.6 Hz, 1H), 7.90 (t, J=7.8 Hz, 1H), 4.58-4.49 (mc, 1H), 3.40 (brd, J=12.0 Hz, 2H), 3.07 (brq, J=11.2 Hz, 2H), 2.30-2.12 (m, 4H). MS(ES+): m/z=405.13/407.13 (88/60) [MH+], 322.07/324.05 (90/64) [MH+-piperidine]. HPLC: $t_R$=1.98 min (polar_5 min, ZQ3). UV: $\lambda_{max}$=210, 244, 352 nm.

4-{4-[6-Amino-5-(8-chloroisoquinolin-3-yl)-pyridin-3-yl]-pyrazol-1-yl}-piperidine-1-carboxylic acid tert-butyl ester To a solution of 4-{4-[6-Amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (70.1 mg, 0.149 mmol), trifluoromethanesulfonic acid 8-chloroisoquinolin-3-yl ester (47.9 mg, 0.154 mmol), and Pd(PPh$_3$)$_4$ (11.5 mg, 0.00995 mmol) in 1,4-dioxane (2.3 mL, 29 mmol in a sealable microwave tube was added a solution of Cs$_2$CO$_3$ (95.5 mg, 0.293 mmol) in H$_2$O (0.65 mL, 36 mmol). The tube was sealed, evacuated and refilled with nitrogen (3×), and heated in the microwave reactor to 105° C. for 30 minutes. The reaction mixture was diluted with DCM, washed with water, sat. NaHCO$_3$ solution, and brine, dried over MgSO$_4$, filtered, and concentrated in vacuo. The crude material was chromatographed on silica gel [20 g/70 mL prepacked cartridge, eluting with DCM→1% MeOH in DCM→2% MeOH in DCM→3% MeOH in DCM]. Fractions containing the title compound were combined and dried in vacuo, yielding the title compound as a glassy, yellow solid. $^1$H NMR (400 MHz, CDCl$_3$): δ=9.70 (t, J=0.8 Hz, 1H), 8.29 (d, J=2.0 Hz, 1H), 8.04 (d, J=0.4 Hz, 1H), 7.96 (d, J=2.4 Hz, 1H), 7.82 (dt, J=5.8, 3.0 Hz, 1H), 7.78 (d, J=1.2 Hz, 1H), 7.67 (d, J=0.8 Hz, 1H), 7.66-7.62 (m, 2H), 6.47 (brs, 2H), 4.40-4.19 (m, 3H), 2.92 (brt, J=11.6 Hz, 2H), 2.19 (brdd, J=12.2 Hz, 2H), 1.95 (dq, J=4.0, 12.0 Hz, 2H), 1.49 (s, 9H). MS(ES+): m/z=505.16/507.13 (100/42) [MH+], 449.05/451.07 (3/1) [MH+-isobutene]. HPLC: $t_R$=3.15 min (polar_5 min, ZQ3).

Trifluoromethanesulfonic acid 8-chloroisoquinolin-3-yl ester

To a suspension of 8-chloroisoquinolin-3-ol (0.260 g, 1.45 mmol) and triethylamine (0.40 mL, 2.9 mmol) in DCM (10 mL, 160 mmol), cooled in an ice bath, was added dropwise trifluoromethanesulfonic anhydride (0.31 mL, 1.8 mmol). The solid dissolved, the color changed from yellow to brown, and the solution was stirred at 0° C. for 1 h. The reaction solution was diluted with more DCM to a total volume of ≈40 mL, washed with water, NaHCO$_3$ solution, and brine, and dried over MgSO$_4$. The extract was filtered through a plug of silica gel (≈1" high in a 60 mL fritted funnel), which was rinsed with DCM until no further product eluted. The fractions containing product were concentrated and dried in vacuo to give the title compound as beige solid. It was used for the next reaction without further purification. $^1$H NMR (400 MHz, CDCl$_3$): δ=9.50 (s, 1H), 7.84 (dd, J=2.8, 6.4 Hz, 1H), 7.74-7.68 (m, 2H), 7.60 (s, 1H). MS(ES+): m/z=311.66/313.63 (66/24) [MH+], 178.88/180.87 (100/38) [MH+—SO$_2$CF$_3$].

8-Chloroisoquinolin-3-ol

Concentrated sulfuric acid (18 M; 7.0 mL) was added to N-(2-chlorobenzyl)-2,2-dimethoxyacetamide (2.21 g, 9.07 mmol) at ambient temperature, and the solution was stirred overnight at ambient temperature and at 60° C. for 5 h. The cooled reaction mixture was added to ≈50 mL of ice, and the pH of the yellow mixture was adjusted to 7 with NaHCO$_3$ solution. The yellow precipitate was filtered off, washed with water, and dried in vacuo, giving the title compound as yellow solid. The material was used in the next step without further purification. $^1$H NMR (400 MHz, DMSO-d$_6$): δ=11.13 (brs, 1H), 9.11 (s, 1H), 7.72 (d, J=8.4 Hz, 1H), 7.54 (dd, J=8.2, 7.2 Hz, 1H), 7.45 (dd, J=0.8, 7.2 Hz, 1H), 7.00 (s, 1H). MS(ES+): m/z=180.07/182.02 (100/38) [MH+]. HPLC: $t_R$=2.45 min (polar_5 min, ZQ3).

N-(2-chlorobenzyl)-2,2-dimethoxyacetamide

A mixture of methyl dimethoxyacetate (1.41 g, 10.4 mmol) and 2-chlorobenzylamine (1.45 g, 9.73 mmol) in a microwave vial was sealed and heated in the microwave reactor to 130° C. for 30 min and then to 140° C. for 40 min. The reaction solution was dissolved in EtOAc (≈60 mL) and washed with dil. HCl, water, sat. Na$_2$CO$_3$ solution, and brine, and dried over MgSO$_4$. The EtOAc extract was filtered, concentrated, and dried in vacuo overnight, giving the title compound as pale yellow oil. $^1$H NMR (400 MHz, CDCl$_3$): δ=7.41-7.35 & 7.27-7.22 (AA'BB', 4H), 6.98 (brs, 1H), 4.74 (s, 1H), 4.58 (d, J=6.0 Hz, 2H), 3.40 (s, 6H). MS(ES+): m/z=266.05/268.01 (41/13) [MNa'], 244.07/246.02 (86/58) [MH+], 212.03/214.02 (56/21) [MH+-MeOH], 180.07/182.05 (63/26) [MH+-2 MeOH]. HPLC: $t_R$=2.87 min (polar_5 min, ZQ3).

Example 4

3-(6-Methylisoquinolin-3-yl)-5-(1-piperidin-4-yl-1H-pyrazol-4-yl)-pyridin-2-ylamine trihydrochloride To a solution of 4-{4-[6-amino-5-(6-methylisoquinolin-3-yl)-pyridin-3-yl]-pyrazol-1-yl}-piperidine-1-carboxylic acid tert-butyl ester (29.5 mg, 0.0609 mmol) in DCM (1.0 mL, 16 mmol) was added 1.0 M of HCl in Et2O (1.7 mL, 1.7 mmol), and the mixture was stirred at ambient temperature for 6 h. Almost immediately a yellow solid precipitated. The solvents were evaporated, and the residue was transferred into a vial and dried in vacuo overnight to give the title compound as yellow solid. It appeared to be slightly hygroscopic. $^1$H NMR (400 MHz, DMSO-d6): δ=14.7 (very brs, 1H), 9.41 (s, 1H), 9.26-9.17 (brm, 1H), 9.14-9.02 (brm, 1H), 8.83 (d, J=2.0 Hz, 1H), 8.79 (brs, 1H), 8.62 (s, 1H), 8.51 (s, 1H), 8.46 (d, J=2.0 Hz, 1H), 8.18 (d, J=8.4 Hz, 1H), 8.15 (d, J=0.4 Hz, 1H), 7.87 (s, 1H), 7.66 (dd, J=1.2, 8.4 Hz, 1H), 7.36 (s, 1H), 7.23 (s, 1H), 7.10 (s, 1H), 4.58-4.49 (m$_c$, 1H), 3.40 (brd, J=12.4 Hz, 2H), 3.11 (brq, J=11.8 Hz, 2H), 2.58 (s, 3H), 2.31-2.13 (m, 4H). MS(ES+): m/z=385.20 (38) [MH$^+$], 302.14 (100) [MH$^+$-piperidine]. HPLC: $t_R$=1.78 min (polar_5 min, ZQ2).

4-{4-[6-Amino-5-(6-methylisoquinolin-3-yl)-pyridin-3-yl]-pyrazol-1-yl}-piperidine-1-carboxylic acid tert-butyl ester To a solution of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (53.7 mg, 0.114 mmol), trifluoromethanesulfonic acid 6-methylisoquinolin-3-yl ester (35.0 mg, 0.120 mmol), and PS-PPh$_3$-Pd (0.10 mmol/g loading; 76 mg, 0.0076 mmol; Argonaut) in 1,4-dioxane (2.0 mL, 25 mmol) in a sealable microwave tube was added a solution of Cs$_2$CO$_3$ (75.6 mg, 0.232 mmol) in H$_2$O (0.60 mL, 33 mmol). The tube was sealed, evacuated and refilled with nitrogen (3×), and heated in the microwave reactor to 105° C. for 30 minutes. The resin was filtered off and washed with DCM. The combined filtrate and washings were washed with 1M NaOH, water and brine, dried over MgSO$_4$, filtered, and concentrated in vacuo. The residue was purified by preparative TLC [20×20 cm plate, 500 μm layer of silica gel, eluting with 3.5% MeOH in DCM (3×)]. Material from the main band was collected and dried in vacuo overnight to give the title compound as a yellow glassy solid. $^1$H NMR (400 MHz, CDCl$_3$): δ=9.22 (s, 1H), 8.26 (d, J=2.0 Hz, 1H), 7.94 (s, 1H), 7.93 (d, J=2.0 Hz, 1H), 7.91 (d, J=8.4 Hz, 1H), 7.77 (d, J=0.4 Hz, 1H), 7.67 (brs, 1H), 7.66 (s, 1H), 7.46 (dd, J=8.4, 1.6 Hz, 1H), 6.43 (brs, 2H), 4.38-4.19 (m, 3H), 2.92 (brt, J=11.0 Hz, 2H), 2.58 (s, 3H), 2.19 (brdd, J=2.0, 12.4 Hz, 2H), 1.98 (dq, J=4.4, 12.0 Hz, 2H), 1.49 (s, 9H). MS(ES+): m/z=485.19 (100) [MH$^+$], 429.13 (7) [MH$^+$-isobutene]. HPLC: $t_R$=2.71 min (polar_5 min, ZQ2).

Trifluoromethanesulfonic acid 6-methylisoquinolin-3-yl ester

To a suspension of 6-methylisoquinolin-3-ol (97.2 mg, 0.611 mmol) and triethylamine (0.17 mL, 1.2 mmol) in DCM (4.8 mL, 74 mmol), cooled in an ice bath, was added dropwise trifluoromethanesulfonic anhydride (0.13 mL, 0.77 mmol). Upon addition, all solid material dissolved, and the solution was stirred at 0° C. for 30 min. The reaction solution was diluted with more DCM to a total volume of ≈40 mL, washed with water, NaHCO$_3$ solution, and brine, and dried over MgSO$_4$. The extract was filtered through a plug of silica gel (≈1" high in a 60 mL fritted funnel), which was rinsed with DCM until no further product eluted. The fraction containing product was concentrated and dried in vacuo overnight to give the title compound as orange oil. The material was used for the next reaction without further purification. $^1$H NMR (400 MHz, CDCl$_3$): δ=9.00 (s, 1H), 7.95 (d, J=8.4 Hz, 1H), 7.67 (s, 1H), 7.52 (dd, J=1.6, 8.4 Hz, 1H), 7.48 (s, 1H), 2.59 (s, 3H). MS(ES+): m/z=292.08 (37) [MH$^+$], 159.17 (100) [MH$^+$-SO$_2$CF$_3$]. HPLC: $t_R$=3.81 min (polar_5 min, ZQ2).

6-Methylisoquinolin-3-ol

Concentrated sulfuric acid (18 M; 11.0 mL) was added to 2,2-dimethoxy-N-(4-methylbenzyl)-acetamide (1.95 g, 8.73 mmol) at ambient temperature, and the solution was stirred overnight at ambient temperature. The reaction mixture was added to ≈100 mL of ice, and the pH of the mixture was adjusted to ≈5 with concentrated aq. NH$_3$ solution. The yellow precipitate was filtered off, washed with water, and dried in vacuo overnight to give the title compound as yellow solid. It was used in the next step without further purification. $^1$H NMR (400 MHz, DMSO-d$_6$): δ=8.79 (s, 1H), 7.81 (d, J=8.4 Hz, 1H), 7.44 (s, 1H), 7.14 (dd, J=1.6, 8.4 Hz, 1H), 6.76 (s, 1H), 2.42 (s, 3H); —OH not apparent. MS(ES+): m/z=160.25 (100) [MH$^+$], 142.13 (12) [MH$^+$-H$_2$O]. HPLC: $t_R$=2.15 min (polar_5 min, ZQ2), 2.25 min (polar_5 min, ZQ3).

2,2-Dimethoxy-N-(4-methylbenzyl)-acetamide

A mixture of methyl dimethoxyacetate (1.35 g, 9.96 mmol) and 4-methylbenzylamine (1.21 g, 9.98 mmol) in a sealable tube was heated in a microwave reactor to 140° C. for 50 min. The reaction mixture was diluted with EtOAc (≈60 mL), washed with diluted aq. HCl, water, sat. NaHCO$_3$ solution, and brine, and dried over MgSO$_4$. The EtOAc extract was filtered, concentrated, and dried in vacuo overnight to give the title compound as pale yellow oil. It was used for the next step without further purification. $^1$H NMR (400 MHz, CDCl$_3$): δ=7.20-7.13 (AA'BB', 4H), 6.82 (brs, 1H), 4.75 (s, 1H), 4.44 (d, J=5.6 Hz, 2H), 3.40 (s, 6H), 2.34 (s, 3H). MS(ES+): m/z=246.10 (43) [MNa$^+$], 224.11 (91) [MH$^+$], 192.14 (8) [MH$^+$-MeOH], 160.06 (80) [MH$^+$-2 MeOH]. HPLC: $t_R$=2.84 min (polar_5 min, ZQ3).

Example 5

3-(8-Methylisoquinolin-3-yl)-5-(1-piperidin-4-yl-1H-pyrazol-4-yl)-pyridin-2-ylamine trihydrochloride To a solution of 4-{4-[6-amino-5-(8-methylisoquinolin-3-yl)-pyridin-3-yl]-pyrazol-1-yl}-piperidine-1-carboxylic acid tert-butyl ester (11.0 mg, 0.0227 mmol) in DCM (0.40 mL, 6.2 mmol) was added 1.0 M of HCl in Et$_2$O (0.60 mL, 0.60 mmol), and the mixture was stirred at ambient temperature for 2 h. Almost immediately an off-white solid precipitated. The solvents were evaporated, and the residue was suspended in Et$_2$O, filtered off, and dried in vacuo overnight, yielding the title compound as yellow solid. It appeared to be hygroscopic during the filtration; however, after the washing and initial drying it appeared to be non-hygroscopic. $^1$H NMR (400 MHz, DMSO-d$_6$): δ=14.6 (very brs, 1H), 9.60 (s, 1H), 9.18-9.07 (brm, 1H), 9.05-8.92 (brm, 1H), 8.88 (d, J=2.0 Hz, 1H), 8.86 (brs, 1H), 8.73 (s, 1H), 8.51 (s, 1H), 8.45 (d, J=2.0 Hz, 1H), 8.16 (d, J=0.4 Hz, 1H), 7.95 (d, J=8.4 Hz, 1H), 7.81 (dd, J=8.4, 6.8 Hz, 1H), 7.61 (d, J=6.8 Hz, 1H), 4.58-4.49 (m, 1H), 3.40 (brd, J=12.4 Hz, 2H), 3.12 (brq, J=12.2 Hz, 2H), 2.83 (s, 3H), 2.30-2.12 (m, 4H). MS(ES+): m/z=385.21 (43) [MH$^+$], 302.15 (100) [MH$^+$-piperidine]. HPLC: t$_R$=1.80 min (polar_5 min, ZQ2).

4-{4-[6-Amino-5-(8-methylisoquinolin-3-yl)-pyridin-3-yl]-pyrazol-1-yl}-piperidine-1-carboxylic acid tert-butyl ester To a solution of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (18.9 mg, 0.0403 mmol), trifluoromethanesulfonic acid 8-methylisoquinolin-3-yl ester (12.0 mg, 0.0412 mmol), and PS-PPh$_3$-Pd (0.10 mmol/g loading; 26 mg, 0.0026 mmol; Argonaut) in 1,4-dioxane (0.70 mL, 9.0 mmol) in a sealable microwave tube was added a solution of Cs$_2$CO$_3$ (26.7 mg, 0.0819 mmol) in H$_2$O (0.20 mL, 11 mmol). The tube was sealed, evacuated and refilled with nitrogen (3×), and heated in the microwave reactor to 105° C. for 30 minutes. The resin was filtered off and washed with DCM. The combined filtrate and washings were washed with water and brine, dried over MgSO$_4$, filtered, and concentrated in vacuo. The residue was purified by preparative TLC [20×20 cm plate, 500 μm layer of silica gel, eluting with 3% MeOH in DCM (2×) and 4% MeOH in DCM (2×)]. Material from the main band was collected and dried in vacuo overnight giving the title compound as a yellow glassy solid. $^1$H NMR (400 MHz, CDCl$_3$): δ=9.50 (s, 1H), 8.26 (d, J=2.0 Hz, 1H), 8.02 (d, J=0.4 Hz, 1H), 7.97 (d, J=2.4 Hz, 1H), 7.78 (d, J=0.8 Hz, 1H), 7.75 (d, J=8.4 Hz, 1H), 7.67 (d, J=0.4 Hz, 1H), 7.62 (dd, J=7.2, 8.4 Hz, 1H), 7.42 (dt, J=7.2, 0.8 Hz, 1H), 6.56 (brs, 2H), 4.38-4.19 (m, 3H), 2.92 (brs, J=11.0 Hz, 2H), 2.83 (s, 3H), 2.19 (brdd, J=2.2, 11.4 Hz, 2H), 1.95 (dq, J=4.0, 12.0 Hz, 2H), 1.49 (s, 9H). MS(ES+): m/z=485.23 (100) [MH$^+$], 429.16 (7) [MH$^+$-isobutene]. HPLC: t$_R$=2.88 min (polar_5 min, ZQ3).

Trifluoromethanesulfonic acid 8-methylisoquinolin-3-yl ester

To a solution of 8-methylisoquinolin-3-ol (40.7 mg, 0.256 mmol) and triethylamine (0.071 mL, 0.51 mmol) in DCM (2.0 mL, 31 mmol), cooled in an ice bath, was added dropwise trifluoromethanesulfonic anhydride (0.054 mL, 0.32 mmol). The color of the reaction mixture changed from yellow to brown, and the solution was stirred at 0° C. for 1 h. The reaction solution was diluted with more DCM to a total volume of ≈40 mL, washed with water, NaHCO$_3$ solution, and brine, and dried over MgSO$_4$. The extract was filtered through a plug of silica gel (≈1" high in a 60 mL fritted funnel), which was rinsed with DCM until no further product eluted. The fraction containing product was concentrated and dried in vacuo overnight, giving the title compound as brown oil. The material was used for the next reaction without further purification. $^1$H NMR (400 MHz, CDCl$_3$): δ=9.27 (s, 1H), 7.75 (d, J=8.4 Hz, 1H), 7.67 (dd, J=6.8, 8.2 Hz, 1H), 7.57 (s, 1H), 7.47 (dt, J=6.8, 1.2 Hz, 1H), 2.82 (s, 3H). MS(ES+): m/z=292.00 (100) [MH$^+$], 159.04 (70) [MH$^+$—SO$_2$CF$_3$]. HPLC: t$_R$=3.92 min (polar_5 min, ZQ3).

8-Methylisoquinolin-3-ol

Concentrated sulfuric acid (18 M; 7.0 mL) was added to 2,2-dimethoxy-N-(2-methylbenzyl)-acetamide (3.04 g, 13.6 mmol) at ambient temperature, and the solution was stirred overnight at ambient temperature and 6 h at 60° C. The cooled reaction mixture was added to ≈50 mL of ice, and the pH of the yellow mixture was adjusted to 7 with NaHCO$_3$ solution. The yellow precipitate was filtered off, washed with water, and dried in vacuo overnight. The yellow solid thus obtained was triturated from EtOH, the mother liquor was concentrated to give a solid, which was triturated against from EtOH. After four such triturations, the mother liquor was adsorbed onto Hydromatrix and chromatographed on silica gel [20 g/70 mL prepacked cartridge, eluting with DCM→2% MeOH in DCM→3% MeOH in DCM→4% MeOH in DCM]. Fractions containing the title compound were combined and dried in vacuo, giving a yellow oil. It was used in the next step without further purification. $^1$H NMR (400 MHz, DMSO-d$_6$): δ=10.9 (brs, 1H), 8.96 (s, 1H), 7.51 (d, J=8.0 Hz, 1H), 7.42 (dd, J=6.8, 8.0 Hz, 1H), 7.12-6.97 (m, 2H), 6.85 (s, 1H), 2.64 (s, 3H). MS(ES+): m/z=160.06 (100) [MH$^+$]. HPLC: t$_R$=2.27 min (polar_5 min, ZQ3).

2,2-Dimethoxy-N-(2-methylbenzyl)-acetamide

A mixture of methyl dimethoxyacetate (2.11 g, 15.6 mmol) and o-xylylamine (1.90 g, 15.4 mmol) in a 15 mL sealed tube was stirred at 55° C. for 11 d. The reaction solution was dissolved in EtOAc (≈60 mL) and washed with dil. HCl, water, sat. NaHCO$_3$ solution, and brine, and dried over MgSO$_4$. The EtOAc extract was filtered, concentrated, and dried in vacuo overnight to give the title compound as pale yellow oil. $^1$H NMR (400 MHz, CDCl$_3$): δ=7.25-7.16 (m, 4H), 6.69 (brs, 1H), 4.75 (s, 1H), 4.48 (d, J=5.6 Hz, 2H), 3.40 (s, 6H), 2.33 (s, 3H). MS(ES+): m/z=246.07 (83) [MNa$^+$], 224.11 (100) [MH$^+$], 192.14 (60) [MH$^+$-MeOH], 160.10 (95) [MH$^+$-2 MeOH]. HPLC: t$_R$=2.82 min (polar_5 min, ZQ3).

Example 6

3-(8-Fluoro-5-methylisoquinolin-3-yl)-5-(1-piperidin-4-yl-1H-pyrazol-4-yl)-pyridin-2-ylamine trihydrochloride To a solution of 4-{4-[6-amino-5-(8-fluoro-5-methylisoquinolin-3-yl)-pyridin-3-yl]-pyrazol-1-yl}-piperidine-1-carboxylic acid tert-butyl ester (11.5 mg, 0.0229 mmol) in DCM (0.60 mL, 9.4 mmol) was added 1.0 M of HCl in Et$_2$O (0.80 mL, 0.80 mmol), and the mixture was stirred at ambient temperature for 2 h. Almost immediately a pale yellow solid precipitated. The solvents were evaporated, and the residue was transferred into a vial and dried in vacuo overnight, yielding the title compound as yellow solid. $^1$H NMR (400 MHz, DMSO-d$_6$): δ=14.6 (very brs, 1H), 9.59 (d, J=0.8 Hz, 1H), 9.19-9.09 (brm, 1H), 9.02-8.91 (brm, 1H), 8.88 (d, J=2.4 Hz, 1H), 8.56 (brs, 1H), 8.54 (s, 1H), 8.48 (s, 1H), 8.47 (d, J=2.4 Hz, 1H), 8.15 (s, 1H), 7.73 (ddd, J=0.8, 6.4, 8.0 Hz, 1H), 7.51 (dd, J=8.0, 10.2 Hz, 1H), 4.59-4.50 (m$_c$, 1H), 3.40 (brd, J=12.2 Hz, 2H), 3.11 (brq, J=11.4 Hz, 2H), 2.76 (s, 3H), 2.30-2.12 (m, 4H). MS(ES+): m/z=403.16 (23) [MH$^+$], 320.12 (100) [MH$^+$-piperidine]. HPLC: t$_R$=1.89 min (polar_5 min, ZQ2).

4-{4-[6-Amino-5-(8-fluoro-5-methylisoquinolin-3-yl)-pyridin-3-yl]-pyrazol-1-yl}-piperidine-1-carboxylic acid tert-butyl ester To a solution of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (56.1 mg, 0.120 mmol), trifluoromethanesulfonic acid 8-fluoro-5-methylisoquinolin-3-yl ester (40.2 mg, 0.130 mmol), and PS-PPh$_3$-Pd (0.10 mmol/g loading; 83 mg, 0.0083 mmol; Argonaut) in 1,4-dioxane (2.0 mL, 26 mmol) in a sealable microwave tube was added a solution of $Cs_2CO_3$ (80.5 mg, 0.247 mmol) in $H_2O$ (0.60 mL, 33 mmol). The tube was sealed, evacuated and refilled with nitrogen (3×), and heated in the microwave reactor to 105° C. for 30 minutes. The resin was filtered off and washed with DCM. The combined filtrate and washings were washed with water and brine, dried over $MgSO_4$, filtered, and concentrated in vacuo. The residue was purified by preparative TLC [20×20 cm plate, 500 μm layer of silica gel, eluting with 3% MeOH in DCM (2×)]. Material from the main band was collected and dried in vacuo overnight giving the title compound as a yellow glassy solid. $^1$H NMR (400 MHz, $CDCl_3$): δ=9.57 (s, 1H), 8.21 (d, J=2.4 Hz, 1H), 8.05 (s, 1H), 7.96 (d, J=2.4 Hz, 1H), 7.77 (s, 1H), 7.66 (d, J=0.4 Hz, 1H), 7.49 (ddd, J=1.0, 5.2, 7.8 Hz, 1H), 7.15 (dd, J=7.8, 9.8 Hz, 1H), 6.89 (brs, 2H), 4.39-4.19 (brm, 3H), 2.92 (brt, J=11.6 Hz, 2H), 2.70 (s, 3H), 2.19 (brdd, J=2.0, 12.4 Hz, 2H), 1.97 (brdq, J=4.2, 12.4 Hz, 2H), 1.49 (s, 9H). MS(ES+): m/z=503.19 (100) [MH$^+$], 447.13 (2) [MH$^+$-isobutene]. HPLC: $t_R$=3.08 min (polar_5 min, ZQ2).

Trifluoromethanesulfonic acid
8-fluoro-5-methylisoquinolin-3-yl ester

To a suspension of 8-fluoro-5-methylisoquinolin-3-ol (114 mg, 0.643 mmol) and triethylamine (0.18 mL, 1.3 mmol) in DCM (4.5 mL, 70 mmol), cooled in an ice bath, was added dropwise trifluoromethanesulfonic anhydride (0.14 mL, 0.81 mmol). The solid dissolved, the color of the reaction mixture changed from yellow to brown, and the solution was stirred at 0° C. for 35 min. The reaction solution was diluted with more DCM to a total volume of ≈40 mL, washed with water, $NaHCO_3$ solution, and brine, and dried over $MgSO_4$. The extract was filtered through a plug of silica gel (≈1" high in a 60 mL fritted funnel), which was rinsed with DCM until no further product eluted. The fraction containing product was concentrated and dried in vacuo overnight, giving the title compound as brown oil. The material was used for the next reaction without further purification. $^1$H NMR (400 MHz, $CDCl_3$): δ=9.34 (d, J=0.8 Hz, 1H), 7.63 (dd, J=0.8, 1.8 Hz, 1H), 7.55 (ddd, J=0.8, 5.2, 8.0 Hz, 1H), 7.21 (dd, J=8.0, 9.8 Hz, 1H), 2.65 (t, J=1.0 Hz, 3H). MS(ES+): m/z=310.00 (100) [MH$^+$], 177.11 (27) [MH$^+$—$SO_2CF_3$]. HPLC: $t_R$=4.01 min (polar_5 min, ZQ3).

8-Fluoro-5-methylisoquinolin-3-ol

A solution of 5-Bromo-8-fluoroisoquinolin-3-ol (76.5 mg, 0.316 mmol), 2.0 M of dimethylzinc in toluene (0.40 mL, 0.80 mmol), and Pd(PPh$_3$)$_4$ (22 mg, 0.019 mmol) in THF in a microwave reactor tube was heated in the microwave reactor to 80° C. for 60 min. The reaction solution was poured into sat. aq. $NH_4Cl$, and the resulting mixture was extracted with DCM (3×25 mL). The combined DCM extracts were washed with brine, dried over $MgSO_4$, filtered, and concentrated in vacuo. The residue was triturated with $Et_2O$. The resulting light greenish-yellow solid was washed with $Et_2O$ and dried in vacuo to give the title compound as light greenish-yellow solid. It was used in the next step without further purification. MS(ES+): m/z=178.17 (100) [MH$^+$]. HPLC: $t_R$=2.36 min (polar_5 min, ZQ2).

5-Bromo-8-fluoroisoquinolin-3-ol

To N-(5-bromo-2-fluorobenzyl)-2,2-dimethoxyacetamide (12.0 g, 39 mmol) were added concentrated $H_2SO_4$ (21 mL) and oleum (30%, 25.0 mL, 394 mmol). The mixture was heated at 85° C. for 2 h. The reaction mixture was cooled to ambient temperature and poured slowly into a cold aqueous satd. solution of $NaHCO_3$ in a beaker with efficient stirring (Note: frothing occurs). The solid that formed was filtered off, washed with water (50 mL), and dried in vacuo to give the title compound as yellow solid. $^1$H NMR (DMSO-d$_6$, 300 MHz) δ=7.03 (s, 1H), 7.11 (dd, J=7.2, 2.1 Hz, 1H), 7.98 (dd, J=7.2, 2.4 Hz, 1H), 9.15 (s, 1H). MS (ES+): m/z 242.11/244.13 [MH$^+$]. HPLC: $t_R$=2.63 min (ZQ2, polar_5 min).

N-(5-Bromo-2-fluorobenzyl)-2,2-dimethoxyacetamide

A mixture of 5-bromo-2-fluorobenzylamine hydrochloride (15.0 g, 62 mmol), methyl dimethoxyacetate (10.0 g, 75 mmol), and DIPEA (10.3 mL, 62 mmol) in methanol (15 mL) was heated at 60° C. for 16 h in a bomb apparatus. After cooling to RT, the solvent was evaporated and DCM (150 mL) was added. The solution was washed with water (2×30 mL), dried over $Na_2SO_4$, filtered, and concentrated under reduced pressure to give the crude product. It was purified by column chromatography on silica gel using EtOAc/Hexanes (1:1) to give the title compound. $^1$H NMR (CDCl$_3$, 300 MHz) δ=3.42 (s, 6H), 4.53 (d, J=4.8 Hz, 2H), 4.81 (s, 1H), 6.96 (t, J=6.8 Hz, 1H), 7.40-7.42 (m, 1H), 7.51-7.54 (m, 1H). MS(ES+): m/z=305.73/307.69 [MH$^+$]. HPLC: $t_R$=2.89 min (polar_5 min, ZQ2).

Example 7

3-(5-Bromo-8-fluoroisoquinolin-3-yl)-5-(1-piperidin-4-yl-1H-pyrazol-4-yl)-pyridin-2-ylamine trihydrochloride To a solution of 4-{4-[6-amino-5-(5-bromo-8-fluoroisoquinolin-3-yl)-pyridin-3-yl]-pyrazol-1-yl}-piperidine-1-carboxylic acid tert-butyl ester (82 mg, 0.14 mmol) in DCM (3.0 mL) was added 1.0 M of HCl in $Et_2O$ (3.0 mL, 3.0 mmol), and the mixture was stirred at ambient temperature for 1 h. Almost immediately a pale yellow solid precipitated. The solvents were evaporated, and the residue was transferred into a vial and dried in vacuo overnight, yielding the title compound as yellow solid. $^1$H NMR (400 MHz, DMSO-d$_6$): δ=2.09-2.28 (m, 4H), 3.03-3.16 (m, 2H), 3.39 (dd, J=13.8, 1.9 Hz, 2H), 4.47-4.58 (m, 1H), 7.61 (dd, J=9.8, 8.4 Hz, 1H), 8.12 (s, 1H), 8.23-8.32 (m, 2H), 8.42 (s, 1H), 8.46 (s, 1H), 8.48 (d, J=2.0 Hz, 1H), 8.71 (d, J=2.0 Hz, 1H), 9.01 (br. s., 1H), 9.16 (br. s., 1H), 9.65 (s, 1H). MS (ES+): m/z=466.73/468.63 [MH$^+$]. HPLC: $t_R$=1.88 min (ZQ2, polar_5 min).

4-{4-[6-Amino-5-(5-bromo-8-fluoroisoquinolin-3-yl)-pyridin-3-yl]-pyrazol-1-yl}-piperidine-1-carboxylic acid tert-butyl ester To a solution of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (370 mg, 0.67 mmol), trifluoromethanesulfonic acid 5-bromo-8-fluoroisoquinolin-3-yl ester (250 mg, 0.67 mmol), and Pd(PPh$_3$)$_4$ (40 mg, 0.03 mmol) in 1,4-dioxane (8.0 mL) in a sealable microwave tube was added a solution of $Cs_2CO_3$ (440 mg, 1.3 mmol) in $H_2O$ (2 mL). The tube was sealed, evacuated and refilled with nitrogen (3×), and heated in the microwave reactor to 100° C. for 30 minutes. The reaction mixture was diluted with EtOAc, washed with water and brine, dried over $Na_2SO_4$, filtered, and concentrated in vacuo. The residue was purified by chromatography on silica gel, eluting with 5% 7M $NH_3$ in MeOH and DCM. One obtained the title compound as a yellow solid. $^1$H NMR (400 MHz, CDCl$_3$): δ=1.24-1.35 (m, 4H), 1.49 (s, 9H), 1.93-2.06 (m, 2H), 2.19 (d, J=2.3 Hz, 1H), 2.86-2.96 (m, 1H), 6.55 (br. s., 2H), 7.17 (dd, J=9.4, 8.3 Hz, 1H), 7.68 (s, 1H), 7.80 (s, 1H), 7.95 (dd, J=8.3, 4.8 Hz, 1H), 8.00 (d, J=2.3 Hz, 1H), 8.31 (s, 1H), 8.32 (d, J=2.3 Hz, 1H), 9.57 (s, 1H). MS (ES+): m/z=566.87/567.69 [MH$^+$]. HPLC: $t_R$=3.08 min (ZQ2, polar_5 min).

Trifluoromethanesulfonic acid 5-bromo-8-fluoroisoquinolin-3-yl ester

A DCM (3 mL) solution of 5-bromo-8-fluoroisoquinolin-3-ol (0.200 g, 0.826 mmol) and triethylamine (0.3 mL, 2.1 mmol) was cooled in an ice bath and charged with trifluoromethanesulfonic anhydride (0.3 mL, 2 mmol); this mixture was allowed to stir for 1 h while slowly warming to rt. The reaction was quenched with some water and then diluted with more DCM, washed with NaHCO$_3$ solution and brine, dried over Na$_2$SO$_4$, filtered and concentrated in vacuo. The crude product was passed through a small SiO$_2$ plug eluting with 10% EtOAc/Hex to yield the title compound as yellow solid. MS (ES+): m/z=373.58/375.55 [MH$^+$]. HPLC: $t_R$=4.03 min (ZQ2, polar_5 min)

Example 8

3-(4-Fluoroisoquinolin-3-yl)-5-(1-piperidin-4-yl-1H-pyrazol-4-yl)-pyridin-2-ylamine trihydrochloride To a solution of 4-{4-[6-amino-5-(4-fluoroisoquinolin-3-yl)-pyridin-3-yl]-pyrazol-1-yl}-piperidine-1-carboxylic acid tert-butyl ester (16.0 mg, 0.0327 mmol) in DCM (0.60 mL, 9.4 mmol) was added 1.0 M of HCl in Et$_2$O (0.90 mL, 0.90 mmol), and the mixture was stirred at ambient temperature for 2 h. Almost immediately a pale yellow solid precipitated. The solvents were evaporated, and the residue was transferred into a vial and dried in vacuo overnight, yielding the title compound as pale yellow solid. $^1$H NMR (400 MHz, DMSO-d$_6$): δ=14.6 (very brs, 1H), 9.38 (s, 1H), 9.08-8.99 (brm, 1H), 8.91-8.80 (brm, 1H), 8.53 (brs, 1H), 8.46 (d, J=2.0 Hz, 1H), 8.40 (s, 1H), 8.37 (d, J=8.4 Hz, 1H), 8.24 (dd, J=8.2, 0.8 Hz, 1H), 8.06 (d, J=0.4 Hz, 1H), 8.03 (ddd, J=0.8, 7.0, 8.2 Hz, 1H), 7.92 (ddd, J=1.0, 7.0, 8.2 Hz, 1H), 7.88 (brs, 1H), 4.54-4.45 (m$_c$, 1H), 3.38 (brd, J=13.2 Hz, 2H), 3.09 (brq, J=11.6 Hz, 2H), 2.27-2.08 (m, 4H). MS(ES+): m/z=389.18 (18) [MH$^+$], 306.13 (100) [MH$^+$-piperidine]. HPLC: $t_R$=1.69 min (polar_5 min, ZQ2).

4-{4-[6-Amino-5-(4-fluoroisoquinolin-3-yl)-pyridin-3-yl]-pyrazol-1-yl}-piperidine-1-carboxylic acid tert-butyl ester To a solution of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (39.0 mg, 0.0831 mmol), trifluoromethanesulfonic acid 4-fluoroisoquinolin-3-yl ester (25.1 mg, 0.0850 mmol), and PS-PPh$_3$-Pd (0.10 mmol/g loading; 55 mg, 0.0055 mmol; Argonaut) in 1,4-dioxane (1.3 mL, 16 mmol) in a sealable microwave tube was added a solution of Cs$_2$CO$_3$ (53.1 mg, 0.163 mmol) in H$_2$O (0.36 mL, 20 mmol). The tube was sealed, evacuated and refilled with nitrogen (3×), and heated in the microwave reactor to 105° C. for 30 minutes. The resin was filtered off and washed with DCM. The combined filtrate and washings were washed with water and brine, dried over MgSO$_4$, filtered, and concentrated in vacuo. The residue was purified by preparative TLC [20×20 cm plate, 500 μm layer of silica gel, eluting with 3.5% MeOH in DCM (3×)]. Material from the main band was collected and dried in vacuo overnight giving the title compound as a yellow glassy solid. $^1$H NMR (400 MHz, CDCl$_3$): δ=9.14 (s, 1H), 8.29 (d, J=2.2 Hz, 1H), 8.18 (dd, J=0.8, 8.2 Hz, 1H), 8.06 (dt, J=8.0, 0.8 Hz, 1H), 8.01 (dd, J=2.6, 2.6 Hz, 1H), 7.84 (ddd, J=1.2, 7.2, 8.2 Hz, 1H), 7.75 (d, J=0.6 Hz, 1H), 7.72 (ddd, J=1.0, 7.0, 8.2 Hz, 1H), 7.64 (d, J=0.6 Hz, 1H), 5.90 (brs, 2H), 4.40-4.15 (m, 3H), 2.91 (brt, J=10.6 Hz, 2H), 2.18 (brdd, J=2.2, 12.4 Hz, 2H), 1.97 (dq, J=4.4, 12.2 Hz, 2H), 1.48 (s, 9H). MS(ES+): m/z=489.16 (100) [MH$^+$], 433.16 (4) [MH$^+$-isobutene]. HPLC: $t_R$=3.05 min (polar_5 min, ZQ3), 2.71 min (polar_5 min, ZQ2).

Trifluoromethanesulfonic acid 4-fluoroisoquinolin-3-yl ester

To a suspension of 4-fluoroisoquinolin-3-ol (95.4 mg, 0.585 mmol) and triethylamine (0.16 mL, 1.2 mmol) in DCM (4.0 mL, 63 mmol), cooled in an ice bath, was added dropwise trifluoromethanesulfonic anhydride (0.12 mL, 0.74 mmol). The solid dissolved, the color of the reaction mixture changed from yellow to brown, and the solution was stirred at 0° C. for 7 h. The reaction solution was diluted with more DCM to a total volume of ≈40 mL, washed with water, NaHCO$_3$ solution, and brine, and dried over MgSO$_4$. The extract was filtered through a plug of silica gel (≈1" high in a 60 mL fritted funnel), which was rinsed with DCM until no further product eluted. The fraction containing product was concentrated and dried in vacuo overnight, giving the title compound as yellow oil. The yellow oil was chromatographed on silica gel [10 g/70 mL prepacked cartridge, eluting with hexanes→9:1 hexanes:EtOAc→5:1 hexanes:EtOAc]. Fractions containing the title compound were combined and dried in vacuo overnight. One obtained the title compound as yellow oil. $^1$H NMR (400 MHz, CDCl$_3$): δ=8.87 (d, J=0.8 Hz, 1H), 8.20 (dd, J=0.8, 8.4 Hz, 1H), 8.10 (dt, J=8.4, 1.0 Hz, 1H), 7.89 (ddd, J=0.8, 6.8, 8.2 Hz, 1H), 7.77 (ddd, J=1.0, 6.8, 8.2 Hz, 1H). MS(ES+): m/z=296.02 (72) [MH$^+$], 163.06 (100) [MH$^+$—SO$_2$CF$_3$]. HPLC: $t_R$=3.92 min (polar_5 min, ZQ3).

4-Fluoroisoquinolin-3-ol

A mixture of 3-hydroxyisoquinoline (84.3 mg, 0.581 mmol) and 1-chloromethyl-4-fluoro-1,4-diazoniabicyclo[2.2.2]octane bis(tetrafluoroborate) (236 mg, 0.666 mmol) in THF (6.0 mL, 74 mmol) was stirred at ambient temperature for 17 d. More 1-chloromethyl-4-fluoro-1,4-diazoniabicyclo[2.2.2]octane bis(tetrafluoroborate) (25 mg, 0.070 mmol) was added, and the reaction mixture was heated to 50° C. for 1d. Solid material was filtered off and rinsed with THF. The filtrate was diluted with DCM (≈75 mL), washed with water (2×) and brine, dried over MgSO$_4$, filtered, and dried in vacuo overnight. One obtained the title compound as yellow solid. It was used in the next step without further purification. $^1$H NMR (400 MHz, DMSO-d$_6$): δ=11.54 (brs, 1H), 8.75 (s, 1H), 8.01 (d, J=8.4 Hz, 1H), 7.84 (d, J=8.0 Hz, 1H), 7.69 (t, J=8.0 Hz, 1H), 7.40 (t, J=7.6 Hz, 1H). MS(ES+): m/z=164.03 (100) [MH$^+$]. HPLC: $t_R$=2.2 min (polar_5 min, ZQ3).

Example 9

3-(5,8-Dichloroisoquinolin-3-yl)-5-(1-piperidin-4-yl-1H-pyrazol-4-yl)-pyridin-2-ylamine trihydrochloride 4-{4-[6-Amino-5-(4,4,5,5-tetramethyl-[1,3,2]dioxaborolan-2-yl)-pyridin-3-yl]-pyrazol-1-yl}piperidine-1-carboxylic acid tert-butyl ester (BB3) (75 mg, 0.16 mmol), trifluoromethanesulfonic acid 5,8-dichloroisoquinolin-3-yl ester (66 mg, 0.19 mmol), Cs$_2$CO$_3$ (87 mg, 0.27 mmol) and Pd(PPh$_3$)$_4$ (8 mg, 0.007 mmol) were placed in a sealable microwave tube and taken up in 1,4-dioxane (2 mL) and H$_2$O (0.619 mL), flushed with nitrogen, sealed and heated in the microwave reactor to 100° C. for 30 minutes. The reaction mixture was diluted with EtOAc, washed with water, brine, dried over sodium sulfate, filtered and concentrated. The crude material was purified by column chromatography on silica gel [eluting with 3% 7N NH$_3$/MeOH in DCM] giving the Boc-protected compound. It was dissolved in 1 mL DCM and charged with 2 mL 1M HCl in ether and stirred at 40° C. overnight. The product precipitated out of solution and was filtered off to afford the title compound as a yellow solid. $^1$H NMR (400 MHz, DMSO-d$_6$): δ=2.09-2.29 (m, 4H), 3.05-3.17 (m, 2H), 3.41 (d, J=11.3 Hz, 2H), 4.47-4.59 (m, 1H), 7.96 (d, J=8.0 Hz, 1H), 8.07-8.14 (m, 1H), 8.45 (s, 2H), 8.59 (s, 1H), 8.73 (br. s., 1H), 8.93 (br. s., 1H), 9.75 (s, 1H). MS (ES+): m/z: 439.07/441.09 (3:2) [MH$^+$]. HPLC: t$_R$=1.94 min (ZQ2, polar__5 min).

Trifluoromethanesulfonic acid 5,8-dichloroisoquinolin-3-yl ester

A solution of 5,8-dichloroisoquinolin-3-ol (0.400 g, 1.87 mmol) and N-phenylbis(trifluoromethanesulphonimide) (0.80 g, 2.2 mmol) in DCM (10 mL) was charged with triethylamine (0.326 mL, 2.34 mmol) and stirred overnight at rt. The reaction mixture was partitioned between DCM and water and separated. The aqueous layer was extracted with DCM (3×) and the combined organic fractions were washed with brine, dried over sodium sulfate, filtered, and concentrated. The residue was purified by column chromatography on silica gel [eluting with 10% EtOAc in hexanes] to afford the title compound as a white solid. $^1$H NMR (400 MHz, CDCl$_3$): δ=7.42 (d, J=7.7 Hz, 1H), 7.50-7.56 (m, 2H), 7.58-7.63 (m, 1H).

5,8-Dichloroisoquinolin-3-ol

A solution of N-(2,5-dichlorobenzyl)-2,2-dimethoxyacetamide (1.0 g, 3.6 mmol) in sulfuric acid (18M; 4 mL) was stirred at 50° C. for 1 h. The reaction mixture was charged with ice and neutralized with NaHCO$_3$. The aqueous mixture was extracted with 5% MeOH in DCM (3×), washed with NaHCO$_3$, dried over sodium sulfate, filtered and concentrated to afford the title compound as yellow solid. MS (ES+): m/z=215.75/217.75 (3:1) [MH$^+$]. HPLC: t$_R$=2.76 min (ZQ2, polar__5 min).

N-(2,5-Dichlorobenzyl)-2,2-dimethoxyacetamide

A solution of methyl dimethoxyacetate (0.823 g, 6.08 mmol) and 2,5-dichlorobenzylamine (1.0 g, 5.7 mmol) was heated to 90° C. in a sealed tube for 48 h. The crude material was purified by column chromatography on silica gel [eluting with 40% EtOAc in hexanes] to afford the title compound as a clear oil. $^1$H NMR (400 MHz, CDCl$_3$) δ=3.41 (s, 6H), 4.53 (d, J=6.6 Hz, 2H), 4.75 (s, 1H), 7.19-7.23 (m, 1H), 7.30 (d, J=8.4 Hz, 1H), 7.35 (d, J=2.5 Hz, 1H). MS (ES+): m/z=278/280/282 [MH$^+$]. HPLC: t$_R$=3.03 min (ZQ2, polar__5 min).

Example 10

3-(5,8-Difluoroisoquinolin-3-yl)-5-(1-piperidin-4-yl-1H-pyrazol-4-yl)-pyridin-2-ylamine trihydrochloride The procedure for the preparation of 3-(5,8-dichloroisoquinolin-3-yl)-5-(1-piperidin-4-yl-1H-pyrazol-4-yl)-pyridin-2-ylamine trihydrochloride was followed, except using trifluoromethanesulfonic acid 5,8-difluoroisoquinolin-3-yl ester in place of trifluoromethanesulfonic acid 5,8-dichloroisoquinolin-3-yl ester, affording the title compound as a yellow solid. $^1$H NMR (400 MHz, DMSO-d$_6$): δ=2.09-2.30 (m, 4H), 3.04-3.17 (m, 2H), 3.41 (d, J=12.1 Hz, 2H), 4.48-4.59 (m, 1H), 7.57-7.68 (m, 1H), 7.79 (td, J=8.8, 3.6 Hz, 1H), 8.15 (s, 1H), 8.47 (s, 1H), 8.68 (s, 1H), 8.83 (br. s., 1H), 9.01 (br. s., 1H), 9.65 (s, 1H). MS (ES+): m/z=407.16 [MH$^+$]. HPLC: t$_R$=1.76 min (ZQ2, polar__5 min).

Trifluoromethanesulfonic acid 5,8-difluoroisoquinolin-3-yl ester

The same procedure as in the previous example was followed, except using 5,8-difluoroisoquinolin-3-ol in place of 5,8-dichloroisoquinolin-3-ol, affording the title compound as a white solid. $^1$H NMR (400 MHz, CDCl$_3$): δ=7.42 (d, J=7.7 Hz, 1H), 7.53 (t, J=7.7 Hz, 2H), 7.57-7.63 (m, 1H).

5,8-Difluoroisoquinolin-3-ol

The same procedure as in the previous example was followed, except using N-(2,5-difluorobenzyl)-2,2-dimethoxyacetamide in place of N-(2,5-dichlorobenzyl)-2,2-dimethoxyacetamide, affording the title compound. MS (ES+): m/z: 181.65 [MH$^+$]. HPLC: t$_R$=2.34 min (ZQ2, polar__5 min).

N-(2,5-Difluorobenzyl)-2,2-dimethoxyacetamide

The same procedure as in the previous example was followed, except using 2,5-difluorobenzylamine in place of 2,5-dichlorobenzylamine to afford the title compound as a clear oil. $^1$H NMR (400 MHz, CDCl$_3$): δ=3.4 (s, 6H), 4.1 (d, J=6.2 Hz, 2H), 4.75 (s, 1H), 6.93-7.08 (m, 3H). MS (ES+): m/z=245.91 [MH$^+$]. HPLC: t$_R$=2.65 min (ZQ2, polar__5 min).

Example 11

3-(5-Chloro-8-fluoroisoquinolin-3-yl)-5-(1-piperidin-4-yl-1H-pyrazol-4-yl)-pyridin-2-ylamine trihydrochloride The procedure for the preparation of 3-(4-fluoroisoquinolin-3-yl)-5-(1-piperidin-4-yl-1H-pyrazol-4-yl)-pyridin-2-ylamine trihydrochloride was followed, except using 4-{4-[6-amino-5-(5-chloro-8-fluoroisoquinolin-3-yl)-pyridin-3-yl]-pyrazol-1-yl}-piperidine-1-carboxylic acid tert-butyl ester in place of 4-{4-[6-amino-5-(4-fluoroisoquinolin-3-yl)-pyridin-3-yl]-pyrazol-1-yl}-piperidine-1-carboxylic acid tert-butyl ester. This afforded the title compound as a yellow solid. $^1$H NMR (400 MHz, DMSO-d$_6$): δ=2.11-2.28 (m, 4H), 3.01-3.17 (m, 2H), 3.32-3.47 (m, 2H), 4.47-4.60 (m, 1H), 7.66 (dd, J=9.85, 8.59 Hz, 1H), 8.08-8.15 (m, 2H), 8.34-8.51 (m, 3H), 8.56 (s, 1H), 8.77 (d, J=2.02 Hz, 1H), 9.00 (br. s., 1H), 9.16 (br. s., 1H), 9.67 (s, 1H). $^1$H NMR (400 MHz, CD$_3$OD): δ=2.29-2.44 (m, 4H), 3.20-3.30 (m, 2H), 3.60 (d, J=12.6 Hz, 2H), 4.54-4.66 (m, 1H), 7.39 (t, J=9.1 Hz, 1H), 7.91 (dd, J=8.3, 4.8 Hz, 1H), 7.94 (s, 1H), 8.14 (s, 1H), 8.18 (s, 1H), 8.29 (s, 1H), 8.43 (s, 1H), 9.61 (s, 1H). MS (ES+): m/z=339.76/341.64 [MH$^+$]. HPLC: t$_R$=2.27 min (ZQ2, polar__5 min).

4-{4-[6-Amino-5-(5-chloro-8-fluoroisoquinolin-3-yl)-pyridin-3-yl]-pyrazol-1-yl}-piperidine-1-carboxylic acid tert-butyl ester 4-{4-[6-Amino-5-(4,4,5,5-tetramethyl-[1,3,2]dioxaborolan-2-yl)-pyridin-3-yl]-pyrazol-1-yl}-piperidine-1-carboxylic acid tert-butyl ester (0.065 g, 0.14 mmol) (BB3), trifluoromethanesulfonic acid 5-chloro-8-fluoroisoquinolin-3-yl ester (0.040 g, 0.12 mmol), $Cs_2CO_3$ (75 mg, 0.23 mmol), and $Pd(PPh_3)_4$ (7 mg, 0.006 mmol) were placed in a sealable microwave tube, taken up in 1,4-dioxane (2 mL, 30 mmol) and $H_2O$ (0.54 mL, 30 mmol), flushed with nitrogen, sealed and heated in the microwave reactor at 100° C. for 30 minutes. The reaction mixture was diluted with EtOAc washed with water, brine, dried over $Na_2SO_4$, filtered and concentrated. The compound was purified by prep-TLC with 5% 7M $NH_3$ in MeOH and DCM mixture yielding the title compound as pale yellow solid. MS (ES+): m/z=523.15/525.12 (100/40) [$MH^+$]. HPLC: $t_R$=3.03 min (ZQ2, polar_5 min).

Trifluoromethanesulfonic acid 5-chloro-8-fluoroisoquinolin-3-yl ester

To a solution of 5-chloro-8-fluoroisoquinolin-3-ol (6.6 g, 33.4 mmol) in $CH_2Cl_2$ (200 mL) under nitrogen at 0° C. were added triethylamine (28 mL, 200 mmol) and triflic anhydride dropwise (11.2 mL, 66.8 mmol). The reaction mixture was stirred for 2 h. Water (50 mL) was added and the layers were separated. The organic layer was washed with aqueous satd. $NaHCO_3$ (50 mL) and water (40 mL), dried over $Na_2SO_4$, filtered and concentrated under reduced pressure. The crude product was purified by passing through a short plug of silica gel using EtOAc/Hexanes (1:9) as eluent to give the title compound as a yellow solid in 62%. $^1$H NMR ($CDCl_3$, 300 MHz): δ=7.25 (t, J=8.1 Hz, 1H), 7.06 (dd, J=8.1, 4.2 Hz, 1H), 7.93 (s, 1H), 9.40 (s, 1H). MS (ES+): m/z=329.71/331.66 [$MH^+$]. HPCL: $t_R$=3.97 min (ZQ2, polar_5 min).

5-Chloro-8-fluoroisoquinolin-3-ol

To N-(5-chloro-2-fluorobenzyl)-2,2-dimethoxyacetamide (9.00 g, 34.3 mmol) were added conc. $H_2SO_4$ (25.0 mL, 465 mmol) and oleum (30%, 25.0 mL, 394 mmol). The mixture was heated at 85° C. for 2 h. Then, the reaction mixture was cooled to RT and poured slowly into a cold aqueous satd. solution of $NaHCO_3$ (2.0 L) in a beaker with efficient stirring (Note: frothing occurs). The solid formed was filtered off, washed with water (50 mL), and dried in vacuo to give the title compound as yellow solid. $^1$H NMR ($CDCl_3$, 300 MHz): δ=6.72 (t, J=8.4 Hz, 1H), 7.15 (s, 1H), 7.43 (dd, J=8.1, 4.2 Hz), 8.80 (s, 1H), —OH not visible. MS (ES+): m/z 197.72/199.77 [$MH^+$]. HPLC: $t_R$=2.58 min (ZQ2, polar_5 min).

N-(5-Chloro-2-fluorobenzyl)-2,2-dimethoxyacetamide

Equimolar amounts of 2-fluoro-5-chlorobenzylamine (10.0 g, 62.5 mmol) and methyl dimethoxyacetate (8.38 g, 62.5 mmol) were heated in a sealed tube at 100° C. for 16 h. After cooling to RT, to the reaction mixture was added n-heptane (40 mL) and cooled at 4° C. overnight. The solid formed was filtered off and dried in vacuo to give the title compound as off-white solid. $^1$H NMR ($CDCl_3$, 300 MHz): δ=3.40 (s, 6H), 4.52 (d, J=5.8 Hz, 2H), 4.74 (s, 1H), 6.89 (bs, 1H), 7.01 (t, J=8.4 Hz, 1H), 7.20-7.25 (m, 1H), 7.31-7.36 (m, 1H). MS (ES+): m/z 261.90/263.78 [$MH^+$]. HPLC: $t_R$=2.85 min (ZQ2, polar_5 min).

Example 12

4-{4-[6-Amino-5-(5-chloro-8-methoxyisoquinolin-3-yl)-pyridin-3-yl]-pyrazol-1-yl}-piperidine trihydrochloride To a suspension of 4-{4-[6-amino-5-(5-chloro-8-fluoroisoquinolin-3-yl)-pyridin-3-yl]-pyrazol-1-yl}-piperidine-1-carboxylic acid tert-butyl ester (40 mg, 0.076 mmol) in MeOH (1.3 mL, 33 mmol), THF (1.3 mL, 16 mmol), and $H_2O$ (0.13 mL, 7.4 mmol) was added sodium hydroxide (40.0 mg, 1.00 mmol), and the mixture was stirred at 55° C. for 24 h. The reaction mixture was concentrated and then diluted with water, this was acidified with Acetic acid and the solid was filtered off and washed with more water and then dried to give the Boc-protected compound; MS (ES+): m/z=535.12/537.13 [$MH^+$]. This material was dissolved in DCM (1 mL) and stirred at ambient temperature with 1M HCl in $Et_2O$ (1.0 mL) for 4 h. The solid that formed was filtered off and dried in vacuo to yield the title compound as pale yellow solid. $^1$H NMR (400 MHz, DMSO-$d_6$): δ=2.11-2.30 (m, 4H), 3.03-3.18 (m, 2H), 3.34-3.43 (m, 2H), 4.08 (s, 3H), 4.48-4.61 (m, 1H), 7.25 (d, J=8.6 Hz, 1H), 8.00 (d, J=8.6 Hz, 1H), 8.14 (s, 1H), 8.47-8.50 (m, 3H), 8.59 (br. s., 1H), 8.78 (d, J=2.0 Hz, 1H), 9.12 (br. s., 1H), 9.28 (br. s., 1H), 9.66 (s, 1H). MS (ES+): m/z=435.09/437.11 [$MH^+$]. HPLC: $t_R$=1.84 min (ZQ2, polar_5 min).

Example 13

3-Isoquinolin-3-yl-5-(1-piperidin-4-yl-1H-pyrazol-4-yl)-pyridin-2-ylamine trihydrochloride The procedure for the preparation of 3-(5,8-dichloroisoquinolin-3-yl)-5-(1-piperidin-4-yl-1H-pyrazol-4-yl)-pyridin-2-ylamine trihydrochloride was followed, except using trifluoromethanesulfonic acid isoquinolin-3-yl ester in place of trifluoromethanesulfonic acid 5,8-dichloroisoquinolin-3-yl ester. This afforded the title compound as a yellow solid. $^1$H NMR (400 MHz, $CD_3OD$): δ=2.39 (br. s., 4H), 3.22-3.31 (m, 2H), 3.57-3.66 (m, 2H), 4.61-4.74 (m, 1H), 7.95 (t, J=7.5 Hz, 1H), 8.04-8.11 (m, 2H), 8.26 (d, J=8.1 Hz, 1H), 8.33 (s, 1H), 8.38 (d, J=8.3 Hz, 1H), 8.41-8.46 (m, 1H), 8.73 (s, 1H), 8.80-8.86 (m, 1H), 9.64 (s, 1H). MS (ES+): m/z=370.94 [$MH^+$]. HPLC: $t_R$=2.21 min (ZQ2, polar_5 min).

Trifluoromethanesulfonic acid isoquinolin-3-yl ester

A DCM (5 mL) solution of 3-hydroxyisoquinoline (0.200 g, 1.38 mmol) and triethylamine (0.4 mL, 3 mmol) was cooled in an ice bath and charged with trifluoromethanesulfonic anhydride (0.5 mL, 3 mmol). This mixture was allowed to stir for 1 h while slowly warming to rt. The reaction was quenched with water and then diluted with more DCM, washed with $NaHCO_3$ solution, brine, dried over $Na_2SO_4$, filtered and concentrated. The crude product was passed through a small silica gel plug eluting with 10% EtOAc/Hex to yield the title compound as yellow solid. $^1$H NMR (400 MHz, $CDCl_3$): δ=7.59 (s, 1H), 7.71 (t, J=7.6 Hz, 1H), 7.81 (dd, J=8.1, 7.1 Hz, 1H), 7.93 (d, J=8.3 Hz, 1H), 8.08 (d, J=8.3 Hz, 1H), 9.09 (s, 1H). MS (ES+): m/z=277.82 [$MH^+$]. HPLC: $t_R$=3.66 min (ZQ2, polar_5 min).

Example 14

5-(1-Piperidin-4-yl-1H-pyrazol-4-yl)-3-(7-trifluoromethoxy-isoquinolin-3-yl)-pyridin-2-ylamine trihydrochloride A mixture of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (75 mg, 0.16 mmol), trifluoromethanesulfonic acid 7-trifluoromethoxy-isoquinolin-3-yl ester (69 mg, 0.19 mmol), potassium carbonate (66 mg, 0.48 mmol), Pd(PPh$_3$)$_4$ (18 mg, 0.016 mmol) in DME (1.5 mL) and H$_2$O (0.5 mL) was evacuated and refilled with N$_2$ (3×), then it was heated at 100° C. for 30 min using the microwave reactor. The reaction mixture was diluted with EtOAc (30 mL), washed with brine (10 mL), and dried over anhydrous sodium sulfate. The residue was purified by silica gel chromatography (Hex.:EtOAc=30:70→15:85) to give a yellow solid. This material was dissolved in DCM (2 mL) and treated with 1M HCl in diethyl ether (3 mL). The resulting mixture was stirred at room temperature overnight. The title compound was collected by filtration as a yellow solid and washed with DCM. MS (ES+): m/z=455.12 [MH$^+$].

Trifluoromethanesulfonic acid 7-trifluoromethoxyisoquinolin-3-yl ester

By following the procedure for the preparation of trifluoromethanesulfonic acid 5-chloro-8-fluoroisoquinolin-3-yl ester, the title compound was prepared from 7-trifluoromethoxyisoquinolin-3-ol (0.98 g, 4.3 mmol), triflic anhydride (0.17 mL, 1.0 mmol), NEt$_3$ (0.8 mL, 3.0 mmol) and CH$_2$Cl$_2$ (10 mL). $^1$H NMR (CDCl$_3$, 300 MHz): δ=7.63 (s, 1H), 7.65 (d, J=6.0 Hz, 1H), 7.89 (s, 1H), 7.98 (d, J=9.0 Hz, 1H), 9.10 (s, 1H).

7-Trifluoromethoxyisoquinolin-3-ol

By following the procedure for the preparation of 5-chloro-8-fluoroisoquinolin-3-ol, the title compound was prepared from 2,2-dimethoxy-N-(3-trifluoromethoxybenzyl)-acetamide (5.0 g, 17 mmol), conc. H$_2$SO$_4$ (9.0 mL) and oleum (30%; 10.8 mL). $^1$H NMR (CDCl$_3$, 300 MHz): δ=6.80 (s, 1H), 7.22 (d, J=6.8 Hz, 1H), 7.42 (s, 1H), 7.43 (d, J=7.2 Hz, 1H), 8.44 (s, 1H).

2,2-Dimethoxy-N-(3-trifluoromethoxybenzyl)-acetamide

By following the procedure for the preparation of N-(5-chloro-2-fluorobenzyl)-2,2-dimethoxyacetamide, the title compound was prepared from 3-(trifluoromethoxy)benzylamine (4.0 g, 21 mmol) and methyl dimethoxyacetate (2.8 g, 21 mmol). $^1$H NMR (CDCl$_3$, 300 MHz): δ=3.40 (s, 6H), 4.44 (d, J=4.2 Hz, 2H), 4.75 (s, 1H), 6.95 (bs, 1H), 7.11 (s, 2H), 7.20 (d, J=2.4 Hz, 1H), 7.35-7.40 (m, 1H).

Example 15

3-(5-Chloro-6,8-difluoroisoquinolin-3-yl)-5-(1-piperidin-4-yl-1H-pyrazol-4-yl)-pyridin-2-ylamine trihydrochloride salt 4-{4-[6-Amino-5-(5-chloro-6,8-difluoroisoquinolin-3-yl)-pyridin-3-yl]-pyrazol-1-yl}-piperidine-1-carboxylic acid tert-butyl ester (0.0311 mmol) was dissolved in DCM (4.4 ml), and 1.0 M of HCl in Et$_2$O (8.8 ml) was added. The mixture was stirred at rt for 16 h. After that time, solvent was removed in vacuo to give the title compound as a yellow powder. $^1$H NMR (400 MHz, DMSO-d$_6$): δ=2.14-2.30 (m, 4H), 3.03-3.18 (m, 2H), 3.36-3.42 (m, 2H), 4.50-4.60 (m, 1H), 4.97 (brs, 2H), 8.07 (t, J=10.0 Hz, 1H), 8.14 (s, 1H), 8.49 (s, 1H), 8.53 (d, J=2.4 Hz, 1H), 8.63 (d, J=0.8 Hz, 1H), 8.81 (d, J=2.4 Hz, 1H), 9.14 (brs, 1H), 9.31 (brs, 1H), 9.66 (s, 1H). MS(ES+): m/z=440.84/442.79 (82/32) [MH$^+$]. HPLC: t$_R$=1.89 min (ZQ3, polar_5 min).

4-{4-[6-Amino-5-(5-chloro-6,8-difluoroisoquinolin-3-yl)-pyridin-3-yl]-pyrazol-1-yl}-piperidine-1-carboxylic acid tert-butyl ester To a solution of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (18.3 mg, 0.0391 mmol), trifluoromethanesulfonic acid 5-chloro-6,8-difluoroisoquinolin-3-yl ester (0.0326 mmol), and Pd(PPh$_3$)$_4$ (2.51 mg, 0.00215 mmol) in 1,4-dioxane (0.90 ml) in a sealable microwave tube was added a solution of Cs$_2$CO$_3$ (21.4 mg, 0.0651 mmol) in H$_2$O (0.30 ml). The tube was sealed, evacuated and refilled with nitrogen (3×), and heated in the microwave reactor to 100° C. for 30 min. The reaction mixture was diluted with EtOAc (40 ml), washed with water (2×20 ml) and brine (20 ml), and dried over MgSO$_4$. After concentration in vacuo, a brown oil was obtained. It was then purified by prep. TLC eluting with 4% MeOH/CH$_2$Cl$_2$ to give the title compound as a brown oil. $^1$H NMR (400 MHz, CDCl$_3$): δ=1.49 (s, 9H), 1.94-2.05 (m, 2H), 2.16-2.24 (m, 2H), 2.87-2.98 (m, 2H), 4.24-4.38 (m, 3H), 6.45 (brs, 2H), 7.18 (t, J=9.6 Hz, 1H), 7.68 (d, J=0.8 Hz, 1H), 7.79 (d, J=0.8 Hz, 1H), 7.99 (d, J=2.4 Hz, 1H), 8.32 (d, J=2.4 Hz, 1H), 8.34 (m, 1H), 9.53 (d, J=1.2 Hz, 1H). MS(ES+): m/z=540.92/542.87 (100/86) [MH$^+$]. HPLC: t$_R$=3.15 min (ZQ3, polar_5 min).

Trifluoromethanesulfonic acid 5-chloro-6,8-difluoroisoquinolin-3-yl ester

A DCM (2 ml) suspension of 5-chloro-6,8-difluoroisoquinolin-3-ol (42.9 mg, 0.199 mmol) and triethylamine (30.6 μl, 0.218 mmol) was charged slowly with N-phenylbis-(trifluoromethanesulfonimide) (73.8 mg, 0.204 mmol) at rt. This mixture was allowed to stir at rt for 24 h. After that time, the reaction mixture was purified by prep. TLC eluting with 40% EtOAc/hexane to give the title compound as an off-white solid. $^1$H NMR (400 MHz, CDCl$_3$): δ=7.26 (t, J=8.8 Hz, 1H), 7.91-7.92 (m, 1H), 9.34 (d, J=0.4 Hz, 1H). MS(ES+): m/z=347.69/349.51 (82/42) [MH$^+$]. HPLC: t$_R$=3.98 min (polar_5 min, ZQ3).

5-Chloro-6,8-difluoroisoquinolin-3-ol

Sulfuric acid (18 M; 2.0 mL, 36 mmol.) was added to N-(5-chloro-2,4-difluorobenzyl)-2,2-dimethoxyacetamide (708 mg, 2.53 mmol) at rt. The solution was stirred at 90° C. overnight. After that time, the mixture was poured into ice and basified with NaOH (10 N) until pH=6-7 forming a solid. The solid was filtered off, washed with water, and dried in vacuo to give the title compound as a yellow solid. $^1$H NMR (400 MHz, CDCl$_3$): δ=6.94 (t, J=9.2 Hz, 1H), 7.48 (s, 1H), 9.04 (s, 1H). MS(ES+): m/z=215.47/217.76 (45/100) [MH$^+$]. HPLC: t$_R$=2.67 min (polar_5 min, ZQ3).

N-(5-Chloro-2,4-difluorobenzyl)-2,2-dimethoxyacetamide

A mixture of methyl dimethoxyacetate (1.45 g, 10.7 mmol) and 5-chloro-2,4-difluorobenzylamine (1.78 g, 10.0 mmol) in a sealed tube was heated at 80° C. for 20 h. After that time, the mixture was diluted with EtOAc (20 ml), washed with HCl (2 N, 10 ml), saturated Na$_2$CO$_3$ (10 ml), H$_2$O (10 ml) and brine (10 ml), and dried over MgSO$_4$. After concentrated in vacuo, the title compound was obtained as a brown oil. $^1$H NMR (400 MHz, CDCl$_3$): δ=3.41 (s, 6H), 4.46 (d, J=6.4 Hz, 2H), 4.74 (s, 1H), 6.92 (t, J=8.8 Hz, 1H), 6.93 (brs, 1H), 7.41 (t, J=8.0 Hz, 1H). MS(ES+): m/z=280.03/282.01 (95/57) [MH$^+$]. HPLC: t$_R$=3.02 min (polar_5 min, ZQ3).

Example 16

5-(1-Piperidin-4-yl-1H-pyrazol-4-yl)-3-(6-trifluoromethylisoquinolin-3-yl)-pyridin-2-ylamine trihydrochloride salt The title compound was obtained as yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt using 4-{4-[6-amino-5-(6-trifluoromethylisoquinolin-3-yl)-pyridin-3-yl]-pyrazol-1-yl}-piperidine-1-carboxylic acid tert-butyl ester. $^1$H NMR (400 MHz, DMSO-d$_6$): δ=2.14-2.34 (m, 4H), 3.07-3.19 (m, 2H), 3.37-3.45 (m, 2H), 4.49-4.62 (m, 1H), 4.70 (brs, 2H), 8.08 (dd, J=2.0 & 8.8 Hz, 1H), 8.16 (d, J=0.4 Hz, 1H), 8.51 (d, J=2.0 Hz, 1H), 8.52 (s, 1H), 8.55 (d, J=9.6 Hz, 2H), 8.71 (brs, 1H), 8.87 (d, J=2.0 Hz, 1H), 8.93 (s, 1H), 9.08 (brs, 1H), 9.22 (brs, 1H), 9.67 (s, 1H). MS(ES+): m/z=438.88 (58) [MH$^+$]. HPLC: t$_R$=1.87 min (ZQ3, polar_5 min).

4-{4-[6-Amino-5-(6-trifluoromethylisoquinolin-3-yl)-pyridin-3-yl]-pyrazol-1-yl}-piperidine-1-carboxylic acid tert-butyl ester The title compound was obtained as a brown oil following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 6-trifluoromethylisoquinolin-3-yl ester. $^1$H NMR (400 MHz, CDCl$_3$): δ=1.49 (s, 9H), 1.92-2.04 (m, 2H), 2.16-2.24 (m, 2H), 2.87-2.98 (m, 2H), 4.24-4.38 (m, 3H), 6.45 (brs, 2H), 7.67 (d, J=0.8 Hz, 1H), 7.77-7.81 (m, 2H), 7.96 (d, J=2.0 Hz, 1H), 8.16 (dd, J=0.8 & 9.2 Hz, 2H), 8.24 (s, 1H), 8.30 (d, J=2.0 Hz, 1H), 9.40 (s, 1H). MS(ES+): m/z=538.49/540.17 (82/100) [MH$^+$]. HPLC: t$_R$=3.01 min (ZQ3, polar_5 min).

Trifluoromethanesulfonic acid 6-trifluoromethylisoquinolin-3-yl ester

The title compound was obtained as an off-white solid following the procedure for trifluoromethanesulfonic acid 5-chloro-6,8-difluoroisoquinolin-3-yl ester, using 6-trifluoromethylisoquinolin-3-ol. $^1$H NMR (400 MHz, CDCl$_3$): δ=7.71 (s, 1H), 7.88 (dd, J=1.6 & 8.4 Hz, 1H), 8.22-8.25 (m, 2H), 9.20 (s, 1H). MS(ES+): m/z=345.74 (100) [MH$^+$]. HPLC: t$_R$=3.92 min (polar_5 min, ZQ3).

6-Trifluoromethylisoquinolin-3-ol

Sulfuric acid (18 M; 2.25 mL, 40.5 mmol) was added to 2,2-dimethoxy-N-(4-trifluoromethylbenzyl)-acetamide (828 mg, 2.96 mmol) at rt. The combined solution was stirred at 50° C. overnight. The mixture was poured into ice, basified with NaOH (10 N) until pH>12, and extracted with EtOAc (3×50 ml). The extracts were washed with water (20 ml), dried over MgSO$_4$, filtered, and concentrated in vacuo. The residue was triturated with 50% EtOAc/hexane (10 ml) to yield a yellow solid that was then purified by Gilson HPLC to give the title compound as yellow solid. $^1$H NMR (400 MHz, CDCl$_3$): δ=7.18 (s, 1H), 7.45-7.51 (m, 1H), 7.96-8.02 (m, 2H), 8.89 (brs, 1H). MS(ES+): m/z=214.32 (100) [MH$^+$]. HPLC: t$_R$=2.64 min (polar_5 min, ZQ3).

2,2-Dimethoxy-N-(4-trifluoromethylbenzyl)-acetamide

The title compound was obtained as a yellow oil following the procedure for preparing N-(5-chloro-2,4-difluorobenzyl)-2,2-dimethoxyacetamide, using 4-trifluoromethylbenzylamine. $^1$H NMR (400 MHz, CDCl$_3$): δ=3.42 (s, 6H), 4.54 (d, J=6.0 Hz, 2H), 4.77 (s, 1H), 6.97 (brs, 1H), 7.39-7.43 (m, 2H), 7.60 (d, J=8.0 Hz, 2H). MS(ES+): m/z=278.12 (100) [MH$^+$]. HPLC: t$_R$=3.06 min (polar_5 min, ZQ3).

Example 17

5-(1-Piperidin-4-yl-1H-pyrazol-4-yl)-3-(7-trifluoromethylisoquinolin-3-yl)-pyridin-2-ylamine trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(7-trifluoromethylisoquinolin-3-yl)-pyridin-3-yl]-pyrazol-1-yl}-1-carboxylic acid tert-butyl ester. $^1$H NMR (400 MHz, DMSO-d$_6$): δ=2.14-2.34 (m, 4H), 3.06-3.19 (m, 2H), 3.37-3.45 (m, 2H), 4.22 (brs, 2H), 4.50-4.60 (m, 1H), 8.16 (dd, J=1.6 & 8.4 Hz, 1H), 8.17 (s, 1H), 8.34 (d, J=8.8 Hz, 1H), 8.52 (d, J=2.4 Hz, 1H), 8.54 (s, 1H), 8.75 (brs, 1H), 8.84 (s, 1H), 8.89 (s, 1H), 8.91 (d, J=2.0 Hz, 1H), 9.16 (brs, 1H), 9.31 (brs, 1H), 9.69 (s, 1H). MS(ES+): m/z 438.81 (38) [MH$^+$]. HPLC: t$_R$ 1.95 min (ZQ3, polar_5 min).

4-{4-[6-Amino-5-(7-trifluoromethylisoquinolin-3-yl)-pyridin-3-yl]-pyrazol-1-yl}-piperidine-1-carboxylic acid tert-butyl ester The title compound was obtained as a brown foam following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 7-trifluoromethylisoquinolin-3-yl ester. $^1$H NMR (400 MHz, CDCl$_3$): δ=1.49 (s, 9H), 1.92-2.04 (m, 2H), 2.16-2.24 (m, 2H), 2.87-2.98 (m, 2H), 4.24-4.38 (m, 3H), 6.47 (brs, 2H), 7.67 (d, J=0.4 Hz, 1H), 7.78 (d, J=0.8 Hz, 1H), 7.90 (dd, J=2.0 & 8.8 Hz, 1H), 7.98 (d, J=2.4 Hz, 1H), 8.03 (d, J=8.0 Hz, 1H), 8.11 (s, 1H), 8.30 (d, J=2.4 Hz, 1H), 8.34 (d, J=0.8 Hz, 1H), 9.41 (s, 1H). MS(ES+): m/z=539.97 (100) [MH$^+$]. HPLC: t$_R$=3.01 min (ZQ3, polar_5 min).

Trifluoromethanesulfonic acid 7-trifluoromethylisoquinolin-3-yl ester

The title compound was obtained as an off-white solid following the procedure for trifluoromethanesulfonic acid 5-chloro-6,8-difluoroisoquinolin-3-yl ester, using the mixture of 7-trifluoromethylisoquinolin-3-ol and 5-trifluoromethylisoquinolin-3-ol mixture followed by separation of the isomers by prep. TLC. $^1$H NMR (400 MHz, CDCl$_3$): δ=7.67 (s, 1H), 7.97 (dd, J=0.8 & 8.4 Hz, 1H), 8.07 (d, J=8.4 Hz, 1H), 8.40 (d, J=0.8 Hz, 1H), 9.21 (s, 1H). MS(ES+): m/z=345.74 (100) [MH$^+$]. HPLC: t$_R$=3.90 min (polar_5 min, ZQ3).

7-Trifluoromethylisoquinolin-3-ol and 5-Trifluoromethylisoquinolin-3-ol

Sulfuric acid (18M; 4.0 mL, 72 mmol) was added to 2,2-dimethoxy-N-(3-trifluoromethylbenzyl)-acetamide (1.43 g, 5.16 mmol) at ambient temperature, and the solution was stirred at 50° C. overnight The solution was poured into ice, basified with NaOH (10 N), and extracted with ether (3×50 ml). The aqueous layer was neutralized with HCl until pH=6-7 forming a precipitate that was filtered off, washed with water, and dried in vacuo to give a mixture of the title compounds as yellow powder. The mixture was used directly for the next step. $^1$H NMR (400 MHz, CDCl$_3$): δ=7.07 (s, 1H), 7.33 (s, 1H), 7.36 (t, J=8.0 Hz, 1H), 7.67 (dd, J=1.6 & 8.8 Hz, 1H), 7.74 (d, J=8.8 Hz, 1H), 7.96 (d, J=7.2 Hz, 1H), 8.01 (d, J=8.0 Hz, 1H), 8.11 (s, 1H), 8.82 (s, 1H), 8.84 (s, 1H). MS(ES+): m/z=214.06 (100) [MH+]. HPLC: t$_R$=2.72 min (polar_5 min, ZQ3).

2,2-Dimethoxy-N-(3-trifluoromethylbenzyl)-acetamide

The title compound was obtained as a yellow oil following the procedure for N-(5-chloro-2,4-difluorobenzyl)-2,2-dimethoxyacetamide, using 3-trifluoromethylbenzylamine. $^1$H NMR (400 MHz, CDCl$_3$): δ=3.42 (s, 6H), 4.54 (d, J=6.0 Hz, 2H), 4.77 (s, 1H), 6.97 (brs, 1H), 7.43-7.57 (m, 4H). MS(ES+): m/z=278.12 (100) [MH$^+$]. HPLC: t$_R$=3.06 min (polar_5 min, ZQ3).

Example 18

5-(1-Piperidin-4-yl-1H-pyrazol-4-yl)-3-(5-trifluoromethylisoquinolin-3-yl)-pyridin-2-ylamine trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(5-trifluoromethylisoquinolin-3-yl)-pyridin-3-yl]-pyrazol-1-yl}-piperidine-1-carboxylic acid tert-butyl ester. $^1$H NMR (400 MHz, DMSO-d$_6$): δ=2.12-2.28 (m, 4H), 3.04-3.17 (m, 2H), 3.36-3.44 (m, 2H), 4.49-4.59 (m, 1H), 4.91 (brs, 2H), 7.97 (t, J=8.0 Hz, 1H), 8.10 (s, 1H), 8.26 (brs, 1H), 8.31 (s, 1H), 8.39 (d, J=7.2 Hz, 1H), 8.43 (s, 1H), 8.49 (d, J=2.4 Hz, 1H), 8.57 (d, J=2.0 Hz, 1H), 8.65 (d, J=8.4 Hz, 1H), 9.06 (brs, 1H), 9.25 (s, 1H), 9.70 (s, 1H). MS(ES+): m/z=438.88 (42) [MH$^+$]. HPLC: t$_R$=1.81 min (ZQ3, polar_5 min).

4-{4-[6-Amino-5-(5-trifluoromethylisoquinolin-3-yl)-pyridin-3-yl]-pyrazol-1-yl}-piperidine-1-carboxylic acid tert-butyl ester The title compound was obtained as a brown foam following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 5-trifluoromethylisoquinolin-3-yl ester. $^1$H NMR (400 MHz, CDCl$_3$): δ=1.49 (s, 9H), 1.92-2.04 (m, 2H), 2.16-2.24 (m, 2H), 2.87-2.98 (m, 2H), 4.24-4.38 (m, 3H), 6.36 (brs, 2H), 7.66 (d, J=0.4 Hz, 1H), 7.69 (t, J=8.0 Hz, 1H), 7.77 (d, J=0.8 Hz, 1H), 7.92 (d, J=2.4 Hz, 1H), 8.12 (d, J=7.2 Hz, 1H), 8.21 (d, J=8.4 Hz, 1H), 8.27 (m, 1H), 8.30 (d, J=2.0 Hz, 1H), 9.39 (d, J=0.8 Hz, 1H). MS(ES+): m/z 540.17 (100) [MH$^+$]. HPLC: t$_R$=2.91 min (ZQ3, polar_5 min).

Trifluoromethanesulfonic acid 5-trifluoromethylisoquinolin-3-yl ester

The title compound was obtained as an off-white solid following the procedure for trifluoromethanesulfonic acid 5-chloro-6,8-difluoroisoquinolin-3-yl ester, using the mixture of 7-trifluoromethylisoquinolin-3-ol and 5-trifluoromethylisoquinolin-3-ol mixture followed by separation of the isomers by prep. TLC. $^1$H NMR (400 MHz, CDCl$_3$): δ=7.77 (dt, J=0.4 & 8.0 Hz, 1H), 7.84-7.85 (m, 1H), 8.19 (dd, J=1.2 & 8.4 Hz, 1H), 8.28 (d, J=8.4 Hz, 1H), 9.19 (d, J=0.8 Hz, 1H). MS(ES+): m/z=345.74 (100) [MH$^+$]. HPLC: t$_R$=3.92 min (polar_5 min, ZQ3).

Example 19

5-(1-Piperidin-4-yl-1H-pyrazol-4-yl)-3-(8-trifluoromethylisoquinolin-3-yl)-pyridin-2-ylamine trihydrochloride salt The title compound was obtained as a yellow oil following the procedure for 3-(5-chloro-6,8-difluoroisoquinolin-3-yl)-5-(1-piperidin-4-yl-1H-pyrazol-4-yl)-pyridin-2-ylamine trihydrochloride using 4-{4-[6-amino-5-(8-trifluoromethylisoquinolin-3-yl)-pyridin-3-yl]-pyrazol-1-yl}-piperidine-1-carboxylic acid tert-butyl ester. $^1$H NMR (400 MHz, CD$_3$OD): δ=2.26-2.42 (m, 4H), 3.19-3.29 (m, 2H), 3.56-3.63 (m, 2H), 4.54-4.62 (m, 1H), 7.89 (t, J=8.0 Hz, 1H), 7.96 (s, 1H), 8.07 (d, J=7.2 Hz, 1H), 8.14 (s, 1H), 8.26 (d, J=9.2 Hz, 2H), 8.29 (d, J=2.8 Hz, 1H), 8.32 (brs, 2H), 8.47 (s, 1H), 9.60 (brs, 1H). MS(ES+): m/z=438.88 (62) [MH$^+$]. HPLC: t$_R$=1.91 min (ZQ3, polar_5 min).

4-{4-[6-Amino-5-(8-trifluoromethylisoquinolin-3-yl)-pyridin-3-yl]-pyrazol-1-yl}-piperidine-1-carboxylic acid tert-butyl ester The title compound was obtained as a brown oil following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 8-trifluoromethylisoquinolin-3-yl ester. $^1$H NMR (400 MHz, CDCl$_3$): δ=1.49 (s, 9H), 1.92-2.02 (m, 2H), 2.18-2.22 (m, 2H), 2.92 (t, J=11.2 Hz, 2H), 4.24-4.38 (m, 3H), 6.54 (brs, 2H), 7.67 (d, J=0.8 Hz, 1H), 7.77 (t, J=8.0 Hz, 1H), 7.78 (d, J=0.8 Hz, 1H), 7.95 (d, J=6.8 Hz, 1H), 7.98 (d, J=2.0 Hz, 1H), 8.09 (d, J=8.4 Hz, 1H), 8.12 (s, 1H), 8.29 (d, J=2.0 Hz, 1H), 9.65 (m, J=2.0 Hz, 1H). MS(ES+): m/z=540.04 (100) [MH$^+$]. HPLC: t$_R$=3.01 min (ZQ3, polar_5 min).

Trifluoromethanesulfonic acid 8-trifluoromethylisoquinolin-3-yl ester

The title compound was obtained as a colorless oil following the procedure for trifluoromethanesulfonic acid 5-chloro-6,8-difluoroisoquinolin-3-yl ester, using 8-trifluoromethylisoquinolin-3-ol. $^1$H NMR (400 MHz, CDCl$_3$): δ=7.59 (s, 1H), 7.86 (dt, J=0.8 & 8.0 Hz, 1H), 8.05 (td, J=0.8 & 7.2 Hz, 1H), 8.11 (d, J=8.8 Hz, 1H), 9.43-9.45 (m, 1H). MS(ES+): m/z=345.74 (100) [MH$^+$]. HPLC: t$_R$=3.96 min (polar_5 min, ZQ3).

8-Trifluoromethylisoquinolin-3-ol

Sulfuric acid (18 M; 3.57 mL, 65.6 mmol) was added to 2,2-dimethoxy-N-(2-trifluoromethylbenzyl)-acetamide (1.33 g, 4.69 mmol) at rt. The solution was stirred at 40° C. overnight. The mixture was poured into ice, basified with NaOH (10 N) until pH>13, extracted with Et$_2$O (3×30 ml), and the extracts were back-washed with water (20 ml). The combined aqueous layers were neutralized with HCl until pH=7-8 and extracted with EtOAc (3×30 ml). The EtOAc extract was washed with water (2×20 ml), brine (20 ml), dried over MgSO4, filtered, and concentrated in vacuo to give the title compound as yellow solid. The material was used in the next step without further purification; a small quantity (15 mg) was purified using the Gilson HPLC for characterization by NMR. $^1$H NMR (400 MHz, DMSO-d$_6$): δ=7.13 (s, 1H), 7.70 (t, 1H, J=8.0 Hz), 7.78 (d, 1H, J=7.2 Hz), 8.06 (d, 1H, J=8.4 Hz), 9.03 (t, 1H, J=1.0 Hz), 11.23 (brs, 1H). MS(ES+): m/z=213.38 (82) [MH$^+$]. HPLC: t$_R$=2.55 min (polar_5 min, ZQ3).

2,2-Dimethoxy-N-(2-trifluoromethylbenzyl)-acetamide

The title compound was obtained as a brown solid following the procedure for N-(5-chloro-2,4-difluorobenzyl)-2,2-dimethoxyacetamide, using 2-trifluoromethylbenzylamine. $^1$H NMR (400 MHz, CDCl$_3$): δ=3.39 (s, 6H), 4.66 (dd, J=1.2 & 6.0 Hz, 2H), 4.74 (s, 1H), 6.94 (brs, 1H), 7.38-7.43 (m, 1H), 7.51-7.59 (m, 2H), 7.66 (d, J=8.0 Hz, 1H).

Example 20

3-(5,8-Dimethylisoquinolin-3-yl)-5-(1-piperidin-4-yl-1H-pyrazol-4-yl)-pyridin-2-ylamine trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(5,8-dimethylisoquinolin-3-yl)-pyridin-3-yl]-pyrazol-1-yl}-piperidine-1-carboxylic acid tert-butyl ester. $^1$H NMR (400 MHz, CD$_3$OD): δ=2.25-2.41 (m, 4H), 2.73 (s, 3H), 2.78 (s, 3H), 3.19-3.28 (m, 2H), 3.55-3.62 (m, 2H), 4.53-4.62 (m, 1H), 7.37 (dd, J=08. & 7.2 Hz, 1H), 7.50 (dd, J=0.8 & 7.2 Hz, 1H), 7.94 (d, J=0.8 Hz, 1H), 8.13 (d, J=0.8, 1H), 8.20 (s, 1H), 8.21 (d, J=6.8 Hz, 1H), 8.26 (s, 1H), 8.30 (brs, 2H), 9.49 (brs, 1H). MS(ES+): m/z=399.97 (100) [MH$^+$]. HPLC: t$_R$=1.84 min (ZQ3, polar_5 min).

4-{4-[6-Amino-5-(5,8-dimethylisoquinolin-3-yl)-pyridin-3-yl]-pyrazol-1-yl}-piperidine-1-carboxylic acid tert-butyl ester The title compound was obtained as a brown solid following the procedure for 4-{4-[6-amino-5-(5-chloro-6,8-difluoroisoquinolin-3-yl)-pyridin-3-yl]-pyrazol-1-yl}-piperidine-1-carboxylic acid ester, using trifluoromethanesulfonic acid 5,8-dimethylisoquinolin-3-yl ester. $^1$H NMR (400 MHz, CDCl$_3$) δ=1.49 (s, 9H), 1.94-2.04 (m, 2H), 2.17-2.21 (m, 2H), 2.70 (s, 3H), 2.78 (s, 3H), 2.82-2.92 (m, 2H), 4.24-4.38 (m, 3H), 6.48 (brs, 2H), 7.29 (d, J=6.8 Hz, 1H), 7.43 (d, J=7.2 Hz, 1H), 7.66 (d, J=0.8 Hz, 1H), 7.77 (d, J=0.8 Hz, 1H), 7.94 (d, J=2.0 Hz, 1H), 8.08 (d, J=0.8 Hz, 1H), 8.26 (d, J=2.0 Hz, 1H), 9.47 (t, J=0.8 Hz, 1H). MS(ES+): m/z 498.62/500.24 (76/100) [MH$^+$]. HPLC: t$_R$=2.84 min (ZQ3, polar_5 min).

Trifluoromethanesulfonic acid 5,8-dimethylisoquinolin-3-yl ester

The title compound was obtained as an off-white solid following the procedure for trifluoromethanesulfonic acid 5-chloro-6,8-difluoroisoquinolin-3-yl ester, using 5,8-dimethylisoquinolin-3-ol. $^1$H NMR (400 MHz, CDCl$_3$): δ=2.65 (s, 3H), 2.77 (s, 3H), 7.34 (dd, J=0.8 & 7.2 Hz, 1H), 7.48 (dd, J=0.8 & 7.2 Hz, 1H), 7.64 (d, J=0.8 Hz, 1H), 9.25 (d, J=0.8 Hz, 1H). MS(ES+): m/z=305.80 (43) [MH$^+$]. HPLC: t$_R$=4.03 min (polar_5 min, ZQ3).

5,8-Dimethylisoquinolin-3-ol

Sulfuric acid (18 M; 3.8 mL, 68 mmol) was added to N-(2,5-dimethylbenzyl)-2,2-dimethoxyacetamide (1.17 g, 4.92 mmol) at rt, and the solution was stirred at rt overnight. The solution was poured into ice, basified with NaOH (10 N) until pH>13, extracted with Et$_2$O (3×30 ml), and the extracts were back-extracted with water (20 ml). The aqueous layer was neutralized with HCl until pH=7-8 and extracted with EtOAc (3×30 ml). The EtOAc extracts were washed with water (2×20 ml), brine (20 ml), dried over MgSO$_4$, filtered, and concentrated in vacuo to give a brown solid. It was purified by prep. TLC eluting with 4% MeOH in DCM to give the title compound as yellow solid. $^1$H NMR (400 MHz, CDCl$_3$): δ=2.46 (s, 3H), 2.55 (s, 3H), 6.84 (d, J=7.6 Hz, 1H), 6.98 (s, 1H), 7.16 (d, J=7.2 Hz, 1H), 8.61 (s, 1H). MS(ES+): m/z=173.43 (100) [MH$^+$]. HPLC: t$_R$=2.35 min (polar_5 min, ZQ3).

N-(2,5-Dimethylbenzyl)-2,2-dimethoxyacetamide

The title compound was obtained as a brown solid following the procedure for N-(5-chloro-2,4-difluorobenzyl)-2,2-dimethoxyacetamide, using 2,5-dimethylbenzylamine. $^1$H NMR (400 MHz, CDCl$_3$): δ=3.28 (s, 3H), 3.31 (s, 3H), 3.40 (s, 6H), 4.43 (d, J=5.6 Hz, 2H), 4.75 (s, 1H), 6.68 (brs, 1H), 7.01-7.09 (m, 3H).

Example 21

3-(7-Bromoisoquinolin-3-yl)-5-(1-piperidin-4-yl-1H-pyrazol-4-yl)-pyridin-2-ylamine trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(7-bromoisoquinolin-3-yl)-pyridin-3-yl]-pyrazol-1-yl}-piperidine-1-carboxylic acid tert-butyl ester. $^1$H NMR (400 MHz, DMSO-d$_6$): δ=2.18-2.32 (m, 4H), 3.06-3.19 (m, 2H), 3.33-3.42 (m, 2H), 4.50-4.60 (m, 1H), 4.78 (brs, 2H), 8.03 (dd, J=1.6 & 8.8 Hz, 1H), 8.09 (d, J=8.8 Hz, 1H), 8.17 (s, 1H), 8.51 (d, J=1.2 Hz, 1H), 8.58 (d, J=9.2 Hz, 2H), 8.83 (s, 1H), 8.88 (d, J=1.2 Hz, 1H), 9.41 (brs, 1H), 9.47 (s, 1H), 9.53 (s, 1H). MS(ES+): m/z=449.09/451.07 (32/32) [MH$^+$]. HPLC: t$_R$=1.86 min (ZQ3, polar_5 min).

4-{4-[6-Amino-5-(7-bromoisoquinolin-3-yl)-pyridin-3-yl]-pyrazol-1-yl}-piperidine-1-carboxylic acid tert-butyl ester The title compound was obtained as a yellow solid following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 7-bromoisoquinolin-3-yl ester. $^1$H NMR (400 MHz, CDCl$_3$): δ=1.49 (s, 9H), 1.94-2.04 (m, 2H), 2.17-2.21 (m, 2H), 2.86-2.98 (m, 2H), 4.20-4.38 (m, 3H), 6.44 (brs, 2H), 7.66 (d, J=0.8 Hz, 1H), 7.77-7.82 (m, 3H), 7.94 (d, J=2.4 Hz, 1H), 8.01 (s, 1H), 8.18 (t, J=0.8 Hz, 1H), 8.28 (d, J=2.4 Hz, 1H), 9.23 (s, 1H). MS(ES+): m/z=549.20/551.15 (100/100) [MH$^+$]. HPLC: t$_R$=2.89 min (ZQ3, polar_5 min).

Trifluoromethanesulfonic acid 7-bromoisoquinolin-3-yl ester

The title compound was obtained as beige solid following the procedure for trifluoromethanesulfonic acid 5-chloro-6,8-difluoroisoquinolin-3-yl ester, using the mixture of 7-bromoisoquinolin-3-ol and 5-bromoisoquinolin-3-ol followed by separation of the isomers by prep. TLC. $^1$H NMR (400 MHz, CDCl$_3$): δ=7.57 (s, 1H), 7.80 (d, J=9.2 Hz, 1H), 7.87 (dd, J=2.0 & 8.8 Hz, 1H), 8.24-8.25 (m, 1H), 9.02 (s, 1H). MS(ES+): m/z=355.96/357.92 (35/45) [MH$^+$]. HPLC: $t_R$=3.90 min (polar__5 min, ZQ3).

5-Bromoisoquinolin-3-ol and 7-Bromoisoquinolin-3-ol

A solution of N-(3-bromobenzyl)-2,2-dimethoxyacetamide (565 mg, 1.96 mmol) and sulfuric acid (18 M; 1.5 mL, 27 mmol) was stirred at 40° C. for 16 h. The mixture was poured into ice, neutralized with NaOH (10 N) until pH=7-8, the solid was filtered off and washed with water. The filtrate was extracted with EtOAc (3×50 ml). The extracts were washed with water (2×20 ml), brine (20 ml), dried over MgSO4, filtered, and concentrated in vacuo. The residue was combined with the precipitate from the neutralization and dried in vacuo, giving a mixture of the two title compounds as yellow solid. Data for 5-bromoisoquinolin-3-ol: $^1$H NMR (400 MHz, DMSO-d$_6$): δ=6.93 (s, 1H), 7.65-7.71 (m, 2H), 8.22-8.23 (m, 1H), 8.91 (s, 1H), 11.04 (brs, 1H). Data for 7-bromoisoquinolin-3-ol: $^1$H NMR (400 MHz, DMSO-d$_6$): δ=7.01 (s, 1H), 7.27 (dd, J=8.0 & 8.0 Hz, 1H), 7.96 (dd, J=1.2 & 7.2 Hz, 1H), 8.02 (d, J=1.2 Hz, 1H), 8.99 (d, J=0.8 Hz, 1H), 11.04 (brs, 1H). Data for mixture: MS(ES+): m/z=224/226 [MH$^+$]. HPLC: $t_R$=2.57 min (polar__5 min, ZQ3).

N-(3-Bromobenzyl)-2,2-dimethoxyacetamide

The title compound was obtained as a brown oil following the procedure for N-(5-chloro-2,4-difluorobenzyl)-2,2-dimethoxyacetamide, using 3-bromobenzylamine. $^1$H NMR (400 MHz, CDCl$_3$): δ=3.42 (s, 6H), 4.45 (d, J=6.0 Hz, 2H), 4.76 (s, 1H), 6.91 (brs, 1H), 7.18-7.24 (m, 2H), 7.38-7.44 (m, 2H). MS(ES+): m/z=287.97/289.95 (90/100) [MH$^+$]. HPLC: $t_R$=2.97 min (polar__5 min, ZQ3).

Example 22

3-(5-Bromoisoquinolin-3-yl)-5-(1-piperidin-4-yl-1H-pyrazol-4-yl)-pyridin-2-ylamine trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(5-bromoisoquinolin-3-yl)-pyridin-3-yl]-pyrazol-1-yl}-piperidine-1-carboxylic acid tert-butyl ester. $^1$H NMR (400 MHz, DMSO-d$_6$): δ=2.11-2.28 (m, 4H), 3.05-3.17 (m, 2H), 3.36-3.44 (m, 2H), 3.64 (brs, 2H), 4.48-4.57 (m, 1H), 7.75 (t, J=8.0 Hz, 1H), 8.13 (d, J=0.4 Hz, 1H), 8.28 (dd, J=1.2 & 7.2 Hz, 1H), 8.36 (d, J=8.4 Hz, 1H), 8.42 (s, 1H), 8.46 (d, J=2.4 Hz, 1H), 8.47 (s, 1H), 8.72 (d, J=2.4 Hz, 1H), 8.93 (brs, 1H), 9.11 (brs, 1H), 9.55 (d, J=0.8 Hz, 1H). MS(ES+): m/z=449.04/451.02 (46/46) [MH$^+$]. HPLC: $t_R$=1.78 min (ZQ3, polar__5 min).

4-{4-[6-Amino-5-(5-bromoisoquinolin-3-yl)-pyridin-3-yl]-pyrazol-1-yl}-piperidine-1-carboxylic acid tert-butyl ester The title compound was obtained as a brown oil following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 5-bromoisoquinolin-3-yl ester. $^1$H NMR (400 MHz, CDCl$_3$): δ=1.49 (s, 9H), 1.94-2.04 (m, 2H), 2.16-2.25 (m, 2H), 2.86-2.98 (m, 2H), 4.22-4.38 (m, 3H), 6.41 (brs, 2H), 7.50 (dd, J=7.2 & 8.0 Hz, 1H), 7.68 (d, J=0.8 Hz, 1H), 7.92 (d, J=0.8 Hz, 1H), 7.99-8.04 (m, 3H), 8.30 (d, J=2.4 Hz, 1H), 8.33 (s, 1H), 9.28 (d, J=0.8 Hz, 1H). MS(ES+): m/z=549.15/551.08 (99/100) [MH$^+$]. HPLC: $t_R$=2.84 min (ZQ3, polar__5 min).

Trifluoromethanesulfonic acid 5-bromoisoquinolin-3-yl ester

The title compound was obtained as beige solid following the procedure for trifluoromethanesulfonic acid 5-chloro-6,8-difluoroisoquinolin-3-yl ester, using the mixture of 7-bromoisoquinolin-3-ol and 5-bromoisoquinolin-3-ol followed by separation of the isomers by prep. TLC. $^1$H NMR (400 MHz, CDCl$_3$): δ=7.57 (dd, J=7.6 & 8.0 Hz, 1H), 7.92 (t, J=0.8 Hz, 1H), 8.05 (td, J=0.8 & 8.4 Hz, 1H), 8.08 (dd, J=0.8 & 7.2 Hz, 1H), 9.08 (d, J=0.4 Hz, 1H). MS(ES+): m/z=355.90/357.85 (36/22) [MH$^+$]. HPLC: $t_R$=3.96 min (polar__5 min, ZQ3).

Example 23

3-(6-Bromoisoquinolin-3-yl)-5-(1-piperidin-4-yl-1H-pyrazol-4-yl)-pyridin-2-ylamine trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(6-bromoisoquinolin-3-yl)-pyridin-3-yl]-pyrazol-1-yl}-piperidine-1-carboxylic acid tert-butyl ester. $^1$H NMR (400 MHz, CD$_3$OD): δ=2.40 (brs, 4H), 3.20-3.35 (m, 2H), 3.53-3.66 (m, 2H), 4.69 (brs, 1H), 7.95-8.01 (m, 1H), 8.05 (s, 1H), 8.20-8.29 (m, 1H), 8.30 (s, 1H), 8.42-8.57 (m, 2H), 8.68 (s, 1H), 8.79 (s, 1H), 9.58 (brs, 1H). MS(ES+): m/z=449.17/451.09 (72/80) [MH$^+$]. HPLC: $t_R$=1.98 min (ZQ3, polar__5 min).

4-{4-[6-Amino-5-(6-bromoisoquinolin-3-yl)-pyridin-3-yl]-pyrazol-1-yl}-piperidine-1-carboxylic acid tert-butyl ester The title compound was obtained as a yellow solid following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 6-bromoisoquinolin-3-yl ester. $^1$H NMR (400 MHz, CDCl$_3$): δ=1.49 (s, 9H), 1.92-2.04 (m, 2H), 2.16-2.23 (m, 2H), 2.86-2.98 (m, 2H), 4.22-4.38 (m, 3H), 6.42 (brs, 2H), 7.67 (d, J=0.8 Hz, 1H), 7.70 (dd, J=2.0 & 8.8 Hz, 1H), 7.77 (d, J=0.8 Hz, 1H), 7.89 (d, J=8.8 Hz, 1H), 7.93 (d, J=2.4 Hz, 1H), 7.95 (s, 1H), 8.10 (m, 1H), 9.29 (d, J=2.0 Hz, 1H), 9.27 (m, 1H). MS(ES+): m/z=549.12/551.08 (100/99) [MH$^+$]. HPLC: $t_R$=2.87 min (ZQ3, polar__5 min).

Trifluoromethanesulfonic acid 6-bromoisoquinolin-3-yl ester

The title compound was obtained as an off-white solid following the procedure for trifluoromethanesulfonic acid 5-chloro-6,8-difluoroisoquinolin-3-yl ester, using 6-bromoisoquinolin-3-ol. $^1$H NMR (400 MHz, CDCl$_3$): δ=7.50 (s, 1H), 7.78 (dd, J=1.6 & 8.4 Hz, 1H), 7.94 (d, J=8.8 Hz, 1H), 8.10-8.12 (m, 1H), 9.06 (s, 1H). MS(ES+): m/z=355.96/357.92 (18/18) [MH+]. HPLC: $t_R$=3.90 min (polar_5 min, ZQ3).

6-Bromoisoquinolin-3-ol

The title compounds was obtained as a yellow solid following the procedure for 5-bromoisoquinolin-3-ol and 7-bromoisoquinolin-3-ol, using N-(4-bromobenzyl)-2,2-dimethoxyacetamide. $^1$H NMR (400 MHz, DMSO-$d_6$): δ=6.87 (s, 1H), 7.42 (dd, J=2.0 & 8.4 Hz, 1H), 7.87 (d, J=8.8 Hz, 1H), 8.00 (d, J=2.0 Hz, 1H), 8.93 (s, 1H), 11.07 (brs, 1H). MS(ES+): m/z=224.04/225.93 (88/100) [MH+]. HPLC: $t_R$=2.41 min (polar_5 min, ZQ3).

N-(4-Bromobenzyl)-2,2-dimethoxyacetamide

The title compound was obtained as a brown oil following the procedure for N-(5-chloro-2,4-difluorobenzyl)-2,2-dimethoxyacetamide, using 4-bromobenzylamine. $^1$H NMR (400 MHz, CDCl$_3$): δ=3.40 (s, 6H), 4.43 (d, J=6.4 Hz, 2H), 4.75 (s, 1H), 6.89 (brs, 1H), 7.16 (d, J=8.4 Hz, 2H), 7.46 (d, J=8.4 Hz, 2H).

Example 24

3-(8-Bromoisoquinolin-3-yl)-5-(1-piperidin-4-yl-1H-pyrazol-4-yl)-pyridin-2-ylamine trihydrochloride salt The title compound was obtained as a yellow solid following the procedures for 3-(5-chloro-6,8-difluoroisoquinolin-3-yl)-5-(1-piperidin-4-yl-1H-pyrazol-4-yl)-pyridin-2-ylamine trihydrochloride salt and 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 8-bromoisoquinolin-3-yl ester. $^1$H NMR (400 MHz, DMSO-d6): δ=2.08-2.35 (m, 4H) 3.04-3.19 (m, 2H) 3.35-3.46 (m, 2H) 4.48-4.58 (m, 1H) 7.80-7.86 (m, 1H) 8.10-8.18 (m, 3H) 8.47 (d, J=1.8 Hz, 1H) 8.51 (s, 1H) 8.71 (br. s., 1H) 8.78 (s, 1H) 8.88 (d, J=2.0 Hz, 1H) 8.99 (br. s., 1H) 9.11 (br. s., 1H) 9.60 (s, 1H). MS(ES+): m/z=449.05/451.06 [MH+]. HPLC: $t_R$=1.89 min (ZQ2, polar_5 min)

Trifluoromethanesulfonic acid 8-bromoisoquinolin-3-yl ester

The title compound was obtained as an off-white solid following the procedure for trifluoromethanesulfonic acid 5-chloro-6,8-difluoroisoquinolin-3-yl ester, using 8-bromoisoquinolin-3-ol. MS (ES+): m/z=355.87/357.88 [MH+]. HPLC: $t_R$=4.08 min (ZQ3, polar_5 min).

8-Bromoisoquinolin-3-ol

The title compounds was obtained as a yellow solid following the procedure for 5-bromoisoquinolin-3-ol and 7-bromoisoquinolin-3-ol, using N-(2-bromobenzyl)-2,2-dimethoxyacetamide. MS (ES+): m/z=224.04/226.03 [MH+]. HPLC: $t_R$=2.39 min (ZQ2, polar_5 min).

N-(2-Bromobenzyl)-2,2-dimethoxyacetamide

Into a sealed tube were added methyl dimethoxyacetate (1.0 g, 7.5 mmol) and 2-bromobenzylamine (1.1 g, 5.8 mmol), this mixture was stirred at 50° C. for 16 h. The completed reaction was transferred to a flask and re-crystallized from heptane yielding the desired product as an off-white solid. MS (ES+): m/z=288.04/289.69 [MH+]. HPLC: $t_R$=2.93 min (ZQ3, polar_5 min).

Example 25

3-(6-Phenylisoquinolin-3-yl)-5-(1-piperidin-4-yl-1H-pyrazol-4-yl)-pyridin-2-ylamine tri-hydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(6-phenylisoquinolin-3-yl)-pyridin-3-yl]-pyrazol-1-yl}-piperidine-1-carboxylic acid tert-butyl ester. $^1$H NMR (400 MHz, CD$_3$OD): δ=2.36 (brs, 4H), 3.21-3.32 (m, 2H), 3.53-3.62 (m, 2H), 4.67 (brs, 1H), 7.55 (t, J=7.2 Hz, 1H), 7.61 (d, J=7.2 Hz, 2H), 7.96 (d, J=7.2 Hz, 2H), 8.05 (brs, 1H), 8.42-8.49 (m, 3H), 8.63-8.72 (m, 2H), 8.73 (brs, 1H), 8.81 (brs, 1H), 9.95 (brs, 1H). MS(ES+): m/z 447.17 (69) [MH+]. HPLC: $t_R$=2.16 min (ZQ3, polar_5 min).

4-{4-[6-Amino-5-(6-phenylisoquinolin-3-yl)-pyridin-3-yl]-pyrazol-1-yl}-piperidine-1-carboxylic acid tert-butyl ester The title compound was obtained as a brown oil from 4-{4-[6-amino-5-(6-bromoisoquinolin-3-yl)-pyridin-3-yl]-pyrazol-1-yl}-piperidine-1-carboxylic acid tert-butyl ester and phenylboronic acid, following the Suzuki coupling procedure described for 4-{4-[6-amino-5-(5-chloro-6,8-difluoroisoquinolin-3-yl)-pyridin-3-yl]-pyrazol-1-yl}-piperidine-1-carboxylic acid tert-butyl ester. $^1$H NMR (400 MHz, CDCl$_3$): δ=1.49 (s, 9H), 1.92-2.05 (m, 2H), 2.16-2.23 (m, 2H), 2.87-2.98 (m, 2H), 4.20-4.38 (m, 3H), 6.50 (brs, 2H), 7.43-7.48 (m, 1H), 7.51-7.57 (m, 2H), 7.67 (d, J=0.4 Hz, 1H), 7.72-7.77 (m, 2H), 7.78 (d, J=0.8 Hz, 1H), 7.89 (dd, J=1.6 & 8.8 Hz, 1H), 7.98 (d, J=2.4 Hz, 1H), 8.07-8.12 (m, 3H), 8.27 (d, J=2.4 Hz, 1H), 9.31 (s, 1H). MS(ES+): m/z=547.23 (100) [MH+]. HPLC: $t_R$=3.02 min (ZQ3, polar_5 min).

Example 26

3-(7-Phenylisoquinolin-3-yl)-5-(1-piperidin-4-yl-1H-pyrazol-4-yl)-pyridin-2-ylamine tri-hydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(7-phenylisoquinolin-3-yl)-pyridin-3-yl]-pyrazol-1-yl}-piperidine-1-carboxylic acid tert-butyl ester. $^1$H NMR (400 MHz, CD$_3$OD): δ=2.38 (brs, 4H), 3.21-3.35 (m, 2H), 3.55-3.65 (m, 2H), 4.66 (brs, 1H), 7.48 (t, J=7.2 Hz, 1H), 7.56 (d, J=7.2 Hz, 2H), 7.86 (d, J=7.6 Hz, 2H), 8.04 (s, 1H), 8.30-8.50 (m, 4H), 8.62 (s, 1H), 8.75 (brs, 2H), 9.74 (s, 1H). MS(ES+): m/z=447.17 (100) [MH+]. HPLC: $t_R$=2.17 min (ZQ3, polar_5 min).

4-{4-[6-Amino-5-(7-phenylisoquinolin-3-yl)-pyridin-3-yl]-pyrazol-1-yl}-piperidine-1-carboxylic acid tert-butyl ester The title compound was obtained as a brown oil from 4-{4-[6-amino-5-(7-bromoisoquinolin-3-yl)-pyridin-3-yl]-pyrazol-1-yl}-piperidine-1-carboxylic acid tert-butyl ester and phenylboronic acid, following the Suzuki coupling procedure described for 4-{4-[6-amino-5-(5-chloro-6,8-difluoroisoquinolin-3-yl)-pyridin-3-yl]-pyrazol-1-yl}-piperidine-1-carboxylic acid tert-butyl ester. $^1$H NMR (400 MHz, CDCl$_3$): δ=1.49 (s, 9H), 1.92-2.05 (m, 2H), 2.16-2.23 (m, 2H), 2.87-2.98 (m, 2H), 4.20-4.38 (m, 3H), 6.47 (brs, 2H), 7.41-7.46 (m, 1H), 7.51-7.56 (m, 2H), 7.68 (d, J=0.4 Hz, 1H), 7.72-7.78 (m, 2H), 7.80 (d, J=1.6 Hz, 1H), 7.97-8.05 (m, 3H), 8.06 (s, 1H), 8.20 (t, J=0.8 Hz, 1H), 8.28 (d, J=2.4 Hz, 1H), 9.35 (s, 1H). MS(ES+): m/z 547.23 (100) [MH$^+$]. HPLC: t$_R$=3.03 min (ZQ3, polar__5 min).

General Procedure for Pd(O) Catalyzed OH Substitution

Into a sealable tube containing a stir bar were added di-tert-butylmethyl-(2',4',6'-triisopropyl-3,4,5,6-tetramethylbiphenyl-2-yl)-1(5)-phosphane (49.5 mg, 0.100 mmol) and tris(dibenzylidenacetone)dipalladium(0) (23.1 mg, 0.0250 mmol). The haloisoquinoline (0.500 mmol) dissolved in H$_2$O (1 ml) and 1,4-dioxane (1 ml) was added into the tube followed by addition of potassium hydroxide (66.0 mg, 1.00 mmol). The tube was evacuated and backfilled with nitrogen three times. The mixture was stirred in a 100° C. preheated oil bath for 1 h. After that time, the mixture was treated with water (5 ml), neutralized with HCl until pH=7-8, and extracted with EtOAc (3×8 ml). The extracts were washed with water (3×8 ml), brine (8 ml), dried over MgSO$_4$, filtered, and concentrated in vacuo. The residue was purified by chromatography to give the target compound.

Example 27

3-[2-Amino-5-(1-piperidin-4-yl-1H-pyrazol-4-yl)-pyridin-3-yl]-isoquinolin-5-ol tri-hydrochloride salt The title compound was obtained as a light-yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(5-hydroxyisoquinolin-3-yl)-pyridin-3-yl]-pyrazol-1-yl}-piperidine-1-carboxylic acid tert-butyl ester. $^1$H NMR (400 MHz, CD$_3$OD): δ=2.35 (brs, 4H), 3.21-3.35 (m, 2H), 3.55-3.62 (m, 2H), 4.64 (brs, 1H), 7.57 (d, J=8.0 Hz, 1H), 7.94 (dd, J=7.6 & 8.0 Hz, 1H), 8.02-8.06 (m, 2H), 8.38 (s, 1H), 8.43 (s, 1H), 8.65 (s, 1H), 8.88 (s, 1H), 9.86 (s, 1H). MS(ES+): m/z=387.14 (78) [MH$^+$]. HPLC: t$_R$=0.63 min (ZQ3, polar__5 min).

4-{4-[6-Amino-5-(5-hydroxyisoquinolin-3-yl)-pyridin-3-yl]-pyrazol-1-yl}-piperidine-1-carboxylic acid tert-butyl ester The title compound was obtained as a brown oil following the General Procedure for Pd(0) Catalyzed OH Substitution, using 4-{4-[6-amino-5-(5-bromoisoquinolin-3-yl)-pyridin-3-yl]-pyrazol-1-yl}-piperidine-1-carboxylic acid tert-butyl ester. $^1$H NMR (400 MHz, CDCl$_3$): δ=1.49 (s, 9H), 1.92-2.04 (m, 2H), 2.13-2.19 (m, 2H), 2.86-2.98 (m, 2H), 4.22-4.38 (m, 3H), 7.20 (d, J=6.8 Hz, 1H), 7.47-7.55 (m, 2H), 7.59 (d, J=5.6 Hz, 2H), 7.77 (s, 1H), 8.04 (d, J=2.0 Hz, 1H), 8.41 (s, 1H), 8.46 (brs, 1H), 9.10 (s, 1H). MS(ES+): m/z=487.14 (100) [MH$^+$]. HPLC: t$_R$=2.35 min (ZQ3, polar__5 min).

Example 28

3-[2-Amino-5-(1-piperidin-4-yl-1H-pyrazol-4-yl)-pyridin-3-yl]-isoquinolin-6-ol trihydrochloride salt The title compound was obtained as a brown oil following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(6-hydroxyisoquinolin-3-yl)-pyridin-3-yl]-pyrazol-1-yl}-piperidine-1-carboxylic acid tert-butyl ester. $^1$H NMR (400 MHz, CD$_3$OD): δ=2.24-2.42 (m, 4H), 3.18-3.28 (m, 2H), 3.55-3.62 (m, 2H), 4.52-4.62 (m, 1H), 7.20 (d, J=2.0 Hz, 1H), 7.25 (dd, J=2.4 & 8.8 Hz, 1H), 7.94 (s, 1H), 7.98 (d, J=9.2 Hz, 1H), 8.01 (s, 1H), 8.11 (s, 1H), 8.14 (d, J=2.4 Hz, 1H), 8.21 (d, J=2.4 Hz, 1H), 8.35 (brs, 2H), 9.12 (s, 1H). MS(ES+): m/z=387.16 (30) [MH$^+$]. HPLC: t$_R$=1.57 min (ZQ3, polar__5 min).

4-{4-[6-Amino-5-(6-hydroxyisoquinolin-3-yl)-pyridin-3-yl]-pyrazol-1-yl}-piperidine-1-carboxylic acid tert-butyl ester The title compound was obtained as a yellow solid following the General Procedure for Pd(0) Catalyzed OH Substitution, using 4-{4-[6-amino-5-(6-bromoisoquinolin-3-yl)-pyridin-3-yl]-pyrazol-1-yl}-piperidine-1-carboxylic acid tert-butyl ester. $^1$H NMR (400 MHz, CD$_3$OD): δ=1.48 (s, 9H), 1.88-2.01 (m, 2H), 2.06-2.14 (m, 2H), 2.85-3.04 (m, 2H), 4.19-4.27 (m, 2H), 4.31-4.41 (m, 1H), 7.18 (d, J=2.0 Hz, 1H), 7.21 (dd, J=2.0 & 8.8 Hz, 1H), 7.85 (s, 1H), 7.94 (d, J=9.2 Hz, 1H), 7.98 (s, 1H), 8.08 (s, 1H), 8.09 (d, J=2.4 Hz, 1H), 8.18 (d, J=2.4 Hz, 1H), 9.08 (s, 1H). MS(ES+): m/z=487.21 (100) [MH$^+$]. HPLC: t$_R$=2.38 min (ZQ3, polar__5 min).

Example 29

3-[2-Amino-5-(1-piperidin-4-yl-1H-pyrazol-4-yl)-pyridin-3-yl]-isoquinolin-7-ol

Into the DCM (5 ml) solution of 4-{4-[6-amino-5-(7-methoxyisoquinolin-3-yl)-pyridin-3-yl]-pyrazol-1-yl}-piperidine-1-carboxylic acid tert-butyl ester (101 mg, 0.171 mmol), cooled in an ice/water bath, was added 1.00 M of boron tribromide in DCM (2.0 ml) over 5 min. The mixture was stirred at 0° C. and warmed to rt overnight. After that time, the mixture was basified with saturated Na$_2$CO$_3$ until pH 10 and extracted with EtOAc (3×30 ml). The extracts were washed with brine (2×20 ml), dried over MgSO$_4$, filtered and concentrated in vacuo, giving the title compound as a light-yellow solid. $^1$H NMR (400 MHz, CD$_3$OD): δ=1.90-2.02 (m, 2H), 2.09-2.18 (m, 2H), 2.74-2.82 (m, 2H), 3.18-3.24 (m, 2H), 4.26-4.36 (m, 1H), 7.27 (d, J=2.4 Hz, 1H), 7.36 (dd, J=2.4 & 9.2 Hz, 1H), 7.84-7.87 (m, 2H), 8.06 (d, J=0.8 Hz, 1H), 8.07 (d, J=3.2 Hz, 1H), 8.10 (s, 1H), 8.17 (d, J=2.4 Hz, 1H), 9.08 (s, 1H). MS(ES+): m/z=387.14 (100) [MH$^+$]. HPLC: t$_R$=0.66 & 1.85 min (ZQ3, polar__5 min; peak splitting).

Example 30

3-(1-Methoxyisoquinolin-3-yl)-5-(1-piperidin-4-yl-1H-pyrazol-4-yl)-pyridin-2-ylamine trihydrochloride salt The title compound was obtained as a light yellow oil following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(1-methoxyisoquinolin-3-yl)-pyridin-3-yl]-pyrazol-1-yl}-piperidine-1-carboxylic acid tert-butyl ester. $^1$H NMR (400 MHz, CD$_3$OD): δ=2.25-2.41 (m, 4H), 3.19-3.28 (m, 2H), 3.55-3.62 (m, 2H), 4.16 (s, 3H), 4.52-4.62 (m, 1H), 7.56-3.61 (m, 1H), 7.71-7.76 (m, 1H), 7.79 (s, 1H), 7.89 (d, J=8.0 Hz, 1H), 7.93 (s, 1H), 8.12 (s, 1H), 8.16 (brs, 1H), 8.20-8.22 (m, 2H), 8.36 (brs, 2H). MS(ES+): m/z=401.19 (100) [MH+]. HPLC: $t_R$=2.00 min (ZQ3, polar_5 min).

4-{4-[6-Amino-5-(1-methoxyisoquinolin-3-yl)-pyridin-3-yl]-pyrazol-1-yl}-piperidine-1-carboxylic acid tert-butyl ester The title compound was obtained as a brown oil following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using 3-chloro-1-methoxyisoquinoline. $^1$H NMR (400 MHz, CDCl$_3$): δ=1.49 (s, 9H), 1.92-2.03 (m, 2H), 2.16-2.22 (m, 2H), 2.86-2.98 (m, 2H), 4.18 (s, 3H), 4.22-4.38 (m, 3H), 6.32 (brs, 2H), 7.53-7.58 (m, 1H), 7.59 (s, 1H), 7.63 (d, J=0.8 Hz, 1H), 7.68-7.72 (m, 1H), 7.77 (d, J=0.4 Hz, 1H), 7.81 (d, J=8.0 Hz, 1H), 7.93 (d, J=2.4 Hz, 1H), 8.24-8.27 (m, 2H). MS(ES+): m/z=501.20 (100) [MH+]. HPLC: $t_R$=3.13 min (ZQ3, polar_5 min).

3-Chloro-1-methoxyisoquinoline

Into a sealed tube were added 1,3-dichloroisoquinoline (501 mg, 2.45 mmol), 2-aminopyridine (31 mg, 0.33 mmol), cuprous monochloride (37.2 mg, 0.162 mmol), MeONa (824 mg, 5.92 mmol), MeOH (3 ml) and diglyne (8 ml). The tube was sealed, evacuated and filled with N$_2$ three times. The combined mixture was heated at 125° C. for 3 days under an atmosphere of nitrogen. After that time, the mixture was treated with water (20 ml) and extracted with EtOAc (3×50 ml). The organic extracts were washed with water (3×30 ml), brine (30 ml), dried over MgSO$_4$, filtered, and concentrated in vacuo to give the title compound as light-yellow solid. $^1$H NMR (400 MHz, CDCl$_3$): δ=4.15 (s, 3H), 7.26 (d, J=0.6 Hz, 1H), 7.51 (ddd, J=3.6, 4.6, 8.2 Hz, 1H), 7.64-7.69 (m, 2H), 8.20 (dd, J=8.4, 1.2 Hz, 1H). MS(ES+): m/z=194.08/196.01 (80/28) [MH+]. HPLC: $t_R$=4.00 min (polar_5 min, ZQ3).

General Procedure for Conversion of Bromo(het)aryl to Cyano(het)aryl

Into a microwave vial were added the bromo(het)aryl compound (220 mg, 0.240 mmol), Pd(PPh$_3$)$_4$ (38.9 mg, 0.0336 mmol), and zinc cyanide (28.2 mg, 0.240 mmol). The vial was sealed, and then DMF (6 ml) was added. The air was removed and N$_2$ was filled for 3 times. The reaction mixture was heated in the microwave reactor to 150° C. for 5 min. The reaction mixture was diluted with EtOAc (30 ml), washed with water (2×50 ml), brine (50 ml), dried over MgSO$_4$, filtered, and concentrated in vacuo. The crude material thus obtained was purified by chromatography if needed.

Example 31

3-[2-Amino-5-(1-piperidin-4-yl-1H-pyrazol-4-yl)-pyridin-3-yl]-isoquinoline-6-carbonitrile trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(6-cyanoisoquinolin-3-yl)-pyridin-3-yl]-pyrazol-1-yl}-piperidine-1-carboxylic acid tert-butyl ester. $^1$H NMR (400 MHz, CD$_3$OD): δ=2.26-2.44 (m, 4H), 3.19-3.32 (m, 2H), 3.56-3.65 (m, 2H), 4.54-4.65 (m, 1H), 7.85-7.92 (m, 1H), 7.95-7.99 (m, 1H), 8.11-8.14 (m, 1H), 8.24-8.39 (m, 5H), 8.41-8.45 (m, 1H), 8.52-8.56 (m, 1H), 9.47-9.53 (m, 1H). MS(ES+): m/z=396.14 (60) [MH+]. HPLC: $t_R$=1.81 min (ZQ3, polar_5 min).

4-{4-[6-Amino-5-(6-cyanoisoquinolin-3-yl)-pyridin-3-yl]-pyrazol-1-yl}-piperidine-1-carboxylic acid tert-butyl ester Following the General Procedure for Conversion of Bromo (het)aryl to Cyano(het)aryl, 4-{4-[6-amino-5-(6-bromoisoquinolin-3-yl)-pyridin-3-yl]-pyrazol-1-yl}-piperidine-1-carboxylic acid tert-butyl ester (220 mg, 0.240 mmol) was reacted with Pd(PPh$_3$)$_4$ (38.9 mg, 0.0336 mmol) and zinc cyanide (28.2 mg, 0.240 mmol) in DMF (6 ml). The crude product was purified by chromatography on silica gel (8 g) eluting with DCM (100 ml), 1% (100 ml), 2% (100 ml), 3% (100 ml) and 4% (50 ml) MeOH/DCM to give the title compound as a yellow solid. MS(ES+): m/z=496.22 (100) [MH+]. HPLC: $t_R$=2.82 min (ZQ3, polar_5 min).

Example 32

3-[2-Amino-5-(1-piperidin-4-yl-1H-pyrazol-4-yl)-pyridin-3-yl]-isoquinoline-7-carbonitrile trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(7-cyanoisoquinolin-3-yl)-pyridin-3-yl]-pyrazol-1-yl}-piperidine-1-carboxylic acid tert-butyl ester. $^1$H NMR (400 MHz, CD$_3$OD): δ=2.30-2.44 (m, 4H), 3.21-3.33 (m, 2H), 3.56-3.64 (m, 2H), 4.62-4.71 (m, 1H), 8.05-8.09 (m, 2H), 8.29-8.34 (m, 2H), 8.48 (s, 1H), 8.75 (s, 1H), 8.34 (s, 1H), 8.93 (s, 1H), 9.56 (s, 1H). MS(ES+): m/z=396.13 (33) [MH+]. HPLC: $t_R$=1.66 min (ZQ3, polar_5 min).

4-{4-[6-Amino-5-(7-cyanoisoquinolin-3-yl)-pyridin-3-yl]-pyrazol-1-yl}-piperidine-1-carboxylic acid tert-butyl ester The title compound was obtained as a brown solid following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 7-cyanoisoquinolin-3-yl ester. $^1$H NMR (400 MHz, CDCl$_3$): δ=1.49 (s, 9H), 1.92-2.03 (m, 2H), 2.16-2.22 (m, 2H), 2.86-2.98 (m, 2H), 4.22-4.38 (m, 3H), 6.53 (brs, 2H), 7.67 (d, J=0.8 Hz, 1H), 7.77 (d, J=0.4 Hz, 1H), 7.85 (dd, J=1.6 & 8.4 Hz, 1H), 7.84 (d, J=2.4 Hz, 1H), 8.01 (d, J=8.8 Hz, 1H), 8.09 (s, 1H), 8.30 (d, J=2.4 Hz, 1H), 8.42 (m, 1H), 9.37 (d, J=1.2 Hz, 1H). MS(ES+): m/z=496.18 (100) [MH+]. HPLC: $t_R$=2.65 min (ZQ3, polar_5 min).

Trifluoromethanesulfonic acid 7-cyanoisoquinolin-3-yl ester

The title compound was obtained as off-white solid following the procedure for trifluoromethanesulfonic acid 5-chloro-6,8-difluoroisoquinolin-3-yl ester, using the mixture of 3-hydroxyisoquinoline-5-carbonitrile and 3-hydroxyisoquinoline-7-carbonitrile followed be separation of the isomers by prep. TLC. $^1$H NMR (400 MHz, CDCl$_3$): δ=7.66 (s, 1H), 7.93 (dd, J=1.2 & 8.4 Hz, 1H), 8.04 (d, J=8.8 Hz, 1H), 8.48 (s, 1H), 9.19 (s, 1H). MS(ES+): m/z=303.08 (65) [MH+]. HPLC: $t_R$=3.50 min (polar_5 min, ZQ3).

3-Hydroxyisoquinoline-5-carbonitrile and 3-Hydroxyisoquinoline-7-carbonitrile

Following the General Procedure for Conversion of Bromo (het)aryl to Cyano(het)aryl, using the mixture of 5-bromoisoquinolin-3-ol and 7-bromoisoquinolin-3-ol, one obtained the mixture of the title compounds as a brown solid. MS(ES+): m/z=171.04 (100) [MH$^+$]. HPLC: $t_R$=2.13 min (polar__5 min, ZQ3).

Example 33

3-[2-Amino-5-(1-piperidin-4-yl-1H-pyrazol-4-yl)-pyridin-3-yl]-isoquinoline-5-carbonitrile trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(5-cyanoisoquinolin-3-yl)-pyridin-3-yl]-pyrazol-1-yl}-piperidine-1-carboxylic acid tert-butyl ester. $^1$H NMR (400 MHz, CD$_3$OD): δ=2.28-2.44 (m, 4H), 3.22-3.33 (m, 2H), 3.56-3.65 (m, 2H), 4.62-4.72 (m, 1H), 7.97 (t, J=8.0 Hz, 1H), 8.07 (s, 1H), 8.33 (s, 1H), 8.39 (s, 1H), 8.46 (d, J=6.4 Hz, 1H), 8.60 (d, J=8.4 Hz, 1H), 8.65 (s, 1H), 8.83 (s, 1H), 9.67 (s, 1H). MS(ES+): m/z=396.13 (14) [MH$^+$]. HPLC: $t_R$=1.64 min (ZQ3, polar__5 min)

4-{4-[6-Amino-5-(5-cyanoisoquinolin-3-yl)-pyridin-3-yl]-pyrazol-1-yl}-piperidine-1-carboxylic acid tert-butyl ester The title compound was obtained as a brown oil following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 5-cyanoisoquinolin-3-yl ester. $^1$H NMR (400 MHz, CDCl$_3$): δ=1.49 (s, 9H), 1.95-2.08 (m, 2H), 2.17-2.23 (m, 2H), 2.87-2.99 (m, 2H), 4.23-4.38 (m, 3H), 6.49 (brs, 2H), 7.69-7.73 (m, 2H), 7.79 (d, J=0.8 Hz, 1H), 8.00 (d, J=2.4 Hz, 1H), 8.17 (dd, J=1.2 & 6.8 Hz, 1H), 8.28 (td, J=0.8 & 8.0 Hz, 1H), 8.32 (d, J=2.0 Hz, 1H), 8.34 (t, J=0.8 Hz, 1H), 9.40 (d, J=0.8 Hz, 1H). MS(ES+): m/z=496.18 (100) [M$^H$+]. HPLC: $t_R$=2.58 min (ZQ3, polar__5 min).

Trifluoromethanesulfonic acid 5-cyanoisoquinolin-3-yl ester

The title compound was obtained as off-white solid following the procedure for trifluoromethanesulfonic acid 5-chloro-6,8-difluoroisoquinolin-3-yl ester, using the mixture of 7-cyanoisoquinolin-3-ol and 5-cyanoisoquinolin-3-ol followed by separation of the isomers by prep. TLC. $^1$H NMR (400 MHz, CDCl$_3$): δ=7.80 (dd, J=7.2 & 8.0 Hz, 1H). 7.92 (m, 1H), 8.24 (dd, J=1.2 & 7.6 Hz, 1H), 8.35 (td, J=1.2 & 8.4 Hz, 1H), 9.22 (d, J=0.8 Hz, 1H). MS(ES+): m/z=303.08 (100) [MH$^+$]. HPLC: $t_R$=3.50 min (polar__5 min, ZQ3).

Example 34

3-(7-Fluoroisoquinolin-3-yl)-5-(1-piperidin-4-yl-1H-pyrazol-4-yl)-pyridin-2-ylamine For the deprotection, 1N HCl in diethyl ether (1.0 mL) was added to a solution of 4-{4-[6-amino-5-(7-fluoroisoquinolin-3-yl)-pyridin-3-yl]-pyrazol-1-yl}-piperidine-1-carboxylic acid tert-butyl ester (entire quantity isolated in the previous step) in DCM (1.0 mL) in a sealed test tube. The reaction stirred at rt for 1 h. The mixture was concentrated in vacuo to give the title compound as yellow solid. $^1$H NMR (400 MHz, CD$_3$OD): δ=2.37 (4H, br.s), 3.54-3.68 (3H, m), 4.20 (1H, d, J=5.6 Hz), 4.64 (1H, br.s), 7.58-7.72 (1H, m), 7.81 (1H, br.s), 7.98 (1H, br.s), 8.06 (1H, br.s), 8.27 (2H, br.s), 8.69-8.90 (2H, m), 9.48 (1H, br.s). HPLC: $t_R$=1.74 min. (ZQ2, polar__5 min.). MS (ES+): m/z=389.18 (95) [MH$^+$].

4-{4-[6-Amino-5-(7-fluoroisoquinolin-3-yl)-pyridin-3-yl]-pyrazol-1-yl}-piperidine-1-carboxylic acid tert-butyl ester A mixture of 4-4-[6-amino-5-(4,4,5,5-tetramethyl-[1,3,2]dioxaborolan-2-yl)-pyridin-3-yl]-pyrazol-1-ylpiperidine-1-carboxylic acid tert-butyl ester (BB3) (30.0 mg, 0.0639 mmol), trifluoromethanesulfonic acid 7-fluoroisoquinolin-3-yl ester (22.6 mg, 0.0767 mmol), KF (7.4 mg, 0.13 mmol), and Pd(PPh$_3$)$_4$ (4 mg, 0.003 mmol) in 1,4-dioxane (1.5 mL) and H$_2$O (0.12 mL) was deg and refilled with nitrogen (3×). The reaction was heated in the microwave reactor to 100° C. for 30 min. The reaction mixture was concentrated in vacuo to a solid and purified by chromatography on silica gel (25 g prepacked column, eluting with DCM to 5% MeOH in DCM] to give the title compound. MS (ES+): m/z=489.19 (100) [MH$^+$]

Trifluoromethanesulfonic acid 7-fluoroisoquinolin-3-yl ester

A DCM (10 mL, 0.2 mol) solution of 7-Fluoroisoquinolin-3-ol (0.476 g, 2.92 mmol) and triethylamine (0.813 mL, 5.84 mmol) was cooled in an ice bath and charged with trifluoromethanesulfonic anhydride (0.982 mL, 5.84 mmol); this mixture was allowed to stir for 1 h while slowly warming to rt. The reaction was quenched with water and then diluted with more DCM, washed with NaHCO$_3$ solution, brine, dried over Na$_2$SO$_4$, filtered and concentrated in vacuo. The crude material was purified by prep. TLC [1000 µm layer of 60 Å silica gel on glass-backed 20×20 cm TLC plate, eluting with 2% 7N (NH$_3$) MeOH in DCM], which afforded the title compound. $^1$H NMR (400 MHz, CD$_3$OD): δ=7.72 (1H, td, J=8.8, 2.5 Hz), 7.87 (1H, s), 7.90 (1H, dd, J=9.0, 2.7 Hz), 8.13 (1H, dd, J=9.2, 5.2 Hz), 9.12 (1H, s). HPLC: $t_R$=3.70 min. (ZQ2, polar__5 min.). MS (ES$^+$): m/z=295.76 (45) [MH$^+$].

7-Fluoroisoquinolin-3-ol

Into a RBF was added N-(3-Fluorobenzyl)-2,2-dimethoxyacetamide (1.53 g, 6.73 mmol) and sulfuric acid (18M; 3.4 mL, 61 mmol); this mixture was stirred at 85° C. for 5 min. Ice water was added and stirred, and then solid NaHCO$_3$ was carefully added until the solution was neutralized. The aqueous layer was extracted with DCM. The DCM layer was dried over Na$_2$SO$_4$, filtered, and concentrated in vacuo to give the title compound. It was carried onto the next step without any further purification. HPLC: $t_R$=2.13 min. (ZQ2, polar__5 min.). MS (ES+): m/z=164.69 (100) [MH$^+$].

N-(3-Fluorobenzyl)-2,2-dimethoxyacetamide

Into a sealable tube were added methyl dimethoxyacetate (0.98 g, 7.3 mmol) and 3-fluorobenzylamine (0.91 g, 7.3 mmol); this mixture was stirred at 60° C. for 2 days. The compound was purified by chromatography on silica gel (10 g/70 mL prepacked column, eluting with 5% EtOAc in hexanes→5% MeOH in hexanes), affording the title compound. HPLC: $t_R$=2.59 min. (ZQ2, polar_5 min.). MS (ES+): m/z=249.92 (29) [MNa+], 227.91 (100) [MH+].

Example 35

3-(6-Fluoroisoquinolin-3-yl)-5-(1-piperidin-4-yl-1H-pyrazol-4-yl)-pyridin-2-ylamine Following the procedure for 5-(1-Piperidin-4-yl-1H-pyrazol-4-yl)-3-(7-trifluoromethoxy-isoquinolin-3-yl)-pyridin-2-ylamine trihydrochloride, using trifluoromethanesulfonic acid 6-fluoroisoquinolin-3-yl ester, the title compound was obtained as a yellow solid. $^1$H NMR (400 MHz, CD$_3$OD): δ=2.27-2.39 (m, 4H), 3.18-3.26 (m, 2H), 3.51-3.60 (m, 2H), 4.57-4.70 (m, 1H), 7.79-7.86 (m, 1H), 7.96-8.04 (m, 2H), 8.36 (s, 1H), 8.40 (s, 1H), 8.56 (dd, J=9.2, 5.4 Hz, 1H), 8.70 (s, 1H), 8.74 (s, 1H), 9.77 (s, 1H). MS (ES+): m/z=389.18 [MH+]. HPLC: $t_R$ 1.68 min (ZQ2, polar_5 min).

Trifluoromethanesulfonic acid 6-fluoroisoquinolin-3-yl ester

A DCM (5 mL) solution of 6-fluoroisoquinolin-3-ol (225 mg, 1.38 mmol) and Triethylamine (0.42 mL, 3.0 mmol) was cooled in an ice bath and charged with trifluoromethanesulfonic anhydride (0.85 g, 3.0 mmol); this mixture was allowed to stir for 1 h while slowly warming to rt. The reaction was quenched with some water and then diluted with more DCM, washed with NaHCO$_3$ solution, brine, dried over Na$_2$SO$_4$, filtered and concentrated. The crude product was passed through a small SiO$_2$ plug eluting with 10% EtOAc/Hexanes to yield the title compound as a yellow solid. MS (ES+): m/z=296.05 [MH+]. HPLC: $t_R$=3.63 min (ZQ2, polar_5 min).

6-Fluoroisoquinolin-3-ol

Into a RBF were added N-(4-Fluorobenzyl)-2,2-dimethoxyacetamide (1.53 g, 6.73 mmol) and sulfuric acid (18M; 3.4 mL, 61 mmol). This mixture was stirred at 85° C. for 5 min. Ice water was added and stirred; then solid NaHCO$_3$ was added until the pH was 7-8. This was allowed to stir, then DCM was added and stirred to dissolve product. A solid precipitated out of the solution after 16 h. It was filtered off and dried in vacuo to give the title compound as yellow solid. HPLC: $t_R$=2.07 min. (ZQ2, polar_5 min.). MS (ES+): m/z 164.24 (100) [MH+].

N-(4-Fluorobenzyl)-2,2-dimethoxyacetamide

Into a sealable tube were added methyl dimethoxyacetate (0.98 g, 7.3 mmol) and 4-fluorobenzylamine (0.91 g, 7.3 mmol); mixture was stirred at 60° C. for 2 days. The compound was purified by column chromatography on silica gel (10 g/70 mL prepacked cartridge, eluting with 5% EtOAc in hexanes→5% MeOH in hexanes), affording the title compound. HPLC: $t_R$=2.58 min. (ZQ2, polar_5 min.). MS (ES+): m/z=249.92 (24) [MNa+], 227.91 (100) [MH+].

Example 36

3-[2-Amino-5-(1-piperidin-4-yl-1H-pyrazol-4-yl)-pyridin-3-yl]-isoquinoline-8-carbonitrile trihydrochloride salt The procedure for the preparation of 3-(5,8-dichloroisoquinolin-3-yl)-5-(1-piperidin-4-yl-1H-pyrazol-4-yl)-pyridin-2-ylamine trihydrochloride was followed, except using trifluoromethanesulfonic acid 8-cyanoisoquinolin-3-yl ester in place of trifluoromethanesulfonic acid 5,8-dichloroisoquinolin-3-yl ester. This afforded the title compound as a yellow solid. $^1$H NMR (400 MHz, CD$_3$OD): δ=2.30-2.42 (m, 4H), 3.21-3.27 (m, 2H), 3.59 (d, J=13.4 Hz, 2H), 4.59-4.71 (m, 1H), 7.97-8.04 (m, 1H), 8.08 (s, 1H), 8.25-8.30 (m, 2H), 8.42-8.49 (m, 2H), 8.86 (s, 1H), 8.93 (d, J=2.0 Hz, 1H), 9.70 (s, 1H). MS (ES+): m/z=396.19 [MH+]. HPLC: $t_R$=1.67 min (ZQ2, polar_5 min).

Trifluoromethanesulfonic Acid 8-cyanoisoquinolin-3-yl ester

Following the procedure for trifluoromethanesulfonic acid 6-fluoroisoquinolin-3-yl ester, using 3-hydroxyisoquinoline-8-carbonitrile in place of 6-fluoroisoquinolin-3-ol, the title compound was obtained as a yellow solid. MS (ES+): m/z=303.04 [MH+]. HPLC: $t_R$=3.55 min (ZQ2, polar_5 min).

3-Hydroxyisoquinoline-8-carbonitrile

The General Procedure for Conversion of Bromo(het)aryl to Cyano(het)aryl was followed, using 8-bromoisoquinolin-3-ol. The crude material was purified by trituration from hexane yielding the title compound as a yellow solid. MS (ES+): m/z=171.04 [MH+]. HPLC: $t_R$=2.22 min (ZQ3, polar_5 min)

Example 37

3-[2-Amino-5-(1-piperidin-4-yl-1H-pyrazol-4-yl)-pyridin-3-yl]-8-fluoro-isoquinoline-5-carbonitrile trihydrochloride The procedure for the preparation of 3-(5,8-dichloroisoquinolin-3-yl)-5-(1-piperidin-4-yl-1H-pyrazol-4-yl)-pyridin-2-ylamine trihydrochloride was followed, except using trifluoromethanesulfonic acid 5-cyano-8-fluoroisoquinolin-3-yl ester in place of trifluoromethanesulfonic acid 5,8-dichloroisoquinolin-3-yl ester. This afforded the title compound as a yellow solid. $^1$H NMR (400 MHz, CD$_3$OD): δ=2.26-2.42 (m, 4H), 3.20-3.29 (m, 2H), 3.55-3.63 (m, 2H), 4.55-4.67 (m, 1H), 7.54 (dd, J=9.7, 8.2 Hz, 1H), 7.95 (s, 1H), 8.15 (s, 1H), 8.26 (d, J=2.0 Hz, 1H), 8.30 (d, J=2.3 Hz, 1H), 8.35 (dd, J=8.1, 5.1 Hz, 1H), 8.39 (s, 1H), 9.70 (d, J=1.0 Hz, 1H). MS (ES+): m/z=414.13 [MH+]. HPLC: $t_R$=1.70 min (ZQ2, polar_5 min).

Trifluoromethanesulfonic acid 5-cyano-8-fluoroisoquinolin-3-yl ester

Following the procedure for trifluoromethanesulfonic acid 6-fluoroisoquinolin-3-yl ester, using 8-fluoro-3-hydroxyisoquinoline-5-carbonitrile in place of 6-fluoroisoquinolin-3-ol, the title compound was obtained as a yellow solid. MS (ES+): m/z=321.06 [MH+]. HPLC: $t_R$=3.58 min (ZQ2, polar_5 min).

8-Fluoro-3-hydroxyisoquinoline-5-carbonitrile

The General Procedure for Conversion of Bromo(het)aryl to Cyano(het)aryl was followed, using 5-bromo-8-fluoroisoquinolin-3-ol. The crude material was purified by trituration from hexane yielding the title compound as a yellow solid. MS (ES+): m/z=189.05 [MH$^+$]. HPLC: $t_R$=2.30 min (ZQ3, polar__5 min).

Example 38

3-(8-Chloro-7-fluoroisoquinolin-3-yl)-5-(1-piperidin-4-yl-1H-pyrazol-4-yl)-pyridin-2-ylamine trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(8-chloro-7-fluoroisoquinolin-3-yl)-pyridin-3-yl]-pyrazol-1-yl}-1-carboxylic acid tert-butyl ester. $^1$H NMR (400 MHz, DMSO-d$_6$): δ=2.14-2.31 (m, 4H), 3.07-3.18 (m, 2H), 3.37-3.44 (m, 2H), 3.59 (brs, 2H), 4.49-4.59 (m, 1H), 8.05 (t, J=9.2 Hz, 1H), 8.16 (s, 1H), 8.23 (dd, J=4.8 & 8.8 Hz, 1H), 8.49 (d, J=2.0 Hz, 1H), 8.52 (s, 1H), 8.70 (brs, 2H), 8.88 (s, 2H), 9.09 (brs, 2H), 9.22 (brs, 1H), 9.68 (s, 1H). MS(ES+): m/z=423.09/425.11 (82/35) [MH$^+$]. HPLC: $t_R$=1.86 min (ZQ3, polar__5 min).

4-{4-[6-Amino-5-(8-chloro-7-fluoroisoquinolin-3-yl)-pyridin-3-yl]-pyrazol-1-yl}-piperidine-1-carboxylic acid tert-butyl ester The title compound was obtained as a yellow solid following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 8-chloro-7-fluoroisoquinolin-3-yl ester. $^1$H NMR (400 MHz, CDCl$_3$): δ=1.49 (s, 9H), 1.88-2.04 (m, 2H), 2.15-2.22 (m, 2H), 2.86-2.98 (m, 2H), 4.20-4.38 (m, 3H), 6.50 (brs, 2H), 7.58 (t, J=8.8 Hz, 1H), 7.67 (s, 1H), 7.77 (d, J=0.4 Hz, 1H), 7.84 (dd, J=4.4 & 8.8 Hz, 1H), 7.94 (d, J=2.4 Hz, 1H), 8.03 (s, 1H), 8.28 (d, J=2.4 Hz, 1H), 9.68 (s, 1H). MS(ES+): m/z=523.17/525.15 (100/88) [MH]. HPLC: $t_R$=3.36 min (ZQ3, polar__5 min).

Trifluoromethanesulfonic acid 8-chloro-7-fluoroisoquinolin-3-yl ester

The title compound was obtained as a beige oil following the procedure for trifluoromethanesulfonic acid 5-chloro-6,8-difluoroisoquinolin-3-yl ester, using 8-chloro-7-fluoroisoquinolin-3-ol. $^1$H NMR (400 MHz, CDCl$_3$): δ=7.61 (s, 1H), 7.66 (dd, J=8.4 & 8.8 Hz, 1H), 7.84-7.88 (m, 1H), 9.47 (t, J=0.8 Hz, 1H). MS(ES+): m/z=329.91/331.89 (100/40) [MH$^+$]. HPLC: $t_R$=4.03 min (polar__5 min, ZQ3).

8-Chloro-7-fluoroisoquinolin-3-ol

Sulfuric acid (18M; 0.19 mL, 3.4 mmol) was added to N-(2-chloro-3-fluorobenzyl)-2,2-dimethoxyacetamide (72.6 mg, 0.250 mmol) at ambient temperature. The mixture was stirred at 50° C. for 16 h. After cooling to rt, the mixture was poured into ice, basified with saturated Na$_2$CO$_3$ until pH=8, and extracted with EtOAc (3×30 ml). The extracts were washed with water (3×20 ml), brine (20 ml), dried over MgSO4, filtered, and concentrated in vacuo to give the title compound as yellow solid. $^1$H NMR (400 MHz, CDCl$_3$): δ=7.05 (s, 1H), 7.41 (dd, J=8.4 & 9.2 Hz, 1H), 7.56-7.60 (m, 1H), 9.11 (s, 1H). MS(ES+): m/z=198.14/200.02 (100/88) [MH$^+$]. HPLC: $t_R$=2.48 min (polar__5 min, ZQ3).

N-(2-Chloro-3-fluorobenzyl)-2,2-dimethoxyacetamide

A mixture of 2-chloro-3-fluorobenzylamine (575 mg, 3.53 mmol), methyl dimethoxyacetate (512 mg, 3.78 mmol), triethylamine (0.62 mL, 4.4 mmol) and MeOH (1 mL, 20 mmol) in a sealed tube was heated at 80° C. for 20 h. After cooling to rt, the mixture was diluted with EtOAc (40 ml), washed with HCl (2N, 2×30 ml), water (2×30 ml), brine (30 ml), dried over MgSO$_4$, filtered, and concentrate vacuo to give the title compound as a brown oil. $^1$H NMR (400 MHz, CDCl$_3$): δ=3.40 (s, 6H), 4.59 (d, J=6.0 Hz, 2H), 4.74 (s, 1H), 6.99 (brs, 1H), 7.07-7.12 (m, 1H), 7.17-7.25 (m, 2H). MS(ES+): m/z=262.06/264.04 (100/62) [MH$^+$]. HPLC: $t_R$=2.91 min (ZQ3, polar__5 min).

2-Chloro-3-fluorobenzylamine

BH$_3$.THF in THF (1.0 M, 50.0 ml) was carefully added into the THF (40.0 ml) solution of 2-chloro-3-fluorobenzonitrile (662 mg, 4.17 mmol) at rt. The resulting mixture was heated at 70° C. under an atmosphere of nitrogen for 16 h. After cooling to ambient temperature, conc. HCl (5.18 ml, 62.5 mmol) was added slowly. The combined mixture was heated at 70° C. for 30 min. After that time, the mixture was concentrated in vacuo to remove most of solvent, water (20 ml) was added, and the mixture was extracted with Et$_2$O (3×30 ml). The extracts were washed with water (20 ml). The combined aqueous layers were basified by saturated Na$_2$CO$_3$ until pH=9 and extracted with EtOAc (3×50 ml). These EtOAc extracts were washed with brine (50 ml) dried over MgSO$_4$, filtered, and concentrated in vacuo to give the title compound as colorless oil. $^1$H NMR (400 MHz, CDCl$_3$): δ=1.67 (brs, 2H), 3.97 (s, 2H), 7.03-7.09 (m, 1H), 7.17-7.26 (m, 2H). MS(ES+): m/z=160.14/162.09 (64/32) [MH$^+$]. HPLC: $t_R$=0.40 & 0.70 min (polar__5 min, ZQ3; peak splitting).

Example 39

3-(8-Fluoroisoquinolin-3-yl)-5-(1-piperidin-4-yl-1H-pyrazol-4-yl)-pyridin-2-ylamine 4-{4-[6-Amino-5-(5-bromo-8-fluoroisoquinolin-3-yl)-pyridin-3-yl]-pyrazol-1-yl}-1-carboxylic acid tert-butyl ester (0.030 g, 0.053 mmol), 2-propaneboronic acid (10 mg, 0.1 mmol), Cs$_2$CO$_3$ (70 mg, 0.22 mmol) and Pd(PPh$_3$)$_4$ (6 mg, 0.005 mmol) were placed in a sealable microwave tube and taken up in 1,4-dioxane (2 mL, 20 mmol) and H$_2$O (0.50 mL, 28 mmol), flushed with nitrogen, sealed and heated in the microwave reactor at 100° C. for 30 min. Pd(dppf)Cl$_2$.DCM (10 mg) was added, and the mixture was heated in the microwave reactor at 100° C. for 30 min. The reaction mixture was diluted with EtOAc washed with water, brine, dried over Na$_2$SO$_4$, filtered and concentrated. The residue was purified on prep-TLC eluting with 5% 7M NH$_3$ in MeOH and DCM to give the Boc-protected title compound; MS (ES+): m/z=488.93 [MH$^+$]. This material was dissolved in DCM (1 mL) and charged with 1M HCl in ether (2.0 mL) and stirred at ambient temperature for 1 h. The solid that formed was filtered off and dried in vacuo overnight, giving the title compound as yellow solid. $^1$H NMR (400 MHz, CD$_3$OD): δ=2.34-2.43 (m, 4H), 2.81 (s, 3H), 2.85-2.89 (m, 2H), 3.56-3.65 (m, 2H), 4.60-4.70 (m, 1H), 7.37 (dd, J=10.1, 7.8 Hz, 1H), 7.70 (dd, J=7.5, 5.4 Hz, 1H), 8.08 (s, 1H), 8.26 (d, J=1.5 Hz, 1H), 8.38 (s, 1H), 8.59 (s, 1H), 8.86 (d, J=1.5 Hz, 1H), 9.62 (s, 1H). MS(ES+): m/z=388.92 (100) [MH$^+$]. HPLC: $t_R$=1.75 min (ZQ2, polar__5 min).

Example 40

3-(6-Chloroisoquinolin-3-yl)-5-(1-piperidin-4-yl-1H-pyrazol-4-yl)-pyridin-2-ylamine trihydrochloride The procedure for the preparation of 3-(5,8-dichloroisoquinolin-3-yl)-5-(1-piperidin-4-yl-1H-pyrazol-4-yl)-pyridin-2-ylamine trihydrochloride was followed, except using trifluoromethanesulfonic acid 6-chloroisoquinolin-3-yl ester in place of trifluoromethanesulfonic acid 5,8-dichloroisoquinolin-3-yl ester. This afforded the title compound as a yellow solid. $^1$H NMR (400 MHz, DMSO-d$_6$): δ=2.14-2.31 (m, 4H), 3.04-3.16 (m, 2H), 3.33-3.41 (m, 2H), 4.47-4.62 (m, 3H), 7.83 (dd, J=8.8, 2.0 Hz, 1H), 8.15 (s, 1H), 8.21 (d, J=1.8 Hz, 1H), 8.34 (d, J=8.8 Hz, 1H), 8.50 (d, J=2.0 Hz, 1H), 8.54 (s, 1H), 8.73 (s, 1H), 8.84 (d, J=2.0 Hz, 1H), 9.22 (br. s., 1H), 9.34 (br. s., 1H), 9.52 (s, 1H), MS(ES+): m/z=404.90/406.78 [MH$^+$]. HPLC: t$_R$=1.80 min (ZQ2, polar__5 min).

Trifluoromethanesulfonic acid 6-chloroisoquinolin-3-yl ester

Following the procedure for trifluoromethanesulfonic acid 6-fluoroisoquinolin-3-yl ester, using 6-chloroisoquinolin-3-ol in place of 6-fluoroisoquinolin-3-ol, the title compound was obtained as a yellow solid. MS (ES+): m/z=311.69/313.63 [MH$^+$]. HPLC: t$_R$=3.88 min (ZQ2, polar__5 min).

6-Chloroisoquinolin-3-ol

The title compound was obtained as a yellow solid following the procedure for 5-chloro-6,8-difluoroisoquinolin-3-ol, using N-(4-chlorobenzyl)-2,2-dimethoxyacetamide. MS (ES+): m/z=179.90/181.83 [MH$^+$]. HPLC: t$_R$=2.34 min (ZQ3, polar__5 min).

N-(4-chlorobenzyl)-2,2-dimethoxyacetamide

Into a vial was added methyl dimethoxyacetate (0.98 g, 7.3 mmol) and 4-chlorobenzylamine (1.0 g, 7.3 mmol), this mixture was stirred at 50° C. for 2 d. The product was recrystallized from Heptane to yield the desired product as an oil that solidified over time. MS (ES+): m/z=244.09/246.05 [MH$^+$]. HPLC: t$_R$=2.80 min (ZQ2, polar__5 min).

Example 41

3-(7-Chloroisoquinolin-3-yl)-5-(1-piperidin-4-yl-1H-pyrazol-4-yl)-pyridin-2-ylamine trihydrochloride The procedure for the preparation of 3-(5,8-dichloroisoquinolin-3-yl)-5-(1-piperidin-4-yl-1H-pyrazol-4-yl)-pyridin-2-ylamine trihydrochloride was followed, except using trifluoromethanesulfonic acid 7-chloroisoquinolin-3-yl ester in place of trifluoromethanesulfonic acid 5,8-dichloroisoquinolin-3-yl ester. This afforded the title compound as a yellow solid. $^1$H NMR (400 MHz, CD$_3$OD): δ=2.29-2.46 (m, 4H), 3.24-3.31 (m, 2H), 3.59-3.67 (m, 2H), 4.61-4.72 (m, 1H), 7.91 (dd, J=8.8, 2.0 Hz 1H), 8.10 (s, 1H), 8.18 (d, J=9.0 Hz, 1H), 8.28 (d, J=2.0 Hz, 1H), 8.30 (d, J=2.0 Hz, 1H), 8.43 (s, 1H), 8.73 (s, 1H), 8.90 (d, J=2.3 Hz, 1H), 9.43 (s, 1H). MS (ES+): m/z=405.09/407.03 [MH$^+$]. HPLC: t$_R$=1.95 min (ZQ3, polar__5 min).

Trifluoromethanesulfonic acid 7-chloroisoquinolin-3-yl ester

The title compound was obtained as beige solid following the procedure for trifluoromethanesulfonic acid 5-chloro-6,8-difluoroisoquinolin-3-yl ester, using the mixture of 7-chloroisoquinolin-3-ol and 5-chloroisoquinolin-3-ol. Isomers were separated via column chromatography eluting with heptane→10% EtOAc/heptane. The higher, less polar spot was the title compound. $^1$H NMR (400 MHz, CDCl$_3$): δ=7.59 (s, 1H), 7.75 (dd, J=8.8, 2.0 Hz, 1H), 7.88 (d, J=8.8 Hz, 1H), 8.07 (d, J=2.0 Hz, 1H), 9.02 (s, 1H). MS (ES+): m/z=311.75/313.70 [MH$^+$]. HPLC: t$_R$=3.87 min (ZQ2, polar__5 min).

5-Chloroisoquinolin-3-ol and 7-Chloroisoquinolin-3-ol

Following the procedure for 5-bromoisoquinolin-3-ol and 7-bromoisoquinolin-3-ol, using N-(3-chlorobenzyl)-2,2-dimethoxyacetamide, the mixture of the title compounds was obtained as a yellow solid. MS (ES+): m/z=311.76/313.68 [MH$^+$]. HPLC: t$_R$=3.86 min (ZQ2, polar__5 min).

N-(3-Chlorobenzyl)-2,2-dimethoxyacetamide

Into a vial were added methyl dimethoxyacetate (1.9 g, 14 mmol) and 3-chlorobenzylamine (2.0 g, 14 mmol), this mixture was stirred at room temperature over two days. The product was triturated with hexane (3×) and re-crystallized from hexane, affording the desired product as oil that solidified over time. $^1$H NMR (400 MHz, CDCl$_3$): δ=3.43 (s, 6H), 4.47 (d, J=6.1 Hz, 2H), 4.77 (s, 1H), 6.91 (br. s., 1H), 7.15-7.21 (m, 1H), 7.25-7.30 (m, 3H). MS (ES+): m/z=243.93/245.81 [MH$^+$]. HPLC: t$_R$=2.80 min (ZQ2, polar__5 min).

Example 42

3-(5-Chloroisoquinolin-3-yl)-5-(1-piperidin-4-yl-1H-pyrazol-4-yl)-pyridin-2-ylamine trihydrochloride The procedure for the preparation of 3-(5,8-dichloroisoquinolin-3-yl)-5-(1-piperidin-4-yl-1H-pyrazol-4-yl)-pyridin-2-ylamine trihydrochloride was followed, except using trifluoromethanesulfonic acid 5-chloroisoquinolin-3-yl ester in place of trifluoromethanesulfonic acid 5,8-dichloroisoquinolin-3-yl ester. This afforded the title compound as a yellow solid. MS (ES+): m/z=405.05/407.03 [MH$^+$]. HPLC: t$_R$=1.91 min (ZQ2, polar__5 min).

Trifluoromethanesulfonic acid 5-chloroisoquinolin-3-yl ester

The title compound was obtained as beige solid following the procedure for trifluoromethanesulfonic acid 5-chloro-6,8-difluoroisoquinolin-3-yl ester, using the mixture of 7-chloroisoquinolin-3-ol and 5-chloroisoquinolin-3-ol. Isomers were separated via column chromatography eluting with heptane→10% EtOAc/heptane. The lower, more polar spot was the title compound. $^1$H NMR (400 MHz, CDCl$_3$): δ=7.65 (dd, J=8.1, 1.0 Hz, 1H), 7.89 (dd, J=7.6, 1.0 Hz, 1H), 7.95 (s, 1H), 8.02 (d, J=8.1 Hz, 1H), 9.11 (s, 1H). MS (ES+): m/z=311.74/313.72 [MH$^+$]. HPLC: t$_R$=3.91 min (ZQ2, polar__5 min).

Example 43

3-(6,8-Dichloroisoquinolin-3-yl)-5-(1-piperidin-4-yl-1H-pyrazol-4-yl)-pyridin-2-ylamine trihydrochloride The procedure for the preparation of 3-(5,8-dichloroisoquinolin-3-yl)-5-(1-piperidin-4-yl-1H-pyrazol-4-yl)-pyridin-2-ylamine trihydrochloride was followed, except using trifluoromethanesulfonic acid 6,8-dichloroisoquinolin-3-yl ester in place of trifluoromethanesulfonic acid 5,8-dichloroisoquinolin-3-yl ester. This afforded the title compound as a yellow solid. $^1$H NMR (400 MHz, DMSO-d$_6$): δ=2.10-2.31 (m, 4H), 3.04-3.18 (m, 2H), 3.33-3.46 (m, 2H), 4.45-4.59 (m, 1H). 8.11 (d, J=1.8 Hz, 1H), 8.14 (s, 1H), 8.22 (d, J=1.3 Hz, 1H), 8.48 (d, J=2.0 Hz, 1H), 8.50 (s, 1H), 8.63 (br. s., 1H), 8.75 (s, 1H), 8.83 (d, J=2.0 Hz, 1H), 8.95 (br. s., 1H), 9.07 (br. s., 1H), 9.65 (s, 1H). MS (ES+): m/z=439.07/441.07/443.06 [MH$^+$]. HPLC: $t_R$=2.00 min (ZQ2, polar_5 min).

Trifluoromethanesulfonic acid 6,8-dichloroisoquinolin-3-yl ester

The title compound was obtained as yellow solid following the procedure for trifluoromethanesulfonic acid 5-chloro-6,8-difluoroisoquinolin-3-yl ester, using 6,8-dichloroisoquinolin-3-ol. MS (ES+): m/z=345.96/347.96/349.94 [MH$^+$]. HPLC: $t_R$=4.16 min (ZQ3, polar_5 min).

6,8-Dichloroisoquinolin-3-ol

The title compound was obtained as a yellow solid following the procedure for 5-chloro-6,8-difluoroisoquinolin-3-ol, using N-(2,4-dichlorobenzyl)-2,2-dimethoxyacetamide. MS (ES+): m/z=214.08/216.10/218.08 [MH$^+$]. HPLC: $t_R$=2.73 min (ZQ2, polar_5 min).

N-(2,4-Dichlorobenzyl)-2,2-dimethoxyacetamide

Into a sealed tube were added methyl dimethoxyacetate (0.78 g, 5.8 mmol) and 2,4-dichlorobenzylamine (1.0 g, 5.8 mmol). This mixture was stirred at 50° C. for 36 h. The completed reaction mixture was transferred to a flask and re-crystallized from heptane yielding the desired product as an off-white solid. MS (ES+): m/z=278.10/280.09/282.08 [MH$^+$]. HPLC: $t_R$=3.03 min (ZQ2, polar_5 min).

Example 44

3-(7-Methoxyisoquinolin-3-yl)-5-(1-piperidin-4-yl-1H-pyrazol-4-yl)-pyridin-2-ylamine trihydrochloride The procedure for the preparation of 3-(5,8-dichloroisoquinolin-3-yl)-5-(1-piperidin-4-yl-1H-pyrazol-4-yl)-pyridin-2-ylamine trihydrochloride was followed, except using trifluoromethanesulfonic acid 7-methoxyisoquinolin-3-yl ester in place of trifluoromethanesulfonic acid 5,8-dichloroisoquinolin-3-yl ester. This afforded the title compound as a yellow solid. $^1$H NMR (400 MHz, CD$_3$OD): δ=2.32-2.44 (m, 4H), 3.23-3.31 (m, 2H), 3.58-3.67 (m, 2H), 4.08 (s, 3H), 4.61-4.72 (m, 1H), 7.67-7.74 (m, 2H), 8.08 (s, 1H), 8.16 (d, J=8.8 Hz, 1H), 8.31 (d, J=2.0 Hz, 1H), 8.40 (s, 1H), 8.65 (s, 1H), 8.79 (d, J=2.0 Hz, 1H), 9.51 (s, 1H). MS (ES+): m/z=401.14 [MH$^+$]. HPLC: $t_R$=1.88 min (ZQ3, polar_5 min).

Trifluoromethanesulfonic acid 7-Methoxyisoquinolin-3-yl ester

The title compound was obtained as yellow solid following the procedure for trifluoromethanesulfonic acid 5-chloro-6,8-difluoroisoquinolin-3-yl ester, using 7-methoxyisoquinolin-3-ol. $^1$H NMR (400 MHz, CDCl$_3$): δ=3.98 (s, 3H), 7.29 (d, J=2.5 Hz, 1H), 7.46 (dd, J=9.1, 2.5 Hz, 1H), 7.52 (s, 1H), 7.81 (d, J=9.1 Hz, 1H), 8.95 (s, 1H). MS (ES+): m/z=307.76 [MH$^+$]. HPLC: $t_R$=3.70 min (ZQ2, polar_5 min).

7-Methoxyisoquinolin-3-ol

The title compound was obtained as a yellow solid following the procedure for 5-chloro-6,8-difluoroisoquinolin-3-ol, using N-(2,4-dichlorobenzyl)-2,2-dimethoxyacetamide. MS (ES+): m/z=176.09 [MH$^+$]. HPLC: $t_R$=2.19 min (ZQ3, polar_5 min).

2,2-Dimethoxy-N-(3-methoxybenzyl)-acetamide

Into a vial was added methyl dimethoxyacetate (2.0 g, 14 mmol) and 3-methoxybenzylamine (2.0 g, 14 mmol), this mixture was stirred at room temperature for 8 d. The product was triturated with heptane (3×) and then dried in vacuo, yielding the desired product as an off-white solid. MS (ES+): m/z=240.84 [MH+]. HPLC: $t_R$=2.55 min (ZQ2, polar_5 min).

Example 45

3-(6-Methoxyisoquinolin-3-yl)-5-(1-piperidin-4-yl-1H-pyrazol-4-yl)-pyridin-2-ylamine trihydrochloride The procedure for the preparation of 3-(5,8-dichloroisoquinolin-3-yl)-5-(1-piperidin-4-yl-1H-pyrazol-4-yl)-pyridin-2-ylamine trihydrochloride was followed, except using trifluoromethanesulfonic acid 6-methoxyisoquinolin-3-yl ester in place of trifluoromethanesulfonic acid 5,8-dichloroisoquinolin-3-yl ester. This afforded the title compound as a yellow solid. $^1$H NMR (400 MHz, DMSO-d$_6$): δ=2.16-2.29 (m, 4H), 3.05-3.17 (m, 2H), 3.38 (d, J=12.6 Hz, 2H), 4.00 (s, 3H), 4.48-4.59 (m, 1H), 7.46-7.54 (m, 2H), 8.13 (s, 1H), 8.27 (d, J=8.8 Hz, 1H), 8.48-8.51 (m, 2H), 8.59 (s, 1H), 8.80 (d, J=2.3 Hz, 1H), 9.19 (br. s., 1H), 9.28 (br. s., 1H), 9.45 (s, 1H). MS (ES+): m/z=318.16 [MH$^+$]. HPLC: $t_R$=1.70 min (ZQ2, polar_5 min).

Trifluoromethanesulfonic acid 6-Methoxyisoquinolin-3-yl ester

The title compound was obtained as yellow solid following the procedure for trifluoromethanesulfonic acid 5-chloro-6,8-difluoroisoquinolin-3-yl ester, using 6-methoxyisoquinolin-3-ol. MS (ES+): m/z=308.07 [MH$^+$]. HPLC: $t_R$=3.68 min (ZQ2, polar_5 min).

6-Methoxyisoquinolin-3-ol

The title compound was obtained as a yellow solid following the procedure for 5-chloro-6,8-difluoroisoquinolin-3-ol, using N-formyl-3-methoxyphenylacetamide. MS (ES+): m/z=176.21 [MH$^+$]. HPLC: $t_R$=2.70 min (ZQ2, polar_5 min).

N-formyl-3-methoxyphenylacetamide

To a stirring solution of (4-methoxyphenyl)acetyl chloride (0.500 g, 2.71 mmol) in acetone (1.0 mL) at 0° C. was added a solution of formamide (0.28 mL, 7.0 mmol) and pyridine (0.28 mL, 3.5 mmol) in acetone (1.0 mL). The resulting solution was stirred at 0° C. for 30 min and then overnight at rt. The reaction mixture was diluted with EtOAc and washed with 1M HCl, sat. NaHCO$_3$ solution, brine, dried over Na$_2$SO$_4$, filtered and concentrated in vacuo. The crude material was purified by column chromatography eluting with 1% MeOH in DCM yielding the title compound as an off-white solid. MS (ES+): m/z=194.11 [MH$^+$]. HPLC: $t_R$=2.57 min (ZQ3, polar_5 min).

General Procedure for the Synthesis of N-Formyl Acetamides

A mixture of (substituted)-phenylacetic acid (2.00 mmol), oxalyl chloride (1.38 ml, 16.0 mmol), and toluene (10 ml) was stirred at 110° C. for 2 h. After that time, the excess reagent and solvent were removed in vacuo to give a light-brown oil. A solution of this oil in acetone (1 ml) was cooled in ice/water, and a solution of formamide (209 μl, 5.20 mmol) and pyridine (212 μl, 2.60 mmol) in acetone (1 ml) was added. The reaction mixture was stirred at 5° C. for 30 min and then at room temperature overnight. After that time, the mixture was diluted with EtOAc (50 ml), washed with HCl (2N; 30 ml), water (2×30 ml), brine (30 ml), dried over $MgSO_4$, filtered, and concentrated in vacuo to give a light-yellow solid. It was then purified by chromatography on silica gel eluting with 10% (100 ml), 20% (100 ml), 30% (100 ml), 40% (100 ml) and 50% (100 ml) EtOAc/hexane to give a light yellow solid that was further purified by trituration with 10% EtOAc/Hexane to give the N-formyl-[(substituted)-phenyl]-acetamide.

Example 46

3-(6,8-Difluoroisoquinolin-3-yl)-5-(1-piperidin-4-yl-1H-pyrazol-4-yl)-pyridin-2-ylamine trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(6,8-difluoroisoquinolin-3-yl)-pyridin-3-yl]-pyrazol-1-yl}-piperidine-1-carboxylic acid tert-butyl ester. $^1$H NMR (400 MHz, DMSO-$d_6$): δ=2.14-2.31 (m, 4H), 3.07-3.18 (m, 2H), 3.37-3.44 (m, 2H), 3.45 (brs, 2H), 4.49-4.59 (m, 1H), 7.75-7.81 (m, 2H), 8.13 (s, 1H), 8.49-8.51 (m, 2H), 8.74 (s, 1H), 8.78 (s, 1H), 9.00 (brs, 1H), 9.15 (brs, 1H), 9.58 (s, 1H). MS(ES+): m/z=407.11 (82) [MH$^+$]. HPLC: $t_R$=1.78 min (ZQ3, polar_5 min).

4-{4-[6-Amino-5-(6,8-difluoroisoquinolin-3-yl)-pyridin-3-yl]-pyrazol-1-yl}-piperidine-1-carboxylic acid tert-butyl ester The title compound was obtained as a yellow solid following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 6,8-difluoroisoquinolin-3-yl ester. $^1$H NMR (400 MHz, CDCl$_3$): δ=1.49 (s, 9H), 1.92-2.05 (m, 2H), 2.16-2.23 (m, 2H), 2.86-2.98 (m, 2H), 4.20-4.38 (m, 3H), 6.48 (brs, 2H), 7.05-7.11 (m, 1H), 7.33-7.35 (m, 1H), 7.66 (d, J=0.8 Hz, 1H), 7.77 (d, J=0.4 Hz, 1H), 7.94 (d, J=2.0 Hz, 1H), 7.99 (d, J=1.6 Hz, 1H), 8.29 (d, J=2.0 Hz, 1H), 9.51 (t, J=1.2 Hz, 1H). MS(ES+): m/z=507.20 (100) [MH$^+$]. HPLC: $t_R$=3.32 min (ZQ3, polar_5 min).

Trifluoromethanesulfonic acid 6,8-Difluoroisoquinolin-3-yl ester

The title compound was obtained as yellow solid following the procedure for trifluoromethanesulfonic acid 5-chloro-6,8-difluoroisoquinolin-3-yl ester, using 6,8-difluoroisoquinolin-3-ol. $^1$H NMR (400 MHz, CDCl$_3$): δ=7.12-7.17 (m, 1H), 7.34-7.37 (m, 1H), 7.54 (s, 1H), 9.30 (s, 1H). MS(ES+): m/z=314.02 (9) [MH$^+$]. HPLC: $t_R$=3.87 min (polar_5 min, ZQ3).

6,8-Difluoroisoquinolin-3-ol

The title compound was obtained as a yellow solid following the procedure for 5-chloro-6,8-difluoroisoquinolin-3-ol, using N-formyl-(3,5-difluorophenyl)acetamide. MS (ES+): m/z=176.21 [MH$^+$]. HPLC: $t_R$=2.70 min (ZQ2, polar_5 min).

N-Formyl-(3,5-difluorophenyl)acetamide

The title compound was obtained as an off-white solid following the General Procedure for the Synthesis of N-Formyl Acetamides, using (3,5-difluorophenyl)acetic acid. $^1$H NMR (400 MHz, CDCl$_3$): δ=3.71 (s, 2H), 6.78-6.85 (m, 3H), 8.00 (brs, 1H), 9.10 (d, J=10.0 Hz, 1H). HPLC: $t_R$=2.67 min (polar_5 min, ZQ3).

Example 47

3-(8-Chloro-6-fluoroisoquinolin-3-yl)-5-(1-piperidin-4-yl-1H-pyrazol-4-yl)-pyridin-2-ylamine trihydrochloride salt The title compound was obtained as a yellow solid following the procedure for 3-(5-chloro-6,8-difluoroisoquinolin-3-yl)-5-(1-piperidin-4-yl-1H-pyrazol-4-yl)-pyridin-2-ylamine trihydrochloride salt, using 4-{4-[6-amino-5-(8-chloro-6-fluoroisoquinolin-3-yl)-pyridin-3-yl]-pyrazol-1-yl}-piperidine-1-carboxylic acid tert-butyl ester. $^1$H NMR (400 MHz, DMSO-$d_6$): δ=2.14-2.31 (m, 4H), 3.07-3.18 (m, 2H), 3.35-3.43 (m, 2H), 4.49-4.59 (m, 1H), 4.97 (brs, 2H), 7.92 (dd, J=2.4 & 8.2 Hz, 1H), 8.07 (dd, J=2.4 & 8.4 Hz, 1H), 8.16 (s, 1H), 8.52 (d, J=1.6 Hz, 1H), 8.55 (s, 1H), 8.76 (brs, 1H), 8.84 (s, 1H), 8.88 (d, J=2.0 Hz, 1H), 9.20 (brs, 1H), 9.33 (brs, 1H), 9.64 (s, 1H). MS(ES+): m/z=423.09/425.04 (58/24) [MH$^+$]. HPLC: $t_R$=1.89 min (ZQ3, polar_5 min).

4-{4-[6-Amino-5-(8-chloro-6-fluoroisoquinolin-3-yl)-pyridin-3-yl]-pyrazol-1-yl}-piperidine-1-carboxylic acid tert-butyl ester The title compound was obtained as a yellow solid following the procedure for 4-{4-[6-amino-5-(5-chloro-6,8-difluoroisoquinolin-3-yl)-pyridin-3-yl]-pyrazol-1-yl}-piperidine-1-carboxylic acid tert-butyl ester, using trifluoromethanesulfonic acid 8-chloro-6-fluoroisoquinolin-3-yl ester. $^1$H NMR (400 MHz, CDCl$_3$): δ=1.49 (s, 9H), 1.92-2.05 (m, 2H), 2.16-2.23 (m, 2H), 2.86-2.98 (m, 2H), 4.20-4.38 (m, 3H), 6.55 (brs, 2H), 7.43-7.48 (m, 2H), 7.66 (d, J=0.8 Hz, 1H), 7.77 (d, J=0.8 Hz, 1H), 7.94 (d, J=2.4 Hz, 1H), 7.98 (d, J=0.8 Hz, 1H), 8.29 (d, J=2.0 Hz, 1H), 9.64 (t, J=0.8 Hz, 1H). MS(ES+): m/z=523.15/525.11 (100/62) [MH$^+$]. HPLC: $t_R$=3.08 min (ZQ3, polar_5 min).

Trifluoromethanesulfonic acid 8-Chloro-6-fluoroisoquinolin-3-yl ester

The title compound was obtained as yellow solid following the procedure for trifluoromethanesulfonic acid 5-chloro-6,8-difluoroisoquinolin-3-yl ester, using the mixture of 8-chloro-6-fluoroisoquinolin-3-ol and 6-chloro-8-fluoroisoquinolin-3-ol mixture. $^1$H NMR (400 MHz, CDCl$_3$): δ=7.46 (dd, J=2.4 & 8.4 Hz, 1H), 7.53 (dd, J=2.4 & 8.4 Hz, 1H), 7.54 (s, 1H), 9.34 (s, 1H). MS(ES+): m/z=329.98/332.00 (27/9) [MH$^+$]. HPLC: $t_R$=4.05 min (polar_5 min, ZQ3).

8-Chloro-6-fluoroisoquinolin-3-ol and 6-Chloro-8-fluoroisoquinolin-3-ol

The mixture of title compounds was obtained as yellow solid following the procedure for 5-chloro-6,8-difluoroisoquinolin-3-ol, using N-formyl-(3-chloro-5-fluorophenyl)acetamide. MS(ES+): m/z=198.04/200.01 (100/85) [MH$^+$]. HPLC: $t_R$=2.57 and 2.68 min (polar__5 min, ZQ3).

N-Formyl-(3-chloro-5-fluorophenyl)acetamide

The title compound was obtained as a white solid following the General Procedure for the Synthesis of N-Formyl Acetamides, using (3-chloro-5-fluorophenyl)acetic acid. $^1$H NMR (400 MHz, CDCl$_3$): δ=3.69 (s, 2H), 6.90-6.95 (m, 1H), 7.06-7.12 (m, 2H), 8.30 (brs, 1H), 9.10 (d, J=9.2 Hz, 1H). HPLC: $t_R$=2.87 min (polar__5 min, ZQ3).

General Procedure S: Suzuki & Stille Couplings on 4-{4-[6-Amino-5-(5-bromo-8-fluoroisoquinolin-3-yl)-pyridin-3-yl]-pyrazol-1-yl}-piperidine-1-carboxylic acid tert-butyl ester To a microwave vial were added 4-{4-[6-Amino-5-(5-bromo-8-fluoro-isoquinolin-3-yl)-pyridin-3-yl]-pyrazol-1-yl}-piperidine-1-carboxylic acid tert-butyl ester (0.0881 mmol), appropriate boronic acid (1.74 mmol), Cs$_2$CO$_3$ (3.3 mmol), and Palladium(0) tetrakis(triphenylphosphine) (0.08 mmol). The mixture was dissolved in 1,4-dioxane (4.0 mL, 63 mmol) and H$_2$O (1.0 mL, 90 mmol) and flushed with nitrogen. The vial was sealed and heated in the microwave reactor at 100° C. for 30 min. For reactions with tributyltin reagents (1.74 mmol), KF (3.3 mmol) was used in place of Cs$_2$CO$_3$, and no water was used. The completed reaction was diluted with EtOAc (25 mL) and washed with water, brine, drying over Na$_2$SO$_4$, filtered and concentrated in vacuo. The product was purified on prep-TLC eluting with 5% 7M NH$_3$ in MeOH/DCM and concentrated. The pure product was dissolved in DCM and charged with excess 1M HCl in Et$_2$O. This mixture was stirred at rt for 30 min to overnight, the solid that formed was filtered off and dried in vacuo, giving the desired pure final compound.

Example 48

3-(8-Fluoro-5-furan-2-ylisoquinolin-3-yl)-5-(1-piperidin-4-yl-1H-pyrazol-4-yl)-pyridin-2-ylamine The title compound was obtained as a yellow solid, following General Procedure S with an extra purification step, passing product through SCX column and elute off of column with 3% 7M NH$_3$ in MeOH/MeOH (1:3). $^1$H NMR (400 MHz, DMSO-d$_6$): δ=1.81-2.08 (m, 4H), 2.70 (t, J=11.4 Hz, 2H), 3.12 (d, J=12.6 Hz, 2H), 4.19-4.31 (m, 1H), 6.72-6.78 (m, 3H), 7.16 (d, J=3.3 Hz, 1H), 7.54-7.66 (m, 2H), 7.87 (s, 1H), 7.96 (d, J=1.3 Hz, 1H), 8.03-8.10 (m, 2H), 8.19 (s, 1H), 8.35 (d, J=2.0 Hz, 1H), 8.58 (s, 1H), 9.64 (s, 1H). MS (ES+): m/z=455.15 [MH$^+$]. HPLC: $t_R$=2.09 min (ZQ3, polar__5 min).

Example 49

3-(8-Fluoro-5-furan-3-ylisoquinolin-3-yl)-5-(1-piperidin-4-yl-1H-pyrazol-4-yl)-pyridin-2-ylamine trihydrochloride The title compound was obtained as a yellow solid, following General Procedure S. $^1$H NMR (400 MHz, DMSO-d$_6$): δ=2.09-2.27 (m, 4H), 3.03-3.16 (m, 2H), 3.34-3.44 (m, 2H), 4.46-4.60 (m, 1H), 7.08 (d, J=1.0 Hz, 1H), 7.68 (dd, J=10.1, 8.1 Hz, 1H), 7.89-7.97 (m, 2H), 8.10 (s, 1H), 8.27-8.34 (m, 2H), 8.42 (s, 1H), 8.45 (d, J=1.8 Hz, 2H), 8.66 (d, J=2.0 Hz, 1H), 8.94 (br, s., 1H), 9.08 (br, s., 1H), 9.68 (s, 1H). MS (ES+): m/z=455.13 [MH$^+$]. HPLC: $t_R$=2.10 min (ZQ3, polar__5 min Example 50

3-(8-Fluoro-5-phenylisoquinolin-3-yl)-5-(1-piperidin-4-yl-1H-pyrazol-4-yl)-pyridin-2-ylamine The title compound was obtained as a yellow solid, following General Procedure S with an extra purification step, passing product through SCX column and elute off of column with 3% 7M NH$_3$ in MeOH/MeOH (1:3). $^1$H NMR (400 MHz, CD$_3$OD): δ=1.98 (dd, J=12.4, 3.8 Hz, 1H), 2.14 (dd, J=12.4, 2.3 Hz, 2H), 2.82 (td, J=12.6, 2.5 Hz, 2H), 3.24 (d, J=12.9 Hz, 2H), 4.26-4.37 (m, 1H), 7.42 (dd, J=10.1, 8.1 Hz, 1H), 7.46-7.52 (m, 1H), 7.52-7.59 (m, 4H), 7.67-7.74 (m, 2H), 7.82 (d, J=2.3 Hz, 1H), 7.95 (s, 1H), 8.06 (s, 1H), 8.18 (d, J=2.3 Hz, 1H), 9.59 (s, 1H). MS (ES+): m/z=465.16 [MH$^+$]. HPLC: $t_R$=2.03 min (ZQ2, polar__5 min).

Example 51

3-[8-Fluoro-5-(1H-pyrazol-4-yl)-isoquinolin-3-yl]-5-(1-piperidin-4-yl-1H-pyrazol-4-yl)-pyridin-2-ylamine trihydrochloride The title compound was obtained as a yellow solid, following General Procedure S. $^1$H NMR (400 MHz, DMSO-d$_6$): δ=2.15-2.27 (m, 4H), 3.03-3.15 (m, 2H), 3.38 (d, J=12.4 Hz, 2H), 4.48-4.60 (m, 1H), 7.66 (dd, J=10.0, 8.2 Hz, 1H), 7.91 (dd, J=8.1, 5.6 Hz, 1H), 8.11 (s, 1H), 8.24 (s, 2H), 8.37 (br. s., 1H), 8.44 (s, 1H), 8.48 (s, 2H), 8.69 (d, J=1.8 Hz, 1H), 9.19 (br. s., 1H), 9.32 (br. s., 1H), 9.66 (s, 1H). MS (ES+): m/z=455.15 [MH$^+$]. HPLC: $t_R$=1.91 min (ZQ3, polar__5 min).

Example 52

3-[8-Fluoro-5-(1-methyl-1H-pyrazol-4-yl)-isoquinolin-3-yl]-5-(1-piperidin-4-yl-1H-pyrazol-4-yl)-pyridin-2-ylamine trihydrochloride The title compound was obtained as a yellow solid, following General Procedure S. $^1$H NMR (400 MHz, DMSO-d$_6$): δ=2.14-2.29 (m, 4H), 3.04-3.15 (m, 2H), 3.38 (d, J=12.6 Hz, 2H), 3.96 (s, 3H), 4.47-4.58 (m, 1H), 7.65 (dd, J=10.1, 8.1 Hz, 1H), 7.88 (dd, J=8.2, 5.4 Hz, 1H), 7.96 (s, 1H), 8.11 (s, 1H), 8.35 (s, 1H), 8.39 (br. s., 1H), 8.46 (s, 1H), 8.47 (d, J=2.0 Hz, 1H), 8.49 (s, 1H, 8.68 (d, J=2.0 Hz, 1H), 9.07 (br. s., 1H), 9.20 (br. s., 1H), 9.65 (s, 1H). MS (ES+): m/z=469.20 [MH$^+$]. HPLC: $t_R$=1.78 min (ZQ2, polar__5 min).

Example 53

3-[8-Fluoro-5-(1H-pyrrol-2-yl)-isoquinolin-3-yl]-5-(1-piperidin-4-yl-1H-pyrazol-4-yl)-pyridin-2-ylamine The title compound was obtained as a yellow solid, following General Procedure S with additional purification: The product was passed through an SCX column eluting with 4M NH$_3$ in MeOH, concentrated in vacuo, and then purified on Prep-TLC eluting with 5% 7MNH$_3$ in MeOH/DCM. $^1$H NMR (400 MHz, CD$_3$OD): δ=1.88-2.01 (m, 2H), 2.08-2.17 (m, 2H), 2.71-2.82 (m, 2H), 3.16-3.24 (m, 2H), 4.24-4.37 (m, 1H), 6.34 (t, J=3.0 Hz, 1H), 6.49 (dd, J=3.4, 1.4 Hz, 1H), 7.00

(dd, J=2.7, 1.4 Hz, 1H), 7.37 (dd, J=10.1, 8.1 Hz, 1H), 7.74 (dd, J=8.1, 5.3 Hz, 1H), 7.78 (s, 1H), 7.97-8.01 (m, 2H), 8.20 (d, J=2.0 Hz, 1H), 8.51 (s, 1H), 9.54 (s, 1H). MS (ES+): m/z=454.19 [MH$^+$]. HPLC: $t_R$=1.96 min (ZQ3, polar_5 min).

Example 54

3-(8-Fluoro-5-pyridin-3-ylisoquinolin-3-yl)-5-(1-piperidin-4-yl-1H-pyrazol-4-yl)-pyridin-2-ylamine trihydrochloride pyridin-2-ylamine trihydrochloride The title compound was obtained as a yellow solid, following General Procedure S. $^1$H NMR (400 MHz, DMSO-d$_6$): δ=1.85 (dd, J=12.0, 3.7 Hz, 2H), 1.97-2.04 (m, 2H), 2.69 (t, J=11.9 Hz, 2H), 3.11 (d, J=12.4 Hz, 2H), 4.22 (dd, J=15.4, 7.3 Hz, 1H), 4.44 (br. s., 1H), 6.66 (br. s., 2H), 7.63 (dd, J=10.6, 8.6 Hz, 2H), 7.78 (s, 1H), 7.86 (dd, J=8.1, 5.6 Hz, 1H), 7.90 (d, J=2.3 Hz, 1H), 7.98 (s, 1H), 8.08-8.10 (m, 1H), 8.11 (s, 1H), 8.30 (d, J=2.3 Hz, 1H), 8.70 (dd, J=4.8, 1.5 Hz, 1H), 8.82 (d, J=1.5 Hz, 1H), 9.68 (s, 1H). MS (ES+): m/z=466.17 [MH$^+$]. HPLC: $t_R$=2.00 min (ZQ3, polar_5 min).

Example 55

3-(8-Fluoro-5-thiazol-2-ylisoquinolin-3-yl)-5-(1-piperidin-4-yl-1H-pyrazol-4-yl)-pyridin-2-ylamine trihydrochloride The title compound was obtained as a yellow solid, following General Procedure S using 2-tributylstannylthiazole. $^1$H NMR (400 MHz, DMSO-d$_6$): δ=2.08-2.29 (m, 4H), 3.02-3.17 (m, 2H), 3.34-3.43 (m, 2H), 4.44-4.58 (m, 1H), 7.05-7.36 (m, 1H), 7.76 (d, J=8.3 Hz, 1H), 8.00 (d, J=3.3 Hz, 1H), 8.07 (s, 1H), 8.15 (d, J=3.3 Hz, 1H), 8.26 (br. s., 1H), 8.34-8.42 (m, 2H), 8.46 (d, J=2.0 Hz, 1H), 8.57 (d, J=1.8 Hz, 1H), 8.97 (br. s., 1H), 9.10 (br. s., 1H), 9.36 (s, 1H), 9.72 (s, 1H). MS (ES+): m/z=412.13 [MH$^+$]. HPLC: $t_R$=2.27 min (ZQ3, polar_5 min).

Example 56

3-(8-Fluoro-5-thiazol-5-ylisoquinolin-3-yl)-5-(1-piperidin-4-yl-1H-pyrazol-4-yl)-pyridin-2-ylamine trihydrochloride The title compound was obtained as a yellow solid, following General Procedure S using 5-tributylstannylthiazole. $^1$H NMR (400 MHz, CD$_3$OD): δ=2.28-2.41 (m, 4H), 3.20-3.27 (m, 2H), 3.55-3.64 (m, 2H), 4.58-4.74 (m, 1H), 7.56-7.67 (m, 1H), 7.97 (s, 1H), 8.01-8.10 (m, 1H), 8.22-8.31 (m, 2H), 8.35 (s, 1H), 8.51 (s, 1H), 8.64 (s, 1H), 9.42 (s, 1H), 9.74 (s, 1H). MS(ES+): m/z=472.41 [MH$^+$]. HPLC: $t_R$=2.41 min (ZQ3, polar_5 min).

Example 57

4-4-[6-Amino-5-(5-chloro-8-fluoroisoquinolin-3-yl)-pyridin-3-yl]-pyrazol-1-ylpiperidine-1-carbaldehyde To a solution of 3-(5-chloro-8-fluoroisoquinolin-3-yl)-5-(1-piperidin-4-yl-1H-pyrazol-4-yl)-pyridin-2-ylamine trihydrochloride (100 mg, 0.188 mmol), EDCI (56.5 mg, 0.295 mmol), DMAP (10 mg, 0.085 mmol), and diisopropylethylamine (160 μL, 0.94 mmol) in DCM (5.1 mL, 80 mmol) was added formic acid (19.9 mg, 0.432 mmol) at ambient temperature, and the reaction mixture was stirred for 1 h at ambient temperature. The reaction was diluted with DCM, washed with NaHCO$_3$ and brine, dried over anhydrous Na$_2$SO$_4$, filtered, and concentrated in vacuo. The residue was purified on prep-TLC developing with 5% 7N NH$_3$(MeOH): DCM solvent system, giving the title compound. $^1$H NMR (400 MHz, CD$_3$OD): δ=2.18-2.32 (m, 2H), 2.89-3.00 (m, 1H), 3.95 (dd, 1H), 4.25 (dd, J=5.6, 1.8 Hz, 3H), 4.46-4.61 (m, 2H), 7.63-7.68 (m, 1H), 7.71-7.77 (m, 1H), 7.90-7.97 (m, 1H), 8.11 (s, 1H), 8.17 (s, 1H), 8.22 (d, J=2.3 Hz, 1H), 8.32 (d, J=2.3 Hz, 1H), 8.48 (s, 1H), 9.64 (s, 1H), MS (ES+): m/z=450.79 [MH$^+$]. HPLC: $t_R$=2.41 min (ZQ2, polar_5 min).

Example 58

3-(5-Chloro-8-fluoroisoquinolin-3-yl)-5-[1-(1-methylpiperidin-4-yl)-1H-pyrazol-4-yl]-pyridin-2-ylamine To a solution of 4-{4-[6-amino-5-(5-chloro-8-fluoroisoquinolin-3-yl)-pyridin-3-yl]-pyrazol-1-yl}-piperidine-1-carbaldehyde (50.0 mg, 0.111 mmol) in THF (5 mL, 60 mmol), cooled to ≈0° C., LiAlH$_4$ (1.0M solution in THF; 0.27 mL, 0.27 mmol) was added, and the reaction mixture was stirred at 0° C.→rt for 30 min. Sodium sulfate decahydrate (0.1 g, 0.4 mmol) and EtOAc were added and the reaction mixture was stirred for 10 min at rt. The solids were filtered off, and the filtrate was concentrated and purified on prep-TLC eluting with 5% 7M NH$_3$ (MeOH)/DCM to give the title compound as pale yellow oil. MS (ES+): m/z=436.79/438.74 [MH$^+$]. HPLC: $t_R$=2.24 min (ZQ2, polar_5 min).

Example 59

3-(5-Chloro-8-fluoroisoquinolin-3-yl)-5-[1-(1-methylpiperidin-4-yl)-1H-pyrazol-4-yl]-pyridin-2-ylamine trihydrochloride To a solution of 3-(5-Chloro-8-fluoroisoquinolin-3-yl)-5-[1-(1-methylpiperidin-4-yl)-1H-pyrazol-4-yl]-pyridin-2-ylamine (25 mg, 0.057 mmol) in DCM (2.8 mL) was added 1.0 M of HCl in Et$_2$O (2.8 mL, 2.8 mmol), causing a solid to precipitate. The solid was filtered off, washed with DCM and heptane, and dried in vacuo, yielding the title compound as yellow solid. $^1$H NMR (400 MHz, CD$_3$OD): δ=2.36-2.47 (m, 4H), 3.67-3.76 (m, 2H), 4.19-4.24 (m, 1H), 4.58-4.69 (m, 1H), 4.70 (s, 1H), 7.47-7.54 (m, 1H), 8.00 (dd, J=8.3, 4.8 Hz, 1H), 8.05-8.09 (m, 1H), 8.29 (s, 1H), 8.38 (s, 1H), 8.71 (s, 1H), 8.83 (s, 1H), 9.68 (s, 1H).

General Procedure for the Preparation of Pinacol Boronates

To degassed dioxane (200 mL) were added Pd$_2$(dba)$_3$ (1.2 g, 2 mol %) and tricyclohexylphosphine (1.47 g, 8 mol %) and stirred for 30 minutes. To this mixture were added the (het) aryl bromide or -iodide (69.3 mmol), bis(pinacolato)diboron (23.0 g, 90.2 mmol), and potassium acetate (10.9 g, 111 mmol), and the mixture was heated under nitrogen at 100° C. for 16 h. After cooling back to RT, the solid that had formed was filtered off. The filtrate was evaporated to give the crude pinacol boronate solid, which was purified by trituration with diisopropyl ether (3×40 mL).

General Procedure for the Bromination of Aminopyridines with NBS

To a solution of the substituted aminopyridine (15.4 mmol) in CH$_2$Cl$_2$ (200 mL) under nitrogen at 0° C. was added N-bromosuccinimide (2.73 g, 15.4 mmol) portionwise. The mixture was stirred for 30 min, washed with water (2×40 mL), dried over MgSO4, filtered, and concentrated to give the crude material, which was purified by trituration with diisopropyl ether (30 mL).

3-(5-Chloro-8-fluoroisoquinolin-3-yl)-5-(4,4,5,5-tetramethyl-[1,3,2]dioxaborolan-2-yl)-pyridin-2-ylamine (BB5)

The title compound was prepared by following the General Procedure for the Preparation of Pinacol Boronates, using 5-bromo-3-(5-chloro-8-fluoroisoquinolin-3-yl)-pyridin-2-ylamine (BB4) (2.0 g, 5.7 mmol), bis(pinacolato)diboron (1.87 g, 7.4 mmol), $Pd_2(dba)_3$ (2 mol %), tricyclohexylphosphine (8 mol %), and KOAc (0.89 g, 9 mmol). $^1$H NMR (CDCl$_3$, 300 MHz): δ=1.38 (s, 12H), 7.19 (t, J=3.8 Hz, 1H), 7.62 (bs, 2H), 7.71 (dd, 6.8, 3.8 Hz, 1H), 8.31 (d, J=1.2 Hz, 1H), 8.38 (d, J=1.2 Hz, 1H), 8.42 (s, 1H), 9.55 (s, 1H). MS(ES+): m/z=399.08/400.10/401.09/402.08 (17/100/25/39) [MH$^+$]. HPLC: $t_R$=3.46 min (polar_5 min, ZQ3).

Data for the corresponding boronic acid: MS(ES+): m/z=317.06/318.04/319.04/320.03 (32/100/15/50) [MH$^+$]. HPLC: $t_R$=2.29 min (polar_5 min, ZQ3).

5-Bromo-3-(5-chloro-8-fluoroisoquinolin-3-yl)-pyridin-2-ylamine (BB4)

The title compound was obtained as a light orange solid following the General Procedure for the Bromination of Aminopyridines with NBS, using 3-(5-chloro-8-fluoroisoquinolin-3-yl)-pyridin-2-ylamine (4.2 g, 15.4 mmol). $^1$H NMR (CDCl$_3$, 300 MHz): δ=6.77 (brs, 2H), 7.22 (t, J=3.9 Hz, 1H), 7.76 (dd, J=6.8, 3.9 Hz, 1H), 8.07 (d, J=1.5 Hz, 1H), 8.17 (d, J=1.5 Hz, 1H), 8.30 (s, 1H), 9.56 (s, 1H). MS(ES+): m/z=351.94/353.92/355.95 (82/100/35) [MH$^+$]. HPLC: $t_R$=3.59 min (nonpolar_5 min, ZQ3).

3-(5-Chloro-8-fluoroisoquinolin-3-yl)-pyridin-2-ylamine

A mixture of trifluoromethanesulfonic acid 5-chloro-8-fluoroisoquinolin-3-yl ester (9.00 g, 27.4 mmol), 3-(4,4,5,5-tetramethyl-[1,3,2]dioxaborolan-2-yl)-pyridin-2-ylamine (8.42 g, 38.3 mmol), Pd(PPh$_3$)$_4$ (0.63 g, 2 mol %), and Cs$_2$CO$_3$ (20.5 g, 62.9 mmol) in dioxane/H$_2$O (4:1, 300 mL) were heated under nitrogen at 100° C. for 16 h. Solvents were evaporated in vacuo, water (100 mL) was added to the residue, and the mixture was extracted with EtOAc (3×75 mL). The EtOAc extract was dried over MgSO$_4$, filtered, and concentrated in vacuo to give the crude product. It was purified by column chromatography on silica gel using EtOAc/Hexanes (1:3) to give the title compound. $^1$H NMR (CDCl$_3$, 300 MHz): δ=6.87 (brs, 2H), 6.81 (dd, J=8.7, 4.8 Hz, 1H), 7.18 (dd, J=9.3, 9.0 Hz, 1H), 7.22 (dd, J=8.1, 4.2 Hz, 1H), 7.99 (dd, J=7.5, 2.1 Hz, 1H), 8.15 (dd, J=6.8, 1.8 Hz, 1H), 8.13 (t, J=1.2 Hz, 1H), 9.56 (d, J=1.2 Hz, 1H).

3-(4,4,5,5-Tetramethyl-[1,3,2]dioxaborolan-2-yl)-pyridin-2-ylamine

The title compound was obtained following the General Procedure for the Preparation of Pinacol Boronates, using 2-amino-3-bromopyridine (12.0 g, 69.3 mmol). $^1$H NMR (CDCl$_3$, 300 MHz): δ=1.42 (s, 12H), 6.65 (dd, J=5.1, 3.6 Hz, 1H), 7.91 (d, J=5.1 Hz, 1H), 8.10 (d, J=3.6 Hz, 1H).

Example 60

3-(5-Chloro-8-fluoroisoquinolin-3-yl)-5-[2-(4-methylpiperazin-1-yl)-thiazol-5-yl]-pyridin-2-ylamine trihydrochloride A solution of 1-(5-bromothiazol-2-yl)-4-methylpiperazine (45 mg, 0.17 mmol), 3-(5-chloro-8-fluoroisoquinolin-3-yl)-5-(4,4,5,5-tetramethyl-1,3,2-dioxaborolan-2-yl)-pyridin-2-ylamine (BB5) (89.2 mg, 0.223 mmol), potassium carbonate (71.2 mg, 0.515 mmol), and Pd(PPh$_3$)$_4$ (11.9 mg, 0.0103 mmol) in previously degassed DME/Water (4:1) (3.0 mL) was placed in a microwave tube and evacuated and charged with N$_2$ (2×). The reaction mixture was heated in the microwave reactor to 100° C. for 45 min. The reaction mixture was partitioned between CHCl$_3$ and H$_2$O, and the layers were separated. The aqueous layer was re-extracted with CHCl$_3$ (3×), and the combined organic fractions were washed with brine, dried over Na$_2$SO$_4$, filtered and concentrated in vacuo. The crude material was purified by chromatography on silica gel [eluting with 1% MeOH in CHCl$_3$] resulting in a pure yellow solid. This sample was then dissolved in a minimum of DCM then charged with 3 equiv of 1M HCl in ether and the reaction mixture was concentrated in vacuo resulting in the title compound as a yellow solid. $^1$H NMR (400 MHz, DMSO-d$_6$): δ=2.83 (d, J=4.0 Hz, 3H), 3.13-3.28 (m, 2H), 3.45-3.60 (m, 4H), 4.07 (d, J=14.3 Hz, 2H), 7.67 (t, J=8.0 Hz, 1H), 7.84 (s, 1H), 8.11 (dd, J=8.4, 4.8 Hz, 1H), 8.27 (d, J=2.2 Hz, 1H), 8.54 (s, 1H), 8.61 (s, 1H), 9.67 (s, 1H), 11.05 (br. s., 1H). MS (ES+): m/z=455.07/457.08 (76/24) [MH$^+$]. HPLC: $t_R$=1.99 min (ZQ2, polar_5 min).

1-(5-Bromothiazol-2-yl)-4-methylpiperazine

A solution of 2,5-dibromothiazole (1.000 g, 4.116 mmol) in DIPEA (3.00 mL) was charged with 1-methylpiperazine (0.457 mL, 4.12 mmol) and heated to 110° C. for 3 h then an additional 48 h at rt. The reaction mixture was partitioned between CHCl$_3$ and H$_2$O, and the layers were separated. The aqueous layer was re-extracted with CHCl$_3$ (3×) and the combined organic fractions were dried over Na$_2$SO$_4$, filtered and concentrated in vacuo. The crude material was purified by chromatography on silica gel [eluting with 5% EtOAc in CHCl$_3$→20% EtOAc in CHCl$_3$] resulting in the title compound as an off-white solid. $^1$H NMR (400 MHz, CDCl$_3$): δ=2.34 (s, 3H), 2.48-2.56 (m, 4H), 3.42-3.51 (m, 4H), 7.07 (s, 1H). MS (ES+): m/z=262.09/264.06 (51/49) [MH$^+$]. HPLC: $t_R$=1.57 & 0.53 min (peak splitting; ZQ2, polar_5 min).

Example 61

3-(5-Chloro-8-fluoroisoquinolin-3-yl)-5-(2-morpholin-4-ylthiazol-5-yl)-pyridin-2-ylamine A solution of 4-(5-bromo-thiazol-2-yl)-morpholine (52.4 mg, 0.210 mmol), 3-(5-chloro-8-fluoroisoquinolin-3-yl)-5-(4,4,5,5-tetramethyl-1,3,2-dioxaborolan-2-yl)-pyridin-2-ylamine (BB5) (70 mg, 0.18 mmol), potassium carbonate (77.5 mg, 0.560 mmol), and Pd(PPh$_3$)$_4$ (0.01 g, 0.01 mmol) in previously degassed DME/water (4:1) (1.95 mL) was placed in a microwave tube and evacuated and charged with N$_2$ (2×). The reaction mixture was heated in the microwave reactor to 100° C. for 45 min. The reaction mixture was partitioned between CHCl$_3$ and H$_2$O, and the layers were separated. The aqueous layer was re-extracted with CHCl$_3$ (3×) and the combined organic fractions were washed with brine, dried over Na$_2$SO$_4$, filtered and concentrated in vacuo. The crude material was purified by chromatography on silica gel [eluting with 1.5% MeOH in CHCl₃] resulting in a yellow solid slightly contaminated with triphenylphosphine oxide. Therefore, this material was dissolved in MeOH/THF and passed through a prewashed 5 g SCX column. The column was washed with 2 volumes of MeOH and 2 volumes of THF then was washed with 1M NH₄OH in MeOH upon which the product was released from the resin. The filtrate was concentrated in vacuo, and the resulting material was chromatographed on silica gel [eluting with 0.5% MeOH in CHCl₃] resulting in the title compound as a yellow solid. $^1$H NMR (400 MHz, DMSO-d₆): δ=3.37-3.49 (m, 4H), 3.68-3.81 (m, 4H), 7.05 (s, 2H), 7.51-7.62 (m, 2H), 8.03 (dd, J=8.4, 4.8 Hz, 1H), 8.07 (d, J=2.2 Hz, 1H), 8.23 (d, J=2.2 Hz, 1H), 8.36 (s, 1H), 9.64 (s, 1H). MS (ES+): m/z=442.06/444.03 (76/24) [MH⁺]. HPLC: $t_R$=3.06 min (ZQ2, polar_5 min).

4-(5-Bromothiazol-2-yl)-morpholine

A solution of 2,5-dibromothiazole (0.500 g, 2.06 mmol) in DIPEA (1.50 mL) was charged with morpholine (0.179 mL, 2.06 mmol) and heated to 110° C. for 2 h. The reaction mixture was allowed to cool then partitioned between EtOAc and H₂O, and the layers were separated. The aqueous layer was re-extracted with EtOAc (3×), and the combined organic extracts were washed with brine (2×), dried over Na₂SO₄, filtered and concentrated in vacuo. The crude material was purified by chromatography on silica gel [eluting with 5% EtOAc in CHCl₃] resulting in the title compound as an off-white solid. $^1$H NMR (400 MHz, CDCl₃): δ=3.35-3.47 (m, 4H), 3.74-3.86 (m, 4H), 7.09 (s, 1H). MS (ES+): m/z=249.06/251.03 (51/49) [MH⁺]. HPLC: $t_R$=2.98 min (ZQ2, polar_5 min).

Example 62

3-(5-Chloro-8-fluoroisoquinolin-3-yl)-5-((R)-1-pyrrolidin-3-yl-1H-pyrazol-4-yl)-pyridin-2-ylamine trihydrochloride A solution of (R)-3-[4-(4,4,5,5-tetramethyl-[1,3,2]dioxaborolan-2-yl)-pyrazol-1-yl]-pyrrolidine-1-carboxylic acid tert-butyl ester (0.0804 g, 0.221 mmol), 5-bromo-3-(5-chloro-8-fluoroisoquinolin-3-yl)-pyridin-2-ylamine (0.065 g, 0.18 mmol), potassium carbonate (0.0815 g, 0.590 mmol), and Pd(PPh₃)₄ (0.015 g, 0.013 mmol) in previously degassed DME/Water (4:1) (2.05 mL) was placed in a microwave tube and evacuated and charged with N₂ (2×). The reaction mixture was heated in the microwave reactor to 100° C. for 45 min. The reaction mixture was diluted with EtOAc and washed with H₂O (2×), brine (2×), dried over Na₂SO₄, filtered and concentrated in vacuo to give a brown oil. This material was purified by chromatography on silica gel [eluting with 1% MeOH in CHCl₃] resulting in (R)-3-{4-[6-Amino-5-(5-chloro-8-fluoroisoquinolin-3-yl)-pyridin-3-yl]-pyrazol-1-yl}-pyrrolidine-1-carboxylic acid tert-butyl ester, MS (ES+): m/z=508.9/510.8 (76/24) [MH⁺]. This compound was dissolved in DCM (2.0 mL) and charged with 1.0 M of HCl in Et₂O (1.1 mL) and stirred at 40° C. for 5 h then at rt for an additional 16 h. The solid that formed was filtered off and washed with diethyl ether (3×), yielding the title compound as a yellow solid. $^1$H NMR (400 MHz, DMSO-d₆): δ=2.23-2.36 (m, 1H), 2.39-2.49 (m, 1H), 3.33-3.48 (m, 1H), 3.51-3.62 (m, 2H), 3.62-3.82 (m, 2H), 5.14-5.28 (m, 1H), 7.66 (t, J=9.2 Hz, 1H), 8.11 (dd, J=8.4, 4.8 Hz, 1H), 8.17 (s, 1H), 8.47 (d, J=1.8 Hz, 1H), 8.54 (d, J=11.7 Hz, 2H), 8.67 (br. s., 1H), 9.41 (br. s., 1H), 9.54 (br. s., 1H), 9.68 (s, 1H) MS (ES+): m/z=408.88/410.77 (76/24) [MH⁺]. HPLC: $t_R$=1.84 min (ZQ2, polar_5 min).

(R)-3-[4-(4,4,5,5-tetramethyl-[1,3,2]dioxaborolan-2-yl)-pyrazol-1-yl]-pyrrolidine-1-carboxlic acid tert-butyl ester A solution of 4-(4,4,5,5-tetramethyl[1,3,2]dioxaborolan-2-yl)-1H-pyrazole (0.856 g, 4.41 mmol), (S)-3-methanesulfonyloxypyrrolidine-1-carboxylic acid tert-butyl ester (1.17 g, 4.41 mmol), and Cs₂CO₃ (2.16 g, 6.61 mmol) in anhydrous DMF (11.7 mL) was heated to 100° C. for 16 h. The re mixture was allowed to cool to rt and was partitioned between EtOAc and H₂O and separated. The aqueous layer was re-extracted with EtOAc (3×) and the combined organic fractions were washed with H₂O (3×), brine (2×), dried over Na₂SO₄, filtered and concentrated in vacuo resulting in a crude brown oil. The reaction mixture was purified by chromatography on silica gel [eluting with 12% EtOAc in CHCl₃] resulting in the title compound as a light yellow oil. $^1$H NMR (400 MHz, CDCl₃): δ=1.31 (s, 12H), 1.46 (s, 9H), 2.36 (q, J=7.0 Hz, 2H), 3.46-3.78 (m, 3H), 3.80-3.91 (m, 1H), 4.89 (quint, J=6.1 Hz, 1H), 7.73 (s, 1H), 7.80 (s, 1H).

(S)-3-Methanesulfonyloxypyrrolidine-1-carboxylic acid tert-butyl ester

A solution of (S)-3-hydroxypyrrolidine-1-carboxylic acid tert-butyl ester (0.750 g, 4.00 mmol) in DCM (10 mL) was cooled to 0° C. and charged with triethylamine (0.67 mL, 4.8 mmol), methanesulfonyl chloride (0.34 mL, 4.4 mmol), and 4-dimethylaminopyridine (0.005 g, 0.04 mmol) and stirred at ambient temperature for 6 h. The reaction mixture was partitioned between CHCl₃ and sat. NaHCO₃ and separated. The aqueous layer was re-extracted with CHCl₃ (3×) and the combined organic fractions were washed with sat. NaHCO₃ (2×), brine (2×), dried over Na₂SO₄, filtered and concentrated in vacuo to give the title compound as a pale yellow oil. This material was taken on to the next step without further purification. $^1$H NMR (400 MHz, CDCl₃): δ=1.47 (s, 9H), 2.05-2.36 (m, 2H), 3.05 (s, 3H), 3.43-3.74 (m, 4H), 5.24-5.30 (m, 1H).

Example 63

3-(5-Chloro-8-fluoroisoquinolin-3-yl)-5-((S)-1-pyrrolidin-3-yl-1H-pyrazol-4-yl)-pyridin-2-ylamine trihydrochloride A solution of (S)-3-[4-(4,4,5,5-tetramethyl-[1,3,2]dioxaborolan-2-yl)-pyrazol-1-yl]-pyrrolidine-1-carboxylic acid tert-butyl ester (0.0804 g, 0.221 mmol), 5-bromo-3-(5-chloro-8-fluoroisoquinolin-3-yl)-pyridin-2-ylamine (0.065 g, 0.18 mmol), potassium carbonate (0.0815 g, 0.590 mmol), and Pd(PPh₃)₄ (0.015 g, 0.013 mmol) in previously degassed DME/Water (4:1) (2.05 mL) was placed in a microwave tube and evacuated and charged with N₂ (2×). The reaction mixture was heated in the microwave reactor to 100° C. for 45 min. The reaction mixture was diluted with EtOAc and washed with H₂O (2×), brine (2×), dried over Na₂SO₄, filtered and concentrated in vacuo to give a brown oil. This material was purified by chromatography on silica gel [eluting with 1% MeOH in CHCl₃] resulting in (R)-3-{4-[6-Amino-5-(5-chloro-8-fluoroisoquinolin-3-yl)-pyridin-3-yl]-pyrazol-1-yl}-pyrrolidine-1-carboxylic acid tert-butyl ester, MS (ES+): m/z=508.9/510.8 (76/24) [MH⁺]. This compound was dissolved in DCM (2.0 mL) and charged with 1.0 M of HCl in Et$_2$O (1.1 mL) and stirred at 40° C. for 5 then at rt for an additional 16 h. The solid that formed was filtered off and washed with diethyl ether (3×), yielding the title compound as a yellow solid. $^1$H NMR (400 MHz, DMSO-d$_6$): δ=2.23-2.36 (m, 1H), 2.39-2.49 (m, 1H), 3.33-3.48 (m, 1H), 3.51-3.62 (m, 2H), 3.62-3.82 (m, 2H), 5.14-5.28 (m, 1H), 7.66 (t, J=9.2 Hz, 1H), 8.11 (dd, J=8.4, 4.8 Hz, 1H), 8.17 (s, 1H), 8.47 (d, J=1.8 Hz, 1H), 8.54 (d, J=11.7 Hz, 2H), 8.67 (br. s., 1H), 9.41 (br. s., 1H), 9.54 (br. s., 1H), 9.68 (s, 1H). MS (ES+): m/z=408.88/ 410.77 (76/24) [MH$^+$]. HPLC: t$_R$=1.84 min (ZQ2, polar_5 min).

(S)-3-[4-(4,4,5,5-tetramethyl-[1,3,2]dioxaborolan-2-yl)-pyrazol-1-yl]-pyrrolidine-1-carboxylic acid tert-butyl ester A solution of 4-(4,4,5,5-tetramethyl[1,3,2]dioxaborolan-2-yl)-1H-pyrazole (0.375 g, 1.93 mmol), (R)-3-methanesulfonyloxypyrrolidine-1-carboxylic acid tert-butyl ester (0.513 g, 1.93 mmol), and Cs$_2$CO$_3$ (0.943 g, 2.90 mmol) in anhydrous DMF (5.1 mL) was heated to 100° C. for 6 h. The reaction mixture was partitioned between EtOAc and H$_2$O and separated. The aqueous layer was re-extracted with EtOAc (3×) and the combined organic fractions were washed with H$_2$O (3×), brine (2×), dried over Na$_2$SO$_4$, filtered and concentrated in vacuo resulting in a brown oil. This material crude was purified by chromatography on silica gel [eluting with 12% EtOAc in CHCl$_3$] resulting in the title compound as a viscous oil. $^1$H NMR (400 MHz, CDCl$_3$): δ=1.32 (s, 12H), 1.47 (s, 9H), 2.36 (q, J=7.0 Hz, 2H), 3.46-3.79 (m, 3H), 3.81-3.92 (m, 1H), 4.90 (quint, J=6.1 Hz, 1H), 7.73 (s, 1H), 7.81 (s, 1H).

(R)-3-Methanesulfonyloxypyrrolidine-1-carboxylic acid tert-butyl ester

A solution of (R)-3-hydroxypyrrolidine-1-carboxylic acid tert-butyl ester (0.500 g, 2.67 mmol) in DCM (6.7 mL) was cooled to 0° C. and charged with triethylamine (0.45 mL, 3.20 mmol), methanesulfonyl chloride (0.23 mL, 2.90 mmol), and 4-dimethylaminopyridine (3.0 mg, 0.03 mmol) and stirred at rt for 6 h. The reaction mixture was partitioned between CHCl$_3$ and sat. NaHCO$_3$ and separated. The aqueous layer was re-extracted with CHCl$_3$ (3×) and the combined organic fractions were washed with sat. NaHCO$_3$ (2×), brine (2×), dried over Na$_2$SO$_4$, filtered and concentrated in vacuo resulting in the title compound as a pale yellow oil. This material was taken on to the next step without further purification. $^1$H NMR (400 MHz, CDCl$_3$): δ=1.47 (s, 9H), 2.06-2.39 (m, 2H), 3.05 (s, 3H), 3.38-3.82 (m, 4H), 5.27 (t, J=4.4 Hz, 1H).

Example 64

3-(5-Chloro-8-fluoroisoquinolin-3-yl)-5-[1-(8-methyl-8-azabicyclo [3.2.1]-oct-3-yl)-1H-pyrazol-4-yl]-pyridin-2-ylamine A solution of 3-(4-iodopyrazol-1-yl)-8-methyl-8-azabicyclo[3.2.1]octane (42.7 mg, 0.135 mmol), 3-(5-chloro-8-fluoroisoquinolin-3-yl)-5-(4,4,5,5-tetramethyl-1,3,2-dioxaborolan-2-yl)-pyridin-2-ylamine (0.070 g, 0.18 mmol), potassium carbonate (55.9 mg, 0.404 mmol), and Pd(PPh$_3$)$_4$ (9 mg, 0.008 mmol) in previously degassed DME/Water (4:1) (3.0 mL) was placed in a microwave tube and evacuated and charged with N$_2$ (2×). The reaction mixture was heated in microwave reactor to 100° C. for 45 min. The reaction mixture was diluted with EtOAc and washed with H$_2$O (2×), brine (2×), dried over Na$_2$SO$_4$, filtered and concentrated in vacuo. The crude material was purified by chromatography on silica gel [eluting with 10% MeOH in CHCl$_3$], passing through an SCX cartridge, and finally by the MDP. The fractions containing product were combined, concentrated in vacuo, and partitioned between CHCl$_3$ and sat. NaHCO$_3$. The organic phase was dried over Na$_2$SO$_4$, filtered and concentrated in vacuo resulting in the title compound as a yellow solid. $^1$H NMR (400 MHz, DMSO-d$_6$): δ=1.64-1.72 (m, 2H), 1.77-1.86 (m, 2H), 1.97-2.06 (m, 2H), 2.07-2.17 (m, 2H), 2.26 (s, 3H), 3.20 (br. s., 2H), 4.47 (tt, J=11.7, 5.9 Hz, 1H), 6.89 (br. s., 2H), 7.54 (dd, J=9.9, 8.4 Hz, 1H), 7.87 (s, 1H), 8.03 (dd, J=8.4, 4.8 Hz, 1H), 8.15 (d, J=2.2 Hz, 1H), 8.25 (s, 1H), 8.35 (d, J=2.2 Hz, 1H), 8.37 (s, 1H), 9.64 (s, 1H). MS (ES+): m/z=463.13/465.15 (76/24) [MH$^+$]. HPLC: t$_R$=1.88 min (ZQ2, polar_5 min).

3-(4-Iodopyrazol-1-yl)-8-methyl-8-azabicyclo[3.2.1]octane

Method C was followed, using methanesulfonic acid 8-methyl-8-aza-bicyclo[3.2.1]oct-3-yl ester (1 eq). After a reaction time of 6.5 h, H$_2$O was added and an aqueous workup, using CH$_2$Cl$_2$ as extracting solvent, was conducted. The crude material was purified by silica gel column chromatography [0.5"×10" column, eluting with 1%→5% 7N NH$_3$ (MeOH):CH$_2$Cl$_2$]. The residue was dissolved in minimal CH$_2$Cl$_2$ and heptane was added. The solution was heated until boiling and then chilled to −20° C. Needles had recrystallized after 16 h and all solvent was decanted. The needles were swirled with fresh heptane, which was decanted, and then allowed to dry in vacuo, to afford the title material. $^1$H NMR (400 MHz, CDCl$_3$): δ=1.66-1.73 (m, 2H), 1.95 (ddd, J=13.0, 5.9, 3.5 Hz, 2H), 2.04-2.17 (m, 4H), 2.37 (s, 3H), 3.30 (dd, J=3.8, 3.0 Hz, 2H), 4.49 (tt, J=11.9, 6.0 Hz, 1H), 7.47 (s, 1H), 7.48 (s, 1H). MS (ES'): m/z=318.03 (87) [MH$^+$]. HPLC: t$_R$=1.55 min (ZQ2, polar_5 min).

Methanesulfonic acid 8-methyl-8-azabicyclo[3.2.1]oct-3-yl ester

A solution of tropine (10.0 g, 70.8 mmol), 4-dimethylaminopyridine (80 mg, 0.60 mmol), and triethylamine (11.0 mL, 78.9 mmol) in DCM (125 mL) was cooled to 0° C., charged with methanesulfonyl chloride (5.50 mL, 71.0 mmol), slowly allowed to warm to rt, and stirred for an additional 16 h at rt. The reaction mixture was partitioned between CHCl$_3$ and sat. NaHCO$_3$, and the layers were separated. The aqueous layer was extracted with CHCl$_3$ (3×) and the combined organic fractions were washed with sat. NaHCO$_3$ (2×), brine (2×), dried over Na$_2$SO$_4$, filtered, and concentrated in vacuo resulting in the title compound as a pale brown solid. This material was taken on to the next step without further purification. $^1$H NMR (400 MHz, CDCl$_3$): δ=1.94-2.09 (m, 6H), 2.20 (dt, J=15.4, 4.2 Hz, 2H), 2.28 (s, 3H), 2.99 (s, 3H), 3.10-3.17 (m, 2H), 4.94 (t, J=5.1 Hz, 1H).

Method A: General Procedure for HCl Salt Formation of 2-aminopyridine Free Base Precursor A solution of the free base (0.21 mmol) in dioxane (3 mL) was charged with 4.0 M of HCl in dioxane (1 mL) at rt. Upon addition, a solid precipitated and all solvent was removed in vacuo. MeOH and heptane were added and the solid was filtered off and dried, giving the title material.

Method B: General Procedure for the Suzuki Coupling of the Brominated 2-aminopyridine Core and the Desired (het) arylboronate A suspension of 3-R1-5-bromopyridin-2-ylamine (0.226 mmol, 1 eq), the (het)arylboronate/boronic acid (0.272 mmol, 1.2 eq), Pd(PPh$_3$)$_4$ (18.6 mg, 0.0161 mmol, 7 mol %), and potassium carbonate (101.1 mg, 0.732 mmol, 3.2 eq) in a 4:1 mixture of DME:H2O (2.5 mL) was evacuated and charged with nitrogen several times, after which the sample was heated in the microwave reactor to 100° C. for 45 min. EtOAc was added to dilute the reaction, which was then washed with water (2×) and brine (1×), dried over anhydrous Na$_2$SO$_4$, filtered, and concentrated in vacuo to dryness. The crude material was purified by column chromatography on silica gel [0.5"×10" glass column, eluting with CH$_2$Cl$_2$:EtOAc 1:0→4:1→1:1→2:3→3:7→1:9→0:1]. Fractions containing product were combined and concentrated in vacuo. DCM and heptane were added to the residue and the solvent was concentrated in vacuo until all CH$_2$Cl$_2$ had been removed; a solid precipitated at this point. The solid was triturated in hot heptane and filtered off, giving the title material.

Method C: General Procedure for N-alkylation of Substituted Pyrazoles, Using Halogenated (Bromo- or Iodo-) and Mesylated Species In a sealed tube, to a suspension of 4-(4,4,5,5-tetramethyl [1,3,2]dioxaborolan-2-yl)-1H-pyrazole (567 mg, 2.92 mmol, 1.0 eq) and Cs$_2$CO$_3$ (1.544 g, 4.739 mmol, 1.6 eq) in DMF (6 mL), the halide or mesylate (4.43 mmol, 1.5 eq) was added and the reaction was allowed to stir at 100° C. for 19 h. Water was added to dilute the reaction and dissolve all salts that had formed, after which EtOAc was added and the two layers were separated. The organic layer was washed with water (2×) and brine (1×). The combined aqueous layers were back extracted with EtOAc (1×), and the combined EtOAc extracts were dried over anhydrous Na$_2$SO$_4$, filtered, and concentrated in vacuo to give the target material.

Method D: General Procedure for N-alkylation/acylation, Using Carbamoyl Chloride, Isocyanate, and Triflate Species To a solution of 4-[4-(4,4,5,5-tetramethyl-[1,3,2]dioxaborolan-2-yl)-pyrazol-1-yl]-piperidine hydrochloride (253.6 mg, 0.809 mmol, 1 eq) in DMF (6 mL), DIPEA (0.7 mL, 4 mmol, 5 eq) was added at rt. The solution was cooled to 0° C. and the carbamoyl chloride/isocyanate/triflate (1.002 mmol, 1.2 eq) in DMF (1 mL) was added. The reaction was stirred from 0° C.→rt for 30 min. MeOH was added and all organic solvent was concentrated in vacuo to dryness. The residue was dissolved in CH$_2$Cl$_2$, washed with water (1×) and brine (1×), dried over anhydrous Na$_2$SO$_4$, filtered, and concentrated in vacuo, giving the title compound.

Method E: General Procedure for the Suzuki Coupling of the Borylated 2-aminopyridine Core and the Desired Iodo-/Bromo-het(aryl) Building Block A solution of the 3-R1-5-(4,4,5,5-tetramethyl-1,3,2-dioxaborolan-2-yl)-pyridin-2-ylamine (0.155 mmol, 1.0 eq), the iodo-/bromo-het(aryl) building block (0.183 mmol, 1.2 eq), Pd(PPh$_3$)$_4$ (12.8 mg, 0.0111 mmol, 7 mol %), and K$_2$CO$_3$ (68.1 mg, 0.493 mmol, 3.2 eq) in a 4:1 mixture of dioxane to H$_2$O (5 mL) was evacuated and charged with nitrogen several times, after which the sample was heated in the microwave reactor to 100° C. for 45 min. EtOAc and water were added to the reaction mixture and the layers were separated. The organic phase was washed with water (2×) and brine (1×), dried over anhydrous Na$_2$SO$_4$, filtered, and concentrated in vacuo. The crude material was purified by pTLC or column chromatography on silica gel.

Example 65

3-(5-Chloro-8-fluoroisoquinolin-3-yl)-5-(1-methyl-1H-pyrazol-4-yl)-pyridin-2-ylamine bis-hydrochloride Method A was followed. $^1$H NMR (400 MHz, DMSO-d$_6$): δ=3.90 (s, 3H), 7.67 (dd, J=9.9, 8.3 Hz, 1H), 8.04 (s, 1H), 8.12 (dd, J=8.3, 4.8 Hz, 1H), 8.34 (s, 1H), 8.42 (d, J=2.3 Hz, 1H), 8.57 (s, 1H), 8.73 (d, J=2.0 Hz, 1H), 9.67 (d, J=0.8 Hz, 1H). MS (ES+): m/z=354.06/356.04 (100/87) [MH$^+$]. HPLC: t$_R$=2.48 min (ZQ3, polar_5 min).

3-(5-Chloro-8-fluoroisoquinolin-3-yl)-5-(1-methyl-1H-pyrazol-4-yl)-pyridin-2-ylamine Method B was followed, except the crude material was purified by pTLC [Silicycle, 1000 μm, 20×20 plate, developed once in 3% 7N NH$_3$(MeOH):CH$_2$Cl$_2$ solvent system]; the desired band was scraped from the plate, the silica gel was rinsed well with copious amounts of the same solvent system, and the filtrate was concentrated in vacuo. $^1$H NMR (400 MHz, CDCl$_3$): δ=3.99 (s, 3H), 6.43 (br s, 2H), 7.21 (dd, J=9.4, 8.3 Hz, 1H), 7.64 (s, 1H), 7.75 (dd, J=8.3, 4.6 Hz, 1H), 7.78 (s, 1H), 8.01 (d, J=2.3 Hz, 1H), 8.32 (d, J=2.0 Hz, 1H), 8.34 (s, 1H), 9.59 (d, J=0.8 Hz, 1H). MS (AP$^+$): m/z=354.06/356.04 (100/37) [MH$^+$]. HPLC: t$_R$=2.45 min (ZQ3, polar_5 min).

Example 66

3-(5-Chloro-8-fluoroisoquinolin-3-yl)-5-(1-isopropyl-1H-pyrazol-4-yl)-pyridin-2-ylamine bis-hydrochloride Method A was followed, except heptane was the only solvent used for recrystallization of the title compound. $^1$H NMR (400 MHz, DMSO-d$_6$): δ=1.46 (d, J=6.6 Hz, 6H), 4.53 (septet, J=6.7 Hz, 1H), 7.67 (dd, J=9.7, 8.5 Hz, 1H), 8.05 (s, 1H), 8.12 (dd, J=8.5, 4.7 Hz, 1H), 8.31 (br s, 1H), 8.43 (d, J=2.0 Hz, 1H), 8.44 (s, 1H), 8.56 (s, 1H), 8.75 (d, J=2.0 Hz, 1H), 9.68 (d, J=0.8 Hz, 1H). MS (AP$^+$): m/z=382.09/384.07 (100/37) [MH$^+$]. HPLC: t$_R$=2.78 min (ZQ3, polar_5 min).

3-(5-Chloro-8-fluoroisoquinolin-3-yl)-5-(1-isopropyl-1H-pyrazol-4-yl)-pyridin-2-ylamine Method B was followed, except 1% MeOH was added to the CH$_2$Cl$_2$:EtOAc mixtures for better separation. $^1$H NMR (400 MHz, CDCl$_3$): δ=1.58 (s, 6H), 4.58 (septet, J=6.7 Hz, 1H), 6.40 (br s, 2H), 7.21 (dd, J=9.4, 8.3 Hz, 1H), 7.69 (d, J=0.8 Hz, 1H), 7.75 (dd, J=8.3, 4.8 Hz, 1H), 7.79 (d, J=0.5 Hz, 1H), 8.01 (d, J=2.0 Hz, 1H), 8.33 (d, J=2.3 Hz, 1H), 8.34-8.36 (m, 1H), 9.59 (d, J=0.8 Hz, 1H). MS (AP$^+$): m/z=382.09/384.09 (100/35) [MH$^+$]. HPLC: t$_R$=2.75 min (ZQ3, polar_5 min).

1-Isopropyl-4-(4,4,5,5-tetramethyl-[1,3,2]dioxaborolan-2-yl)-1H-pyrazole

Method C was followed, using isopropyl iodide (753.3 mg, 4.431 mmol, 1.5 eq). The title compound was obtained as a yellow oil that was used without further purification. $^1$H NMR (400 MHz, CDCl$_3$): δ=1.33 (s, 12H), 1.51 (d, J=6.8 Hz, 6H), 4.53 (septet, J=6.7 Hz, 1H), 7.75 (s, 1H), 7.80 (s, 1H). MS (AP$^+$): m/z=235.98 (76) [MH$^+$]. HPLC: t$_R$=3.22 min (ZQ3, polar_5 min).

Example 67

4-4-[6-Amino-5-(5-chloro-8-fluoroisoquinolin-3-yl)-pyridin-3-yl]-pyrazol-1-ylpiperidine-1-carboxylic acid dimethylamide bis-hydrochloride Method A was followed, except a mixture of CH$_2$Cl$_2$ and heptane was used to recrystallize the title compound. $^1$H NMR (400 MHz, DMSO-d$_6$): δ=1.89 (qd, J=12.1, 3.9 Hz, 2H), 2.05 (dd, J=12.3, 2.4 Hz, 2H), 2.76 (s, 6H), 2.90 (t, J=11.8 Hz, 2H), 3.66 (d, J=13.4 Hz, 2H), 4.33-4.45 (m, 1H), 7.66 (dd, J=9.9, 8.6 Hz, 1H), 8.07 (s, 1H), 8.12 (dd, J=8.5, 4.7 Hz, 1H), 8.30 (br s, 2H), 8.42 (d, J=2.0 Hz, 1H), 8.49 (s, 1H), 8.55 (s, 1H), 8.74 (d, J=2.0 Hz, 1H), 9.68 (d, J=0.8 Hz, 1H). MS (AP$^+$): m/z=494.12/496.12 (100/39) [MH$^+$]. HPLC: t$_R$=2.59 min (ZQ3, polar__5 min).

4-4-[6-Amino-5-(5-chloro-8-fluoroisoquinolin-3-yl)-pyridin-3-yl]-pyrazol-1-ylpiperidine-1-carboxylic acid dimethylamide Method B was followed, except 7N NH$_3$(MeOH):EtOAc mixtures were necessary for silica gel chromatography. $^1$H NMR (400 MHz, CDCl$_3$): δ=2.01-2.16 (m, 2H), 2.18-2.27 (m, 2H), 2.88 (s, 6H), 2.91-3.01 (m, 2H), 3.84 (d, J=13.4 Hz, 2H), 4.29-4.40 (m, 1H), 6.42 (br s, 2H), 7.21 (dd, J=9.4, 8.3 Hz, 1H), 7.70 (d, J=0.5 Hz, 1H), 7.75 (dd, J=8.3, 4.8 Hz, 1H), 7.80 (d, J=0.5 Hz, 1H), 8.00 (d, J=2.3 Hz, 1H), 8.32 (d, J=2.3 Hz, 1H), 8.34-8.37 (m, 1H), 9.59 (d, J=0.8 Hz, 1H). MS (ES$^+$): m/z=493.97/496.11 (78/100) [MH$^+$]. HPLC: t$_R$=2.53 min (ZQ3, polar__5 min).

4-[4-(4,4,5,5-Tetramethyl-[1,3,2]dioxaborolan-2-yl)-pyrazol-1-yl]-piperidine-1-carboxylic acid dimethylamide To a solution of 4-[4-(4,4,5,5-tetramethyl-[1,3,2]dioxaborolan-2-yl)-pyrazol-1-yl]-piperidine hydrochloride (253.6 mg, 0.809 mmol, 1 eq) in DMF (6 mL), DIPEA (0.7 mL, 4 mmol, 5 eq) was added at rt. The solution was cooled to 0° C. and N,N-dimethylcarbamoyl chloride (107.7 mg, 1.002 mmol, 1.2 eq) in DMF (1 mL) was added. The reaction was stirred from 0° C.→rt for 30 min. MeOH was added and all organic solvent was concentrated in vacuo to dryness. The residue was dissolved in CH$_2$Cl$_2$, washed with water (1×) and brine (1×), dried over anhydrous Na$_2$SO$_4$, filtered, and concentrated in vacuo, giving 292.5 mg (98%, 0.798 mmol) of the title compound, as a waxy white solid that had solidified upon drying. $^1$H NMR (400 MHz, CDCl$_3$): δ=1.32 (s, 12H), 1.94-2.07 (m, 2H), 2.16 (dd, J=12.3, 2.4 Hz, 2H), 2.85 (s, 6H), 2.87-2.95 (m, 2H), 3.78 (d, J=13.4 Hz, 2H), 4.24-4.34 (m, 1H), 7.76 (s, 1H), 7.80 (s, 1H). MS (AP$^+$): m/z=349.13 (100) [MH$^+$]. HPLC: t$_R$=2.91 min (ZQ3, polar__5 min).

4-[4-(4,4,5,5-Tetramethyl-[1,3,2]dioxaborolan-2-yl)-pyrazol-1-yl]-piperidine hydrochloride To a solution of 4-[4-(4,4,5,5-tetramethyl-1,3,2-dioxaborolan-2-yl)-pyrazol-1-yl]-piperidine-1-carboxylic acid tert-butyl ester (1.011 g, 2.68 mmol, 1 eq.) in dioxane (5 mL), 4.0 M of HCl in dioxane (10 mL, 20 eq) was added and the reaction was stirred at 35° C. for 2.5 h. The reaction mixture was concentrated in vacuo, yielding the title material, as a white solid. $^1$H NMR (400 MHz, CDCl$_3$): δ=1.32 (s, 12H), 2.46 (br s, 4H), 3.18 (br s, 2H), 3.57-3.70 (m, 2H), 4.48 (br s, 1H), 7.78 (s, 1H), 7.79 (s, 1H), 9.54-10.04 (m, 2H). MS (ES$^+$): m/z=278.14 (100) [MH$^+$]. HPLC: t$_R$=1.89 min (ZQ2, polar__5 min).

Example 68

4-4-[6-Amino-5-(5-chloro-8-fluoroisoquinolin-3-yl)-pyridin-3-yl]-pyrazol-1-ylpiperidine-1-carboxamide bis-hydrochloride Method A was followed, except a mixture of CH$_2$Cl$_2$ and heptane was used to recrystallize the title compound. $^1$H NMR (400 MHz, DMSO-d$_6$): δ=1.77 (qd, J=12.1, 4.0 Hz, 2H), 2.01 (dd, J=11.8, 2.4 Hz, 2H), 2.87 (t, J=11.9 Hz, 2H), 4.06 (d, J=13.4 Hz, 2H), 4.33-4.44 (m, 1H), 6.04 (br s, 1H), 7.66 (dd, J=9.9, 8.6 Hz, 1H), 8.06 (d, J=0.5 Hz, 1H), 8.12 (dd, J=8.3, 4.8 Hz, 1H), 8.27 (br s, 1H), 8.41 (d, J=2.0 Hz, 1H), 8.48 (s, 1H), 8.55 (s, 1H), 8.73 (d, J=1.5 Hz, 1H), 9.68 (d, J=0.8 Hz, 1H). MS (ES$^+$): m/z=466.12/468.04 (100/63) [MH$^+$]. HPLC: t$_R$=2.33 min (ZQ3, polar__5 min).

4-4-[6-Amino-5-(5-chloro-8-fluoroisoquinolin-3-yl)-pyridin-3-yl]-pyrazol-1-ylpiperidine-1-carboxamide Method B was followed, except 7N NH$_3$(MeOH):EtOAc mixtures were necessary for silica gel chromatography. $^1$H NMR (400 MHz, CDCl$_3$): δ=2.07 (qd, J=12.3, 4.0 Hz, 2H), 2.26 (dd, J=12.4, 2.5 Hz, 2H), 3.01-3.11 (m, 2H), 4.13 (d, J=13.4 Hz, 2H), 4.38 (tt, J=11.4, 4.1 Hz, 1H), 4.50 (br s, 2H), 6.44 (br s, 2H), 7.21 (dd, J=9.4, 8.3 Hz, 1H), 7.69 (d, J=0.5 Hz, 1H), 7.75 (dd, J=8.3, 4.8 Hz, 1H), 7.80 (d, J=0.8 Hz, 1H), 8.00 (d, J=2.3 Hz, 1H), 8.32 (d, J=2.3 Hz, 1H), 8.33-8.35 (m, 1H), 9.59 (d, J=0.8 Hz, 1H). MS (ES$^+$): m/z=466.11/468.09 (100/72) [MH$^+$]. HPLC: t$_R$=2.33 min (ZQ3, polar__5 min).

4-[4-(4,4,5,5-Tetramethyl-1,3,2-dioxaborolan-2-yl)-pyrazol-1-yl]-piperidine-1-carboxamide Method D was followed, using trimethylsilyl isocyanate (2.3 eq) and DIPEA (3 eq). After a total reaction time of 3.5 h, EtOAc was added and a standard aqueous workup was performed. $^1$H NMR (400 MHz, CDCl$_3$): δ=1.31 (s, 12H), 1.88-2.02 (m, 2H), 2.17 (dd, J=12.3, 2.4 Hz, 2H), 2.92-3.05 (m, 2H), 4.06 (d, J=13.6 Hz, 2H), 4.31 (tt, J=11.3, 3.9 Hz, 1H), 4.77 (br s, 2H), 7.73 (s, 1H), 7.78 (s, 1H). MS (ES$^+$): m/z=321.18 (100) [MH$^+$]. HPLC: t$_R$=2.57 min (ZQ3, polar__5 min).

Example 69

3-(5-Chloro-8-fluoroisoquinolin-3-yl)-5-1-[1-(2,2,2-trifluoroethyl)-piperidin-4-yl]-1H-pyrazol-4-yl-pyridin-2-ylamine bis-hydrochloride Method A was followed, except a mixture of CH$_2$Cl$_2$ and heptane was used to recrystallize the title compound. $^1$H NMR (400 MHz, DMSO-d$_6$): δ=2.15 (br s, 4H), 2.86 (br s, 2H), 3.23 (d, J=8.8 Hz, 2H), 3.57-3.71 (m, 2H), 4.26-4.39 (m, 1H), 7.67 (dd, J=9.9, 8.6 Hz, 1H), 8.07-8.14 (m, 2H), 8.46 (d, J=2.0 Hz, 1H), 8.51 (s, 1H), 8.56 (s, 1H), 8.76 (d, J=2.0 Hz, 1H), 9.67 (d, J=0.8 Hz, 1H). MS (ES$^+$): m/z=505.12/507.09 (100/79) [MH$^+$]. HPLC: t$_R$=3.08 min (ZQ3, polar__5 min).

3-(5-Chloro-8-fluoroisoquinolin-3-yl)-5-1-[1-(2,2,2-trifluoroethyl)-piperidin-4-yl]-1H-pyrazol-4-yl-pyridin-2-ylamine Method B was followed, except 1% 7N NH$_3$(MeOH) was added to the CH$_2$Cl$_2$:EtOAc mixtures for better separation. $^1$H NMR (400 MHz, CDCl$_3$): δ=2.09-2.27 (m, 4H), 2.62 (td, J=11.5, 3.0 Hz, 2H), 3.07 (q, J=9.6 Hz, 2H), 3.11-3.18 (m, 2H), 4.15-4.26 (m, 1H), 6.43 (br s, 2H), 7.21 (dd, J=9.4, 8.3 Hz, 1H), 7.70 (s, 1H), 7.75 (dd, J=8.2, 4.7 Hz, 1H), 7.79 (d, J=0.8 Hz, 1H), 8.00 (d, J=2.3 Hz, 1H), 8.32 (d, J=2.3 Hz, 1H), 8.34-8.36 (m, 1H), 9.59 (d, J=0.8 Hz, 1H). MS (AP$^+$): m/z=505.09/507.10 (83/29) [MH$^+$]. HPLC: t$_R$=3.05 min (ZQ3, polar__5 min).

4-[4-(4,4,5,5-Tetramethyl-1,3,2-dioxaborolan-2-yl)-pyrazol-1-yl]-1-(2,2,2-trifluoroethyl)-piperidine Method D was followed, using 2,2,2-trifluoroethyl triflate (1.6 eq). After reacting for 3 h, EtOAc was added and a standard aqueous workup was performed. The crude was purified using a short silica gel plug [eluting with 2:1 CH$_2$Cl$_2$:EtOAc]. $^1$H NMR (400 MHz, CDCl$_3$): δ=1.33 (s, 12H), 1.58 (s, 2H), 2.00-2.11 (m, 2H), 2.11-2.19 (m, 2H), 2.59 (td, J=11.7, 2.2 Hz, 2H), 3.06-3.12 (m, 2H), 4.15 (tt, J=11.3, 4.3 Hz, 1H), 7.75 (s, 1H), 7.80 (s, 1H). MS (AP$^+$): m/z=360.14 (100) [MH$^+$]. HPLC: t$_R$=3.54 min (ZQ3, polar_5 min).

Example 70

3-(5-Chloro-8-fluoroisoquinolin-3-yl)-5-1-[1-(2-methoxyethyl)-piperidin-4-yl]-1H-pyrazol-4-yl-pyridin-2-ylamine Method B was followed, except the crude material was purified by pTLC [Silicycle, 1000 μm, 20×20 cm plate, developed once in 4% 7N NH$_3$(MeOH):EtOAc solvent system]; the desired band was scraped from the plate, the silica gel was rinsed well with copious amounts of the same solvent system, and the filtrate was concentrated in vacuo. The title compound was recrystallized from hot heptane. $^1$H NMR (400 MHz, CDCl$_3$): δ=2.08-2.28 (m, 6H), 2.65 (t, J=5.6 Hz, 2H), 3.14 (d, J=11.4 Hz, 2H), 3.39 (s, 3H), 3.55 (t, J=5.6 Hz, 2H), 4.15-4.28 (m, 1H), 6.43 (br s, 2H), 7.20 (dd, J=9.4, 8.3 Hz, 1H), 7.70 (s, 1H), 7.75 (dd, J=8.3, 4.8 Hz, 1H), 7.78 (d, J=0.8 Hz, 1H), 8.00 (d, J=2.3 Hz, 1H), 8.32 (d, J=2.3 Hz, 1H), 8.35 (s, 1H), 9.59 (d, J=0.8 Hz, 1H). MS (ES+): m/z=481.14/483.12 (60/35) [MH$^+$]. HPLC: t$_R$=2.02 min (ZQ3, polar_5 min).

1-(2-Methoxyethyl)-4-[4-(4,4,5,5-tetramethyl-1,3,2-dioxaborolan-2-yl)-pyrazol-1-yl]-piperidine Method C was followed, using 1-bromo-2-methoxyethane (2 eq) and Cs$_2$CO$_3$ (3 eq). The crude material was also quickly purified over a short plug of silica gel. $^1$H NMR (400 MHz, CDCl$_3$): δ=1.32 (s, 12H), 2.06 (td, J=11.9, 3.7 Hz, 2H), 2.11-2.24 (m, 4H), 2.59-2.64 (m, 2H), 3.07 (d, J=12.1 Hz, 2H), 3.37 (s, 3H), 3.53 (t, J=5.6 Hz, 2H), 4.15 (tt, J=11.4, 4.1 Hz, 1H), 7.74 (s, 1H), 7.79 (s, 1H).

Example 71

(2S,4S)-4-{4-[6-Amino-5-(5-chloro-8-fluoroisoquinolin-3-yl)-pyridin-3-yl]-pyrazol-1-yl}-pyrrolidine-2-carboxylic acid dimethylamide To a solution of (2S,4S)-4-{4-[6-amino-5-(5-chloro-8-fluoroisoquinolin-3-yl)-pyridin-3-yl]-pyrazol-1-yl}-pyrrolidine-2-carboxylic acid (5.00 mg, 0.00889 mmol) in DCM (2 mL, 0.02 mol) was added dimethylamine hydrochloride (20 mg, 0.2 mmol) and DIPEA (0.2 mL, 1.0 mmol), and stirred for 1 min. TBTU (5.71 mg, 0.0178 mmol) was then added, and the solution was stirred at rt for 10 min. The material was transferred to a separatory funnel. The organic layer was washed with water, and concentrated in vacuo. The material was loaded onto a prep TLC plate, eluting with 6% (7N NH$_3$ in MeOH/DCM. The band containing the product was collected and the product was eluted with 1:1 MeOH/DCM. The solution was concentrated in vacuo to afford the title compound as a yellow solid. $^1$H NMR (400 MHz, CD$_3$OD): δ=2.15-2.22 (m, 1H), 2.82-2.90 (m, 1H), 2.99 (s, 3H), 3.10-3.13 (m, 3H), 3.21-3.26 (m, 1H), 3.49 (dd, J=12.3, 3.2 Hz, 1H), 4.15 (t, J=8.2 Hz, 1H), 4.99-5.05 (m, 1H), 7.38 (dd, J=9.6, 8.3 Hz, 1H), 7.84-7.91 (m, 2H), 8.13-8.17 (m, 2H), 8.27 (d, J=2.3 Hz, 1H), 8.43 (s, 1H), 9.60 (s, 1H). MS (ES$^+$): m/z=480.13/482.11 (100/36) [MH$^+$]. HPLC: t$_R$=1.89 min (ZQ2, polar_5 min).

Example 72

((2S,4S)-4-{4-[6-Amino-5-(5-chloro-8-fluoroisoquinolin-3-yl)-pyridin-3-yl]-pyrazol-1-yl}-pyrrolidin-2-yl)-morpholin-4-ylmethanone The title compound was prepared according to the procedures described for (2S,4S)-4-{4-[6-amino-5-(5-chloro-8-fluoroisoquinolin-3-yl)-pyridin-3-yl]-pyrazol-1-yl}-pyrrolidine-2-carboxylic acid dimethylamide. $^1$H NMR (400 MHz, CD$_3$OD): δ=2.23 (s, 1H), 2.79-2.86 (m, 1H), 3.23 (dd, J=12.3, 6.4 Hz, 1H), 3.46-3.51 (m, 1H), 3.57-3.70 (m, 8H), 4.13 (t, J=8.3 Hz, 1H), 4.99-5.04 (m, 1H), 7.38 (dd, J=9.6, 8.3 Hz, 1H), 7.85-7.92 (m, 2H), 8.12-8.18 (m, 2H), 8.27 (d, J=2.3 Hz, 1H), 8.43 (s, 1H), 9.60 (s, 1H). MS (ES+): m/z=522.14/524.13 (100/40) [MH$^+$]. HPLC: t$_R$=1.95 min (ZQ2, polar_5 min).

Example 73

((2S,4S)-4-{4-[6-Amino-5-(5-chloro-8-fluoroisoquinolin-3-yl)-pyridin-3-yl]-pyrazol-1-yl}-pyrrolidin-2-yl)-pyrrolidin-1-ylmethanone The title compound was prepared according to the procedures described for (2S,4S)-4-{4-[6-amino-5-(5-chloro-8-fluoroisoquinolin-3-yl)-pyridin-3-yl]-pyrazol-1-yl}-pyrrolidine-2-carboxylic acid dimethylamide. $^1$H NMR (400 MHz, CD$_3$OD): δ=1.91-2.02 (m, 4H), 2.78-2.86 (m, 1H), 3.21-3.26 (m, 1H), 3.45-3.52 (m, 4H), 3.61-3.67 (m, 1H), 4.01 (t, J=8.2 Hz, 1H), 4.21 (dd, J=5.6, 1.8 Hz, 1H), 4.99-5.03 (m, 1H), 7.38 (dd, J=9.6, 8.3 Hz, 1H), 7.87 (s, 1H), 7.90 (dd, J=8.3, 4.8 Hz, 1H), 8.17 (s, 2H), 8.27 (d, J=2.3 Hz, 1H), 8.44 (s, 1H), 9.60 (d, J=1.0 Hz, 1H). MS (ES'): m/z=506.16/507.15 (100/41) [MH$^+$]. HPLC: t$_R$=2.23 min (ZQ2, polar_5 min).

Example 74

(2S,4S)-4-{4-[6-Amino-5-(5-chloro-8-fluoroisoquinolin-3-yl)-pyridin-3-yl]-pyrazol-1-yl}-pyrrolidine-2-carboxylic acid (2-methoxyethyl)-amide The title compound was prepared according to the procedures described for (2S,4S)-4-{4-[6-amino-5-(5-chloro-8-fluoroisoquinolin-3-yl)-pyridin-3-yl]-pyrazol-1-yl}-pyrrolidine-2-carboxylic a dimethylamide. $^1$H NMR (400 MHz, CD$_3$OD): δ=2.33-2.40 (m, 1H), 2.76-2.82 (m, 1H), 1H), 3.27 (s, 3H), 3.37 (d, J=4.8 Hz, 2H), 3.41 (d, J=4.5 Hz, 2H), 3.81-3.90 (m, 1H), 4.22 (dd, J=5.6, 1.8 Hz, 2H), 4.96 (br. s., 1H), 7.38 (dd, J=9.9, 8.3 Hz, 1H), 7.87 (s, 1H), 7.90 (dd, J=8.3, 4.8 Hz, 1H), 8.14 (s, 1H), 8.18 (d, J=2.3 Hz, 1H), 8.29 (d, J=2.3 Hz, 1H), 8.45 (d, J=1.8 Hz, 1H), 9.61 (s, 1H). MS (ES+): m/z=510.14/512.16 (100/43) [MH$^+$]. HPLC: t$_R$=2.05 min (ZQ2, polar_5 min).

Example 75

(2S,4S)-4-{4-[6-Amino-5-(5-chloro-8-fluoroisoquinolin-3-yl)-pyridin-3-yl]-pyrazol-1-yl}-pyrrolidine-2-carboxylic acid A mixture of 3-(5-chloro-8-fluoroisoquinolin-3-yl)-5-(4,4,5,5-tetramethyl-[1,3,2]dioxaborolan-2-yl)-pyridin-2- ylamine (100 mg, 0.250 mmol), (2S,4S)-4-(4-iodopyrazol-1-yl)-pyrrolidine-1,2-dicarboxylic acid 1-benzyl ester 2-methyl ester (137.0 mg, 0.300 mmol), Pd(PPh$_3$)$_4$ (29 mg, 0.025 mmol), potassium fluoride (43.6 mg, 0.751 mmol) and 4:1 dioxane:water (3 mL) was heated in the microwave reactor to 85° C. for 30 min. The material was concentrated in vacuo, then dry-loaded onto silica gel for column chromatography. The product was eluted with 2→5% MeOH/DCM, and the fractions containing the product were concentrated in vacuo. The material was dissolved in conc. HCl, transferred to a sealed tube and heated at 60° C. for 2 h. The solvent was removed in vacuo to afford the title compound as a brown solid. MS (ES$^+$): m/z=453.09/455.10 (100/37) [MH$^+$]. HPLC: t$_R$=1.94 min (ZQ2, polar_5 min).

Example 76

3-(5-Chloro-8-fluoroisoquinolin-3-yl)-5-thiophen-3-ylpyridin-2-amine

A mixture of 5-bromo-3-(5-chloro-8-fluoroisoquinolin-3-yl)-pyridin-2-ylamine (BB4) (25 mg, 0.070 mmol), 3-thienylboronic acid (20 mg, 0.10 mmol) and potassium carbonate (29 mg, 0.21 mmol) in 1,4-dioxane (1.0 mL) and H$_2$O (0.4 mL) was degassed and refilled with argon (3×) prior to the addition of Pd(dppf)Cl$_2$ (5 mg, 0.01 mmol). The reaction mixture was degassed and refilled with argon (2×) and left to stir at 100° C. in the microwave reactor for 30 min. Then, the mixture was passed through PL-Thiol MP SPE resin and concentrated in vacuo. The residual oil was partitioned between DCM and H$_2$O. The combined organic layers were washed with brine, dried over anhydrous Na$_2$SO$_4$, filtered, and concentrated in vacuo. Purification via MDP afforded the title compound as a yellow solid. MS (ES+): m/z=356.03/358.05 (100/50) [MH$^+$]. HPLC: t$_R$=3.22 min (ZQ2, polar_5 min).

The following examples 77-89 were prepared following the same procedure.

Example 77

3-(5-Chloro-8-fluoroisoquinolin-3-yl)-5-phenylpyridin-2-amine

MS (ES+): m/z=350.03/352.05 (100/45) [MH$^+$]. HPLC: t$_R$=3.37 min (ZQ2, polar_5 min).

Example 78

5-(5-Chloro-8-fluoroisoquinolin-3-yl)-3,3'-bipyridin-6-amine

MS (ES+): m/z=351.04/353.07 (100/40) [MH$^+$]. HPLC: t$_R$=2.66 min (ZQ2, polar_5 min).

Example 79

5-(5-Chloro-8-fluoroisoquinolin-3-yl)-3,4'-bipyridin-6-amine

MS (ES+): m/z=351.04/353.07 (100/30) [MH$^+$]. HPLC: t$_R$=2.35 min (ZQ2, polar_5 min).

Example 80

5-(5-Chloro-8-fluoroisoquinolin-3-yl)-1',2',3',6'-tetrahydro-3,4'-bipyridin-6-yl-tert-butyl carboxylate MS (ES+): m/z=455.15/457.06 (100/55) [MH$^+$]. HPLC: t$_R$=3.87 min (ZQ3, polar_5 min).

Example 81

5-(5-Chloro-8-fluoroisoquinolin-3-yl)-3,3'-bipyridine-6,6'-diamine

MS (ES+): m/z=366.06/368.04 (100/35) [MH$^+$]. HPLC: t$_R$=3.37 min (ZQ2, polar_5 min).

Example 82

N-4-[6-Amino-5-(5-chloro-8-fluoroisoquinolin-3-yl)pyridin-3-yl]phenylacetamide

MS (ES+): m/z=407.06/409.04 (100/50) [MH$^+$]. HPLC: t$_R$=3.01 min (ZQ3, polar_5 min).

Example 83

Ethyl-[4-(6-amino-5-(5-chloro-8-fluoroisoquinolin-3-yl)pyridin-3-yl)phenoxy]acetate MS (ES+): m/z=452.08/454.06 (100/90) [MH$^+$]. HPLC: t$_R$=3.48 min (ZQ3, polar_5 min).

Example 84

6'-Amino-5'-(5-chloro-8-fluoroisoquinolin-3-yl)-3,3'-bipyridin-6-ol

MS (ES+): m/z=367.09/369.06 (100/50) [MH$^+$]. HPLC: t$_R$=2.49 min (ZQ3, polar_5 min).

Example 85

3-(5-Chloro-8-fluoroisoquinolin-3-yl)-5-furan-3-ylpyridin-2-amine

MS (ES+): m/z=340.08/341.99 (100/80) [MH$^+$]. HPLC: t$_R$=3.26 min (ZQ3, polar_5 min).

Example 86

3-(5-Chloro-8-fluoroisoquinolin-3-yl)-5-furan-2-ylpyridin-2-amine

MS (ES+): m/z=340.08/341.99 (100/70) [MH]. HPLC: t$_R$=3.72 min (ZQ3, polar_5 min).

Example 87

3-(5-Chloro-8-fluoroisoquinolin-3-yl)-5-(1H-pyrazol-4-yl)pyridin-2-amine

MS (ES+): m/z=340.08/341.99 (100/80) [MH$^+$]. HPLC: t$_R$=2.49 min (ZQ3, polar_5 min).

Example 88

3-(5-Chloro-8-fluoroisoquinolin-3-yl)-5-N6'-(2-morpholin-4-ylethyl)-3,3'-bipyridine-6,6'-diamine MS (ES+): m/z=479.16/481.07 (100/75) [MH$^+$]. HPLC: t$_R$=2.18 min (ZQ3, polar_5 min).

Example 89

3-(5-Chloro-8-fluoroisoquinolin-3-yl)-5-(1H-indol-2-yl)pyridin-2-amine

1-Boc-indole-2-boronic acid was used. The resulting Boc-protected intermediate was treated with (1:1) DCM:TFA mixture at rt for 15 min. Filtration and drying in vacuo afforded the title compound. MS (ES+): m/z=389.12/391.10 (100/60) [MH$^+$]. HPLC: t$_R$=3.72 min (ZQ3, polar_5 min).

Example 90

4-[6-Amino-5-(5-chloro-8-methoxyisoquinolin-3-yl)-pyridin-3-yl]benzoic acid

To a solution of methyl 4-[6-amino-5-(5-chloro-8-fluoroisoquinolin-3-yl)-pyridin-3-yl]-benzoate (0.13 g, 0.32 mmol) in methanol (5 mL) and water (0.5 mL) was added NaOH (0.24 g, 6 mmol), and the mixture was heated at 50° C. for 16 h. The solvents were evaporated at reduced pressure, and the residue was neutralized with acetic acid. The solid formed was filtered off and dried in vacuo to give the title compound. $^1$H NMR (400 MHz, DMSO-d$_6$): δ=12.82 (very brs, 1H), 9.63 (s, 1H), 8.51 (d, J=2.4 Hz, 1H), 8.35 (s, 1H), 8.31 (d, J=2.4 Hz, 1H), 8.03-7.98 & 7.90-7.85 (AA'BB', 4H), 7.92 (d, J=8.0 Hz, 1H), 7.27 (brs, 2H), 7.15 (d, J=8.0 Hz, 1H), 4.07 (s, 3H). MS(ES+): m/z=406.08/408.03 (100/53) [MH$^+$]. HPLC: t$_R$=3.00 min (polar_5 min, ZQ3).

Methyl 4-[6-Amino-5-(5-chloro-8-fluoroisoquinolin-3-yl)-pyridin-3-yl]-benzoate A mixture of 5-bromo-3-(5-chloro-8-fluoroisoquinolin-3-yl)-pyridin-2-ylamine (BB4) (0.40 g, 1.1 mmol), 4-(carbomethoxyphenyl)boronic acid (0.21 g, 1.2 mmol), Pd(PPh$_3$)$_4$ (5 mol %) and Cs$_2$CO$_3$ (0.89 g, 2.3 mmol) in dioxane/H$_2$O (4:1, 5.0 mL) was heated under nitrogen at 90° C. for 5 h. The solvents were removed under reduced pressure. The residue was dissolved in EtOAc (30 mL) and washed with water (20 mL). The EtOAc solution was dried over MgSO$_4$, filtered, and concentrated. The crude material was purified by column chromatography on silica gel using EtOAc/Hexanes (1:4) to give the title compound.

Example 91

3-[6-Amino-5-(5-chloro-8-methoxyisoquinolin-3-yl)-pyridin-3-yl]benzoic acid

To a solution of methyl 4-[6-amino-5-(5-chloro-8-fluoroisoquinolin-3-yl)-pyridin-3-yl]-benzoate (0.13 g, 0.32 mmol) in methanol (5 mL) and water (0.5 mL) was added NaOH (0.24 g, 6 mmol), and the mixture was heated at 50° C. for 16 h. The solvents were evaporated at reduced pressure, and the residue was neutralized with acetic acid. The solid formed was filtered off and dried in vacuo to give the title compound. $^1$H NMR (400 MHz, DMSO-d$_6$): δ=12.99 (very brs, 1H), 9.64 (d, J=1.2 Hz, 1H), 8.44 (d, J=2.4 Hz, 1H), 8.34 (d, J=0.4 Hz, 1H), 8.26 (d, J=2.4 Hz, 1H), 8.20 (t, J=1.6 Hz, 1H), 7.99 (dt, J=8.0, 1.0 Hz, 1H), 7.91 (d, J=8.0 Hz, 1H), 7.90 (dt, J=8.0, 1.4 Hz, 1H), 7.59 (t, J=8.0 Hz, 1H), 7.17 (brs, 2H), 7.15 (d, J=8.0 Hz, 1H), 4.07 (s, 3H). MS(ES+): m/z=406.09/408.07 (100/45) [MH$^+$]. HPLC: t$_R$=3.00 min (polar_5 min, ZQ3).

Methyl 3-[6-Amino-5-(5-chloro-8-fluoroisoquinolin-3-yl)-pyridin-3-yl]-benzoate Following the procedure for methyl 4-[6-amino-5-(5-chloro-8-fluoroisoquinolin-3-yl)-pyridin-3-yl]-benzoate, the title compound was prepared from 5-bromo-3-(5-chloro-8-fluoroisoquinolin-3-yl)-pyridin-2-ylamine (BB4) (0.4 g, 1.13 mmol), 3-(carbomethoxy)phenylboronic acid (0.214 g, 1.2 mmol), Pd(PPh$_3$)$_4$ (5 mol %) and Cs$_2$CO$_3$ (0.89 g, 2.3 mmol). $^1$H NMR (CDCl$_3$, 300 MHz): δ=6.59 (bs, 2H), 7.20 (dd, J=8.4, 7.8 Hz, 1H), 7.55 (t, J=7.8 Hz, 1H), 7.43 (dd, J=5.2, 4.8 Hz, 1H), 7.80 (dd, J=6.8, 2.4 Hz, 1H), 8.01 (dd, J=6.8, 2.4 Hz, 1H), 8.17 (d, J=2.1 Hz, 1H), 8.28 (t, J=1.8 Hz, 1H), 8.44 (d, J=2.4 Hz, 1H), 9.59 (s, 1H).

Example 92

3-Benzofuran-2-yl-5-(1-piperidin-4-yl-1H-pyrazol-4-yl)-pyridin-2-ylamine dihydrochloride To a solution of 4-[4-(6-amino-5-benzofuran-2-ylpyridin-3-yl)-pyrazol-1-yl]-piperidine-1-carboxylic acid tert-butyl ester (83.2 mg, 0.181 mmol) in DCM (2 mL) was added 1M HCl in Et$_2$O (3.0 mL, 3.0 mmol), and the mixture was stirred at ambient temperature for 30 min to overnight. The solid that formed was filtered off and dried in vacuo to give the title compound. $^1$H NMR (400 MHz, DMSO-d$_6$): δ=2.11-2.30 (m, 4H), 3.04-3.16 (m, 2H), 3.39 (d, J=12.1 Hz, 2H), 4.47-4.57 (m, 1H), 7.35 (t, J=7.4 Hz, 1H), 7.43 (t, J=7.4 Hz, 1H), 7.63 (s, 1H), 7.71 (d, J=8.4 Hz, 1H), 7.77 (d, J=7.6 Hz, 1H), 8.00 (brs, 1H), 8.11 (s, 1H), 8.47 (s, 1H), 8.48 (d, J=1.8 Hz, 1H), 8.67 (d, J=1.8 Hz, 1H), 9.07 (brs, 1H), 9.21 (brs, 1H). MS (ES+): m/z 360.16 [MH]. HPLC: t$_R$=2.02 min (ZQ3, polar_5 min).

4-[4-(6-Amino-5-benzofuran-2-ylpyridin-3-yl)-pyrazol-1-yl]-piperidine-1-carboxylic acid tert-butyl ester To a solution of 3-Benzofuran-2-yl-5-bromopyridin-2-ylamine (61.1 mg, 0.211 mmol) and 4-[4-(4,4,5,5-tetramethyl-1,3,2-dioxaborolan-2-yl)-pyrazol-1-yl]-piperidine-1-carboxylic acid tert-butyl ester (94.4 mg, 0.250 mmol) in 1,4-dioxane (2.9 mL, 38 mmol) in a microwave reactor tube were added PS-PPh$_3$-Pd (0.10 mmol/g loading; 120 mg, 0.0120 mmol; Argonaut) and a solution of Cs$_2$CO$_3$ (142 mg, 0.436 mmol) in H$_2$O (0.90 mL, 50 mmol). The tube was sealed, evacuated and refilled with nitrogen (3×), and heated in the microwave reactor to 105° C. for 60 min. The resin was filtered off and washed with DCM. The combined filtrate and washings were diluted with DCM to 50 mL, washed with water and brine, dried over MgSO$_4$, filtered and concentrated in vacuo. The residue was chromatographed on silica gel [10 g/70 mL prepacked cartridge, eluting with DCM→1% MeOH in DCM→2% MeOH in DCM]. Fractions containing product were combined and dried in vacuo. One obtained the title compound as a yellow solid. $^1$H NMR (400 MHz, CDCl$_3$): δ=8.26 (d, J=2.4 Hz, 1H), 7.98 (d, J=2.4 Hz, 1H), 7.77 (s, 1H), 7.66 (s, 1H), 7.62 (dd, J=7.6, 0.8 Hz, 1H), 7.55 (d, J=8.4 Hz, 1H), 7.33 (ddd, J=1.6, 7.2, 8.2 Hz, 1H), 7.28 (ddd, J=1.0, 7.8, 8.4 Hz, 1H), 7.05 (d, J=0.8 Hz, 1H), 5.27

(brs, 2H), 4.40-4.16 (m, 3H), 2.92 (brt, J=11.4 Hz, 2H), 2.19 (brdd, J=2.2, 12.6 Hz, 2H), 1.97 (dq, J=4.4, 12.4 Hz, 2H), 1.49 (s, 9H). MS(ES+): m/z=460.20 (100) [MH$^+$]. HPLC: $t_R$=2.92 min (nonpolar__5 min, ZQ3).

In an alternative synthesis of the title compound, 4-[4-(6-Amino-5-bromopyridin-3-yl)-pyrazol-1-yl]-piperidine-1-carboxylic acid tert-butyl ester (70 mg, 0.17 mmol), 1-benzofuran-2-ylboronic acid (40 mg, 0.25 mmol), $Cs_2CO_3$ (110 mg, 0.33 mmol), and $Pd(PPh_3)_4$ (10 mg, 0.0087 mmol) were placed in a sealable microwave tube, taken up in 1,4-dioxane (3 mL) and $H_2O$ (0.8 mL), flushed with nitrogen, sealed and irradiated in a microwave reactor at 100° C. for 30 min. The reaction mixture was diluted with EtOAc and washed with water (2×), brine, dried over $Na_2SO_4$, filtered, and concentrated. The crude product was purified via prep-TLC eluting with 5% $NH_3$ in MeOH and (1:1) EtOAc/Hep mixtures to give the title compound.

3-Benzofuran-2-yl-5-bromopyridin-2-ylamine (BB6)

To a mixture of 5-bromo-3-(3-bromobenzofuran-2-yl)-pyridin-2-ylamine (2.5 g, 6.8 mmol) in ethanol (95%, 75 mL), $CH_2Cl_2$ (25 mL) and $NH_4Cl$ (9.0 g) in water (20 mL) at 60° C. was added Zinc (8.0 g) portion wise. After 30 minutes, the reaction mixture was filtered while hot and the filtrate was evaporated in vacuo. The crude material was chromatographed on silica gel using EtOAc/Hexanes (1:4) to give the title compound as a pale yellow solid. $^1$H NMR ($CDCl_3$, 300 MHz): δ=7.02 (s, 1H), 7.28-7.37 (m, 2H), 7.35 (d, J=8.1 Hz, 1H), 7.62 (d, J=8.1 Hz, 1H), 7.99 (d, J=2.4 Hz, 1H), 8.13 (d, J=2.4 Hz, 1H). MS(ES+): m/z=288.99/290.92 (90/100) [MH$^+$]. HPLC: $t_R$=3.30 min.

5-Bromo-3-(3-bromobenzofuran-2-yl)-pyridin-2-ylamine

Following the General Procedure for the Bromination of Aminopyridines with N-bromosuccinimide, but using 2.0 equivalents of NBS, the title compound was prepared from 3-benzofuran-2-ylpyridin-2-ylamine. $^1$H NMR ($CDCl_3$, 300 MHz): δ=5.56 (brs, 2H), 7.36-7.44 (m, 2H), 7.52 (d, J=7.5 Hz, 1H), 7.60 (d, J=7.5 Hz, 1H), 8.12 (d, J=2.4 Hz, 1H), 8.18 (d, J=2.4 Hz, 1H).

3-Benzofuran-2-ylpyridin-2-ylamine

A mixture of 2-amino-3-bromopyridine (1.0 g, 5.7 mmol), benzofuran-2-boronic acid (1.03 g, 6.4 mmol), $Pd(dppf)_2Cl_2$ (50 mg) and $K_2CO_3$ (1.83 g, 13.3 mmol) in dioxane/$H_2O$ (4:1, 5 under nitrogen at 80° C. for 16 h, cooled to RT, and concentrated in vacuo. The solid residue thus obtained was dissolved in EtOAc (30 mL) and washed with water (20 mL) and dried in vacuo. The crude material was purified by chromatography on silica gel using EtOAc/Hexanes (1:4) to give the title compound. $^1$H NMR ($CDCl_3$, 300 MHz): δ=5.61 (brs, 2H), 6.82 (dd, J=7.2, 4.1 Hz, 1H), 7.05 (s, 1H), 7.25-7.28 (m, 2H), 7.60 (d, J=7.2 Hz, 1H), 7.66 (d, J=7.2 Hz, 1H), 7.94 (d, J=2.4 Hz, 1H), 8.19 (d, 2.4 Hz).

Example 93

3-(3-Chlorobenzofuran-2-yl)-5-(1-piperidin-4-yl-1H-pyrazol-4-yl)-pyridin-2-ylamine dihydrochloride To a solution of 4-{4-[6-Amino-5-(3-chlorobenzofuran-2-yl)-pyridin-3-yl]-pyrazol-1-yl}-piperidine-1-carboxylic acid tert-butyl ester (78.0 mg, 0.158 mmol) in DCM (2.5 mL, 39 mmol) was added 1.0 M of HCl in $Et_2O$ (1.5 mL; 1.5 mmol), and the mixture was stirred at ambient temperature for 8.5 h. The solid formed was filtered off, washed with DCM, and dried in vacuo overnight, yielding the title compound as yellow solid. $^1$H NMR (400 MHz, DMSO-$d_6$): δ=9.20-9.09 (brm, 1H), 9.02-8.91 (brm, 1H), 8.57 (d, J=2.0 Hz, 1H), 8.52 (d, J=2.0 Hz, 1H), 8.39 (s, 1H), 8.05 (s, 1H), 7.96 (very brs, 2H), 7.76 (d, J=8.4 Hz, 1H), 7.74 (dd, J=8.4, 0.8 Hz, 1H), 7.55 (ddd, J=1.2, 7.2, 8.4 Hz, 1H), 7.48 (ddd, J=0.8, 7.2, 8.4 Hz, 1H), 4.55-4.46 ($m_c$, 1H), 3.38 (brd, J=12.8 Hz, 2H), 3.08 (q, J=12.2 Hz, 2H), 2.26-2.08 (m, 4H). MS(ES+): m/z=394.10/396.09 (65/21) [MH$^+$], 311.04/313.07 (100/34) [MH$^+$-piperidine]. HPLC: $t_R$=2.28 min (polar__5 min, ZQ3).

4-{4-[6-Amino-5-(3-chlorobenzofuran-2-yl)-pyridin-3-yl]-pyrazol-1-yl}-piperidine-1-carboxylic acid tert-butyl ester To a solution of 5-Bromo-3-(3-chlorobenzofuran-2-yl)-pyridin-2-ylamine (57.9 mg, 0.179 mmol) and 4-[4-(4,4,5,5-tetramethyl-1,3,2-dioxaborolan-2-yl)-pyrazol-1-yl]-piperidine-1-carboxylic acid tert-butyl ester (69.5 mg, 0.184 mmol) in 1,4-dioxane (2.5 mL, 32 mmol) in a microwave reactor tube were added PS-$PPh_3$-Pd (0.10 mmol/g loading; 100 mg, 0.0100 mmol; Argonaut) and a solution of $Cs_2CO_3$ (117 mg, 0.358 mmol) in $H_2O$ (0.75 mL, 42 mmol). The tube was sealed, evacuated and refilled with nitrogen (3×), and heated in the microwave reactor to 105° C. for 30 min. More 4-[4-(4,4,5,5-tetramethyl-1,3,2-dioxaborolan-2-yl)-pyrazol-1-yl]-piperidine-1-carboxylic acid tert-butyl ester (21 mg, 0.056 mmol) was added, the tube was evacuated and refilled with nitrogen again (3×) and heated in the microwave reactor to 105° C. for 45 min. The resin was filtered off and washed with DCM. The combined filtrate and washings were diluted with DCM to ≈50 mL, washed with water and brine, dried over $MgSO_4$, filtered, and concentrated in vacuo. The residue was chromatographed on silica gel [10 g/70 mL prepacked cartridge, eluting with DCM→1% MeOH in DCM→2% MeOH in DCM]. Fractions containing product were combined and dried in vacuo. One obtained the title compound as a yellow solid. $^1$H NMR (400 MHz, $CDCl_3$): δ=8.30 (d, J=2.4 Hz, 1H), 8.09 (d, J=2.4 Hz, 1), 7.74 (s, 1H), 7.65 (dd, J=7.2, 1.2 Hz, 1H), 7.63 (s, 1H), 7.52 (dd, J=7.0, 1.4 Hz, 1H), 7.41 (ddd, J=1.6, 7.2, 7.2 Hz, 1H), 7.38 (ddd, J=1.4, 7.0, 7.0 Hz, 1H), 5.27 (brs, 2H), 4.37-4.17 (m, 3H), 2.91 (brt, J=11.2 Hz, 2H), 2.18 (brdd, J=2.2, 12.8 Hz, 2H), 1.97 (dq, J=12.4, 4.0 Hz, 2H), 1.48 (s, 9H). MS(ES+): m/z=494.15/496.08 (100/48) [MH$^+$]. HPLC: $t_R$=3.23 min (nonpolar__5 min, ZQ3).

5-Bromo-3-(3-chlorobenzofuran-2-yl)-pyridin-2-ylamine

A solution of 3-Benzofuran-2-yl-5-bromopyridin-2-ylamine (76.1 mg, 0.263 mmol) and NCS (37.3 mg, 0.279 mmol) in DCM (5.0 mL, 78 mmol) was stirred at ambient temperature for 2 d and then at reflux for 3 d. The reaction mixture was diluted with DCM to 50 mL, washed with 1M NaOH, water containing $Na_2S_2O_3$, and brine, and dried over $MgSO_4$. The DCM solution was filtered through a plug of silica gel (≈1" in a 60 mL fritted funnel) that was washed with more DCM until no more product eluted. The filtrate containing product was concentrated in vacuo. The residue was triturated with $Et_2O$. The solid was filtered off, rinsed with $Et_2O$, and dried in vacuo overnight. One obtained the title compound as light beige solid. $^1$H NMR (400 MHz, $CDCl_3$): δ=8.19 (d, J=2.2 Hz, 1H), 8.10 (d, J=2.2 Hz, 1H), 7.64 (dd, J=1.2, 7.2 Hz, 1H), 7.52 (dd, J=1.4, 7.4 Hz, 1H), 7.41 (ddd, J=1.4, 7.4, 7.4 Hz, 1H), 7.38 (ddd, J=1.2, 7.2, 7.2 Hz, 1H), 5.32 (brs, 2H). MS(ES+): m/z=322.96/324.94/326.91 (87/100/29) [MH+]. HPLC: t_R=3.56 min (nonpolar__5 min, ZQ3).

Example 94

3-(3-Methylbenzofuran-2-yl)-5-(1-piperidin-4-yl-1H-pyrazol-4-yl)pyridin-2-ylamine bishydrochloride To the powder of Boc protected compound was added 2 mL of 1.0M HCl in ether. The mixture was shaken at room temperature overnight. Evaporation of solvents yielded the hydrochloride salt of the title compound as yellow powder. $^1$H NMR (400 MHz, CD$_3$OD): δ=2.36 (br. s., 4H), 2.41 (s, 3H), 3.22 (br. s., 2H), 3.58 (br. s., 2H), 4.63 (br. s., 1H), 7.31-7.38 (m, 1H), 7.43 (td, J=7.7, 1.3 Hz, 1H), 7.57 (d, J=8.1 Hz, 1H), 7.70 (d, J=6.6 Hz, 1H), 8.00 (s, 1H), 8.25 (d, J=2.0 Hz, 1H), 8.29 (s, 1H), 8.40 (d, J=2.0 Hz, 1H). MS (ES+): m/z=374.26 (100) [MH+]. HPLC: t_R=0.52 min (UPLC-ACQUITY, Analytical).

4-{4-[6-Amino-5-(3-methylbenzofuran-2-yl)-pyridin-3-yl]-pyrazol-1-yl}-piperidine-1-carboxylic acid tert-butyl ester To the DME solution of 3-methyl-2-(4,4,5,5-tetramethyl-[1,3,2]dioxaborolan-2-yl)benzofuran (2.3 mL, 0.58 mmol, 2 eq.) from the previous step were added 4-[4-(6-amino-5-bromopyridin-3-yl)-pyrazol-1-yl]piperidine-1-carboxylic acid tert-butyl ester (BB3) (120 mg, 0.29 mmol, 1 eq.), potassium carbonate (120 mg, 0.87 mmol, 3 eq.), water (0.5 mL), and 1,1'-bis(diphenylphosphino)ferrocene]dichloropalladium DCM (10 mg, 0.01 mmol, 0.05 eq.). The mixture was evacuated and filled with nitrogen (3×) and heated in a microwave reactor to 100° C. for 30 min. The crude was passed through Thiol-SPE to remove Pd. The clear solution was purified with the MDPS. $^1$H NMR (400 MHz, CD$_3$OD): δ=1.48 (s, 9H), 1.96 (dq, J=4.3, 12.3 Hz, 2H), 2.09 (br. s., 2H), 2.35 (s, 3H), 2.96 (br. s., 2H), 4.21 (br. s., 2H), 4.33-4.43 (m, 1H), 7.29 (dt, J=0.8, 7.4 Hz, 1H), 7.34 (dt, J=1.4, 7.2 Hz, 1H), 7.51 (d, J=7.8 Hz, 1H), 7.59-7.65 (m, 1H), 7.82 (s, 1H), 7.85 (d, J=2.3 Hz, 1H), 8.07 (s, 1H), 8.26 (d, J=2.3 Hz, 1H). MS (ES+): m/z=474.38 (100) [MH+]. HPLC: t_R=0.94 min (UPLC-ACQUITY, Analytical).

3-Methyl-2-(4,4,5,5-tetramethyl-[1,3,2]dioxaborolan-2-yl)benzofuran

A flask containing [Ir(OMe)(COD)]$_2$ (20 mg, 0.030 mmol), 4,4'-di-tert-butyl-[2,2']bipyridinyl (20 mg, 0.060 mmol) and 4,4,5,5,4',4',5',5'-octamethyl-[2,2']bi[[1,3,2]dioxaborolane (250 mg, 1.0 mmol) was evacuated and refilled with argon (3×), then charged with anhydrous DME (5 mL) and 3-methylbenzofuran (264 mg, 2.0 mmol). The resulting mixture was evacuated and refilled with argon (3×) again and kept stirring under argon at ambient temperature overnight. The resulting boronate was not isolated, but the reaction solution was used directly in the Suzuki coupling step. MS (ES+): m/z=259.20 (100) [MH+]. HPLC: t_R=1.39 min (UPLC-ACQUITY, Analytical).

Example 95

3-(3-Bromobenzofuran-2-yl)-5-(1-piperidin-4-yl-1H-pyrazol-4-yl)-pyridin-2-ylamine trifluoroacetate A solution of 4-[4-(6-amino-5-benzofuran-2-yl-pyridin-3-yl)pyrazol-1-yl]piperidine-1-carboxylic acid tert-butyl ester (10 mg, 0.020 mmol) and NBS (8.6 mg, 0.048 mmol) in acetonitrile (1 mL) was left to stir at 55° C. for 2 h. The mixture was concentrated in vacuo, and the residue was partitioned between EtOAc and an aqueous saturated solution of Na$_2$S$_2$O$_3$ (2×). The organic layer was washed with water (1×). The combined organic extracts were treated with brine, dried over sodium sulfate and concentrated in vacuo. Purification via prep TLC (5% MeOH in DCM) afforded 4-{4-[6-amino-5-(3-bromobenzofuran-2-yl)pyridine-3-yl]pyrazol-1-yl}piperidine-1-carboxylic acid tert-butyl ester. This compound was left to stir in a 1:1 DCM/TFA mixture (1 mL) for 15 min at rt. The mixture was concentrated in vacuo, affording the title compound as a tan solid. $^1$H NMR (400 MHz, CD$_3$OD): δ=2.23-2.38 (m, 4H), 3.18-3.26 (m, 2H), 3.57 (dd, J=9.5, 3.9 Hz, 2H), 4.57 (dd, J=10.1, 5.1 Hz, 1H), 7.46 (dd, J=8.2, 1.4 Hz, 2H), 7.62 (d, J=8.6 Hz, 1H), 7.90 (s, 1H), 8.09 (s, 1H), 8.26-8.31 (m, 2H). MS (ES+): m/z=438.03/440.01 (60/70) [MH+]. HPLC: t_R=2.50 min (ZQ3, polar__5 min).

4-{4-[6-Amino-5-(3-bromobenzofuran-2-yl)pyridine-3-yl]pyrazol-1-yl}piperidine-1-carboxylic acid tert-butyl ester A solution of 4-[4-(6-Amino-5-benzofuran-2-ylpyridin-3-yl)pyrazol-1-yl]piperidine-1-carboxylic acid tert-butyl ester (795 mg, 1.73 mmol) and NBS (616 mg, 3.46 mmol) in acetonitrile (30 mL) was left to stir at rt for 16 h. The mixture was quenched with Na$_2$S$_2$O$_3$ saturated solution (15 mL) and left to stir for an additional 5 min at rt. The mixture was partitioned between EtOAc and H$_2$O (3×). The combined organic extracts were treated with brine, dried over Na$_2$SO$_4$, and concentrated in vacuo. Purification via silica gel chromatography (5% MeOH in DCM) afforded the title compound as a brown solid. $^1$H NMR (400 MHz, DMSO-d$_6$): δ=1.42 (s, 9H), 1.71-1.85 (m, 2H), 1.97-2.08 (m, 2H), 2.83-3.03 (m, 2H), 3.99-4.11 (m, 2H), 4.31-4.40 (m, 1H), 6.21 (br. s., 2H), 7.42 (dd, J=7.5, 1.1 Hz, 1H), 7.45 (td, J=7.6, 1.6 Hz, 1H), 7.58 (dd, J=7.6, 1.0 Hz, 1H), 7.69 (d, J=7.8 Hz, 1H), 7.83 (s, 1H), 7.95 (d, J=2.3 Hz, 1H), 8.22 (s, 1H), 8.38 (d, J=2.3 Hz, 1H). MS (ES+): m/z=538.11/540.09 (90/100) [MH+]. HPLC: t_R=3.84 min (ZQ3, polar__5 min).

Example 96

3-(3-Phenylbenzofuran-2-yl)-5-(1-piperidin-4-yl-1H-pyrazol-4-yl)pyridine-2-ylamine A mixture of 4-{4-[6-amino-5-(3-bromobenzofuran-2-yl)pyridine-3-yl]pyrazol-1-yl}piperidine-1-carboxylic acid tert-butyl ester (50 mg, 0.093 mmol), phenylboronic acid (28 mg, 0.23 mmol), potassium fluoride (16 mg, 0.28 mmol), and palladium acetate (1.0 mg, 0.0050 mmol) in 1,4-dioxane (2.25 mL) and H$_2$O (0.75 mL) was degassed and refilled with argon (2×). The reaction mixture was left to stir at 100° C. in the microwave reactor for 30 min. Then, the mixture was passed through PL-Thiol MP SPE+ resin and concentrated in vacuo. The residual oil was partitioned between DCM and H$_2$O. The organic layers were treated with brine, dried over anhydrous Na$_2$SO$_4$ and concentrated in vacuo to give 4-{4-[5-(3-Phenylbenzofuran-2-yl)pyridin-3-yl]pyrazol-1-yl}piperidine-1-carboxylic and tert-butyl ester, MS (ES+): m/z=536.13 (100) [MH+]; HPLC: t_R=3.38 min (ZQ3, polar__5 min). This compound was left to stir in a 1:1 DCM/TFA mixture (1 mL) for 30 min at rt. Purification via MDP afforded the title compound as a yellow solid. $^1$H NMR (400 MHz, CD$_3$OD): δ=2.13-2.22 (m, 2H), 2.23-2.30 (m, 2H), 3.10-3.19 (m, 2H), 3.47-3.54 (m, 2H), 4.43-4.53 (m, 1H), 7.33 (td, J=7.5, 0.8 Hz, 1H), 7.38-7.46 (m, 3H), 7.47-7.52 (m, 3H), 7.53 (s, 1H), 7.62 (d, J=8.3 Hz, 1H), 7.64 (d, J=2.3 Hz, 1H), 7.67 (d, J=7.8 Hz, 1H), 7.82 (s, 1H), 8.20 (d, J=2.5 Hz, 1H), 8.53 (br. s., 2H). MS (ES+): m/z=436.12 (60) [MH$^+$]. HPLC: $t_R$=2.56 min (ZQ3, polar__5 min).

Example 97

3-[3-(3-Chloro-2-fluorophenyl)benzofuran-2-yl]-5-(1-piperidin-4-yl-1H-pyrazol-4-yl)pyridine-2-ylamine The title compound was obtained following the procedure for 3-(3-phenylbenzofuran-2-yl)-5-(1-piperidin-4-yl-1H-pyrazol-4-yl)pyridine-2-ylamine, using 4-(4-{5-[3-(3-chloro-2-fluorophenyl)-benzofuran-2-yl]pyridin-3-yl}pyrazol-1-yl)-piperidine-1-carboxylic acid tert-butyl ester. $^1$H NMR (400 MHz, CD$_3$OD): δ=2.13-2.18 (m, 2H), 2.22-2.28 (m, 2H), 3.07-3.11 (m, 2H), 3.42-3.49 (m, 2H), 4.40-4.49 (m, 1H), 7.28 (dd, J=15.8, 0.9 Hz, 1H), 7.32-7.37 (m, 1H), 7.41-7.47 (m, 2H), 7.51 (d, J=7.8 Hz, 1H), 7.54 (s, 1H), 7.56 (d, J=1.3 Hz, 1H), 7.58 (d, J=2.3 Hz, 1H), 7.66 (d, J=8.1 Hz, 1H), 7.85 (s, 1H), 8.22 (d, J=2.3 Hz, 1H), 8.54 (br. s., 2H). MS (ES+): m/z=488.03/490.01 (60/20) [MH$^+$]. HPLC: $t_R$=2.63 min (ZQ3, polar__5 min).

4-(4-{5-[3-(3-Chloro-2-fluorophenyl)-benzofuran-2-yl]pyridin-3-yl}pyrazol-1-yl)-piperidine-1-carboxylic acid tert-butyl ester The title compound was obtained following the procedure for 4-{4-[5-(3-phenylbenzofuran-2-yl)pyridin-3-yl]pyrazol-1-yl}piperidine-1-carboxylic acid tert-butyl ester in the previous example, using 3-chloro-2-fluorophenylboronic acid. It was used in the next step without further purification. MS (ES+): m/z=588.12/590.03 (100/50) [MH$^+$]. HPLC: $t_R$=3.55 min (ZQ3, polar__5 min).

Example 98

3-[3-(2,3-Difluorophenyl)benzofuran-2-yl]-5-(1-piperidin-4-yl-1H-pyrazol-4-yl)pyridine-2-ylamine The title compound was obtained following the procedure for 3-(3-phenylbenzofuran-2-yl)-5-(1-piperidin-4-yl-1H-pyrazol-4-yl)pyridine-2-ylamine, using 4-(4-{5-[3-(2,3-difluorophenyl)benzofuran-2-yl]pyridin-3-yl}pyrazol-1-yl)-piperidine-1-carboxylic acid tert-butyl ester. $^1$H NMR (400 MHz, CD$_3$OD): δ=2.12-2.23 (m, 2H), 2.24-2.31 (m, 2H), 3.07-3.16 (m, 2H), 4.47-4.55 (m, 1H), 7.28 (td, J=8.4, 3.4 Hz, 2H), 7.32-7.38 (m, 2H), 7.44 (dd, J=15.4, 1.3 Hz, 1H), 7.53 (d, J=7.6 Hz, 1H), 7.56 (s, 1H), 7.60 (d, J=2.3 Hz, 1H), 7.66 (d, J=8.3 Hz, 1H), 7.86 (s, 1H), 8.22 (d, J=2.3 Hz, 1H), 8.54 (br. s., 2H). MS (ES+): m/z=472.07 (50) [MH$^+$]. HPLC: $t_R$=2.60 min (ZQ3, polar__5 min).

4-(4-{5-[3-(2,3-Difluorophenyl)benzofuran-2-yl]pyridin-3-yl}pyrazol-1-yl)piperidine-1-carboxylic acid tert-butyl ester The title compound was obtained following the procedure for 4-{4-[5-(3-phenylbenzofuran-2-yl)pyridin-3-yl]pyrazol-1-yl}piperidine-1-carboxylic acid tert-butyl ester in the previous example, using 2,3-difluorophenylboronic acid. It was used in the next step without further purification. MS (ES+): m/z=572.15 (100) [MH$^+$]. HPLC: $t_R$=3.92 min (ZQ3, polar__5 min).

Example 99

3-Benzofuran-2-yl-5-((R)-1-pyrrolidin-3-yl-1H-pyrazol-4-yl)-pyridin-2-ylamine dihydrochloride A solution of (R)-3-[4-(4,4,5,5-tetramethyl-[1,3,2]dioxaborolan-2-yl)-pyrazol-1-yl]-pyrrolidine-1-carboxylic acid tert-butyl ester (0.0980 g, 0.270 mmol), 3-benzofuran-2-yl-5-bromopyridin-2-ylamine (0.065 g, 0.220 mmol), potassium carbonate (0.0994 g, 0.719 mmol), and Pd(PPh$_3$)$_4$ (0.02 g, 0.020 mmol) in previously degassed DME/H$_2$O (4:1) (2.5 mL) was placed in a microwave tube and evacuated and charged with N$_2$ (2×). The reaction mixture was heated in a microwave reactor to 100° C. for 45 min. The reaction mixture was diluted with EtOAc and washed with H$_2$O (2×), brine (2×), dried over Na$_2$SO$_4$, filtered and concentrated in vacuo. The crude material was further purified by chromatography on silica gel [eluting with 3% MeOH in CHCl$_3$] resulting in 50 mg of a yellow oil which was still slightly impure with triphenylphosphine oxide. Therefore the material was purified again by chromatography on silica gel [eluting with 1% MeOH in CHCl$_3$] to give (R)-3-[4-(6-amino-5-benzofuran-2-ylpyridin-3-yl)-pyrazol-1-yl]-pyrrolidine-1-carboxylic acid tert-butyl ester. This material was dissolved in DCM (1.0 mL), charged with HCl (1.0 M solution in Et$_2$O; 0.67 mL, 0.67 mmol) and stirred at ambient temperature for 3 h. The reaction was charged with another portion of DCM (1 mL) and HCl (1.0 M solution in Et$_2$O; 0.67 mL, 0.67 mmol) and was heated to 40° C. for 7 h and the at ambient temperature for an additional 16 h. The precipitate that had formed was filtered off, washed with diethyl ether (4×), and dried in vacuo to give the title compound as a yellow solid. $^1$H NMR (400 MHz, DMSO-d$_6$): δ=2.26-2.37 (m, 1H), 2.39-2.48 (m, 1H), 3.33-3.60 (m, 3H), 3.62-3.74 (m, 1H), 5.15-5.26 (m, 1H), 7.35 (t, J=7.5 Hz, 1H), 7.43 (t, J=7.2 Hz, 1H), 7.60 (s, 1H), 7.71 (d, J=8.1 Hz, 1H), 7.76 (d, J=7.7 Hz, 1H), 8.15 (s, 1H), 8.44 (d, J=2.2 Hz, 1H), 8.55 (s, 1H), 8.59 (s, 1H), 9.36 (broad s, 2H). MS (ES+): m/z=263.90 (100) [MH$^+$]. HPLC: $t_R$=2.63 min (ZQ2, polar__5 min).

Example 100

3-Benzofuran-2-yl-5-((S)-1-pyrrolidin-3-yl-1H-pyrazol-4-yl)-pyridin-2-ylamine dihydrochloride A solution of (S)-3-[4-(4,4,5,5-tetramethyl-1,3,2-dioxaborolan-2-yl)-pyrazol-1-yl]-pyrrolidine-1-carboxylic acid tert-butyl ester (0.0980 g, 0.270 mmol), 3-benzofuran-2-yl-5-bromopyridin-2-ylamine (0.0650 g, 0.225 mmol), potassium carbonate (0.0994 g, 0.719 mmol), and Pd(PPh$_3$)$_4$ (0.02 g, 0.02 mmol) in previously degassed DME/Water (4:1) (2.50 mL) was placed in a microwave tube and evacuated and charged with N$_2$ (2×). The reaction mixture was heated in a microwave reactor to 100° C. for 45 min. Another portion of (S)-3-[4-(4,4,5,5-tetramethyl-1,3,2-dioxaborolan-2-yl)-pyrazol-1-yl]-pyrrolidine-1-carboxylic acid tert-butyl ester (0.0163 g, 0.0450 mmol) was added, and heating to 100° C. was continued for 30 min. The reaction mixture was diluted with EtOAc and washed with H$_2$O (2×), brine (2×), dried over Na$_2$SO$_4$, filtered and concentrated in vacuo. The crude oil was purified by chromatography on silica gel [eluting with 1% MeOH in CHCl$_3$] to give (S)-3-[4-(6-amino-5-benzofuran-2-ylpyridin-3-yl)-pyrazol-1-yl]-pyrrolidine-1-carboxylic acid tert-butyl ester. This material was dissolved in DCM (2.0 mL, 31 mmol) and charged with 1.00 M of HCl in Et$_2$O (1.35 mL, 1.35 mmol) and stirred at 40° C. for 5 h then at rt for an additional 16 h. The solid that had formed was filtered off, washed with diethyl ether (3×), and dried in vacuo to give the title compound as a yellow solid. $^1$H NMR (400 MHz, DMSO-$d_6$): δ=2.25-2.37 (m, 1H), 2.39-2.49 (m, 1H), 3.32-3.50 (m, 2H), 3.62-3.74 (m, 1H), 5.15-5.25 (m, 1H), 7.37 (d, J=8.4 Hz, 1H), 7.44 (t, J=7.2 Hz, 1H), 7.63 (s, 1H), 7.71 (d, J=8.0 Hz, 1H), 7.77 (d, J=7.3 Hz, 1H), 8.17 (s, 1H), 8.46 (d, J=1.8 Hz, 1H), 8.58 (s, 1H), 8.64 (s, 1H), 9.34-9.68 (m, 2H). MS (ES+): m/z=345.92 (100) [MH$^+$]. HPLC: $t_R$=1.84 min (ZQ2, nonpolar_5 min).

Example 101

3-Benzofuran-2-yl-5-(1-methyl-1H-pyrazol-4-yl)-pyridin-2-ylamine bis-hydrochloride A solution of 3-benzofuran-2-yl-5-(1-methyl-1H-pyrazol-4-yl)-pyridin-2-ylamine (60 mg, 0.207 mmol) in dioxane (3 mL) was charged with 4.0 M of HCl in dioxane (1 mL) at rt. Upon addition, a solid precipitated and all solvent was removed in vacuo. MeOH and heptane were added and the solid was filtered off and dried, giving the title compound as a yellow solid. $^1$H NMR (400 MHz, DMSO-$d_6$): δ=3.89 (s, 3H), 7.31-7.38 (m, 1H), 7.43 (ddd, J=8.3, 7.1, 1.3 Hz, 1H), 7.64 (d, J=0.8 Hz, 1H), 7.71 (dd, J=8.2, 0.6 Hz, 1H), 7.77 (dd, J=7.8, 0.5 Hz, 1H), 8.02 (d, J=0.5 Hz, 1H), 8.32 (s, 1H), 8.42 (d, J=2.0 Hz, 1H), 8.64 (d, J=2.3 Hz, 1H). MS (ES+): m/z=291.07 (100) [MH$^+$]. HPLC: $t_R$=2.67 min (ZQ3, polar_5 min).

3-Benzofuran-2-yl-5-(1-methyl-1H-pyrazol-4-yl)-pyridin-2-ylamine

A suspension of 3-benzofuran-2-yl-5-bromopyridin-2-ylamine (65.2 mg, 0.226 mmol, 1 eq), 1-methyl-4-(4,4,5,5-tetramethyl-1,3,2-dioxaborolan-2-yl)-1H-pyrazole (56.7 mg, 0.272 mmol, 1.2 eq), Pd(PPh$_3$)$_4$ (18.6 mg, 0.0161 mmol, 7 mol %), and potassium carbonate (101.1 mg, 0.732 mmol, 3.2 eq) in a 4:1 mixture of DME:H$_2$O (2.5 mL) was evacuated and charged with nitrogen several times, after which the sample was heated in the microwave reactor to 100° C. for 45 min. EtOAc was added to dilute the reaction, which was then washed with water (2×) and brine (1×), dried over anhydrous Na$_2$SO$_4$, filtered, and concentrated in vacuo to dryness. The crude material was purified by column chromatography on silica gel [0.5"×10" glass column, eluting with CH$_2$Cl$_2$:EtOAc 1:0→4:1→1:1→2:3→3:7→1:9→0:1]. Fractions containing product were combined and concentrated in vacuo. DCM and heptane were added to the residue and the solvent was concentrated in vacuo until all CH$_2$Cl$_2$ had been removed; a solid precipitated at this point. The solid was triturated in hot heptane and filtered off, giving the title compound as a yellow solid. $^1$H NMR (400 MHz, DMSO-$d_6$): δ=3.86 (s, 3H), 6.28 (br s, 2H), 7.24-7.37 (m, 2H), 7.39 (d, J=0.8 Hz, 1H), 7.64-7.70 (m, 2H), 7.86 (d, J=0.8 Hz, 1H), 8.11 (d, J=2.3 Hz, 1H), 8.13 (s, 1H), 8.31 (d, J=2.3 Hz, 1H). MS (ES$^+$): m/z=291.09 (100) [MH$^+$]. HPLC: $t_R$=2.65 min (ZQ3, polar_5 min).

Example 102

3-Benzofuran-2-yl-5-(1-isopropyl-1H-pyrazol-4-yl)-pyridin-2-ylamine bis-hydrochloride Method A was followed, except a mixture of CH$_2$Cl$_2$ and heptane was used to recrystallize the title compound. $^1$H NMR (400 MHz, DMSO-$d_6$): δ=1.46 (d, J=6.8 Hz, 6H), 4.45-4.58 (m, 3H), 7.32-7.38 (m, 1H), 7.40-7.46 (m, 1H), 7.64 (d, J=0.8 Hz, 1H), 7.71 (dd, J=8.3, 0.8 Hz, 1H), 7.77 (d, J=7.1 Hz, 1H), 8.03 (d, J=0.8 Hz, 1H), 8.43 (d, J=2.0 Hz, 1H), 8.45 (s, 1H), 8.66 (d, J=2.0 Hz, 1H). MS (ES$^+$): m/z=319.12 (100) [MH$^+$]. HPLC: $t_R$=2.96 min (ZQ3, polar_5 min).

3-Benzofuran-2-yl-5-(1-isopropyl-1H-pyrazol-4-yl)-pyridin-2-ylamine

Method B was followed, except the free base was recrystallized from heptane (2×) to afford the title compound. $^1$H NMR (400 MHz, DMSO-$d_6$): δ=1.45 (d, J=6.8 Hz, 6H), 4.50 (spt, J=6.7 Hz, 1H), 6.27 (s, 2H), 7.31 (td, J=14.0, 6.6 Hz, 2H), 7.39 (d, J=0.8 Hz, 1H), 7.64-7.69 (m, 2H), 7.87 (d, J=0.5 Hz, 1H), 8.14 (d, J=2.3 Hz, 1H), 8.24 (d, J=0.5 Hz, 1H), 8.33 (d, J=2.3 Hz, 1H). MS (ES$^+$): m/z=319.12 (100) [MH$^+$]. HPLC: $t_R$=2.99 min (ZQ3, polar_5 min).

Example 103

4-[4-(6-Amino-5-benzofuran-2-yl-pyridin-3-yl)-pyrazol-1-yl]-piperidine-1-carboxylic acid dimethylamide bis-hydrochloride Method A was followed, except a mixture of CH$_2$Cl$_2$ and heptane was used to recrystallize the title compound. $^1$H NMR (400 MHz, DMSO-$d_6$): δ=1.88 (qd, J=12.0, 3.4 Hz, 2H), 2.05 (d, J=10.9 Hz, 2H), 2.77 (s, 6H), 2.91 (t, J=12.1 Hz, 2H), 3.66 (d, J=13.1 Hz, 2H), 4.33-4.42 (m, 1H), 7.32-7.39 (m, 1H), 7.41-7.47 (m, 1H), 7.63 (s, 1H), 7.71 (d, J=8.1 Hz, 1H), 7.77 (d, J=7.8 Hz, 1H), 8.06 (s, 1H), 8.42-8.45 (m, 1H), 8.50 (s, 1H), 8.66-8.69 (m, 1H). MS (ES$^+$): m/z=430.98 (95) [MH$^+$]. HPLC: $t_R$=2.74 min (ZQ3, polar_5 min).

4-[4-(6-Amino-5-benzofuran-2-yl-pyridin-3-yl)-pyrazol-1-yl]-piperidine-1-carboxylic acid dimethylamide Method B was followed, except EtOAc and MeOH mixtures were used to purify the title material. $^1$H NMR (400 MHz, CDCl$_3$): δ=2.00-2.14 (m, 2H), 2.18-2.25 (m, 2H), 2.88 (s, 6H), 2.91-3.00 (m, 2H), 3.83 (d, J=13.4 Hz, 2H), 4.28-4.38 (m, 1H), 5.28 (br s, 2H), 7.06 (d, J=1.0 Hz, 1H), 7.26-7.31 (m, 1H), 7.32-7.37 (m, 1H), 7.54-7.58 (m, 1H), 7.63 (dd, J=7.6, 1.0 Hz, 1H), 7.70 (d, J=0.5 Hz, 1H), 7.78 (d, J=0.8 Hz, 1H), 7.99 (d, J=2.3 Hz, 1H), 8.27 (d, J=2.3 Hz, 1H). MS (ES$^+$): m/z=431.14 (100) [MH$^+$]. HPLC: $t_R$=2.72 min (ZQ3, polar_5 min).

Example 104

3-Benzo[b]thiophen-2-yl-5-(1-piperidin-4-yl-1H-pyrazol-4-yl)-pyridin-2-ylamine bishydrochloride In a microwave vial, 4-[4-(6-amino-5-bromopyridin-3-yl)-pyrazol-1-yl]-piperidine-1-carboxylic acid tert-butyl ester (BB2) (50 mg, 0.12 mmol), 2-benzo[b]thiopheneboronic acid (32 mg, 0.18 mmol), Cs$_2$CO$_3$ (77 mg, 0.24 mmol), and Palladium(0) tetrakis(triphenylphosphine) (7 mg, 0.006 mmol) were dissolved in 1,4-dioxane (2.0 mL) and H$_2$O (0.55 mL), flushed with nitrogen, sealed and heated in the microwave reactor to 100° C. for 30 min. The completed reaction was diluted with EtOAc (25 mL), washed with water and brine, dried over Na$_2$SO$_4$, filtered and concentrated. The product was purified on prep-TLC eluting with 5% 7M NH$_3$ in MeOH/DCM and concentrated to give the Boc compound; MS (ES+): m/z=476.14 [MH$^+$]. This compound was dissolved in DCM (3.0 mL) and charged with 1.0 M HCl in Et$_2$O (3.0 mL, 3.0 mmol). This mixture was stirred at rt for 2 h. The solid that had formed was filtered off and dried in vacuo, giving the title compound as yellow solid. $^1$H NMR (400 MHz, DMSO-$d_6$): δ=2.06-2.27 (m, 4H), 3.01-3.15 (m, 2H), 3.33-3.43 (m, 2H), 4.45-4.54 (m, 1H), 7.43-7.50 (m, 2H), 7.75 (s, 1H), 7.86 (br. s., 1H), 7.94-7.98 (m, 1H), 8.06-8.10 (m, 2H), 8.37 (d, J=2.0 Hz, 1H), 8.41 (d, J=2.0 Hz, 1H), 8.42 (s, 1H), 8.91 (br. s., 1H), 9.05 (br. s., 1H), MS (ES+): m/z=376.12 [MH$^+$]. HPLC: $t_R$=1.99 min (ZQ3, polar_5 min).

Example 105

3-(3-Methylbenzo[b]thiophen-2-yl)-5-(1-piperidin-4-yl-1H-pyrazol-4-yl)pyridin-2-ylamine bishydrochloride To the powder of Boc protected compound was added 2 mL of 1.0M HCl in ether. The mixture was shaken at room temperature overnight. Evaporation of solvents yielded the hydrochloride salt of the title compound as yellow powder. $^1$H NMR (400 MHz, CD$_3$OD): δ=2.26-2.39 (m, 7H), 3.19-3.28 (m, 2H), 3.54-3.61 (m, 2H), 4.55-4.68 (m, 1H), 7.43-7.53 (m, 2H), 7.88 (dd, J=7.1, 1.5 Hz, 1H), 7.93 (dd, J=7.2, 1.4 Hz, 1H), 7.98 (s, 1H), 8.24-8.28 (m, 2H), 8.31 (d, J=2.0 Hz, 1H). MS (ES+): m/z=390.25 (100) [MH$^+$]. HPLC: $t_R$=0.53 min (UPLC-ACQUITY, Analytical)

4-{4-[6-Amino-5-(3-methylbenzo[b]thiophen-2-yl)-pyridin-3-yl]-pyrazol-1-yl}-piperidine-1-carboxylic acid tert-butyl ester To the DME solution of 4,4,5,5-tetramethyl-2-(3-methylbenzo[b]thiophen-2-yl)-[1,3,2]dioxaborolane (2.3 mL, 0.50 mmol, 2 eq.) from the previous step were added 4-[4-(6-amino-5-bromopyridin-3-yl)-pyrazol-1-yl]piperidine-1-carboxylic acid tert-butyl ester (BB3) (120 mg, 0.29 mmol, 1 eq.), potassium carbonate (104 mg, 0.75 mmol, 3 eq.), water (0.5 mL), and 1,1'-bis(diphenylphosphino)ferrocene]dichloropalladium DCM (10 mg, 0.01 mmol, 0.05 eq.). The mixture was evacuated and filled with nitrogen (3×) and heated in a microwave reactor to 100° C. for 30 min. The crude was passed through Thiol-SPE to remove Pd. The clear solution was purified with the MDPS. $^1$H NMR (400 MHz, CD$_3$OD): δ=1.47 (s, 9H), 1.87-2.00 (m, 2H), 2.09 (d, J=10.4 Hz, 2H). 2.31 (s, 3H), 2.95 (br. s., 2H), 3.35 (s, 2H), 4.22 (d, J=13.4 Hz, 2H), 4.37 (tt, J=11.6, 4.1 Hz, 1H), 7.36-7.47 (m, 2H), 7.75-7.82 (m, 3H), 7.87 (d, J=7.6 Hz, 1H), 8.05 (s, 1H), 8.25 (d, J=1.8 Hz, 1H). MS (ES+): m/z=490.37 (100) [MH$^+$]. HPLC: $t_R$=0.93 min (UPLC-ACQUITY, Analytical).

4,4,5,5-Tetramethyl-2-(3-methylbenzo[b]thiophen-2-yl)-[1,3,2]dioxaborolane

A flask containing [Ir(OMe)(COD)]$_2$ (20 mg, 0.030 mmol), 4,4'-di-tert-butyl-[2,2']bipyridinyl (20 mg, 0.060 mmol) and 4,4,5,5,4',4',5',5'-octamethyl-[2,2']bi[[1,3,2]dioxaborolane (250 mg, 1.0 mmol) was evacuated and refilled with argon (3×), then charged with anhydrous DME (5 mL) and 3-methylbenzothiophene (296 mg, 2.0 mmol). The resulting mixture was evacuated and refilled with argon (3×) again and kept stirring under argon at ambient temperature overnight. The resulting boronate was not isolated, but the reaction solution was used directly in the Suzuki coupling step. MS (ES+): m/z=275.14 (100) [MH$^+$]. HPLC: $t_R$=1.49 min (UPLC-ACQUITY, Analytical).

Example 106

3-Benzoxazol-2-yl-5-(1-piperidin-4-yl-1H-pyrazol-4-yl)-pyridin-2-ylamine dihydrochloride A solution of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB3) (0.075 g, 0.16 mmol) and 2-chlorobenzoxazole (0.029 g, 0.19 mmol) in 1,4-dioxane (1.8 mL) and H$_2$O (0.6 mL) was charged with potassium carbonate (0.066 g, 0.48 mmol) and (1,1'bis-(diphenylphosphino)-ferrocene) palladium dichloride (0.002 g, 0.003 mmol) under an atmosphere of nitrogen and the reaction was irradiated in the microwave reactor at 100° C. for 30 minutes. The reaction mixture was partitioned between EtOAc and water and separated. The aqueous was extracted with EtOAc (3×) and the combined organic fractions were washed with brine, dried over sodium sulfate, filtered, and concentrated. The residue was purified by chromatography on silica gel [eluting w/3% MeOH in DCM] to afford the Boc-protected product; MS (ES+): m/z=460.8 [MH$^+$]. This product was taken up in DCM, charged with 0.25 mL of 1.0 M HCl in ether, and stirred at rt overnight. A solid precipitated out of solution, which was filtered off and dried in vacuo to afford the title compound as a yellow solid. $^1$H NMR (400 MHz, DMSO-$d_6$): δ=2.09-2.31 (m, 4H), 3.06-3.18 (m, 2H), 3.42 (d, J=12.8 Hz, 2H), 4.46-4.57 (m, 1H), 7.42-7.50 (m, 2H), 7.80 (dd, J=6.2, 2.2 Hz, 1H), 7.86 (dd, J=5.8, 2.2 Hz, 1H), 8.02 (s, 1H), 8.35 (s, 1H), 8.51 (br. s., 1H), 8.56 (d, J=2.2 Hz, 1H). MS (ES+): m/z=360.83 [MH$^+$]. HPLC: $t_R$=2.03 min (ZQ2, polar_5 min).

Example 107

3-Benzothiazol-2-yl-5-(1-piperidin-4-yl-1H-pyrazol-4-yl)-pyridin-2-ylamine dihydrochloride The procedure for 3-benzoxazol-2-yl-5-(1-piperidin-4-yl-1H-pyrazol-4-yl)-pyridin-2-ylamine dihydrochloride except using 2-chlorobenzothiazole in place of 2-chlorobenzoxazole to afford the title compound as a yellow solid. $^1$H NMR (400 MHz, DMSO-$d_6$): δ=2.10-2.22 (m, 2H), 2.27 (d, J=13.5 Hz, 2H), 3.07-3.18 (m, 2H), 3.43 (d, J=13.2 Hz, 2H), 4.47-4.57 (m, 1H), 7.50 (t, J=7.5 Hz, 1H), 7.55-7.61 (m, 1H), 8.02 (s, 1H), 8.10 (d, J=8.0 Hz, 1H), 8.16 (d, J=7.7 Hz, 1H), 8.21 (br. s., 1H), 8.33 (s, 1H), 8.50 (d, J=2.2 Hz, 1H). MS (ES+): m/z=376.80 [MH$^+$]. HPLC: $t_R$=2.02 min (ZQ2, polar_5 min).

Example 108

3-Benzothiazol-2-yl-5-[1-(8-methyl-8-azabicyclo[3.2.1]oct-3-yl)-1H-pyrazol-4-yl]-pyridin-2-ylamine trihydrochloride Method A was followed, except the title material was dissolved in minimal CH$_2$Cl$_2$ and then recrystallized from hot heptane. $^1$H NMR (400 MHz, DMSO-$d_6$): δ=2.05-2.14 (m, 2H), 2.19-2.37 (m, 4H), 2.71 (d, J=5.1 Hz, 2H), 4.02 (br s, 2H), 4.79 (tt, J=11.5, 5.7 Hz, 1H), 7.48-7.55 (m, 1H), 7.57-7.63 (m, 1H), 8.05 (s, 1H), 8.13 (d, J=7.6 Hz, 1H), 8.19 (d, J=7.3 Hz, 1H), 8.29-8.35 (m, 2H), 8.49 (d, J=2.3 Hz, 1H), 10.28 (br s, 1H); 3H singlet for N-methyl is hidden beneath DMSO peak. MS (ES$^+$): m/z=417.16 (29) [MH$^+$]. HPLC: $t_R$=2.04 min (ZQ2, polar_5 min).

Example 109

3-Benzothiazol-2-yl-5-[1-(8-methyl-8-azabicyclo[3.2.1]oct-3-yl)-1H-pyrazol-4-yl]-pyridin-2-ylamine A suspension of 3-benzothiazol-2-yl-5-(4,4,5,5-tetramethyl-1,3,2-dioxaborolan-2-yl)-pyridin-2-ylamine (BB8) (95.6 mg, 0.271 mmol, 1.2 eq), 3-(4-iodopyrazol-1-yl)-8-methyl-8-azabicyclo[3.2.1]octane (69.1 mg, 0.218 mmol, 1.0 eq), (1,1'-bis-(diphenylphosphino)-ferrocene) palladium dichloride (16.0 mg, 0.0219 mmol, 10 mol %), and $K_2CO_3$ (92.0 mg, 0.666 mmol, 3 eq) in a 4:1 ratio of DME to $H_2O$ (2.5 mL) was evacuated and charged with nitrogen several times, after which the sample was heated in the microwave reactor to 80° C. for 30 min. The reaction mixture was partitioned between EtOAc and water and the layers were separated. The aqueous layer was back extracted with EtOAc (3×) and the combined organic layers were washed with water (1×) and brine (1×), dried over anhydrous $Na_2SO_4$, filtered, and concentrated in vacuo to dryness. The emulsion that had formed was collected separately and extracted with $CH_2Cl_2$ (2×), washed with brine (1×), dried over anhydrous $Na_2SO_4$, filtered, and concentrated in vacuo. All organics were combined. The crude material was adsorbed onto silica gel and purified by column chromatography on silica gel [10"×0.5" column, eluting with neat EtOAc→7N $NH_3$(MeOH):EtOAc 2%→3%→5%]. Fractions containing product were pooled and concentrated in vacuo. The product was recrystallized from neat acetonitrile [heated until boiling, cooled to −20° C. for 16 h], giving the title material as a yellow solid. $^1$H NMR (400 MHz, $CDCl_3$): δ=1.72-1.79 (m, 2H), 2.05 (ddd, J=13.1, 5.8, 3.3 Hz, 2H), 2.13-2.25 (m, 4H), 2.40 (s, 3H), 3.29-3.40 (m, 2H), 4.49-4.63 (m, 1H), 7.12 (br s, 2H), 7.39-7.44 (m, 1H), 7.50 (ddd, J=8.2, 7.2, 1.3 Hz, 1H), 7.71 (s, 1H), 7.72 (s, 1H), 7.92 (dd, J=7.9, 0.6 Hz, 1H), 7.99 (d, J=2.0 Hz, 1H), 8.02 (dd, J=8.1, 0.5 Hz, 1H), 8.32 (d, J=2.0 Hz, 1H). MS (ES$^+$): m/z=417.13 (24) [MH$^+$]. HPLC: $t_R$=2.12 min (ZQ2, polar_5 min).

3-Benzothiazol-2-yl-5-(4,4,5,5-tetramethyl-[1,3,2]dioxaborolan-2-yl)-pyridin-2-ylamine (BB8)

The title compound was prepared as a light brown solid by following the General Procedure for the Preparation of Pinacol Boronates, using 3-benzothiazol-2-yl-5-bromopyridin-2-ylamine (BB7) (15.3 g, 50 mmol), bis(pinacolato)diboron (16.5 g, 65 mmol), $Pd_2(dba)_3$ (3 mol %), tricyclohexylphosphine (12 mol %) and KOAc (7.85 g, 80 mmol). $^1$H NMR ($CDCl_3$, 300 MHz): δ=7.43-7.58 (m, 4H), 7.94 (d, J=8.1 Hz, 1H), 8.05 (d, J=8.1 Hz, 1H), 8.40 (d, J=1.8 Hz, 1H), 8.60 (d, J=1.5 Hz). MS(ES+): m/z=353.14/354.09/355.15 (33/100/35) [MH$^+$]. HPLC: $t_R$=4.19 min (polar_5 min, ZQ3).

Data for the corresponding boronic acid: MS(ES+): m/z=271.06/272.00/273.06 (60/100/45) [MH$^+$]. HPLC: $t_R$=2.39 min (polar_5 min, ZQ3).

3-Benzothiazol-2-yl-5-bromopyridin-2-ylamine (BB7)

The title compound was prepared from 3-benzothiazol-2-ylpyridin-2-ylamine (22.7 g, 100 mmol) and NBS (17.8 g, 100 mmol) as a brown solid following the General Procedure for the Bromination of Aminopyridines with NBS. $^1$H NMR ($CDCl_3$, 300 MHz): δ=7.17 (brs, 2H), 7.41 (t, J=6.9 Hz, 1H), 7.50 (t, J=6.9 Hz, 1H), 7.89 (d, J=2.4 Hz, 1H), 7.95 (d, J=2.4 Hz, 1H), 8.03 (d, J=2.1 Hz, 1H), 8.20 (d, J=2.1 Hz, 1H). MS(ES+): m/z=305.98/307.94 (91/100) [MH$^+$]. HPLC: $t_R$=3.62 min (nonpolar_5 min, ZQ3).

3-Benzothiazol-2-ylpyridin-2-ylamine

The title compound was prepared following the procedure for 3-(5-chloro-8-fluoroisoquinolin-3-yl)-pyridin-2-ylamine, using 3-(4,4,5,5-tetramethyl-[1,3,2]dioxaborolan-2-yl)-pyridin-2-ylamine (30.0 g, 136 mmol), 2-chlorobenzothiazole (16.5 g, 97 mmol), Pd(PPh$_3$)$_4$ (3.3 g, 3 mol %), and $Cs_2CO_3$ (72.6 g, 223 mmol). $^1$H NMR ($CDCl_3$, 300 MHz): δ=6.71 (dd, J=6.8, 3.6 Hz, 1H), 7.13 (brs, 2H), 7.38 (t, J=8.4 Hz, 1H), 7.47 (t, J=8.4 Hz, 1H), 7.87 (d, J=6.0 Hz, 1H), 7.95 (dd, J=6.2, 1.5 Hz, 1H), 7.99 (d, J=6.0 Hz, 1H), 8.18 (dd, J=6.2, 1.2 Hz, 1H).

Example 110

5-[1-(8-Azabicyclo[3.2.1]oct-3-yl)-1H-pyrazol-4-yl]-3-benzothiazol-2-ylpyridin-2-ylamine To a stirring solution of 3-[4-(5-benzothiazol-2-yl-6-ethoxycarbonylaminopyridin-3-yl)-pyrazol-1-yl]-8-azabicyclo[3.2.1]octane-8-carboxylic acid ethyl ester (7.1 mg, 0.013 mmol, 1 eq) and potassium hydroxide (22.2 mg, 0.396 mmol, 30 eq) in 1,2-ethanediol (3 mL), hydrazine hydrate (7 μL, 0.1 mmol, 10 eq) was added and the solution was stirred at reflux (T=200° C.) for 9 h. The reaction mixture was poured into water and extracted with ether. The combined organic layers were dried over anhydrous $Na_2SO_4$, filtered, and concentrated in vacuo. The residue was purified by prep. TLC [Silicycle, 1000 μm, 20×20 cm plate, developed twice in a 8% 7N $NH_3$(MeOH):$CH_2Cl_2$ solvent system.] The desired band was scraped from the plate, the silica gel was completely rinsed of all product, and the filtrate was concentrated in vacuo, giving the title compound as a yellow solid. MS (ES$^+$): m/z=403.17 (40) [MH$^+$]. HPLC: $t_R$=2.37 min (ZQ3, polar_5 min).

3-[4-(6-Amino-5-benzothiazol-2-ylpyridin-3-yl)-pyrazol-1-yl]-8-azabicyclo[3.2.1]octane-8-carboxylic acid ethyl ester To a solution of 3-benzothiazol-2-yl-5-[1-(8-methyl-8-azabicyclo[3.2.1]oct-3-yl)-1H-pyrazol-4-yl]-pyridin-2-ylamine (50.8 mg, 0.122 mmol; 1 eq) and $K_2CO_3$ (1.2 mg, 0.0087 mmol, 7 mol %) in toluene (3 mL), ethyl chloroformate (67.0 mg, 0.617 mmol, 5 eq) in toluene (1 mL) was added. The solution was heated to reflux for a total of 10 h (temp=110° C.). The residue was dissolved in water. The aqueous mixture was extracted with $CH_2Cl_2$ (3×) and the combined organic layers were dried over anhydrous $Na_2SO_4$, filtered, and concentrated in vacuo. The crude was purified by column chromatography on silica gel [0.5"×10" column, eluting with $CH_2Cl_2$:EtOAc 1:0→2:1→1:1→1:2→0:1]. Fractions containing product were combined and concentrated in vacuo to give the title compound. MS (ES$^+$): m/z=475.13 (100) [MH$^+$]. HPLC: $t_R$=3.41 min (ZQ2, polar_5 min).

3-[4-(5-Benzothiazol-2-yl-6-ethoxycarbonylaminopyridin-3-yl)-pyrazol-1-yl]-8-azabicyclo[3.2.1]octane-8-carboxylic acid ethyl ester From above reaction, the title material was also isolated. MS (ES$^+$): m/z=547.10 (65) [MH$^+$]. HPLC: $t_R$=3.76 min (ZQ2, polar_5 min).

Example 111

3-Benzothiazol-2-yl-5-[1-(tetrahydropyran-4-yl)-1H-pyrazol-4-yl]-pyridin-2-ylamine Method E was followed. Trituration gave the title compound as a yellow solid. $^1$H NMR (400 MHz, CDCl$_3$): δ=2.09-2.23 (m, 4H), 3.55-3.63 (m, 2H), 4.12-4.20 (m, 2H), 4.37-4.48 (m, 1H), 7.13 (br s, 2H), 7.37-7.46 (m, 1H), 7.51 (ddd, J=8.2, 7.2, 1.3 Hz, 1H), 7.69 (d, J=0.8 Hz, 1H), 7.78 (d, J=0.8 Hz, 1H), 7.89-7.94 (m, 1H), 7.99-8.05 (m, 2H), 8.34 (d, J=2.3 Hz, 1H). MS (ES$^+$): m/z=378.13 (100) [MH$^+$]. HPLC: t$_R$=3.20 min (ZQ3, polar_5 min).

4-Iodo-1-(tetrahydropyran-4-yl)-1H-pyrazole

Method C was followed, using 4-iodotetrahydro-2H-pyran. The crude material was purified by column chromatography on silica gel [0.5"×10" glass column, eluting with neat CH$_2$Cl$_2$→CH$_2$Cl$_2$:EtOAc 1%→2%→neat EtOAc]. The resulting material was contaminated with the 4-iodopyrazole starting material but was carried on to the next step without further purification. $^1$H NMR (400 MHz, CDCl$_3$): δ=1.97-2.17 (m, 4H), 3.54 (td, J=11.6, 2.9 Hz, 2H), 4.06-4.15 (m, 2H), 4.40-4.42 (m, 1H), 7.49 (s, 1H), 7.53 (s, 1H). MS (ES$^+$): m/z=278.98 (100) [MH$^+$]. HPLC: t$_R$=2.89 min (ZQ3, polar_5 min).

Example 112

3-Benzothiazol-2-yl-5-(1H-pyrazol-4-yl)-pyridin-2-ylamine

Method E was followed, giving the title compound as a yellow solid. $^1$H NMR (400 MHz, CDCl$_3$): δ=7.16 (br s, 2H), 7.42 (td, J=7.6, 1.0 Hz, 1H), 7.48-7.54 (m, 1H), 7.87 (s, 2H), 7.90-7.94 (m, 1H), 8.01-8.04 (m, 1H), 8.06 (d, J=2.0 Hz, 1H), 8.38 (d, J=2.3 Hz, 1H), 10.25 (br s, 1H). MS (ES$^+$): m/z=294.08 (100) [MH$^+$]. HPLC: t$_R$=2.83 min (ZQ3, polar_5 min).

Example 113

3-Benzothiazol-2-yl-5-(1-cyclohexyl-1H-pyrazol-4-yl)-pyridin-2-ylamine bis-hydrochloride Method A was followed. $^1$H NMR (400 MHz, DMSO-d$_6$): δ=1.16-1.31 (m, 1H), 1.36-1.51 (m, 2H), 1.64-1.79 (m, 3H), 1.80-1.89 (m, 2H), 2.08 (dd, J=12.6, 2.3 Hz, 2H), 4.15 (tt, J=11.5, 3.8 Hz, 1H), 7.50-7.56 (m, 1H), 7.57-7.63 (m, 1H), 7.97 (s, 1H), 8.13 (d, J=7.6 Hz, 1H), 8.20 (d, J=7.33 Hz, 1H), 8.37-8.43 (m, 2H), 8.48 (d, J=2.0 Hz, 1H). MS (ES+): m/z=376.16 (100) [MH$^+$]. HPLC: t$_R$=4.03 min (ZQ3, polar_5 min).

3-Benzothiazol-2-yl-5-(1-cyclohexyl-1H-pyrazol-4-yl)-pyridin-2-ylamine

Method B was followed, except the crude reaction mixture was concentrated in vacuo first, after which a standard aqueous workup was performed using CH$_2$Cl$_2$ as extraction solvent. Prep-TLC purification [Silicycle, 1000 µm, 20×20 cm plate, one development in 1:1 EtOAc:CH$_2$Cl$_2$ solvent system] was utilized; the desired band was scraped from the plate, the silica gel was rinsed well with copious amounts of the same solvent system, and the filtrate was concentrated in vacuo. The title material was recrystallized from heptane. $^1$H NMR (400 MHz, CDCl$_3$): δ=1.24-1.37 (m, 1H), 1.40-1.54 (m, 2H), 1.72-1.87 (m, 3H), 1.95 (dt, J=13.6, 3.1 Hz, 2H), 2.19-2.30 (m, 2H), 4.17 (tt, J=11.8, 3.8 Hz, 1H), 7.11 (br s, 2H), 7.38-7.45 (m, 1H), 7.51 (ddd, J=8.2, 7.1, 1.1 Hz, 1H), 7.67 (d, J=0.5 Hz, 1H), 7.76 (d, J=0.8 Hz, 1H), 7.91 (dd, J=8.0, 0.6 Hz, 1H), 7.99-8.06 (m, 2H), 8.34 (d, J=2.0 Hz, 1H). MS (ES$^+$): m/z=376.15 (100) [MH$^+$]. HPLC: t$_R$=4.06 min (ZQ3, polar_5 min).

1-Cyclohexyl-4-(4,4,5,5-tetramethyl-1,3,2-dioxaborolan-2-yl)-1H-pyrazole

Method C was followed, using bromocyclohexane equivalents (2 eq). The crude material was also purified by column chromatography on silica gel [0.5"×10" glass column, eluting with CH$_2$Cl$_2$:EtOAc mixtures]. $^1$H NMR (400 MHz, CDCl$_3$): δ=1.32 (s, 12H), 1.39-1.50 (m, 2H), 1.60-1.80 (m, 4H), 1.88 (d, J=13.4 Hz, 2H), 2.16 (d, J=11.1 Hz, 2H), 4.04-4.20 (m, 1H), 7.74 (s, 1H), 7.78 (s, 1H). MS (ES$^+$): m/z=277.16 (100) [MH$^+$]. HPLC: t$_R$=3.75 min (ZQ3, polar_5 min).

Example 114

3-Benzothiazol-2-yl-5-1-[1-(2-methoxyethyl)-piperidin-4-yl]-1H-pyrazol-4-yl-pyridin-2-ylamine Method B was followed, except the crude material was purified by pTLC [Silicycle, 1000 µm, 20×20 cm plate, developed once in 2% 7N NH$_3$(MeOH):EtOAc solvent system]; the desired band was scraped from the plate, the silica gel was rinsed well with copious amounts of the same solvent system, and the filtrate was concentrated in vacuo. The title material was recrystallized from hot heptane. $^1$H NMR (400 MHz, CDCl$_3$): δ=2.07-2.30 (m, 6H), 2.66 (t, J=5.6 Hz, 2H), 3.14 (d, J=11.6 Hz, 2H), 3.39 (s, 3H), 3.56 (t, J=5.6 Hz, 2H), 4.16-4.27 (m, 1H), 7.13 (br s, 2H), 7.42 (td, J=7.6, 1.1 Hz, 1H), 7.51 (ddd, J=8.2, 7.2, 1.3 Hz, 1H), 7.68 (d, J=0.5 Hz, 1H), 7.75 (d, J=0.8 Hz, 1H), 7.89-7.95 (m, 1H), 7.99-8.05 (m, 2H), 8.33 (d, J=2.3 Hz, 1H). MS (ES$^+$): m/z=435.16 (53) [MH$^+$]. HPLC: t$_R$=2.57 min (ZQ3, polar_5 min).

Example 115

3-Benzothiazol-2-yl-5-1-[1-(2,2,2-trifluoroethyl)-piperidin-4-yl]-1H-pyrazol-4-yl-pyridin-2-ylamine dihydrochloride Method A was followed. $^1$H NMR (400 MHz, DMSO-d$_6$) δ 2.16 (br s, 4H), 2.87 (br s, 2H), 3.24 (br s, 2H), 3.64 (br s, 2H), 4.23-4.40 (m, 2H), 7.53-7.60 (m, 1H), 7.60-7.66 (m, 1H), 8.09 (s, 1H), 8.17 (dd, J=7.7, 0.4 Hz, 1H), 8.22-8.27 (m, 1H), 8.53-8.57 (m, 2H), 8.63 (d, J=1.8 Hz, 1H), 8.91 (br s, 1H). MS (AP$^+$): m/z 459.11 (100) [MH$^+$]. HPLC: t$_R$=3.69 min (ZQ3, polar_5 min).

3-Benzothiazol-2-yl-5-1-[1-(2,2,2-trifluoroethyl)-piperidin-4-yl]-1H-pyrazol-4-yl-pyridin-2-ylamine Method B was followed, except 7N NH$_3$(MeOH):CH$_2$Cl$_2$ mixtures were required for column chromatography. $^1$H NMR (400 MHz, CDCl$_3$): δ=2.08-2.25 (m, 4H), 2.62 (td, J=11.5, 2.8 Hz, 2H), 3.06 (q, J=9.4 Hz, 2H), 3.14 (d, J=11.9 Hz, 2H), 4.15-4.26 (m, 1H), 7.12 (br s, 2H), 7.38-7.44 (m, 1H), 7.50 (ddd, J=8.3, 7.2, 1.1 Hz, 1H), 7.67 (d, J=0.5 Hz, 1H), 7.76 (d, J=0.5 Hz, 1H), 7.91 (dd, J=7.9, 0.6 Hz, 1H), 7.98-8.04 (m, 2H), 8.33 (d, J=2.0 Hz, 1H). MS (AP$^+$): m/z=459.11 (100) [MH$^+$]. HPLC: $t_R$=3.69 min (ZQ3, polar_5 min).

Example 116

4-[4-(6-Amino-5-benzothiazol-2-yl-pyridin-3-yl)-pyrazol-1-yl]-piperidine-1-carboxamide bis-hydrochloride Method A was followed, except the reaction was never concentrated in vacuo. The solid mixture was filtered off directly and rinsed with heptane. $^1$H NMR (400 MHz, DMSO-d$_6$): δ=1.68-1.88 (m, 2H), 2.03 (dd, J=12.1, 2.5 Hz, 2H), 2.88 (t, J=11.8 Hz, 2H), 4.07 (d, J=13.4 Hz, 2H), 4.39 (t, J=11.5, 4.1 Hz, 1H), 5.99 (br s, 1H), 7.52-7.59 (m, 1H), 7.60-7.67 (m, 1H), 8.06 (s, 1H), 8.17 (d, J=7.6 Hz, 1H), 8.24 (dd, J=7.8, 0.8 Hz, 1H), 8.49-8.55 (m, 2H), 8.61 (s, 1H), 8.86 (br s, 1H). MS (ES$^+$): m/z=420.12 (100) [MH$^+$]. HPLC: $t_R$=2.66 min (ZQ3, polar_5 min).

4-[4-(6-Amino-5-benzothiazol-2-yl-pyridin-3-yl)-pyrazol-1-yl]-piperidine-1-carboxamide Method B was followed, except 7N NH$_3$(MeOH):EtOAc mixtures were required to isolate the title material. $^1$H NMR (400 MHz, CDCl$_3$): δ=1.99-2.17 (m, 2H), 2.26 (d, J=12.4 Hz, 2H), 3.01-3.13 (m, 2H), 4.14 (d, J=13.6 Hz, 2H), 4.38 (tt, J=11.3, 4.1 Hz, 1H), 4.51 (brs, 2H), 7.14 (br s, 2H), 7.39-7.45 (m, 1H), 7.51 (td, J=7.7, 1.3 Hz, 1H), 7.67 (s, 1H), 7.78 (s, 1H), 7.92 (d, J=8.1 Hz, 1H), 7.99-8.05 (m, 2H), 8.33 (d, J=2.3 Hz, 1H). MS (ES$^+$): m/z=420.13 (100) [MH$^+$]. HPLC: $t_R$=2.66 min (ZQ3, polar_5 min).

Example 117

4-[4-(6-Amino-5-benzothiazol-2-yl-pyridin-3-yl)-pyrazol-1-yl]-piperidine-1-carboxylic acid dimethylamide bis-hydrochloride Method A was followed, except a mixture of CH$_2$Cl$_2$ and heptane was used to recrystallize the title compound. $^1$H NMR (400 MHz, DMSO-d$_6$): δ=1.84-1.97 (m, 2H), 2.06 (dd, J=12.3, 2.7 Hz, 2H), 2.77 (s, 6H), 2.85-2.96 (m, 2H), 3.63-3.71 (m, 2H), 4.38 (tt, J=11.5, 4.1 Hz, 1H), 7.52-7.58 (m, 1H), 7.59-7.65 (m, 1H), 8.04 (s, 1H), 8.15 (d, J=7.6 Hz, 1H), 8.22 (d, J=7.3 Hz, 1H), 8.50 (s, 1H), 8.51-8.54 (m, 2H), 8.67 (br s, 1H). MS (ES$^+$): m/z=448.17 (100) [MH$^+$]. HPLC: $t_R$=3.05 min (ZQ3, polar_5 min).

4-[4-(6-Amino-5-benzothiazol-2-yl-pyridin-3-yl)-pyrazol-1-yl]-piperidine-1-carboxylic acid dimethylamide Method B was followed, except, in addition to CH$_2$Cl$_2$:EtOAc mixtures, 7N NH$_3$(MeOH) was required to completely elute the title compound. $^1$H NMR (400 MHz, CDCl$_3$): δ=2.01-2.16 (m, 2H), 2.17-2.28 (m, 2H), 2.89 (s, 6H), 2.91-3.01 (m, 2H), 3.84 (d, J=13.4 Hz, 2H), 4.28-4.40 (m, 1H), 7.13 (br s, 2H), 7.37-7.45 (m, 1H), 7.51 (ddd, J=8.2, 7.2, 1.3 Hz, 1H), 7.69 (d, J=0.5 Hz, 1H), 7.77 (d, J=0.5 Hz, 1H), 7.92 (dd, J=7.8, 0.5 Hz, 1H), 7.98-8.05 (m, 2H), 8.34 (d, J=2.0 Hz, 1H). MS (ES$^+$): m/z=448.13 (100) [MH$^+$]. HPLC: $t_R$=3.05 min (ZQ3, polar_5 min).

Example 118

3-Benzothiazol-2-yl-5-(1-isopropyl-1H-pyrazol-4-yl)-pyridin-2-ylamine bis-hydrochloride Method A was followed, except heptane was used to recrystallize the title compound. $^1$H NMR (400 MHz, DMSO-d$_6$): δ=1.41 (d, J=6.8 Hz, 6H), 4.41-4.53 (m, 1H), 7.45-7.53 (m, 1H), 7.56 (dd, J=8.1, 1.0 Hz, 1H), 7.98 (s, 1H), 8.10 (d, J=8.1 Hz, 1H), 8.18 (d, J=7.8 Hz, 1H), 8.42 (s, 1H), 8.47 (d, J=2.0 Hz, 1H), 8.55 (d, J=1.8 Hz, 1H), 8.81 (br s, 1H). MS (ES$^+$): m/z=336.12 (100) [MH$^+$]. HPLC: $t_R$=3.39 min (ZQ3, polar_5 min).

3-Benzothiazol-2-yl-5-(1-isopropyl-1H-pyrazol-4-yl)-pyridin-2-ylamine

Method B was followed, except heptane and EtOAc mixtures were used to purify the title compound, which was then recrystallized from heptane. $^1$H NMR (400 MHz, CDCl$_3$): δ=1.59 (d, J=6.6 Hz, 6H), 4.58 (septet, J=6.7 Hz, 1H), 7.12 (br s, 2H), 7.39-7.44 (m, 1H), 7.51 (ddd, J=8.2, 7.2, 1.3 Hz, 1H), 7.67 (d, J=0.5 Hz, 1H), 7.76 (d, J=0.5 Hz, 1H), 7.91 (dd, J=8.0, 0.6 Hz, 1H), 8.00-8.04 (m, 2H), 8.35 (d, J=2.0 Hz, 1H). MS (ES$^+$): m/z=336.12 (100) [MH$^+$]. HPLC: $t_R$=3.39 min (ZQ3, polar_5 min).

Example 119

3-Benzothiazol-2-yl-5-(1-methyl-1H-pyrazol-4-yl)-pyridin-2-ylamine bis-hydrochloride Method A was followed, except hot heptane was used for trituration of the title compound. $^1$H NMR (400 MHz, DMSO-d$_6$): δ=3.90 (s, 3H), 7.53-7.60 (m, 1H), 7.60-7.67 (m, 1H), 8.05 (d, J=0.5 Hz, 1H), 8.17 (d, J=7.6 Hz, 1H), 8.25 (d, J=7.3 Hz, 1H), 8.38 (s, 1H), 8.54 (d, J=2.3 Hz, 1H), 8.63 (d, J=2.0 Hz, 1H), 9.03 (br s, 1H). MS (ES$^+$): m/z=308.09 (100) [MH$^+$]. HPLC: $t_R$=3.04 min (ZQ3, polar_5 min).

3-Benzothiazol-2-yl-5-(1-methyl-1H-pyrazol-4-yl)-pyridin-2-ylamine

Method B was followed. $^1$H NMR (400 MHz, CDCl$_3$): δ=3.99 (s, 3H), 7.13 (br s, 2H), 7.38-7.44 (m, 1H), 7.51 (ddd, J=8.2, 7.1, 1.1 Hz, 1H), 7.62 (s, 1H), 7.75 (d, J=0.8 Hz, 1H), 7.91 (dd, J=7.8, 0.5 Hz, 1H), 7.98-8.05 (m, 2H), 8.33 (d, J=2.0 Hz, 1H). MS (ES$^+$): m/z=308.09 (100) [MH$^+$]. HPLC: $t_R$=3.01 min (ZQ3, polar_5 min).

Example 120

3-Benzothiazol-2-yl-5-(2-morpholin-4-ylthiazol-5-yl)-pyridin-2-ylamine

A solution of 4-(5-bromothiazol-2-yl)-morpholine (0.0600 g, 0.241 mmol), 3-benzothiazol-2-yl-5-(4,4,5,5-tetramethyl-1,3,2-dioxaborolan-2-yl)-pyridin-2-ylamine (BB8) (0.110 g, 0.313 mmol), potassium carbonate (0.106 g, 0.771 mmol), and Pd(PPh$_3$)$_4$ (0.02 g, 0.02 mmol) in previously degassed DME/Water (4:1) (2.7 mL) was placed in a microwave tube and evacuated and charged with N$_2$ (2×). The reaction mixture was heated in the microwave reactor at 100° C. for 45 min. The reaction mixture was partitioned between CHCl$_3$ and H$_2$O and the layers were separated. The aqueous layer was re-extracted with CHCl$_3$ (3×), and the combined organic extracts were washed with brine (1×), dried over Na$_2$SO$_4$, filtered and concentrated in vacuo. The crude material was submitted for MDP for purification. The pure fractions were combined and the organic was concentrated in vacuo then diluted with CHCl$_3$ and neutralized with sat. NaHCO$_3$. The layers were separated, and the aqueous layer was re-extracted with CHCl$_3$ (3×). The combined organic extracts were dried over Na$_2$SO$_4$, filtered and concentrated in vacuo, giving the title compound as a yellow solid. $^1$H NMR (400 MHz, DMSO-d$_6$): δ=3.44 (d, J=5.1 Hz, 4H), 3.73 (d, J=5.1 Hz, 4H), 7.49 (t, J=7.7 Hz, 1H), 7.57 (t, J=7.7 Hz, 1H), 7.61 (s, 1H), 8.00 (d, J=2.2 Hz, 1H), 8.03 (br. s., 2H), 8.10 (d, J=7.7 Hz, 1H), 8.15 (d, J=7.3 Hz, 1H), 8.36 (d, J=2.2 Hz, 1H). MS (ES+): m/z=396.07 (100) [MH$^+$]. HPLC: t$_R$=3.57 min (ZQ2, polar__5 min).

Example 121

3-Benzothiazol-2-yl-5-[2-(4-methylpiperazin-1-yl)-thiazol-5-yl]-pyridin-2-ylamine dihydrochloride A solution of 1-(5-bromothiazol-2-yl)-4-methylpiperazine (0.0600 g, 0.229 mmol), 3-benzothiazol-2-yl-5-(4,4,5,5-tetramethyl-1,3,2-dioxaborolan-2-yl)-pyridin-2-ylamine (BB8) (0.105 g, 0.298 mmol), potassium carbonate (0.101 g, 0.732 mmol), and Pd(PPh$_3$)$_4$ (0.02 g, 0.02 mmol) in previously degassed DME/Water (4:1) (2.54 mL) was placed in a microwave tube and evacuated and charged with N$_2$ (2×). The reaction mixture was heated in the microwave reactor to 100° C. for 45 min. A precipitate had formed from the reaction mixture and was filtered through a fritted funnel resulting in a brown solid. This solid was purified by chromatography on silica gel [eluting with 5% MeOH in CHCl$_3$] resulting in the title compound as a yellow solid. The solid was then dissolved in MeOH and charged with 3 equiv of 1M HCl in ether and concentrated in vacuo resulting in the title compound as a dark yellow solid. $^1$H NMR (400 MHz, DMSO-d$_6$): δ=2.82 (d, J=4.0 Hz, 3H), 3.13-3.26 (m, 2H), 3.46-3.58 (m, 4H), 4.07 (d, J=15.4 Hz, 2H), 7.53 (t, J=7.2 Hz, 1H), 7.60 (t, J=7.0 Hz, 1H), 7.74 (s, 1H), 8.13 (d, J=7.7 Hz, 1H), 8.18 (s, 1H), 8.21 (d, J=5.5 Hz, 1H), 8.39 (d, J=2.2 Hz, 1H), 11.07 (br, s., 1H). MS (ES+): m/z=409.07 (100) [MH$^+$]. HPLC: t$_R$=2.13 min (ZQ2, polar__5 min).

Example 122

3-Benzothiazol-2-yl-5-(2-piperazin-1-ylthiazol-5-yl)-pyridin-2-ylamine dihydrochloride A solution of 4-(5-bromothiazol-2-yl)-piperazine-1-carboxylic acid tert-butyl ester (0.079 g, 0.229 mmol), 3-benzothiazol-2-yl-5-(4,4,5,5-tetramethyl-1,3,2-dioxaborolan-2-yl)-pyridin-2-ylamine (BB8) (0.105 g, 0.298 mmol), potassium carbonate (0.101 g, 0.732 mmol), and Pd(PPh$_3$)$_4$ (0.018 g, 0.016 mmol) in previously degassed DME/H$_2$O (4:1) (4.0 mL) was placed in a microwave tube and evacuated and charged with N$_2$ (2×). The reaction mixture was heated in the microwave reactor to 100° C. for 30 min. The reaction mixture was diluted with EtOAc, washed with water and brine, dried over Na$_2$SO$_4$, filtered and concentrated in vacuo. The crude material was purified on prep-TLC eluting with 3% 7M NH$_3$ in MeOH/DCM yielding 4-[5-(6-amino-5-benzothiazol-2-ylpyridin-3-yl)-thiazol-2-yl]-piperazine-1-carboxylic acid tert-butyl ester, MS (ES+): m/z=495.06 [MH$^+$]. To a solution of this compound in DCM (1.0 mL) was added 1M HCl in ether (2.0 mL, 2.0 mmol), and the mixture was stirred at room temperature overnight. The solid that formed was filtered off and purified on the MDP. To a solution of the material thus obtained in DCM (1.0 mL) was added 1M HCl in ether (1.0 mL, 1.0 mmol). The precipitate was filtered off and dried in vacuo, yielding the title compound as yellow solid. $^1$H NMR (400 MHz, CD$_3$OD): δ=2.95-3.00 (m, 4H), 3.46-3.53 (m, 4H), 7.40 (s, 1H), 7.42-7.48 (m, 1H), 7.53 (dd, J=15.3, 1.1 Hz, 1H), 7.98-8.05 (m, 2H), 8.07 (d, J=2.3 Hz, 1H), 8.23 (d, J=2.3 Hz, 1H). MS (ES+): m/z=395.06 (55) [MH$^+$]. HPLC: t$_R$=2.11 min (ZQ2, polar__5 min).

4-(5-Bromothiazol-2-yl)-piperazine-1-carboxylic acid tert-butyl ester

A solution of 2,5-dibromothiazole (1.00 g, 4.12 mmol) in DIPEA (3.00 mL) was charged with tert-butyl 1-piperazinecarboxylate (0.767 g, 4.12 mmol) and heated to 110° C. for 3 h and then an additional 16 h at rt. The reaction mixture was partitioned between CHCl$_3$ and H$_2$O, and the layers were separated. The aqueous layer was re-extracted with CHCl$_3$ (3×) and the combined organic fractions were dried over Na$_2$SO$_4$, filtered and concentrated in vacuo. The crude material was purified by chromatography on silica gel [eluting with 0.5% EtOAc in CHCl$_3$] resulting in the title compound as a light orange solid. $^1$H NMR (400 MHz, CDCl$_3$): δ=1.47 (s, 9H), 3.37-3.44 (m, 4H), 3.51-3.59 (m, 4H), 7.08 (s, 1H). MS (ES+): m/z=348.09 (51/49) [MH$^+$]. HPLC: t$_R$=3.73 min (ZQ2, polar__5 min).

Example 123

4-[4-(6-Amino-5-benzothiazol-2-ylpyridin-3-yl)-pyrazol-1-yl]-cyclohexanone

To a solution of 3-benzothiazol-2-yl-5-[1-(1,4-dioxaspiro[4.5]dec-8-yl)-1H-pyrazol-4-yl]-pyridin-2-ylamine (0.750 g, 1.7 mmol) in dioxane (5 mL) was added 2 N HCl (1 mL), and the solution was stirred at RT for 1 h. The solvents were evaporated, and aq. satd. NaHCO$_3$ solution (30 mL) was added to the residue. The mixture was extracted with CH$_2$Cl$_2$ (3×40 mL), and the combined extracts were washed with water, dried over Na$_2$SO$_4$, filtered, and concentrated in vacuo. The crude material was purified by column chromatography on silica gel using EtOAc/Hexanes (1:1) to give the title compound as yellow solid. $^1$H NMR (400 MHz, CDCl$_3$): δ=8.33 (d, J=2.2 Hz, 1H), 8.02 (dd, J=8.4, 0.4 Hz, 1H), 8.01 (d, J=2.4 Hz, 1H), 7.91 (ddd, J=8.4, 1.2, 0.4 Hz, 1H), 7.79 (d, J=0.6 Hz, 1H), 7.71 (d, J=0.6 Hz, 1H), 7.51 (ddd, J=8.4, 7.4, 1.2 Hz, 1H), 7.41 (ddd, J=8.0, 7.4, 1.4 Hz, 1H), 7.14 (brs, 2H), 4.72-4.64 (m$_c$, 1H), 2.70-2.47 (m, 6H), 2.46-2.34 (m, 2H). MS(ES+): m/z=390.14 (100) [MH$^+$]. HPLC: t$_R$=3.13 min (polar__5 min, ZQ3).

Example 124

3-Benzothiazol-2-yl-5-[1-(1,4-dioxaspiro[4.5]dec-8-yl)-1H-pyrazol-4-yl]-pyridin-2-ylamine The title compound was obtained as yellow solid following the procedure for 3-(5-chloro-8-fluoroisoquinolin-3-yl)-pyridin-2-ylamine, using 1-(1,4-dioxaspiro[4.5]dec-8-yl)-4-iodo-1H-pyrazole (1.42 g, 4.2 mmol), 3-benzothiazol-2-yl-5-(4,4,5,5-tetramethyl-[1,3,2]dioxaborolan-2-yl)-pyridin-2-ylamine (BB8) (1.47 g, 4.2 mmol), Pd(PPh$_3$)$_4$ (0.08 g, 2 mol %), Cs$_2$CO$_3$ (3.28 g, 10 mmol). $^1$H NMR (400 MHz, CDCl$_3$): δ=8.33 (d, J=2.2 Hz, 1H), 8.02 (dd, J=8.4, 0.4 Hz, 1H), 8.01 (d, J=2.0 Hz, 1H), 7.91 (ddd, J=8.4, 1.2, 0.4 Hz, 1H), 7.75 (d, J=0.6 Hz, 1H), 7.69 (d, J=0.6 Hz, 1H), 7.50 (ddd, J=8.4, 7.0, 1.2 Hz, 1H), 7.41 (ddd, J=8.0, 7.4, 1.4 Hz, 1H), 7.12 (brs, 2H), 4.33-4.25 (m$_c$, 1H), 4.00 (s, 4H), 2.27-2.09 (m, 4H), 1.97-1.90 (m, 2H), 1.78 (ddd, J=4.4, 13.2, 13.2 Hz, 2H). MS(ES+): m/z=434.14 (100) [MH$^+$]. HPLC: t$_R$=3.36 min (polar_5 min, ZQ3).

1-(1,4-Dioxaspiro[4.5]dec-8-yl)-4-iodo-1H-pyrazole

A mixture of toluene-4-sulfonic acid 1,4-dioxaspiro[4.5]dec-8-yl ester (2.0 g, 6.4 mmol; prepared according to U.S. Pat. No. 4,360,531 example I.B), 4-iodopyrazole (1.36 g, 7.01 mmol), K$_2$CO$_3$ (1.06 g, 7.7 mmol), 18-crown-6 (0.2 g, 0.7 mmol) in DMF (5 mL) was heated under nitrogen at 50° C. for 16 h. Water (50 mL) was added, and the reaction mixture was extracted with EtOAc (3×40 mL). The EtOAc extracts were washed with water (30 mL), dried over Na$_2$SO$_4$, filtered, and concentrated at reduced pressure. The crude material was purified by column chromatography on silica gel using EtOAc/CH$_2$Cl$_2$ (1:9) to give the title compound. $^1$H NMR (CDCl$_3$, 300 MHz): δ=1.66-2.17 (m, 8H), 3.97 (s, 4H), 4.17-4.23 (m, 1H), 7.27 (d, J=3.3 Hz, 1H), 7.48 (d, J=3.3 Hz, 1H).

Example 125

[3-(6-Amino-5-benzothiazol-2-ylpyridin-3-yl)-prop-2-ynyl]-carbamic acid tert-butyl ester To a solution of 3-benzothiazol-2-yl-5-bromopyridin-2-ylamine (BB7) (3.37 g, 11.0 mmol) in dioxane (50 mL) were added N-(Boc)-propargylamine (1.705 g, 11.0 mmol), Pd(PPh$_3$)$_4$ (0.250 g, 2 mol %), CuI (0.04 g), and NEt$_3$ (1.85 mL, 13.2 mmol). The mixture was heated under nitrogen at 80° C. for 48 h. The reaction mixture was concentrated, taken up with CH$_2$Cl$_2$ (120 mL), washed with water (3×30 mL), dried over Na$_2$SO$_4$, filtered, and concentrated at reduced pressure. The crude material was purified by column chromatography on silica gel using EtOAc/Hexanes (1:4) to give the title compound. $^1$H NMR (CDCl$_3$, 300 MHz): δ=1.56 (s, 9H), 4.22 (d, J=2.4 Hz, 2H), 4.99 (bs, 1H), 7.40-7.61 (m, 4H), 7.88 (d, J=6.8 Hz, 1H), 8.05-8.08 (m, 2H), 8.32 (d, J=1.8 Hz, 1H), MS (ES$^+$): m/z=381.14 (100) [MH$^+$]. HPLC: t$_R$=3.87 min (ZQ3, polar_5 min).

Example 126

5-(3-Aminoprop-1-ynyl)-3-benzothiazol-2-ylpyridin-2-ylamine

To a solution of [3-(6-amino-5-benzothiazol-2-ylpyridin-3-yl)-prop-2-ynyl]-carbamic acid tert-butyl ester (0.225 g, 0.6 mmol) in CH$_2$Cl$_2$ (5 mL) was added trifluoroacetic acid (0.5 mL, 6 mmol), the mixture was stirred at RT for 2 h. Aq. satd. NaHCO$_3$ (20 mL) was added, and the mixture was extracted with CH$_2$Cl$_2$/MeOH (10%, 4×30 mL). The organic extracts were dried over Na$_2$SO$_4$, filtered, and concentrated at reduced pressure to give the title compound. $^1$H NMR (CDCl$_3$, 300 MHz): δ=3.78 (s, 2H), 7.42-7.58 (m, 2H), 7.88 (d, J=6.8 Hz, 1H), 8.05-8.07 (m, 2H), 8.32 (d, J=1.8 Hz, 1H). MS (ES$^+$): m/z=281.14 (100) [MH$^+$]. HPLC: t$_R$=2.01 min (ZQ2, polar_5 min).

Example 127

3-[3-(6-Amino-5-benzothiazol-2-ylpyridin-3-yl)-prop-2-ynyl]-1,1-dimethylurea

A mixture of 5-(3-aminoprop-1-ynyl)-3-benzothiazol-2-ylpyridin-2-ylamine (10.0 mg, 0.0357 mmol), N,N-dimethylcarbamoyl chloride (3.60 uL, 0.0392 mmol), DMF (1 mL, 0.01 mol) and DIPEA (0.03 mL, 0.2 mmol) was stirred at rt for 30 min. The solution was used directly for HPLC purification. The fractions containing the pure product were concentrated in vacuo to afford the title compound as a yellow solid. $^1$H NMR (400 MHz, CD$_3$OD): δ=2.93 (s, 6H), 4.13-4.18 (m, 2H), 7.39-7.45 (m, 1H), 7.51 (td, J=7.7, 1.3 Hz, 1H), 7.96 (d, J=7.3 Hz, 1H), 8.01 (d, J=8.1 Hz, 1H), 8.09 (d, J=2.0 Hz, 1H), 8.14 (s, 1H). MS (ES$^+$): m/z=352.11 (100) [MH$^+$]. HPLC: t$_R$=3.11 min (ZQ3, polar_5 min).

Example 128

4-Ethylpiperazine-1-carboxylic acid [3-(6-amino-5-benzothiazol-2-ylpyridin-3-yl)-prop-2-ynyl]-amide The title compound was prepared according to the procedures described for 3-[3-(6-amino-5-benzothiazol-2-ylpyridin-3-yl)-prop-2-ynyl]-1,1-dimethylurea. $^1$H NMR (400 MHz, CD$_3$OD): δ=1.13 (t, J=7.3 Hz, 3H), 2.44-2.51 (m, 6H), 3.42-3.51 (m, 4H), 4.17 (s, 2H), 7.43-7.48 (m, 1H), 7.54 (td, J=7.7, 1.3 Hz, 1H), 8.02 (dd, J=12.6, 7.8 Hz, 2H), 8.13 (d, J=2.0 Hz, 1H), 8.17 (d, J=2.0 Hz, 1H). MS (ES$^+$): m/z=422.11 (100) [MH$^+$]. HPLC: t$_R$=2.46 min (ZQ3, polar_5 min).

Example 129

[3-(6-Amino-5-benzothiazol-2-ylpyridin-3-yl)-prop-2-ynyl]-urea

A mixture of 5-(3-aminoprop-1-ynyl)-3-benzothiazol-2-ylpyridin-2-ylamine (10.0 mg, 0.0357 mmol), trimethylsilyl isocyanate (5.31 uL, 0.0392 mmol), DMF (1 mL, 0.01 mol) and DIPEA (0.03 mL, 0.2 mmol) was stirred at rt for 3 h. The solution was used directly for HPLC purification. The fractions containing the pure product were concentrated in vacuo to afford the title compound as a yellow solid. $^1$H NMR (400 MHz, CD$_3$OD): δ=4.14 (s, 2H), 7.39-7.45 (m, 1H), 7.47-7.52 (m, 1H), 7.93 (s, 1H), 8.00 (d, J=7.8 Hz, 1H), 8.06 (d, J=2.0 Hz, 1H). MS (ES$^+$): m/z=324.10 (100) [MH$^+$]. HPLC: t$_R$=2.85 min (ZQ3, polar_5 min).

Example 130

N-[3-(6-Amino-5-benzothiazol-2-ylpyridin-3-yl)-prop-2-ynyl]-2-dimethylaminoacetamide A mixture of 5-(3-aminoprop-1-ynyl)-3-benzothiazol-2-ylpyridin-2-ylamine (10.0 mg, 0.0357 mmol), dimethylaminoacetic acid (4.05 mg, 0.0392 mmol), TBTU (17.2 mg, 0.0535 mmol), DMF (1 mL, 0.01 mol) and DIPEA (0.03 mL, 0.0002 mol) was stirred at rt for 30 min. The solution was used directly for HPLC purification. The fractions containing the pure product were concentrated in vacuo to afford the title compound as a yellow solid. $^1$H NMR (400 MHz, CD$_3$OD): δ=2.66 (br. s., 6H), 3.54 (br. s., 2H), 4.28 (s, 2H), 7.42-7.47 (m, 1H), 7.53 (td, J=7.7, 1.3 Hz, 1H), 7.99 (d, J=7.3 Hz, 1H), 8.03 (d, J=7.6 Hz, 1H), 8.09 (d, J=2.0 Hz, 1H), 8.15 (d, J=1.8 Hz, 1H). MS (ES$^+$): m/z=366.13 (100) [MH$^+$]. HPLC: t$_R$=2.43 min (ZQ3, polar_5 min).

Example 131

N-[3-(6-Amino-5-benzothiazol-2-ylpyridin-3-yl)-prop-2-ynyl]-2-pyrrolidin-1-ylacetamide The title compound was prepared according to the procedures described for N-[3-(6-amino-5-benzothiazol-2-ylpyridin-3-yl)-prop-2-ynyl]-2-dimethylaminoacetamide. $^1$H NMR (400 MHz, CD$_3$OD): δ=2.06 (br. s., 4H), 3.27 (br. s., 4H), 3.88 (s, 2H), 4.29 (s, 2H), 7.41-7.47 (m, 1H), 7.49-7.55 (m, 1H), 7.97 (d, J=8.1 Hz, 1H), 8.02 (d, J=8.1 Hz, 1H), 8.06 (d, J=2.0 Hz, 1H), 8.15 (d, J=1.8 Hz, 1H). MS (ES$^+$): m/z=392.12 [MH$^+$]. HPLC: t$_R$=2.49 min (ZQ3, polar_5 min).

Example 132

2-[4-(6-Amino-5-benzothiazol-2-ylpyridin-3-yl)-pyrazol-1-yl]-1-morpholin-4-ylethanone A mixture of [4-(6-amino-5-benzothiazol-2-ylpyridin-3-yl)-pyrazol-1-yl]-acetic acid (5.00 mg, 0.0142 mmol), morpholine (10.0 mg, 0.11 mmol), TBTU (9.14 mg, 0.0284 mmol), DIPEA (0.02 mL, 0.1 mmol) and DMF (2 mL, 0.03 mol) was stirred at rt for 10 min. The solution was transferred to a separatory funnel, diluted with EtOAc and washed 3× with water. The organic layer was concentrated in vacuo and loaded onto a prep TLC plate, eluting with 5% MeOH/DCM. The band containing the pure product was filtered off using 1:1 MeOH/DCM, and the filtrate was concentrated in vacuo to afford the title compound as a yellow solid. $^1$H NMR (400 MHz, CD$_3$OD): δ=3.60-3.64 (m, 4H), 3.72 (dt, J=12.8, 4.7 Hz, 4H), 5.17 (s, 2H), 7.40-7.45 (m, 1H), 7.48-7.54 (m, 1H), 7.85 (s, 1H), 7.94-7.98 (m, 2H), 8.02 (d, J=7.8 Hz, 1H), 8.16 (d, J=2.3 Hz, 1H), 8.30 (d, J=2.3 Hz, 1H). MS (ES$^+$): m/z=421.12 (100) [MH$^+$]. HPLC: t$_R$=2.79 min (ZQ3, polar_5 min).

[4-(6-Amino-5-benzothiazol-2-ylpyridin-3-yl)-pyrazol-1-yl]-acetic acid

A mixture of (4-iodopyrazol-1-yl)-acetic acid methyl ester (124 mg, 0.467 mmol), 3-benzothiazol-2-yl-5-(4,4,5,5-tetramethyl-1,3,2-dioxaborolan-2-yl)-pyridin-2-ylamine (BB8) (150.0 mg, 0.4246 mmol), Pd(PPh$_3$)$_4$ (40 mg, 0.03 mmol), potassium fluoride (74.0 mg, 1.27 mmol) and 4:1 dioxane:water (4:1, 1,4-dioxane:H$_2$O, 6 mL) was heated in the microwave reactor at 85° C. for 30 min. The solution was concentrated in vacuo and dry-loaded onto silica gel for column chromatography. The material was eluted with 2% MeOH/DCM. The fractions containing the product were concentrated in vacuo. The material was redissolved in 1,4-dioxane (5 mL), and 4M HCl in 1,4-dioxane (1 mL) was added. The solution was heated to 50° C. in a sealed tube for 3 h. The solvent was removed in the corrosive pump to afford the title compound as an orange solid. MS (ES$^+$): m/z=352.08 (100) [MH$^+$]. HPLC: t$_R$=2.78 min (ZQ3, polar_5 min).

(4-Iodopyrazol-1-yl)-acetic acid methyl ester

A mixture of 4-iodopyrazole (1.000 g, 5.155 mmol), Cs$_2$CO$_3$ (2.016 g, 6.186 mmol) and DMF (20 mL, 0.2 mol) was added chloroacetic acid methyl ester (0.5440 mL, 6.186 mol) at 0° C. The reaction was allowed to stir for 1 h at rt. The material was transferred to a separatory funnel, diluted with EtOAc, and washed with water several times to remove DMF. The organic layer was dry-loaded onto silica gel, and column chromatography was used to purify, eluting with 3:1 Hexanes/EtOAc, affording the title compound as a clear liquid. $^1$H NMR (400 MHz, CDCl$_3$): δ=3.79 (s, 3H), 4.93 (s, 2H), 7.54 (s, 1H), 7.57 (s, 1H). MS (ES$^+$): m/z=266.95 (100) [MH$^+$]. HPLC: t$_R$=2.73 min (ZQ3, polar_5 min).

Example 133

2-[4-(6-Amino-5-benzothiazol-2-ylpyridin-3-yl)-pyrazol-1-yl]-1-pyrrolidin-1-ylethanone The title compound was prepared according to the procedures described for 2-[4-(6-amino-5-benzothiazol-2-ylpyridin-3-yl)-pyrazol-1-yl]-1-morpholin-4-ylethanone. $^1$H NMR (400 MHz, CD$_3$OD): δ=1.89-1.95 (m, 2H), 2.05 (quintet, J=6.8 Hz, 2H), 3.49 (t, J=6.9 Hz, 2H), 3.58 (t, J=6.8 Hz, 2H), 5.03 (s, 2H), 7.38-7.43 (m, 1H), 7.49 (td, J=7.6, 1.4 Hz, 1H), 7.80 (s, 1H), 7.90-7.94 (m, 2H), 7.99 (d, J=7.6 Hz, 1H), 8.12 (d, J=2.3 Hz, 1H), 8.27 (d, J=2.0 Hz, 1H). MS (ES$^+$): m/z=405.15 (100) [MH$^+$]. HPLC: t$_R$=2.88 min (ZQ3, polar_5 min).

Example 134

2-[4-(6-Amino-5-benzothiazol-2-ylpyridin-3-yl)-pyrazol-1-yl]-N-(2-methoxyethyl)-acetamide The title compound was prepared according to the procedures described for 2-[4-(6-amino-5-benzothiazol-2-ylpyridin-3-yl)-pyrazol-1-yl]-1-morpholin-4-ylethanone. $^1$H NMR (400 MHz, CD$_3$OD): δ=3.35 (s, 3H), 3.41-3.45 (m, 2H), 3.45-3.49 (m, 2H), 4.88 (s, 2H), 7.41 (t, J=7.6 Hz, 1H), 7.49 (t, J=7.7 Hz, 1H), 7.84 (s, 1H), 7.93 (d, J=8.1 Hz, 1H), 7.96 (s, 1H), 7.99 (d, J=8.1 Hz, 1H), 8.12 (d, J=2.0 Hz, 1H), 8.27 (d, J=2.3 Hz, 1H). MS (ES$^+$): m/z=409.12 (100) [MH$^+$]. HPLC: t$_R$=2.75 min (ZQ3, polar_5 min).

Example 135

2-[4-(6-Amino-5-benzothiazol-2-ylpyridin-3-yl)-pyrazol-1-yl]-1-(3-hydroxypyrrolidin-1-yl)-ethanone The title compound was prepared according to the procedures described for 2-[4-(6-amino-5-benzothiazol-2-ylpyridin-3-yl)-pyrazol-1-yl]-1-morpholin-4-ylethanone. $^1$H NMR (400 MHz, CD$_3$OD): δ=1.98 (dd, J=8.5, 4.2 Hz, 1H), 2.11 (dd, J=9.1, 4.3 Hz, 1H), 3.52-3.75 (m, 4H), 4.43-4.53 (m, 1H), 5.01-5.09 (m, 2H), 7.38-7.43 (m, 1H), 7.49 (td, J=7.7, 1.3 Hz, 1H), 7.81 (s, 1H), 7.94 (t, J=3.7 Hz, 2H), 8.00 (d, J=7.8 Hz, 1H), 8.13 (d, J=2.3 Hz, 1H), 8.27 (d, J=2.3 Hz, 1H). MS (ES$^+$): m/z=421.07 (100) [MH$^+$]. HPLC: t$_R$=2.29 min (ZQ2, polar_5 min).

Example 136

2-[4-(6-Amino-5-benzothiazol-2-ylpyridin-3-yl)-pyrazol-1-yl]-N-(2-hydroxyethyl)-acetamide The title compound was prepared according to the procedures described for 2-[4-(6-amino-5-benzothiazol-2-ylpyridin-3-yl)-pyrazol-1-yl]-1-morpholin-4-ylethanone. $^1$H NMR (400 MHz, CD$_3$OD): δ=3.35-3.39 (m, 2H), 3.63 (td, J=5.4, 2.0 Hz, 2H), 4.89 (d, J=1.8 Hz, 2H), 7.40-7.45 (m, 1H), 7.51 (t, J=7.7 Hz, 1H), 7.85 (d, J=1.5 Hz, 1H), 7.95 (d, J=7.8 Hz, 1H), 7.98 (d, J=1.5 Hz, 1H), 8.01 (d, J=8.1 Hz, 1H), 8.14 (t, J=2.3 Hz, 1H), 8.29 (t, J=2.1 Hz, 1H). MS (ES'): m/z=395.07 (100) [MH$^+$]. HPLC: t$_R$=2.27 min (ZQ2, polar_5 min).

Example 137

2-[4-(6-Amino-5-benzothiazol-2-ylpyridin-3-yl)-pyrazol-1-yl]-N-methylacetamide

The title compound was prepared according to the procedures described for 2-[4-(6-amino-5-benzothiazol-2-ylpyridin-3-yl)-pyrazol-1-yl]-1-morpholin-4-ylethanone. $^1$H NMR (400 MHz, CD$_3$OD): δ=2.79 (s, 3H), 4.86 (s, 2H), 7.39-7.44 (m, 1H), 7.47-7.53 (m, 1H), 7.84 (s, 1H), 7.92-7.97 (m, 2H), 8.01 (d, J=7.6 Hz, 1H), 8.14 (d, J=2.3 Hz, 1H), 8.28 (d, J=2.3 Hz, 1H). MS (ES$^+$): m/z=365.11 (100) [MH$^+$]. HPLC: t$_R$=2.63 min (ZQ3, polar_5 min).

Example 138

2-[4-(6-Amino-5-benzothiazol-2-ylpyridin-3-yl)-pyrazol-1-yl]-N,N-bis-(2-methoxyethyl)-acetamide The title compound was prepared according to the procedures described for 2-[4-(6-amino-5-benzothiazol-2-ylpyridin-3-yl)-pyrazol-1-yl]-1-morpholin-4-ylethanone. $^1$H NMR (400 MHz, CD$_3$OD): δ=3.34 (s, 3H), 3.43 (s, 3H), 3.54-3.58 (m, 2H), 3.60-3.64 (m, 4H), 3.71 (t, J=4.9 Hz, 2H), 5.28 (s, 2H), 7.40-7.46 (m, 1H), 7.49-7.53 (m, 1H), 7.83 (s, 1H), 7.93 (s, 1H), 7.97 (d, J=7.3 Hz, 1H), 8.02 (d, J=7.6 Hz, 1H), 8.16 (d, J=2.0 Hz, 1H), 8.30 (d, J=2.0 Hz, 1H). MS (ES$^+$): m/z=467.16 (100) [MH$^+$]. HPLC: t$_R$=2.95 min (ZQ3, polar_5 min).

Example 139

2-[4-(6-Amino-5-benzothiazol-2-ylpyridin-3-yl)-pyrazol-1-yl]-1-(4-hydroxypiperidin-1-yl)-ethanone The title compound was prepared according to the procedures described for 2-[4-(6-amino-5-benzothiazol-2-ylpyridin-3-yl)-pyrazol-1-yl]-1-morpholin-4-ylethanone. $^1$H NMR (400 MHz, CD$_3$OD): δ=1.46-1.60 (m, 2H), 1.84-1.96 (m, 2H), 3.26 (ddd, J=13.2, 9.4, 3.4 Hz, 1H), 3.33-3.40 (m, 1H), 3.80-3.93 (m, 2H), 4.01 (d, J=4.3 Hz, 1H), 5.16 (s, 2H), 7.41 (t, J=7.6 Hz, 1H), 7.50 (t, J=7.7 Hz, 1H), 7.82 (s, 1H), 7.92 (s, 1H), 7.95 (d, J=8.1 Hz, 1H), 8.00 (d, J=8.1 Hz, 1H), 8.14 (d, J=2.3 Hz, 1H), 8.28 (d, J=2.3 Hz, 1H). MS (ES$^+$): m/z=435.15 (100) [MH$^+$]. HPLC: t$_R$=2.54 min (ZQ3, polar_5 min).

Example 140

2-[4-(6-Amino-5-benzothiazol-2-ylpyridin-3-yl)-pyrazol-1-yl]-N,N-dimethylacetamide The title compound was prepared according to the procedures described for 2-[4-(6-amino-5-benzothiazol-2-ylpyridin-3-yl)-pyrazol-1-yl]-1-morpholin-4-ylethanone. $^1$H NMR (400 MHz, CD$_3$OD): δ=3.01 (s, 3H), 3.15 (s, 3H), 5.15 (s, 2H), 7.40-7.45 (m, 1H), 7.51 (td, J=7.7, 1.3 Hz, 1H), 7.83 (s, 1H), 7.94 (s, 1H), 7.96 (d, J=7.3 Hz, 1H), 8.01 (d, J=7.6 Hz, 1H), 8.15 (d, J=2.3 Hz, 1H), 8.29 (d, J=2.3 Hz, 1H). MS (ES'): m/z=379.15 (100) [MH$^+$]. HPLC: t$_R$=2.70 min (ZQ3, polar_5 min).

Example 141

2-[4-(6-Amino-5-benzothiazol-2-ylpyridin-3-yl)-pyrazol-1-yl]-1-piperidin-1-ylethanone The title compound was prepared according to the procedures described for 2-[4-(6-amino-5-benzothiazol-2-ylpyridin-3-yl)-pyrazol-1-yl]-1-morpholin-4-ylethanone. $^1$H NMR (400 MHz, CD$_3$OD): δ=1.59 (d, J=5.1 Hz, 2H), 1.64-1.74 (m, 4H), 3.52-3.60 (m, 4H), 5.13 (s, 2H), 7.42 (t, J=7.6 Hz, 1H), 7.50 (t, J=7.7 Hz, 1H), 7.82 (s, 1H), 7.91 (s, 1H), 7.95 (d, J=7.8 Hz, 1H), 8.00 (d, J=7.8 Hz, 1H), 8.14 (t, J=2.3 Hz, 1H), 8.27-8.30 (m, 1H). MS (ES$^+$): m/z=419.17 (100) [MH$^+$]. HPLC: t$_R$=3.08 min (ZQ3, polar_5 min).

Example 142

2-[4-(6-Amino-5-benzothiazol-2-ylpyridin-3-yl)-pyrazol-1-yl]-1-morpholin-4-ylpropan-1-one A mixture of 2-[4-(6-amino-5-benzothiazol-2-ylpyridin-3-yl)-pyrazol-1-yl]-propionic acid (5.00 mg, 0.0142 mmol), morpholine (10.0 mg, 0.11 mmol), TBTU (9.14 mg, 0.0284 mmol), DIPEA (0.02 mL, 0.1 mmol) and DMF (2 mL, 0.03 mol) was stirred at rt for 10 min. The solution was transferred to a separatory funnel, diluted with EtOAc and washed 3× with water. The organic layer was concentrated in vacuo and loaded onto a prep TLC plate, eluting with 5% MeOH/DCM. The band containing the pure product was filtered off using 1:1 MeOH/DCM, and the filtrate was concentrated in vacuo to afford the title compound as a yellow solid. $^1$H NMR (400 MHz, CD$_3$OD): δ=1.74 (d, J=7.1 Hz, 3H), 3.50-3.72 (m, 8H), 5.62 (q, J=7.1 Hz, 1H), 7.42-7.47 (m, 1H), 7.50-7.56 (m, 1H), 7.88 (s, 1H), 8.01 (dd, J=10.7, 8.2 Hz, 2H), 8.17 (s, 1H), 8.21 (d, J=2.0 Hz, 1H), 8.34 (d, J=2.3 Hz, 1H). MS (ES$^+$): m/z=435.16 (100) [MH$^+$]. HPLC: t$_R$=2.89 min (ZQ3, polar_5 min).

2-[4-(6-Amino-5-benzothiazol-2-ylpyridin-3-yl)-pyrazol-1-yl]-propionic acid

The title compound was prepared according to the procedures described for [4-(6-amino-5-benzothiazol-2-ylpyridin-3-yl)-pyrazol-1-yl]-acetic acidmethyl ester. MS (ES$^+$): m/z=366.13 (100) [MH$^+$]. HPLC: t$_R$=2.90 min (ZQ3, polar_5 min).

2-(4-Iodopyrazol-1-yl)-propionic acid methyl ester

The title compound was prepared according to the procedures described for (4-iodopyrazol-1-yl)-acetic acid methyl ester. $^1$H NMR (400 MHz, CDCl$_3$): δ=1.79 (d, J=7.6 Hz, 3H), 3.76 (s, 3H), 5.11 (q, J=7.3 Hz, 1H), 7.55 (s, 1H), 7.60 (s, 1H).

Example 143

2-[4-(6-Amino-5-benzothiazol-2-ylpyridin-3-yl)-pyrazol-1-yl]-N,N-bis-(2-methoxyethyl)-propionamide The title compound was prepared according to the procedures described for 2-[4-(6-amino-5-benzothiazol-2-ylpyridin-3-yl)-pyrazol-1-yl]-1-morpholin-4-ylpropan-1-one. $^1$H NMR (400 MHz, CD$_3$OD): δ=1.70 (d, J=6.8 Hz, 3H), 3.30 (s, 3H), 3.38 (s, 3H), 3.48-3.67 (m, 7H), 3.88-3.98 (m, 1H), 5.72 (q, J=6.8 Hz, 1H), 7.40-7.45 (m, 1H), 7.51 (td, J=7.7, 1.3 Hz, 1H), 7.84 (s, 1H), 7.96-8.03 (m, 2H), 8.10 (s, 1H), 8.17 (d, J=2.0 Hz, 1H), 8.31 (d, J=2.3 Hz, 1H). MS (ES$^-$): m/z=481.14 (100) [MH$^+$]. HPLC: t$_R$=2.96 min (ZQ2, polar_5 min).

Example 144

2-[4-(6-Amino-5-benzothiazol-2-ylpyridin-3-yl)-pyrazol-1-yl]-N-methylpropionamide The title compound was prepared according to the procedures described for 2-[4-(6-amino-5-benzothiazol-2-ylpyridin-3-yl)-pyrazol-1-yl]-1-morpholin-4-ylpropan-1-one. $^1$H NMR (400 MHz, CD$_3$OD): δ=1.78 (d, J=7.1 Hz, 3H), 2.76 (s, 3H), 5.02 (q, J=7.1 Hz, 1H), 7.38-7.44 (m, 1H), 7.49 (td, J=7.7, 1.3 Hz, 1H), 7.83 (s, 1H), 7.94 (d, J=8.1 Hz, 1H), 8.00 (d, J=8.1 Hz, 1H), 8.07 (s, 1H), 8.14 (d, J=2.3 Hz, 1H), 8.29 (d, J=2.0 Hz, 1H). MS (ES$^+$): m/z=379.14 (100) [MH$^+$]. HPLC: $t_R$=2.79 min (ZQ3, polar_5 min).

Example 145

2-[4-(6-Amino-5-benzothiazol-2-ylpyridin-3-yl)-pyrazol-1-yl]-propionamide

The title compound was prepared according to the procedures described for 2-[4-(6-amino-5-benzothiazol-2-ylpyridin-3-yl)-pyrazol-1-yl]-1-morpholin-4-ylpropan-1-one. $^1$H NMR (400 MHz, CD$_3$OD): δ=1.81 (d, J=7.3 Hz, 3H), 5.07 (q, J=7.3 Hz, 1H), 7.39-7.45 (m, 1H), 7.50 (td, J=7.7, 1.3 Hz, 1H), 7.86 (s, 1H), 7.96 (d, J=7.8 Hz, 1H), 8.01 (d, J=8.3 Hz, 1H), 8.09 (s, 1H), 8.16 (d, J=2.3 Hz, 1H), 8.30 (d, J=2.3 Hz, 1H). MS (ES$^+$): m/z=365.11 (100) [MH$^+$]. HPLC: $t_R$=2.68 min (ZQ3, polar_5 min).

Example 146

2-[4-(6-Amino-5-benzothiazol-2-ylpyridin-3-yl)-pyrazol-1-yl]-N-(2-methoxyethyl)-propionamide The title compound was prepared according to the procedures described for 2-[4-(6-amino-5-benzothiazol-2-ylpyridin-3-yl)-pyrazol-1-yl]-1-morpholin-4-ylpropan-1-one. $^1$H NMR (400 MHz, CD$_3$OD): δ=1.79 (d, J=7.1 Hz, 3H), 3.34 (s, 3H), 3.37-3.42 (m, 2H), 3.43-3.48 (m, 2H), 5.05 (q, J=7.2 Hz, 1H), 7.38-7.44 (m, 1H), 7.47-7.52 (m, 1H), 7.83 (s, 1H), 7.94 (d, J=7.6 Hz, 1H), 8.00 (d, J=7.8 Hz, 1H), 8.04 (s, 1H), 8.12 (d, J=2.3 Hz, 1H), 8.28 (d, J=2.0 Hz, 1H). MS (ES$^+$): m/z=423.16 (100) [MH$^+$]. HPLC: $t_R$=2.87 min (ZQ3, polar_5 min).

Example 147

2-[4-(6-Amino-5-benzothiazol-2-ylpyridin-3-yl)-pyrazol-1-yl]-N-(2-hydroxyethyl)-propionamide The title compound was prepared according to the procedures described for 2-[4-(6-amino-5-benzothiazol-2-ylpyridin-3-yl)-pyrazol-1-yl]-1-morpholin-4-ylpropan-1-one. $^1$H NMR (400 MHz, CD$_3$OD): δ=1.80 (d, J=7.1 Hz, 3H), 3.33-3.37 (m, 2H), 3.62 (t, J=5.6 Hz, 2H), 5.06 (q, J=7.2 Hz, 1H), 7.40-7.45 (m, 1H), 7.48-7.53 (m, 1H), 7.85 (s, 1H), 7.95 (d, J=7.3 Hz, 1H), 8.01 (d, J=7.8 Hz, 1H), 8.08 (s, 1H), 8.16 (d, J=2.0 Hz, 1H), 8.29 (d, J=2.3 Hz, 1H). MS (ES'): m/z=409.14 (100) [MH$^+$]. HPLC: $t_R$=2.61 min (ZQ3, polar_5 min).

Example 148

2-[4-(6-Amino-5-benzothiazol-2-ylpyridin-3-yl)-pyrazol-1-yl]-N,N-dimethylpropionamide The title compound was prepared according to the procedures described for 2-[4-(6-amino-5-benzothiazol-2-ylpyridin-3-yl)-pyrazol-1-yl]-1-morpholin-4-ylpropan-1-one. $^1$H NMR (400 MHz, CD$_3$OD): δ=1.72 (d, J=7.1 Hz, 3H), 2.99 (s, 3H), 3.12-3.18 (m, 3H), 5.55 (q, J=6.9 Hz, 1H), 7.40 (t, J=7.6 Hz, 1H), 7.46-7.52 (m, 1H), 7.77 (s, 1H), 7.93 (d, J=7.8 Hz, 1H), 7.98-8.01 (m, 2H), 8.11 (d, J=2.3 Hz, 1H), 8.27 (d, J=2.3 Hz, 1H). MS (ES$^+$): m/z=393.14 (100) [MH$^+$]. HPLC: $t_R$=2.90 min (ZQ3, polar_5 min).

Example 149

2-[4-(6-Amino-5-benzothiazol-2-ylpyridin-3-yl)-pyrazol-1-yl]-1-(3-hydroxypyrrolidin-1-yl)-propan-1-one The title compound was prepared according to the procedures described for 2-[4-(6-amino-5-benzothiazol-2-ylpyridin-3-yl)-pyrazol-1-yl]-1-morpholin-4-ylpropan-1-one. $^1$H NMR (400 MHz, CD$_3$OD): δ=1.76 (td, J=7.2, 3.5 Hz, 3H), 1.89-2.14 (m, 2H), 3.49-3.67 (m, 3H), 3.73-3.81 (m, 1H), 4.39-4.52 (m, 1H), 5.36-5.50 (m, 1H), 7.44 (t, J=7.3 Hz, 1H), 7.50-7.55 (m, 1H), 7.87 (s, 1H), 8.01 (dd, J=10.7, 8.0 Hz, 2H), 8.16-8.21 (m, 2H), 8.34 (br. s., 1H). MS (ES$^+$): m/z=435.16 (100) [MH$^+$]. HPLC: $t_R$=2.65 min (ZQ3, polar_5 min).

Example 150

2-[4-(6-Amino-5-benzothiazol-2-ylpyridin-3-yl)-pyrazol-1-yl]-1-(4-hydroxypiperidin-1-yl)-propan-1-one The title compound was prepared according to the procedures described for 2-[4-(6-amino-5-benzothiazol-2-ylpyridin-3-yl)-pyrazol-1-yl]-1-morpholin-4-ylpropan-1-one. $^1$H NMR (400 MHz, CD$_3$OD): δ=1.31-1.45 (m, 1H), 1.46-1.58 (m, J=16.5, 8.3, 8.3, 3.9 Hz, 1H), 1.72 (t, J=6.9 Hz, 3H), 1.77-1.93 (m, 2H), 3.32-3.48 (m, 2H), 3.80-3.99 (m, 2H), 4.18 (d, J=12.9 Hz, 1H), 5.60-5.68 (m, 1H), 7.40-7.45 (m, 1H), 7.51 (td, J=7.7, 1.3 Hz, 1H), 7.86 (d, J=5.8 Hz, 1H), 7.97-8.03 (m, 2H), 8.14 (s, 1H), 8.18 (d, J=2.0 Hz, 1H), 8.32 (s, 1H). MS (ES$^+$): m/z=449.15 (100) [MH$^+$]. HPLC: $t_R$=2.69 min (ZQ3, polar_5 min).

Example 151

2-[4-(6-Amino-5-benzothiazol-2-ylpyridin-3-yl)-pyrazol-1-yl]-1-pyrrolidin-1-ylpropan-1-one The title compound was prepared according to the procedures described for 2-[4-(6-amino-5-benzothiazol-2-ylpyridin-3-yl)-pyrazol-1-yl]-1-morpholin-4-ylpropan-1-one. $^1$H NMR (400 MHz, CD$_3$OD): δ=1.75 (d, J=7.1 Hz, 3H), 1.87-1.95 (m, 2H), 1.97-2.05 (m, 2H), 3.47 (t, J=7.1 Hz, 2H), 3.53-3.70 (m, 2H), 5.43 (q, J=7.1 Hz, 1H), 7.41-7.46 (m, 1H), 7.50-7.55 (m, 1H), 7.87 (s, 1H), 8.01 (dd, J=11.0, 7.7 Hz, 2H), 8.18 (s, 1H), 8.20 (d, J=2.3 Hz, 1H), 8.34 (d, J=2.0 Hz, 1H). MS (ES$^+$): m/z=419.15 (100) [MH$^+$]. HPLC: $t_R$=3.05 min (ZQ3, polar_5 min).

Example 152

2-[4-(6-Amino-5-benzothiazol-2-ylpyridin-3-yl)-pyrazol-1-yl]-1-piperidin-1-ylpropan-1-one The title compound was prepared according to the procedures described for 2-[4-(6-amino-5-benzothiazol-2-ylpyridin-3-yl)-pyrazol-1-yl]-1-morpholin-4-ylpropan-1-one. $^1$H NMR (400 MHz, CD$_3$OD): δ=1.44 (td, J=7.3, 3.9 Hz, 1H), 1.53-1.62 (m, 3H), 1.64-1.68 (m, 2H), 1.72 (d, J=7.1 Hz, 3H), 3.41-3.50 (m, 1H), 3.52-3.59 (m, 1H), 3.61-3.75 (m, 2H), 5.62 (q, J=6.9 Hz, 1H), 7.40-7.46 (m, 1H), 7.52 (td, J=7.6, 1.3 Hz, 1H), 7.86 (s, 1H), 8.00 (dd, J=10.9, 7.8 Hz, 2H), 8.14 (s, 1H), 8.18-8.20 (m, 1H), 8.32 (d, J=2.3 Hz, 1H). MS (ES$^+$): m/z=433.18 (100) [MH$^+$]. HPLC: $t_R$=3.30 min (ZQ3, polar_5 min).

Example 153

3-[4-(6-Amino-5-benzothiazol-2-ylpyridin-3-yl)-pyrazol-1-yl]-1-pyrrolidin-1-ylpropan-1-one A mixture of 3-[4-(6-amino-5-benzothiazol-2-ylpyridin-3-yl)-pyrazol-1-yl]-propionic acid (7.0 mg, 0.013 mmol), pyrrolidine (9 mg, 0.1 mmol), TBTU (8.24 mg, 0.0257 mmol), DIPEA (0.02 mL, 0.1 mmol), and DMF (2 mL, 0.02 mol) was stirred at rt for 10 min. The solution was transferred to a separatory funnel, diluted with EtOAc and washed 3× with water. The organic layer was concentrated in vacuo and loaded onto a prep TLC plate, eluting with 5% MeOH/DCM. The band containing the pure product was filtered off using 1:1 MeOH/DCM, and the filtrate was concentrated in vacuo to afford the title compound as a yellow solid. $^1$H NMR (400 MHz, CD$_3$OD): δ=1.85 (q, J=6.4 Hz, 2H), 1.88-1.96 (m, 2H), 2.92 (t, J=6.6 Hz, 2H), 3.39 (q, J=7.1 Hz, 4H), 4.49 (t, J=6.6 Hz, 2H), 7.39-7.44 (m, 1H), 7.47-7.52 (m, 1H), 7.81 (s, 1H), 7.94-7.97 (m, 2H), 8.00 (d, J=7.8 Hz, 1H), 8.12 (d, J=2.3 Hz, 1H), 8.27 (d, J=2.3 Hz, 1H). MS (ES$^+$): m/z=419.13 (100) [MH$^+$]. HPLC: t$_R$=2.99 min (ZQ3, polar_5 min).

3-[4-(6-Amino-5-benzothiazol-2-ylpyridin-3-yl)-pyrazol-1-yl]-propionic acid

A mixture of 3-(4-iodopyrazol-1-yl)-propionic acid methyl ester (174 mg, 0.623 mmol), 3-benzothiazol-2-yl-5-(4,4,5,5-tetramethyl-1,3,2-dioxaborolan-2-yl)-pyridin-2-ylamine (200.0 mg, 0.5662 mmol), Pd(PPh$_3$)$_4$ (50 mg, 0.04 mmol), potassium fluoride (98.7 mg, 1.70 mmol), and 4:1 dioxane:water (4:1, 1,4-dioxane:H$_2$O, 8 mL) was heated in the microwave reactor at 85° C. for 30 min. The solution was concentrated in vacuo, and dry-loaded onto silica gel for column chromatography. The material was eluted with 2% MeOH/DCM. The fractions containing the product were concentrated in vacuo. The material was dissolved in conc. HCl (4 mL) and heated to 60° C. for 30 min in a sealed tube. The solvent was removed using the corrosive pump to afford the title compound as an orange solid. MS (ES$^+$): m/z=366.14 (100) [MH$^+$]. HPLC: t$_R$=2.59 min (ZQ2, polar_5 min).

3-(4-Iodopyrazol-1-yl)-propionic acid methyl ester

To a mixture of 4-iodopyrazole (1.000 g, 5.155 mmol), Cs$_2$CO$_3$ (2.016 g, 6.186 mmol), and DMF (20 mL, 0.2 mol) was added methyl 3-chloropropanoate (758.1 mg, 6.186 mmol) at 0° C. The reaction was heated to 50° C. for 1 h. The material was transferred to a separatory funnel, diluted with EtOAc, and washed with water several times to remove DMF. The organic layer was dry-loaded onto silica gel, and column chromatography was used for purification, eluting with 3:1 Hexanes/EtOAc, affording the title compound as a clear liquid. MS (ES$^+$): m/z=280.95 (100) [MH$^+$]. HPLC: t$_R$=2.91 min (ZQ3, polar_5 min).

Example 154

(2S,4S)-4-[4-(6-Amino-5-benzothiazol-2-ylpyridin-3-yl)-pyrazol-1-yl]-pyrrolidine-2-carboxylic acid A mixture of 3-benzothiazol-2-yl-5-(4,4,5,5-tetramethyl-[1,3,2]dioxaborolan-2-yl)-pyridin-2-ylamine (BB8) (200 mg, 0.566 mmol), (2S,4S)-4-(4-iodopyrazol-1-yl)-pyrrolidine-1,2-dicarboxylic acid 1-benzyl ester 2-methyl ester (309.0 mg, 0.679 mmol), Pd(PPh$_3$)$_4$ (60 mg, 0.06 mmol), potassium fluoride (98.7 mg, 1.70 mmol), and 4:1 dioxane: water (5 mL) was heated in the microwave reactor at 85° C. for 30 min. The material was concentrated in vacuo, then dry-loaded onto silica gel for column chromatography. The product was eluted with 2→5% MeOH/DCM, and the fractions containing the product were concentrated in vacuo. The material was dissolved in conc. HCl, transferred to a sealed tube and heated at 60° C. for 2 h. The solvent was removed using the corrosive pump to afford the title compound as a brown solid. $^1$H NMR (400 MHz, CD$_3$OD): δ=2.73 (ddd, J=14.0, 6.5, 4.5 Hz, 1H), 3.07 (ddd, J=14.1, 10.0, 7.5 Hz, 1H), 3.81-3.93 (m, 2H), 4.68 (dd, J=10.0, 6.7 Hz, 1H), 5.36 (ddd, J=6.8, 3.8, 3.5 Hz, 1H), 7.56-7.63 (m, 2H), 8.05 (s, 1H), 8.08-8.11 (m, 1H), 8.16 (d, J=7.6 Hz, 1H), 8.32-8.36 (m, 2H), 8.72 (d, J=2.0 Hz, 1H). MS (ES'): m/z=407.13 (100) [MH$^+$]. HPLC: t$_R$=2.28 min (ZQ2, polar_5 min).

Example 155

(2S,4S)-4-[4-(6-Amino-5-benzothiazol-2-ylpyridin-3-yl)-pyrazol-1-yl]-pyrrolidine-2-carboxylic acid dimethylamide To a solution of (2S,4S)-4-[4-(6-amino-5-benzothiazol-2-ylpyridin-3-yl)-pyrazol-1-yl]-pyrrolidine-2-carboxylic acid (5.00 mg, 0.00969 mmol) in DMF (2 mL) at rt were added dimethylamine hydrochloride (20 mg, 0.25 mmol) and DIPEA (0.1 mL, 0.6 mmol), and the mixture was stirred for 1 min. TBTU (6.22 mg, 0.0194 mmol) was then added, and the solution was stirred for 10 min. The material was transferred to a separatory funnel. The organic layer was washed with water, and concentrated in vacuo. The material was loaded onto a prep TLC plate, eluting with 6% (7N NH$_3$ in MeOH)/DCM. The band containing the product was collected and filtered off with 1:1 MeOH/DCM. The filtrate was concentrated in vacuo to afford the title compound as a yellow solid. $^1$H NMR (400 MHz, CD$_3$OD): δ=2.15-2.21 (m, 1H), 2.82-2.91 (m, 1H), 3.00 (s, 3H), 3.12 (s, 3H), 3.23 (dd, J=12.4, 6.3 Hz, 1H), 3.49 (dd, J=12.0, 3.4 Hz, 1H), 4.15 (t, J=8.3 Hz, 1H), 4.98-5.05 (m, 1H), 7.42-7.47 (m, 1H), 7.53 (td, J=7.7, 1.3 Hz, 1H), 7.85 (s, 1H), 8.02 (dd, J=11.6, 7.8 Hz, 2H), 8.13 (s, 1H), 8.20 (d, J=2.3 Hz, 1H), 8.32 (d, J=2.0 Hz, 1H). MS (ES+): m/z=434.14 (100) [MH$^+$]. HPLC: t$_R$=2.12 min (ZQ2, polar_5 min).

Example 156

{(2S,4S)-4-[4-(6-Amino-5-benzothiazol-2-ylpyridin-3-yl)-pyrazol-1-yl]-pyrrolidin-2-yl}-pyrrolidin-1-ylmethanone The title compound was prepared according to the procedures described for (2S,4S)-4-[4-(6-amino-5-benzothiazol-2-ylpyridin-3-yl)-pyrazol-1-yl]-pyrrolidine-2-carboxylic acid dimethylamide. $^1$H NMR (400 MHz, CD$_3$OD): δ=1.92 (q, J=6.8 Hz, 2H), 1.98-2.03 (m, 2H), 2.21 (ddd, J=13.4, 7.8, 5.3 Hz, 1H), 2.85 (dt, J=13.6, 8.2 Hz, 1H), 3.23 (dd, J=12.4, 6.6 Hz, 1H), 3.43-3.53 (m, 4H), 3.64 (dt, J=10.3, 6.6 Hz, 1H), 4.01 (t, J=8.1 Hz, 1H), 4.98-5.04 (m, 1H), 7.41-7.46 (m, 1H), 7.49-7.54 (m, 1H), 7.84 (s, 1H), 8.00 (dd, J=11.4, 7.8 Hz, 2H), 8.15 (s, 1H), 8.16-8.19 (m, 1H), 8.31 (d, J=2.3 Hz, 1H). MS (ES$^+$): m/z=460.10 (100) [MH$^+$]. HPLC: t$_R$=2.12 min (ZQ2, polar_5 min).

Example 157

{(2S,4S)-4-[4-(6-Amino-5-benzothiazol-2-ylpyridin-3-yl)-pyrazol-1-yl]-pyrrolidin-2-yl}-morpholin-4-ylmethanone The title compound was prepared according to the procedures described for (2S,4S)-4-[4-(6-amino-5-benzothiazol- 2-ylpyridin-3-yl)-pyrazol-1-yl]-pyrrolidine-2-carboxylic acid dimethylamide. $^1$H NMR (400 MHz, CD$_3$OD): δ=2.17-2.27 (m, 1H), 2.84 (dt, J=13.6, 8.3 Hz, 1H), 3.24 (dd, J=12.4, 6.6 Hz, 1H), 3.50 (dd, J=12.5, 3.4 Hz, 1H), 3.58-3.74 (m, 8H), 4.14 (t, J=8.2 Hz, 1H), 4.98-5.03 (m, 1H), 7.43-7.47 (m, 1H), 7.53 (td, J=7.7, 1.3 Hz, 1H), 7.85 (s, 1H), 8.02 (dd, J=11.2, 7.5 Hz, 2H), 8.13 (s, 1H), 8.19 (d, J=2.3 Hz, 1H), 8.32 (d, J=2.3 Hz, 1H). MS (ES$^+$): m/z=476.14 (100) [MH$^+$]. HPLC: $t_R$=2.10 min (ZQ2, polar__5 min).

Example 158

{(2S,4S)-4-[4-(6-Amino-5-benzothiazol-2-ylpyridin-3-yl)-pyrazol-1-yl]-pyrrolidin-2-yl}-piperidin-1-ylmethanone The title compound was prepared according to the procedures described for (2S,4S)-4-[4-(6-amino-5-benzothiazol-2-ylpyridin-3-yl)-pyrazol-1-yl]-pyrrolidine-2-carboxylic acid dimethylamide. $^1$H NMR (400 MHz, CD$_3$OD): δ=1.55-1.72 (m, 6H), 2.13-2.19 (m, 1H), 2.84 (dt, J=13.6, 8.2 Hz, 1H), 3.22 (dd, J=12.4, 6.6 Hz, 1H), 3.47-3.61 (m, 5H), 4.13 (t, J=8.3 Hz, 1H), 4.98-5.04 (m, 1H), 7.42-7.47 (m, 1H), 7.53 (td, J=7.7, 1.3 Hz, 1H), 7.85 (s, 1H), 8.01 (dd, J=11.9, 7.8 Hz, 2H), 8.11 (s, 1H), 8.19 (d, J=2.0 Hz, 1H), 8.32 (d, J=2.3 Hz, 1H). MS (ES'): m/z=474.13 (100) [MH$^+$]. HPLC: $t_R$=2.21 min (ZQ2, polar__5 min).

Example 159

{(2S,4S)-4-[4-(6-Amino-5-benzothiazol-2-ylpyridin-3-yl)-pyrazol-1-yl]-pyrrolidin-2-yl}-(3-hydroxypyrrolidin-1-yl)-methanone The title compound was prepared according to the procedures described for (2S,4S)-4-[4-(6-amino-5-benzothiazol-2-ylpyridin-3-yl)-pyrazol-1-yl]-pyrrolidine-2-carboxylic acid dimethylamide. $^1$H NMR (400 MHz, CD$_3$OD): δ=1.86-1.95 (m, 1H), 1.97-2.07 (m, 1H), 2.16 (s, 1H), 2.78 (d, J=8.8 Hz, 1H), 3.15 (dd, J=11.9, 5.8 Hz, 1H), 3.37-3.44 (m, 2H), 3.47-3.56 (m, 2H), 3.64 (d, J=14.7 Hz, 1H), 3.91-3.99 (m, 1H), 4.30-4.42 (m, 1H), 4.89-4.96 (m, 1H), 7.33-7.38 (m, 1H), 7.41-7.46 (m, 1H), 7.75 (s, 1H), 7.92 (dd, J=11.0, 8.2 Hz, 2H), 8.05-8.08 (m, 1H), 8.10 (t, J=1.8 Hz, 1H), 8.23 (s, 1H). MS (ES$^+$): m/z=476.09 (100) [MH$^+$]. HPLC: $t_R$=2.00 min (ZQ2, polar__5 min).

Example 160

{(2S,4S)-4-[4-(6-Amino-5-benzothiazol-2-ylpyridin-3-yl)-pyrazol-1-yl]-pyrrolidin-2-yl}-azetidin-1-yl-methanone The title compound was prepared according to the procedures described for (2S,4S)-4-[4-(6-amino-5-benzothiazol-2-ylpyridin-3-yl)-pyrazol-1-yl]-pyrrolidine-2-carboxylic acid dimethylamide. $^1$H NMR (400 MHz, CD$_3$OD): δ=2.23 (ddd, J=13.6, 8.0, 5.4 Hz, 1H), 2.32-2.41 (m, 2H), 2.70-2.79 (m, 1H), 3.21-3.27 (m, 1H), 3.40-3.48 (m, 1H), 3.82 (t, J=8.2 Hz, 1H), 4.02-4.11 (m, 2H), 4.24-4.39 (m, 2H), 4.99 (br. s., 1H), 7.43-7.47 (m, 1H), 7.53 (td, J=7.7, 1.3 Hz, 1H), 7.85 (s, 1H), 8.02 (dd, J=11.2, 8.0 Hz, 2H), 8.18 (s, 1H), 8.20 (d, J=2.3 Hz, 1H), 8.33 (d, J=2.3 Hz, 1H). MS (ES$^+$): m/z=446.09 (100) [MH$^+$]. HPLC: $t_R$=2.05 min (ZQ2, polar__5 min).

Example 161

{4-[4-(6-Amino-5-benzothiazol-2-ylpyridin-3-yl)-pyrazol-1-yl]-piperidin-1-yl}-acetic acid A mixture of 3-benzothiazol-2-yl-5-(1-piperidin-4-yl-1H-pyrazol-4-yl)-pyridin-2-ylamine (211.0 mg, 0.5604 mmol), Cs$_2$CO$_3$ (730 mg, 2.24 mmol), and DMF (10 mL, 0.1 mol) at 0° C. was charged with methyl chloroacetate (0.0493 mL, 0.560 mmol) and then heated at 40° C. overnight. The solvent was removed in vacuo, and the material was dry-loaded onto silica gel for column chromatography, eluting with 2→5% MeOH/DCM. The fractions containing the pure ester were concentrated in vacuo and redissolved in conc. HCl. The material was transferred to a sealed tube, and heated overnight at 50° C. The HCl was removed using the corrosive pump to afford the title compound as a yellow solid. $^1$H NMR (400 MHz, DMSO-d6): δ=2.36 (br. s., 4H), 3.34 (d, J=11.4 Hz, 2H), 3.71 (d, J=9.1 Hz, 2H), 4.19 (br. s., 2H), 4.31-4.41 (m, 1H), 4.51 (br. s., 2H), 7.54-7.60 (m, 1H), 7.61-7.67 (m, 1H), 8.12-8.20 (m, 2H), 8.24 (d, J=7.1 Hz, 1H), 8.52 (d, J=1.3 Hz, 1H), 8.58-8.65 (m, 2H), 10.49 (br, s., 1H). MS (ES$^+$): m/z=435.09 (100) [MH$^+$]. HPLC: $t_R$=2.24 min (ZQ2, polar__5 min).

Example 162

2-{4-[4-(6-Amino-5-benzothiazol-2-ylpyridin-3-yl)-pyrazol-1-yl]-piperidin-1-yl}-acetamide A mixture of {4-[4-(6-amino-5-benzothiazol-2-ylpyridin-3-yl)-pyrazol-1-yl]-piperidin-1-yl}-acetic acid (10.0 mg, 0.0184 mmol), NH$_4$Cl (2.0 mg, 0.037 mmol), TBTU (8.86 mg, 0.0276 mmol) and DMF (1 mL) was charged with DIPEA (0.03 mL, 0.2 mmol) and allowed to stir at rt for 10 min. The solution was used directly for HPLC purification. The fractions containing the pure product were concentrated in vacuo to afford the title compound as a white solid. $^1$H NMR (400 MHz, CD$_3$OD): δ=2.17-2.35 (m, 4H), 2.69 (td, J=11.9, 2.5 Hz, 2H), 3.28 (d, J=12.4 Hz, 2H), 3.37 (s, 2H), 4.29-4.40 (m, 1H), 7.41-7.47 (m, 1H), 7.53 (td, J=7.6, 1.3 Hz, 1H), 7.89 (s, 1H), 8.01 (dd, J=12.3, 8.0 Hz, 2H), 8.11 (s, 1H), 8.19 (d, J=2.0 Hz, 1H), 8.32 (d, J=2.3 Hz, 1H).

Example 163

2-{4-[4-(6-Amino-5-benzothiazol-2-ylpyridin-3-yl)-pyrazol-1-yl]-piperidin-1-yl}-N-methylacetamide The title compound was prepared according to the procedures described for 2-{4-[4-(6-amino-5-benzothiazol-2-ylpyridin-3-yl)-pyrazol-1-yl]-piperidin-1-yl}-acetamide. $^1$H NMR (400 MHz, CD$_3$OD): δ=2.10-2.32 (m, 4H), 2.52 (t, J=9.5 Hz, 2H), 2.81 (s, 3H), 3.11 (d, J=12.4 Hz, 2H), 3.20 (s, 2H), 4.21-4.33 (m, 1H), 7.40-7.47 (m, 1H), 7.49-7.56 (m, 1H), 7.88 (s, 1H), 8.01 (dd, J=12.0, 8.0 Hz, 2H), 8.11 (s, 1H), 8.19 (d, J=2.0 Hz, 1H), 8.33 (d, J=2.0 Hz, 1H).

Example 164

2-{4-[4-(6-Amino-5-benzothiazol-2-ylpyridin-3-yl)-pyrazol-1-yl]-piperidin-1-yl}-N,N-dimethylacetamide The title compound was prepared according to the procedures described for 2-{4-[4-(6-amino-5-benzothiazol-2-ylpyridin-3-yl)-pyrazol-1-yl]-piperidin-1-yl}-acetamide. $^1$H NMR (400 MHz, CD₃OD): δ=2.28-2.50 (m, 4H), 2.98-3.04 (m, 3H), 3.04-3.13 (m, 5H), 3.56 (d, J=12.1 Hz, 2H), 4.02 (s, 2H), 4.44-4.56 (m, 1H), 7.44 (t, J=7.6 Hz, 1H), 7.50-7.57 (m, 1H), 7.90 (s, 1H), 8.01 (dd, J=12.8, 8.0 Hz, 2H), 8.12 (s, 1H), 8.18 (d, J=2.0 Hz, 1H), 8.32 (d, J=2.3 Hz, 1H).

Example 165

2-{4-[4-(6-Amino-5-benzothiazol-2-ylpyridin-3-yl)-pyrazol-1-yl]-piperidin-1-yl}-1-azetidin-1-yletha-none The title compound was prepared according to the procedures described for 2-{4-[4-(6-amino-5-benzothiazol-2-ylpyridin-3-yl)-pyrazol-1-yl]-piperidin-1-yl}-acetamide. ¹H NMR (400 MHz, CD₃OD): δ=2.14-2.31 (m, 4H), 2.36 (dt, J=15.7, 7.8 Hz, 2H), 2.58-2.73 (m, 2H), 3.26 (br. s., 2H), 3.41 (s, 2H), 4.07 (t, J=8.0 Hz, 2H), 4.28-4.39 (m, 3H), 7.40-7.48 (m, 1H), 7.53 (td, J=7.7, 1.3 Hz, 1H), 7.88 (s, 1H), 8.02 (dd, J=12.1, 8.1 Hz, 2H), 8.13 (s, 1H), 8.20 (d, J=2.3 Hz, 1H), 8.33 (d, J=2.3 Hz, 1H).

Example 166

2-{4-[4-(6-Amino-5-benzothiazol-2-ylpyridin-3-yl)-pyrazol-1-yl]-piperidin-1-yl}-1-pyrrolidin-1-yletha-none The title compound was prepared according to the procedures described for 2-{4-[4-(6-amino-5-benzothiazol-2-ylpyridin-3-yl)-pyrazol-1-yl]-piperidin-1-yl}-acetamide. ¹H NMR (400 MHz, CD₃OD): δ=1.86-1.97 (m, 2H), 1.98-2.07 (m, 2H), 2.27-2.47 (m, 4H), 2.97-3.08 (m, 2H), 3.44-3.61 (m, 6H), 3.89 (s, 2H), 4.42-4.53 (m, 1H), 7.41-7.47 (m, 1H), 7.53 (td, J=7.6, 1.1 Hz, 1H), 7.90 (s, 1H), 8.01 (dd, J=13.4, 7.8 Hz, 2H), 8.13 (s, 1H), 8.19 (d, J=2.3 Hz, 1H), 8.33 (d, J=2.0 Hz, 1H).

Example 167

2-{4-[4-(6-Amino-5-benzothiazol-2-ylpyridin-3-yl)-pyrazol-1-yl]-piperidin-1-yl}-1-(3-hydroxypyrroli-din-1-yl)ethanone The title compound was prepared according to the procedures described for 2-{4-[4-(6-amino-5-benzothiazol-2-ylpyridin-3-yl)-pyrazol-1-yl]-piperidin-1-yl}-acetamide. ¹H NMR (400 MHz, CD₃OD): δ=1.91-2.16 (m, 2H), 2.25-2.43 (m, 4H), 2.92-3.07 (m, 2H), 3.44-3.69 (m, 3.76-3.96 (m, 2H), 4.41-4.53 (m, 2H), 7.40-7.48 (m, 1H), 7.48-7.56 (m, 1H), 7.89 (s, 1H), 8.01 (dd, J=13.3, 7.7 Hz, 2H), 8.13 (s, 1H), 8.19 (d, J=2.0 Hz, 1H), 8.32 (d, J=2.3 Hz, 1H).

Example 168

2-{4-[4-(6-Amino-5-benzothiazol-2-ylpyridin-3-yl)-pyrazol-1-yl]-piperidin-1-yl}-1-piperidin-1-yletha-none The title compound was prepared according to the procedures described for 2-{4-[4-(6-amino-5-benzothiazol-2-ylpyridin-3-yl)-pyrazol-1-yl]-piperidin-1-yl}-acetamide. ¹H NMR (400 MHz, CD₃OD): δ=1.51-1.76 (m, 6H), 2.25-2.45 (m, 4H), 2.94-3.08 (m, 2H), 3.42-3.48 (m, 3.48-3.61 (m, 4H), 3.98 (s, 2H), 4.47 (ddd, J=10.2, 5.6, 5.2 Hz, 1H), 7.39-7.47 (m, 1H), 7.48-7.56 (m, 1H), 7.89 (s, 1H), 8.00 (dd, J=13.4, 7.8 Hz, 2H), 8.11 (s, 1H), 8.18 (d, J=2.0 Hz, 1H), 8.31 (d, J=2.0 Hz, 1H).

Example 169

2-{4-[4-(6-Amino-5-benzothiazol-2-ylpyridin-3-yl)-pyrazol-1-yl]-piperidin-1-yl}-1-(4-hydroxypiperidin-1-yl)ethanone The title compound was prepared according to the procedures described for 2-{4-[4-(6-amino-5-benzothiazol-2-ylpyridin-3-yl)-pyrazol-1-yl]-piperidin-1-yl}-acetamide. ¹H NMR (400 MHz, CD₃OD): δ=1.42-1.64 (m, 2H), 1.83-2.00 (m, 2H), 2.27-2.44 (m, 4H), 2.94-3.05 (m, 2H), 3.19-3.31 (m, 2H), 3.51 (d, J=12.4 Hz, 2H), 3.77 (td, J=9.2, 4.2 Hz, 1H), 3.86-4.11 (m, 4H), 4.42-4.54 (m, 1H), 7.41-7.48 (m, 1H), 7.50-7.57 (m, 1H), 7.90 (s, 1H), 8.01 (dd, J=13.5, 8.0 Hz, 2H), 8.13 (s, 1H), 8.20 (d, J=2.3 Hz, 1H), 8.33 (d, J=2.0 Hz, 1H).

Example 170

2-{4-[4-(6-Amino-5-benzothiazol-2-ylpyridin-3-yl)-pyrazol-1-yl]-piperidin-1-yl}-1-morpholin-4-yletha-none The title compound was prepared according to the procedures described for 2-{4-[4-(6-amino-5-benzothiazol-2-ylpyridin-3-yl)-pyrazol-1-yl]-piperidin-1-yl}-acetamide. ¹H NMR (400 MHz, CD₃OD): δ=2.26-2.43 (m, 4H), 2.85-3.02 (m, 2H), 3.48 (d, J=12.6 Hz, 2H), 3.53-3.58 (m, 2H), 3.63 (t, J=4.5 Hz, 2H), 3.67-3.77 (m, 4H), 4.46 (ddd, J=10.2, 5.3, 5.2 Hz, 1H), 7.42-7.49 (m, 1H), 7.50-7.57 (m, 1H), 7.91 (s, 1H), 8.02 (dd, J=12.9, 8.1 Hz, 2H), 8.14 (s, 1H), 8.20 (d, J=2.3 Hz, 1H), 8.33 (d, J=2.0 Hz, 1H).

Example 171

2-{4-[4-(6-Amino-5-benzothiazol-2-ylpyridin-3-yl)-pyrazol-1-yl]-piperidin-1-yl}-N-(2-hydroxyethyl)-acetamide The title compound was prepared according to the procedures described for 2-{4-[4-(6-amino-5-benzothiazol-2-ylpyridin-3-yl)-pyrazol-1-yl]-piperidin-1-yl}-acetamide. ¹H NMR (400 MHz, CD₃OD): δ=2.15-2.34 (m, 4H), 2.55-2.65 (m, 2H), 3.18 (d, J=12.1 Hz, 2H), 3.29 (s, 2H), 3.39 (t, J=5.6 Hz, 2H), 3.60-3.68 (m, 2H), 4.25-4.37 (m, 1H), 7.41-7.48 (m, 1H), 7.53 (td, J=7.6, 1.3 Hz, 1H), 7.88 (s, 1H), 8.02 (dd, J=12.6, 7.8 Hz, 2H), 8.12 (s, 1H), 8.20 (d, J=2.0 Hz, 1H), 8.33 (d, J=1.8 Hz, 1H).

Example 172

2-{4-[4-(6-Amino-5-benzothiazol-2-ylpyridin-3-yl)-pyrazol-1-yl]-piperidin-1-yl}-N-(2-methoxyethyl)-acetamide The title compound was prepared according to the procedures described for 2-{4-[4-(6-amino-5-benzothiazol-2-ylpyridin-3-yl)-pyrazol-1-yl]-piperidin-1-yl}-acetamide. ¹H NMR (400 MHz, CD₃OD): δ=2.12-2.30 (m, 4H), 2.52 (t, J=10.6 Hz, 2H), 3.12 (d, J=11.9 Hz, 2H), 3.21 (s, 2H), 3.37 (s, 3H), 3.42-3.47 (m, 2H), 3.47-3.52 (m, 2H), 4.22-4.34 (m, 1H), 7.40-7.47 (m, 1H), 7.49-7.55 (m, 1H), 7.87 (s, 1H), 8.00 (dd, J=11.5, 8.0 Hz, 2H), 8.10 (s, 1H), 8.17 (d, J=2.3 Hz, 1H), 8.31 (d, J=2.0 Hz, 1H).

Example 173

2-{4-[4-(6-Amino-5-benzothiazol-2-ylpyridin-3-yl)-pyrazol-1-yl]-piperidin-1-yl}-N,N-bis-(2-methoxyethyl)-acetamide

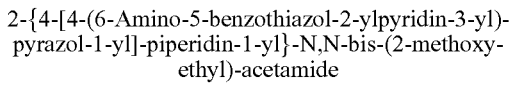

The title compound was prepared according to the procedures described for 2-{4-[4-(6-amino-5-benzothiazol-2-ylpyridin-3-yl)-pyrazol-1-yl]-piperidin-1-yl}-acetamide. $^1$H NMR (400 MHz, CD$_3$OD): δ=2.22-2.42 (m, 4H), 2.91 (td, J=11.6, 2.8 Hz, 2H), 3.34 (s, 3H), 3.38 (s, 3H), 3.43 (d, J=12.4 Hz, 2H), 3.53-3.68 (m, 8H), 3.94 (s, 2H), 4.38-4.49 (m, 1H), 7.41-7.47 (m, 1H), 7.53 (td, J=7.6, 1.3 Hz, 1H), 7.89 (s, 1H), 8.01 (dd, J=12.9, 7.8 Hz, 2H), 8.12 (s, 1H), 8.18 (d, J=2.3 Hz, 1H), 8.32 (d, J=2.0 Hz, 1H).

Example 174

(2R,4S)-4-[4-(6-Amino-5-benzothiazol-2-ylpyridin-3-yl)-pyrazol-1-yl]-pyrrolidine-2-carboxylic acid

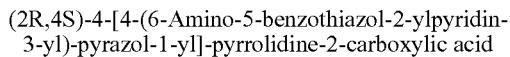

A mixture of 3-benzothiazol-2-yl-5-(4,4,5,5-tetramethyl-[1,3,2]dioxaborolan-2-yl)-pyridin-2-ylamine (BB8) (151 mg, 0.428 mmol), (2R,4S)-4-(4-iodopyrazol-1-yl)-pyrrolidine-1,2-dicarboxylic acid 1-benzyl ester 2-methyl ester (177 mg, 0.389 mmol), Pd(PPh$_3$)$_4$ (20 mg, 0.02 mmol), potass fluoride (67.8 mg, 1.17 mmol), and 4:1 dioxane:water (4 mL) was heated in the microwave reactor at 85° C. for 30 min. The solution was dry-loaded onto silica gel for column chromatography, eluting with 2→5% MeOH/DCM. The fractions containing the product were concentrated in vacuo and dissolved in conc. HCl. The material was heated to 60° C. for 3 h in a sealed tube. The solvent was removed on the corrosive pump to afford the title compound as an orange solid. $^1$H NMR (400 MHz, CD$_3$OD): δ=2.55-2.67 (m, 1H), 2.74 (br. s., 1H), 3.76-3.87 (m, 2H), 4.45 (t, J=8.6 Hz, 1H), 5.25 (dd, J=6.1, 3.0 Hz, 1H), 7.44 (t, J=7.6 Hz, 1H), 7.49-7.55 (m, 1H), 7.88 (s, 1H), 7.97 (d, J=7.6 Hz, 1H), 8.02 (d, J=7.8 Hz, 1H), 8.06 (s, 1H), 8.16 (d, J=2.0 Hz, 1H), 8.30 (d, J=2.0 Hz, 1H).

Example 175

(2R,4S)-4-[4-(6-Amino-5-benzothiazol-2-ylpyridin-3-yl)-pyrazol-1-yl]-pyrrolidine-2-carboxylic acid dimethylamide A mixture of (2R,4S)-4-[4-(6-amino-5-benzothiazol-2-ylpyridin-3-yl)-pyrazol-1-yl]-pyrrolidine-2-carboxylic acid (10.00 mg, 0.019 mmol), dimethylamine (0.009 g, 0.2 mmol), TBTU (12.4 mg, 0.0388 mmol), and DMF (1 mL) was charged with DIPEA (0.03 mL, 0.2 mmol) and allowed to stir at rt for 10 min. The solution was used directly for HPLC purification. The fractions containing the pure product were concentrated in vacuo to afford the title compound as a yellow solid. $^1$H NMR (400 MHz, CD$_3$OD): δ=2.40-2.51 (m, 1H), 2.87 (d, J=6.1 Hz, 1H), 3.04 (s, 3H), 3.09 (s, 3H), 3.72 (br. s., 1H), 3.85 (dd, J=12.5, 6.4 Hz, 1H), 5.02 (t, J=8.7 Hz, 1H), 5.29 (br. s., 1H), 7.42-7.48 (m, 1H), 7.54 (td, J=7.7, 1.3 Hz, 1H), 7.96 (s, 1H), 8.02 (dd, J=15.2, 7.6 Hz, 2H), 8.14 (s, 1H), 8.21 (d, J=2.3 Hz, 1H), 8.33 (d, J=2.3 Hz, 1H).

Example 176

{(2R,4S)-4-[4-(6-Amino-5-benzothiazol-2-ylpyridin-3-yl)-pyrazol-1-yl]-pyrrolidin-2-yl}-pyrrolidin-1-ylmethanone

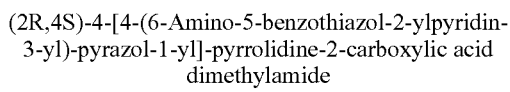

The title compound was prepared according to the procedures described for (2R,4S)-4-[4-(6-amino-5-benzothiazol-2-ylpyridin-3-yl)-pyrazol-1-yl]-pyrrolidine-2-carboxylic acid dimethylamide. $^1$H NMR (400 MHz, CD$_3$OD): δ=1.89-2.07 (m, 4H), 2.41-2.55 (m, 1H), 2.86 (s, 1H), 3.43-3.67 (m, 5H), 3.78-3.87 (m, 1H), 4.79 (t, J=8.6 Hz, 1H), 5.27 (br. s., 1H), 7.42-7.48 (m, 1H), 7.51-7.57 (m, 1H), 7.95 (s, 1H), 8.02 (dd, J=15.3, 8.0 Hz, 2H), 8.14 (s, 1H), 8.21 (d, J=2.0 Hz, 1H), 8.34 (d, J=2.3 Hz, 1H).

Example 177

{(2R,4S)-4-[4-(6-Amino-5-benzothiazol-2-ylpyridin-3-yl)-pyrazol-1-yl]-pyrrolidin-2-yl}-(3-hydroxypyrrolidin-1-yl)methanone

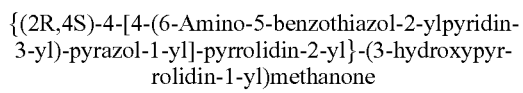

The title compound was prepared according to the procedures described for (2R,4S)-4-[4-(6-amino-5-benzothiazol-2-ylpyridin-3-yl)-pyrazol-1-yl]-pyrrolidine-2-carboxylic acid dimethylamide. $^1$H NMR (400 MHz, CD$_3$OD): δ=1.93-2.18 (m, 2H), 2.44-2.56 (m, 1H), 2.79-2.93 (m, 1H), 3.55 (d, J=16.9 Hz, 2H), 3.61-3.79 (m, 3H), 3.85 (d, J=14.4 Hz, 1H), 4.48 (d, J=18.4 Hz, 1H), 4.72-4.84 (m, 1H), 5.30 (br. s., 1H), 7.42-7.49 (m, 1H), 7.51-7.58 (m, 1H), 7.96 (s, 1H), 8.02 (dd, J=15.0, 8.0 Hz, 2H), 8.14 (s, 1H), 8.20 (d, J=2.0 Hz, 1H), 8.34 (d, J=2.0 Hz, 1H).

Example 178

{(2R,4S)-4-[4-(6-Amino-5-benzothiazol-2-ylpyridin-3-yl)-pyrazol-1-yl]-pyrrolidin-2-yl}-piperidin-1-ylmethanone

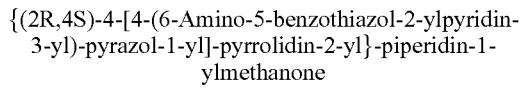

The title compound was prepared according to the procedures described for (2R,4S)-4-[4-(6-amino-5-benzothiazol-2-ylpyridin-3-yl)-pyrazol-1-yl]-pyrrolidine-2-carboxylic acid dimethylamide. $^1$H NMR (400 MHz, CD$_3$OD): δ=1.54-1.77 (m, 6H), 2.49 (dd, J=9.1, 7.1 Hz, 1H), 2.83-2.92 (m, 1H), 3.48 (t, J=5.4 Hz, 2H), 3.57-3.69 (m, 2H), 3.75 (br. s., 1H), 3.84-3.92 (m, 1H), 5.05 (t, J=9.0 Hz, 1H), 5.31 (br. s., 1H), 7.43-7.50 (m, 1H), 7.53-7.58 (m, 1H), 7.98 (s, 1H), 8.04 (dd, J=15.5, 8.0 Hz, 2H), 8.15 (s, 1H), 8.22 (d, J=2.3 Hz, 1H), 8.35 (d, J=2.3 Hz, 1H).

Example 179

{(2R,4S)-4-[4-(6-Amino-5-benzothiazol-2-ylpyridin-3-yl)-pyrazol-1-yl]-pyrrolidin-2-yl}-morpholin-4-ylmethanone

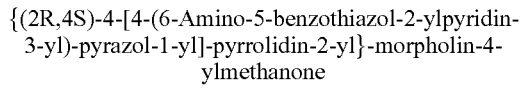

The title compound was prepared according to the procedures described for (2R,4S)-4-[4-(6-amino-5-benzothiazol-2-ylpyridin-3-yl)-pyrazol-1-yl]-pyrrolidine-2-carboxylic acid dimethylamide. $^1$H NMR (400 MHz, CD$_3$OD): δ=2.43-2.56 (m, 1H), 2.78-2.90 (m, 1H), 3.55 (br. s., 2H), 3.62-3.75 (m, 7H), 3.79-3.91 (m, 1H), 4.97-5.03 (m, 1H), 5.21-5.34 (m, 1H), 7.42-7.49 (m, 1H), 7.51-7.57 (m, 1H), 7.96 (br. s., 1H), 8.02 (dd, J=15.3, 7.7 Hz, 2H), 8.11-8.16 (m, 1H), 8.20 (d, J=2.3 Hz, 1H), 8.33 (d, J=2.3 Hz, 1H).

Example 180

{(S)-4-[4-(6-Amino-5-benzothiazol-2-ylpyridin-3-yl)-pyrazol-1-yl]-pyrrolidin-2-yl}-methanol

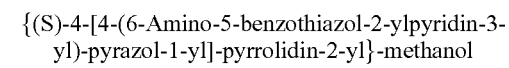

A solution of (2S,4S)-4-[4-(6-amino-5-benzothiazol-2-ylpyridin-3-yl)-pyrazol-1-yl]-pyrrolidine-2-carboxylic acid (10.0 mg, 0.0155 mmol) in THF (4 mL, 0.05 mol) was cooled to −78° C. LiAlH$_4$ (1.0 M in THF; 0.2 mL, 0.2 mmol) was added slowly, and the mixture was allowed to warm to rt overnight. The material was concentrated in vacuo, then dissolved in DCM, transferred to a separatory funnel, and washed with sat. NaHCO$_3$. The organic layer was loaded onto a prep TLC plate, eluting with 8% (7N NH$_3$ in MeOH)/DCM. The band containing the product was filtered off using 1:1 MeOH/DCM. The filtrate was concentrated in vacuo to afford the title compound (mixture of diastereomers) as a yellow solid. MS (ES+): m/z=393.14 [MH$^+$].

Example 181

5-(1-Azetidin-3-yl-1H-pyrazol-4-yl)-3-benzothiazol-2-ylpyridin-2-ylamine trifluoroacetate A solution of 3-benzothiazol-2-yl-5-(4,4,5,5-tetramethyl-1,3,2-dioxaborolan-2-yl)pyridin-2-ylamine (BB8) (30 mg, 0.080 mmol), 3-(4-iodopyrazol-1-yl)-azetidine-1-carboxylic acid tert-butyl ester (59 mg, 0.17 mmol), potassium carbonate (40 mg, 0.20 mmol), and Pd(dppf)Cl$_2$ (3 mg, 0.01 mmol) in 1,4-dioxane (1.5 mL) and H$_2$O (0.5 mL) was left to stir at 100° C. for 30 min in the microwave reactor. The mixture was passed through PL-Thiol MP SPE and the residue was concentrated in vacuo. The resulting oil was partitioned between EtOAc and water (3×). The combined organic extracts were treated with brine, dried over anhydrous Na$_2$SO$_4$, filtered, and concentrated in vacuo. The residue was purified by prep TLC (EtOAc:hexane (3:2)), giving 3-[4-(6-Amino-5-benzothiazol-2-ylpyridin-3-yl)-pyrazol-1-yl]-azetidine-1-carboxylic acid tert-butyl ester, MS (ES+): m/z=449 [MH$^+$]. This material was left to stir at rt in a (1:1) DCM:TFA mixture for 15 min. The solid that formed was filtered off and dried in vacuo, affording the title compound as a yellow solid. $^1$H NMR (400 MHz, CD$_3$OD): δ=4.53 (d, J=8.1 Hz, 1H), 4.58 (d, J=7.3 Hz, 4H), 5.49 (quint, J=7.4 Hz, 1H), 7.49-7.56 (m, 1H), 7.60 (dd, J=15.4, 1.3 Hz, 1H), 8.07 (d, J=8.1 Hz, 1H), 8.12 (d, J=7.8 Hz, 1H), 8.16 (s, 1H), 8.21 (s, 1H), 8.33 (d, J=2.3 Hz, 1H), 8.57 (d, J=2.0 Hz, 1H). MS (ES+): m/z=349.16 (100) [MH$^+$]. HPLC: $t_R$=1.99 min (ZQ2, polar_5 min).

3-(4-Iodopyrazol-1-yl)-1-azetidine-1-carboxylic acid tert-butyl ester

A mixture of 3-methanesulfonyloxyazetidine-1-carboxylic acid tert-butyl ester (4.0 g, 15.9 mmol), 4-iodopyrazole (3.1 g, 15.9 mmol), potassium carbonate (2.85 g, 20.6 mmol, 1.3 eq), and 18-crown-6 (400 mg) in dry DMF (15 mL) was heated at 85° C. for 24 h. The reaction mixture was cooled to RT, poured into water and extracted with EtOAc (3×20 mL). The combined organic layers were washed with water (2×10 mL), dried over anhydrous sodium sulfate, filtered, and concentrated in vacuo. The residue was purified by column chromatography using hexanes/DCM/EtOAc (8:1:1) to give the title compound. $^1$H NMR (300 MHz, CDCl$_3$): δ=1.47 (s, 9H), 4.29 (m, 2H), 4.36 (m, 2H), 5.05 (m, 1H), 7.59 (s, 1H), 7.60 (s, 1H).

General Procedure F for Libraries Based on BB7

To a solution of 3-benzothiazol-2-yl-5-bromopyridin-2-ylamine (BB7) (25.0 mg, 0.0529 mmol, 1 eq.), boronic acid or ester (0.118 mmol, 2 eq.), and potassium carbonate (24.5 mg, 0.178 mmol, 3 eq.) in dioxane (0.9 mL) and water (0.3 mL) was added 1,1'-bis(diphenylphosphino)-ferrocene]dichloropalladium(II) DCM (2 mg, 0.003 mmol, 0.05 eq.). The mixture was evacuated and filled with nitrogen 3 times and heated in the microwave reactor to 100° C. for 30 min. The reaction mixture was passed through 500 mg Thiol-SPE to remove palladium. The clear solution was submitted to MDPS for purification.

The following examples were prepared using General Procedure F.

Example 182

[4-(6-Amino-5-benzothiazol-2-ylpyridin-3-yl)phenyl]-(4-methylpiperazin-1-yl)methanone MS (ES+): m/z=430.10 (100) [MH$^+$]. HPLC: $t_R$=2.10 min (ZQ2, polar_5 min).

Example 183

4-(6-Amino-5-benzothiazol-2-ylpyridin-3-yl)-N,N-dimethylbenzamide

MS (ES+): m/z=375.10 (100) [MH$^+$]. HPLC: $t_R$3.18 min (ZQ2, polar_5 min). $^1$H NMR (400 MHz, DMSO-d$_6$): δ=2.99 (br. s., 6H), 7.45-7.54 (m, 3H), 7.54-7.60 (m, 1H), 7.76-7.82 (m, 2H), 8.07-8.13 (m, 3H), 8.16 (d, J=7.3 Hz, 1H), 8.25 (d, J=2.3 Hz, 1H), 8.58 (d, J=2.3 Hz, 1H).

Example 184

[3-(6-Amino-5-benzothiazol-2-ylpyridin-3-yl)phenyl]-(4-methylpiperazin-1-yl)methanone MS (ES+): m/z=430.10 (100) [MH$^+$]. HPLC: $t_R$=2.11 min (ZQ2, polar_5 min).

Example 185

4-(6-Amino-5-benzothiazol-2-ylpyridin-3-yl)-N-(2-dimethylaminoethyl)benzamide

MS (ES+): m/z=418.11 (100) [MH$^+$]. HPLC: $t_R$=2.15 min (ZQ2, polar_5 min).

Example 186

3-(6-Amino-5-benzothiazol-2-ylpyridin-3-yl)-N,N-dimethylbenzamide

MS (ES+): m/z=375.10 (100) [MH$^+$]. HPLC: $t_R$3.19 min (ZQ2, polar_5 min). $^1$H NMR (400 MHz, DMSO-d$_6$): δ=2.97 (s, 3H), 3.02 (s, 3H), 7.34-7.39 (m, 1H), 7.45-7.60 (m, 3H), 7.72 (t, J=1.6 Hz, 1H), 7.76-7.82 (m, 1H), 8.05-8.18 (m, 4H), 8.24 (d, J=2.3 Hz, 1H), 8.56 (d, J=2.5 Hz, 1H).

Example 187

3-(6-Amino-5-benzothiazol-2-ylpyridin-3-yl)-N-(2-dimethylaminoethyl)benzamide

MS (ES+): m/z=418.10 (100) [MH$^+$]. HPLC: $t_R$=2.16 min (ZQ2, polar_5 min).

Example 188

5-Benzothiazol-2-yl-6'-(3-dimethylaminopropoxy)-[3,3']bipyridinyl-6-ylamine

MS (ES+): m/z=406.10 (100) [MH$^+$]. HPLC: $t_R$=2.18 min (ZQ2, polar_5 min).

Example 189

[4-(6-Amino-5-benzothiazol-2-ylpyridin-3-yl)phenyl]morpholin-4-ylmethanone

MS (ES+): m/z=417.09 (100) [MH$^+$]. HPLC: $t_R$=2.18 min (ZQ2, polar_5 min).

Example 190

4-(6-Amino-5-benzothiazol-2-ylpyridin-3-yl)benzamide

MS (ES+): m/z=347.07 (100) [MH$^+$]. HPLC: $t_R$=2.86 min (ZQ2, polar_5 min).

Example 191

4-(6-Amino-5-benzothiazol-2-ylpyridin-3-yl)-N,N-diethylbenzamide

MS (ES+): m/z=403.14 (100) [MH$^+$]. HPLC: $t_R$=3.58 min (ZQ2, polar_5 min).

Example 192

3-(6-Amino-5-benzothiazol-2-ylpyridin-3-yl)-N-furan-2-ylmethylbenzamide

MS (ES+): m/z=427.07 (100) [MH$^+$]. HPLC: $t_R$=3.47 min (ZQ2, polar_5 min).

Example 193

4-(6-Amino-5-benzothiazol-2-ylpyridin-3-yl)-N-furan-2-ylmethylbenzamide

MS (ES+): m/z=427.07 (100) [MH$^+$]. HPLC: $t_R$=3.44 min (ZQ2, polar_5 min).

Example 194

3-(6-Amino-5-benzothiazol-2-ylpyridin-3-yl)-N-methylbenzamide

MS (ES+): m/z=361.08 (100) [MH$^+$]. HPLC: $t_R$=3.06 min (ZQ2, polar_5 min).

Example 195

[4-(6-Amino-5-benzothiazol-2-ylpyridin-3-yl)phenyl]piperidin-1-ylmethanone

MS (ES+): m/z=415.13 (100) [MH$^+$]. HPLC: $t_R$=3.71 min (ZQ2, polar_5 min).

Example 196

3-(6-Amino-5-benzothiazol-2-ylpyridin-3-yl)benzamide

MS (ES+): m/z=347.07 (100) [MH$^+$]. HPLC: $t_R$=3.89 min (ZQ2, polar_5 min).

Example 197

3-Benzothiazol-2-yl-5-[1-(2-morpholin-4-ylethyl)-1H-pyrazol-4-yl]pyridin-2-ylamine MS (ES+): m/z=407.11 (100) [MH$^+$]. HPLC: $t_R$=2.08 min (ZQ2, polar_5 min).

Example 198

4-(6-Amino-5-benzothiazol-2-ylpyridin-3-yl)-N-cyclopropylbenzamide

MS (ES+): m/z=387.10 (100) [MH$^+$]. HPLC: $t_R$=3.20 min (ZQ2, polar_5 min).

Example 199

4-(6-Amino-5-benzothiazol-2-ylpyridin-3-yl)-N-methylbenzamide

MS (ES+): m/z=361.08 (100) [MH$^+$]. HPLC: $t_R$=3.00 min (ZQ2, polar_5 min).

Example 200

3-(6-Amino-5-benzothiazol-2-ylpyridin-3-yl)-benzoic acid

To a solution of 3-(6-amino-5-benzothiazol-2-ylpyridin-3-yl)-benzoic acid methyl ester (0.980 g, 2.7 mmol) in dioxane/H$_2$O (5:1, 30 mL) was added K$_2$CO$_3$ (1.5 g, 11 mmol), and the mixture was heated at 50° C. for 16 h. Evaporation of the solvents and neutralization with acetic acid gave a precipitate that was filtered off and dried in vacuo to give the title compound. $^1$H NMR (DMSO-d$_6$, 300 MHz): δ=7.51-7.66 (m, 3H), 7.95-8.00 (m, 2H), 8.14-8.18 (m, 4H), 8.24 (d, J=8.4 Hz, 2H), 8.29 (d, J=1.8 Hz, 1H), 8.61 (d, J=2.1 Hz, 1H). MS(ES+): m/z=348.06 (100) [MH$^+$]. HPLC: $t_R$=3.42 min (polar_5 min, ZQ3).

3-(6-Amino-5-benzothiazol-2-ylpyridin-3-yl)-benzoic acid methyl ester

A mixture of 3-benzothiazol-2-yl-5-bromopyridin-2-ylamine (BB7) (1.37 g, 4.5 mmol), 3-(carbomethoxy)phenylboronic acid (0.85 g, 4.7 mmol), Pd(PPh$_3$)$_4$ (5 mol %), and Cs$_2$CO$_3$ (3.5 g, 10.8 mmol) in dioxane/H$_2$O (4:1, 30 mL) were heated under nitrogen at 90° C. for 5 h. Solvents were removed in vacuo, water (10 mL) was added to the residue, and the mixture was extracted with EtOAc (3×10 mL). The combined EtOAc extracts were dried over Na$_2$SO$_4$, filtered, and concentrated in vacuo. The crude material thus obtained was purified by column chromatography on silica gel using mixtures of EtOAc/Hexanes to give the title compound. $^1$H NMR (CDCl$_3$, 300 MHz): δ=7.28 (brs, 2H), 7.41 (t, J=6.9 Hz, 1H), 7.51 (t, J=6.9 Hz, 1H), 7.64 (d, J=7.5 Hz, 1H), 7.77 (d, J=6.3 Hz, 1H), 7.92 (d, J=7.8 Hz, 1H), 8.01-8.05 (m, 2H), 8.18 (d, J=2.1 Hz, 1H), 8.26 (t, J=1.8 Hz, 1H), 8.47 (d, J=2.1 Hz, 1H).

Example 201

4-(6-Amino-5-benzothiazol-2-ylpyridin-3-yl)-benzoic acid

Following the procedure for 3-(6-amino-5-benzothiazol-2-ylpyridin-3-yl)-benzoic acid methyl ester, the title compound was prepared from 4-(6-amino-5-benzothiazol-2-ylpyridin-3-yl)-benzoic acid methyl ester (1.2 g, 3.3 mmol) and K$_2$CO$_3$ (1.5 g, 11 mmol) in dioxane/H$_2$O (5:1, 30 mL). $^1$H NMR (400 MHz, DMSO-d$_6$): δ=13.0 (very brs, 1H), 8.62 (d, J=2.2 Hz, 1H), 8.29 (d, J=2.2 Hz, 1H), 8.19-8.13 (m, 3H), 8.12 (d, J=7.8 Hz, 1H), 8.04-8.00 & 7.88-7.84 (AA'BB', 4H), 7.57 (ddd, J=1.0, 7.0, 8.0 Hz, 1H), 7.49 (ddd, J=1.0, 7.4, 8.0 Hz, 1H). MS(ES+): m/z=348.08 (100) [MH$^+$]. HPLC: t$_R$=3.29 min (polar__5 min, ZQ2).

4-(6-Amino-5-benzothiazol-2-ylpyridin-3-yl)-benzoic acid methyl ester

Following the procedure for 4-(6-Amino-5-benzothiazol-2-ylpyridin-3-yl)-benzoic acid methyl ester, the title compound was prepared from 3-benzothiazol-2-yl-5-bromopyridin-2-ylamine (BB7) (2.0 g, 6.5 mmol), 4-(carbomethoxyphenyl)boronic acid (0.85 g, 4.7 mmol), Pd(PPh$_3$)$_4$ (5 mol %) and Cs$_2$CO$_3$ (3.5 g, 10.8 mmol).

Example 202

6'-Amino-5'-benzothiazol-2-yl-[3,3']bipyridinyl-6-carboxylic acid

Following the procedures for 3-(6-amino-5-benzothiazol-2-ylpyridin-3-yl)-benzoic acid methyl ester and the benzoic acid, the title compound was prepared from 3-benzothiazol-2-yl-5-bromopyridin-2-ylamine (BB7) (1.1 g, 3.6 mmol), 5-(4,4,5,5-tetramethyl-[1,3,2]dioxaborolan-2-yl)-pyridine-2-carboxylic acid methyl ester (1.0 g, 3.8 mmol), Pd(PPh$_3$)$_4$ (2 mol %), and Cs$_2$CO$_3$ (2.83 g, 8.7 mmol) in DMF/H$_2$O (24 mL, 5:1). $^1$H NMR (400 MHz, DMSO-d$_6$): δ=8.90 (s, 1H), 8.61 (d, J=2.0 Hz, 1H), 8.31 (d, J=2.0 Hz, 1H), 8.20-8.07 (m, 5H), 7.96 (brd, J=8.4 Hz, 1H), 7.57 (dt, J=1.0, 8.0 Hz, 1H), 7.49 (dt, J=1.0, 8.0 Hz, 1H); COOH proton not visible. MS(ES+): m/z=349.08 (100) [MH$^+$], 305.09 (8) [MH$^+$—CO$_2$]. HPLC: t$_R$=2.89 min (polar__5 min, ZQ3).

Example 203

6-Amino-5-benzothiazol-2-yl-[3,4']bipyridinyl-2'-carboxylic acid

Following the procedure for 3-(6-amino-5-benzothiazol-2-ylpyridin-3-yl)-benzoic acid methyl ester, the title compound was prepared from 6-amino-5-benzothiazol-2-yl-[3,4']bipyridinyl-2'-carboxylic acid methyl ester (1.14 g, 3.2 mmol) and NaOH (0.48 g, 12 mmol) in MeOH (10 mL). $^1$H NMR (400 MHz, DMSO-d$_6$): δ=13.0 (very brs, 1H), 8.62 (d, J=2.2 Hz, 1H), 8.29 (d, J=2.2 Hz, 1H), 8.19-8.13 (m, 3H), 8.12 (d, J=7.8 Hz, 1H), 8.04-8.00 & 7.88-7.84 (AA'BB', 4H), 7.57 (ddd, J=1.0, 7.0, 8.0 Hz, 1H), 7.49 (ddd, J=1.0, 7.4, 8.0 Hz, 1H). MS(ES+): m/z=348.08 (100) [MH$^+$]. HPLC: t$_R$=3.29 min (polar__5 min, ZQ2).

6-Amino-5-benzothiazol-2-yl-[3,4']bipyridinyl-2'-carboxylic acid methyl ester Following the procedure for 4-(6-Amino-5-benzothiazol-2-ylpyridin-3-yl)-benzoic acid methyl ester, the title compound was prepared from 3-benzothiazol-2-yl-5-(4,4,5,5-tetramethyl-[1,3,2]dioxaborolan-2-yl)-pyridin-2-ylamine (BB8) (1.41 g, 4.0 mmol), 4-iodopyridine-2-carboxylic acid methyl ester (0.85 g, 3.2 mmol), Pd(PPh$_3$)$_4$ (2 mol %) and Cs$_2$CO$_3$ (2.5 g, 7.7 mmol) in dioxane/water (5:1; 18 mL). $^1$H NMR (CD$_3$OD, 300 MHz): δ=4.01 (s, 3H), 7.38-7.45 (m, 2H), 7.70 (dd, J=7.2, 2.4 Hz, 1H), 7.85 (d, J=6.8 Hz, 1H), 7.95 (d, J=6.8 Hz, 1H), 8.21 (d, J=2.4 Hz, 1H), 8.31 (d, J=2.4 Hz, 1H), 8.44 (d, J=2.4 Hz, 1H), 8.70 (d, J=7.2 Hz, 1H).

General Procedure G for (Het)aryl Amides

To a suspension of 3-(6-amino-5-benzothiazol-2-ylpyridin-3-yl)benzoic acid (20 mg, 0.058 mmol, 1 eq.) in 1 mL DCM were added TBTU (19.4 mg, 0.060 mmol, 1.05 eq.), DIPEA (10 μL, 0.058 mmol, 1 eq.), and the amine (0.116 mmol, 2 eq.). The mixture was stirred at room temperature overnight. If the mixture was heterogeneous, the solid was filtered off and dried in vacuo. Otherwise, DCM was evaporated, and the residue was dissolved in DMSO for MDP purification.

The following examples were prepared using General Procedure G.

Example 204

[3-(6-Amino-5-benzothiazol-2-ylpyridin-3-yl)phenyl]pyrrolidin-1-ylmethanone MS (ES+): m/z=401.11 (100) [MH$^+$]. HPLC: t$_R$=3.39 min (ZQ2, polar__5 min).

Example 205

N-(2-Acetylaminoethyl)-3-(6-amino-5-benzothiazol-2-ylpyridin-3-yl)benzamide MS (ES+): m/z=432.07 (100) [MH$^+$]. HPLC: t$_R$=2.75 min (ZQ2, polar__5 min).

Example 206

[3-(6-Amino-5-benzothiazol-2-ylpyridin-3-yl)phenyl]piperidin-1-ylmethanone

MS (ES+): m/z=415.13 (100) [MH$^+$]. HPLC: t$_R$=3.68 min (ZQ2, polar__5 min).

Example 207

3-(6-Amino-5-benzothiazol-2-ylpyridin-3-yl)-N-(2-diethylaminoethyl)benzamide MS (ES+): m/z=446.14 (100) [MH$^+$]. HPLC: t$_R$=2.26 min (ZQ2, polar__5 min).

Example 208

[3-(6-Amino-5-benzothiazol-2-ylpyridin-3-yl)phenyl]-(cis-3,5-dimethylpiperazin-1-yl)methanone MS (ES+): m/z=444.12 (100) [MH$^+$]. HPLC: t$_R$=2.20 min (ZQ2, polar__5 min).

Example 209

3-(6-Amino-5-benzothiazol-2-ylpyridin-3-yl)-N-(3-pyrrolidin-1-ylpropyl)benzamide MS (ES+): m/z=458.15 (100) [MH$^+$]. HPLC: t$_R$=2.23 min (ZQ2, polar__5 min).

Example 210

3-(6-Amino-5-benzothiazol-2-ylpyridin-3-yl)-N-methyl-N-(1-methylpiperidin-4-yl)benzamide MS (ES+): m/z=458.15 (100) [MH$^+$]. HPLC: $t_R$=2.14 min (ZQ2, polar_5 min).

Example 211

2-{4-[3-(6-Amino-5-benzothiazol-2-ylpyridin-3-yl)benzoyl]piperazin-1-pyrrolidin-1-yl}-1-ylethanone MS (ES+): m/z=527.15 (100) [MH$^+$]. HPLC: $t_R$=2.26 min (ZQ2, polar_5 min).

Example 212

1-{4-[3-(6-Amino-5-benzothiazol-2-ylpyridin-3-yl)benzoyl]piperazin-1-yl}ethanone MS (ES+): m/z=458.08 (100) [MH$^+$]. HPLC: $t_R$=2.81 min (ZQ2, polar_5 min).

Example 213

[3-(6-Amino-5-benzothiazol-2-ylpyridin-3-yl)phenyl]-(3-hydroxypiperidin-1-yl)methanone MS (ES+): m/z=431.10 (100) [MH$^+$]. HPLC: $t_R$=2.90 min (ZQ2, polar_5 min).

Example 214

[3-(6-Amino-5-benzothiazol-2-ylpyridin-3-yl)phenyl]-(cis-2,6-dimethylmorpholin-4-yl)methanone MS (ES+): m/z=445.13 (100) [MH$^+$]. HPLC: $t_R$=3.47 min (ZQ2, polar_5 min).

Example 215

2-{4-[3-(6-Amino-5-benzothiazol-2-ylpyridin-3-yl)benzoyl]piperazin-1-yl}-N,N-dimethylacetamide MS (ES+): m/z=501.12 (100) [MH$^+$]. HPLC: $t_R$=2.19 min (ZQ2, polar_5 min).

Example 216

3-(6-Amino-5-benzothiazol-2-ylpyridin-3-yl)-N,N-bis-(2-methoxyethyl)benzamide

MS (ES+): m/z=463.13 (100) [MH$^+$]. HPLC: $t_R$=3.31 min (ZQ2, polar_5 min).

Example 217

[3-(6-Amino-5-benzothiazol-2-ylpyridin-3-yl)phenyl]-(4-pyrrolidin-1-ylpiperidin-1-yl)methanone MS (ES+): m/z=484.29 (100) [MH$^+$]. HPLC: $t_R$=2.16 min (ZQ2, polar_5 min).

Example 218

3-(6-Amino-5-benzothiazol-2-ylpyridin-3-yl)-N-(1-methylpiperidin-4-yl)benzamide

MS (ES+): m/z=444.28 (100) [MH$^+$]. HPLC: $t_R$=2.19 min (ZQ2, polar_5 min).

Example 219

1-[3-(6-Amino-5-benzothiazol-2-ylpyridin-3-yl)benzoyl]piperidine-4-carboxylic acid amide MS (ES+): m/z=458.23 (100) [MH$^+$]. HPLC: $t_R$=2.68 min (ZQ2, polar_5 min).

Example 220

3-(6-Amino-5-benzothiazol-2-ylpyridin-3-yl)-N-(2-dimethylaminoethyl)-N-methylbenzamide MS (ES+): m/z=432.25 (100) [MH$^+$]. HPLC: $t_R$=2.15 min (ZQ2, polar_5 min).

Example 221

3-(6-Amino-5-benzothiazol-2-ylpyridin-3-yl)-N-((1S,2S)-2-hydroxycyclohexyl)benzamide MS (ES+): m/z=445.13 (100) [MH$^+$]. HPLC: $t_R$=2.23 min (ZQ2, polar_5 min).

Example 222

[3-(6-Amino-5-benzothiazol-2-ylpyridin-3-yl)phenyl]-(3-hydroxypyrrolidin-1-yl)methanone MS (ES+): m/z=417.19 (100) [MH$^+$]. HPLC: $t_R$=0.73 min (UPLC-ACQUITY, Analytical).

Example 223

3-(6-Amino-5-benzothiazol-2-ylpyridin-3-yl)-N-(3-imidazol-1-ylpropyl)benzamide

MS (ES+): m/z=455.25 (100) [MH$^+$]. HPLC: $t_R$=0.65 min (UPLC-ACQUITY, Analytical).

Example 224

[3-(6-Amino-5-benzothiazol-2-ylpyridin-3-yl)phenyl]-(3-dimethylaminopyrrolidin-1-yl)methanone MS (ES+): m/z=444.24 (100) [MH$^+$]. HPLC: $t_R$=2.18 min (ZQ2, polar_5 min).

Example 225

3-(6-Amino-5-benzothiazol-2-ylpyridin-3-yl)-N-(3-morpholin-4-ylpropyl)benzamide

MS (ES+): m/z=474.21 (100) [MH$^+$]. HPLC: $t_R$=3.28 min (ZQ2, polar_5 min).

Example 226

[3-(6-Amino-5-benzothiazol-2-ylpyridin-3-yl)phenyl]-(4-methyl-[1,4]diazepan-1-yl)methanone MS (ES+): m/z=444.20 (100) [MH$^+$]. HPLC: t$_R$=0.62 min (UPLC-ACQUITY, Analytical).

Example 227

[3-(6-Amino-5-benzothiazol-2-ylpyridin-3-yl)phenyl]-(3,3-difluoropyrrolidin-1-yl)methanone MS (ES+): m/z=437.18 (100) [MH$^+$]. HPLC: t$_R$=0.99 min (UPLC-ACQUITY, Analytical).

Example 228

[3-(6-Amino-5-benzothiazol-2-ylpyridin-3-yl)phenyl]-(cis-3,4,5-trimethylpiperazin-1-yl)methanone MS (ES+): m/z=458.24 (100) [MH$^+$]. HPLC: t$_R$=0.63 min (UPLC-ACQUITY, Analytical).

Example 229

3-(1,3-Benzothiazol-2-yl)-5-(1H-indol-2-yl)pyridin-2-amine

A mixture of 3-benzothiazol-2-yl-5-bromopyridin-2-ylamine (BB7) (25 mg, 0.080 mmol), 1-Boc-indole-2-boronic acid (40 mg, 0.20 mmol) and potassium carbonate (34 mg, 0.24 mmol) in 1,4-dioxane (1.4 mL) and H$_2$O (0.5 mL) was degassed and refilled with argon (3×) prior to the addition of Pd(dppf)Cl$_2$ (6 mg, 0.01 mmol). The reaction mixture was degassed and refilled with argon (2×) and left to stir at 100° C. in the microwave reactor for 30 min. Then, the mixture was passed through PL-Thiol MP SPE resin and concentrated in vacuo. The residual oil was partitioned between DCM and H$_2$O. The combined organic layers were treated with brine, dried over anhydrous Na$_2$SO$_4$ and concentrated in vacuo. The resulting Boc-protected intermediate was left to stir in (1:1) DCM:TFA mixture (1.0 mL) at rt for 15 min. Purification via MDP afforded the title compound as a yellow solid. MS (ES+): m/z=343.08 (100) [MH$^+$]. HPLC: t$_R$=4.00 min (ZQ3, polar_5 min).

Example 230

3-(1,3-Benzothiazol-2-yl)-5-(1H-pyrrol-2-yl)pyridin-2-amine

The procedure for 3-(1,3-benzothiazol-2-yl)-5-(1H-indol-2-yl)pyridin-2-amine was followed. MS (ES+): m/z=293.09 (100) [MH$^+$]. HPLC: t$_R$=3.44 min (ZQ3, polar_5 min).

Example 231

N-4-[6-Amino-5-(1,3-benzothiazol-2-yl)pyridin-3-yl]phenylmethanesulfonamide

The procedure for 3-(1,3-benzothiazol-2-yl)-5-(1H-indol-2-yl)pyridin-2-amine was followed, except the treatment with TFA/DCM was omitted. MS (ES+): m/z=397.10 (100) [MH$^+$]. HPLC: t$_R$=3.32 min (ZQ3, polar_5 min).

Example 232

5-(1,3-Benzothiazol-2-yl)-1',2',3',6'-tetrahydro-3,4'-bipyridin-6-amine

The procedure for 3-(1,3-benzothiazol-2-yl)-5-(1H-indol-2-yl)pyridin-2-amine was followed. MS (ES+): m/z=309.11 (100) [MH$^+$]. HPLC: t$_R$=2.17 min (ZQ3, polar_5 min).

Example 233

3-[6-Amino-5-(1,3-benzothiazol-2-yl)pyridin-3-yl]phenol

A mixture of 3-benzothiazol-2-yl-5-bromopyridin-2-ylamine (BB7) (100 mg, 0.330 mmol), 3-hydroxyphenylboronic acid (68 mg, 0.49 mmol) and potassium carbonate (140 mg, 0.980 mmol) in 1,4-dioxane (4.5 mL) and H$_2$O (1.5 mL) was degassed and refilled with argon (3×) prior to the addition of Pd(dppf)Cl$_2$ (10 mg, 0.020 mmol). The reaction mixture was degassed and refilled with argon (2×) and left to stir at 100° C. for 30 min in the microwave reactor. Then, the mixture was passed through a pad of Celite and to the filtrate was partitioned between EtOAc and NaHCO$_3$ aq. soln. (3×). The combined organic extracts were treated with brine, dried over anhydrous Na$_2$SO$_4$, filtered, and concentrated in vacuo. Purification via silica gel chromatography (5% MeOH in DCM) afforded the title compound as a yellow solid. $^1$H NMR (400 MHz, DMSO-d$_6$): δ=6.75-6.77 (m, 1H), 7.04-7.04 (m, 1H), 7.10-7.12 (m, 1H), 7.27 (t, J=8.0 Hz, 1H), 7.46-7.50 (m, 1H), 7.55-7.58 (m, 1H), 8.02 (br.s, 2H), 8.10-8.16 (m, 3H), 8.46 (d, J=4.0 Hz, 1H), 9.54 (s, 1H). MS (ES+): m/z=320.09 (100) [MH$^+$]. HPLC: t$_R$=3.44 min (ZQ3, polar_5 min).

Example 234

Methyl 3-[6-amino-5-(1,3-benzothiazol-2-yl)pyridin-3-yl]phenoxyacetate

A solution of 3-[6-amino-5-(1,3-benzothiazol-2-yl)pyridin-3-yl]phenol (80 mg, 0.20 mmol), potassium carbonate (100 mg, 0.700 mmol) and chloroacetic acid methyl ester (33 mg, 0.30 mmol) in DMF was left to stir at rt overnight. To the mixture was added EtOAc (10 mL), which was left to stir at rt for 10 min. Then, the mixture was washed with NaHCO$_3$ aq. soln. (2×). The combined organic extracts were treated with brine, dried over anhydrous Na$_2$SO$_4$ and concentrated in vacuo. Purification via silica gel chromatography (5% MeOH in DCM) afforded the title compound as a yellow solid. MS (ES+): m/z=392.02 (100) [MH$^+$]. HPLC: t$_R$=3.63 min (ZQ3, polar_5 min).

Example 235

[3-(6-Amino-5-benzothiazol-2-yl-pyridin-3-yl)-phenoxy]acetic acid

To a suspension of methyl 3-[6-amino-5-(1,3-benzothiazol-2-yl)pyridin-3-yl]phenoxyacetate (75 mg, 0.19 mmol) in EtOH (4.0 mL) and H$_2$O (4.0 mL) was added 3M aqueous NaOH (0.30 mL, 1.0 mmol). The reaction mixture was left to stir at rt overnight. Then, the mixture was acidified with 1M HCl aqueous to pH=2. Vacuum filtration afforded the title compound as a yellow solid. $^1$H NMR (400 MHz, DMSO-d$_6$): δ=4.80 (s, 2H), 6.93 (dd, J=7.7, 2.1 Hz, 1H), 7.25-7.29 (m, 1H), 7.31 (d, J=7.8 Hz, 1H), 7.40 (t, J=7.8 Hz, 1H), 7.48-7.54 (m, 1H), 7.55-7.62 (m, 1H), 8.15 (dd, J=18.4, 7.6 Hz, 2H), 8.31 (d, J=2.0 Hz, 1H), 8.55 (d, J=2.3 Hz, 1H), 13.06 (br. s., 1H). MS (ES+): m/z=378.07 (100) [MH$^+$]. HPLC: t$_R$=3.50 min (ZQ3, polar_5 min).

Example 236

Ethyl 4-[6-amino-5-(1,3-benzothiazol-2-yl)pyridin-3-yl]phenoxyacetate

A mixture of 3-benzothiazol-2-yl-5-bromopyridin-2-ylamine (BB7) (100 mg, 0.330 mmol), 4-(2-ethoxy-2-oxoethoxy)benzeneboronic acid (100 mg, 0.600 mmol) and potassium fluoride (57 mg, 0.98 mmol) in 1,4-dioxane (9.0 mL) and H$_2$O (3.0 mL) was degassed and refilled with argon (3×) prior to the addition of Pd(dppf)Cl$_2$ (10 mg, 0.020 mmol). The reaction mixture was degassed and refilled with argon (2×) and left to stir at 100° C. for 2 h. The mixture was quickly passed through a silica gel pad (5% MeOH in DCM), which afforded the title compound as a yellow solid. MS (ES+): m/z=406.10 (100) [MH$^+$]. HPLC: t$_R$=3.90 min (ZQ3, polar_5 min).

Example 237

4-[6-Amino-5-(1,3-benzothiazol-2-yl)pyridin-3-yl]phenoxyacetic acid

To a suspension of ethyl 4-[6-amino-5-(1,3-benzothiazol-2-yl)pyridin-3-yl]phenoxyacetate (132 mg, 0.330 mmol) in EtOH (2.0 mL) was added 3M aqueous NaOH (0.50 mL, 1.5 mmol). Then, the mixture was acidified to pH=2 with 1M aq. HCl. Vacuum filtration afforded the title compound as a yellow solid. MS (ES+): m/z=506.88 (100) [MH$^+$]. HPLC: t$_R$=3.14 min (ZQ3, polar_5 min).

Example 238

2-[4-(6-Amino-5-benzothiazol-2-ylpyridin-3-yl)-phenoxy]-N-methylacetamide

To a suspension of 4-[6-amino-5-(1,3-benzothiazol-2-yl)pyridin-3-yl]phenoxyacetic acid (20 mg, 0.050 mmol) in DMF (1.0 mL) were added methylammonium chloride (4 mg, 0.06 mmol), TBTU (19 mg, 0.060 mmol) and DIEA (0.05 mL, 0.3 mmol). The mixture was left to stir at rt for 30 min. Purification via MDP afforded the title compound as a yellow solid. $^1$H NMR (400 MHz, DMSO-d$_6$): δ=2.67 (d, J=4.8 Hz, 3H), 4.51 (s, 2H), 7.04-7.10 (m, 2H), 7.45-7.52 (m, 1H), 7.54-7.59 (m, 1H), 7.63-7.68 (m, 2H), 7.97 (s, 2H), 8.10 (d, J=7.8 Hz, 1H), 8.13-8.17 (m, 2H), 8.48 (d, J=2.3 Hz, 1H). MS (ES+): m/z=391.10 (100) [MH$^+$]. HPLC: t$_R$=3.20 min (ZQ3, polar_5 min).

Example 239

2-[4-(6-Amino-5-benzothiazol-2-ylpyridin-3-yl)-phenoxy]-N,N-dimethylacetamide

The procedure for 2-[4-(6-amino-5-benzothiazol-2-ylpyridin-3-yl)-phenoxy]-N-methylacetamide was followed. $^1$H NMR (400 MHz, DMSO-d$_6$): δ=2.86 (s, 3H), 3.02 (s, 3H), 4.86 (s, 2H), 6.99-7.05 (m, 2H), 7.45-7.51 (m, 1H), 7.53-7.59 (m, 1H), 7.59-7.64 (m, 2H), 7.96 (s, 2H), 8.08-8.17 (m, 3H), 8.47 (d, J=2.3 Hz, 1H). MS (ES+): m/z=405.15 (100) [MH$^+$]. HPLC: t$_R$=3.23 min (ZQ3, polar_5 min).

Example 240

2-[4-(6-Amino-5-benzothiazol-2-ylpyridin-3-yl)-phenoxy]-N-benzylacetamide

The procedure for 2-[4-(6-amino-5-benzothiazol-2-ylpyridin-3-yl)-phenoxy]-N-methylacetamide was followed. MS (ES+): m/z=467.09 (100) [MH$^+$]. HPLC: t$_R$=3.81 min (ZQ3, polar_5 min).

Example 241

2-[4-(6-Amino-5-benzothiazol-2-ylpyridin-3-yl)phenoxy]-1-pyrrolidin-1-ylethanone The procedure for 2-[4-(6-amino-5-benzothiazol-2-ylpyridin-3-yl)-phenoxy]-N-methylacetamide was followed. MS (ES+): m/z=431.14 (100) [MH$^+$]. HPLC: t$_R$=3.41 min (ZQ3, polar_5 min).

Example 242

2-[4-(6-Amino-5-benzothiazol-2-ylpyridin-3-yl)-phenoxy]-N-[3-(2-oxopyrrolidin-1-yl)-propyl]acetamide The procedure for 2-[4-(6-amino-5-benzothiazol-2-ylpyridin-3-yl)-phenoxy]-N-methylacetamide was followed. MS (ES+): m/z=502.15 (100) [MH$^+$]. HPLC: t$_R$=3.09 min (ZQ3, polar_5 min).

Example 243

2-[4-(6-Amino-5-benzothiazol-2-ylpyridin-3-yl)phenoxy]-N-(2-hydroxycyclohexyl)acetamide The procedure for 2-[4-(6-amino-5-benzothiazol-2-ylpyridin-3-yl)-phenoxy]-N-methylacetamide was followed. MS (ES+): m/z=475.14 (100) [MH$^+$]. HPLC: t$_R$=3.32 min (ZQ3, polar_5 min).

Example 244

2-[4-(6-Amino-5-benzothiazol-2-ylpyridin-3-yl)phenoxy]-1-morpholin-4-ylethanone

The procedure for 2-[4-(6-amino-5-benzothiazol-2-ylpyridin-3-yl)-phenoxy]-N-methylacetamide was followed. MS (ES+): m/z=447.10 (100) [MH$^+$]. HPLC: t$_R$=3.24 min (ZQ3, polar_5 min).

Example 245

2-[4-(6-Amino-5-benzothiazol-2-ylpyridin-3-yl)phenoxy]-N-cyclohexylmethylacetamide The procedure for 2-[4-(6-amino-5-benzothiazol-2-ylpyridin-3-yl)-phenoxy]-N-methylacetamide was followed. MS (ES+): m/z=473.16 (100) [MH$^+$]. HPLC: t$_R$=4.15 min (ZQ3, polar_5 min).

Example 246

2-[4-(6-Amino-5-benzothiazol-2-yl-pyridin-3-yl) phenoxy]-1-[4-(2-hydroxyethyl)piperazin-1-yl]ethanone The procedure for 2-[4-(6-amino-5-benzothiazol-2-ylpyridin-3-yl)-phenoxy]-N-methylacetamide was followed. MS (ES+): m/z=490.15 (100) [MH$^+$]. HPLC: $t_R$=2.44 min (ZQ3, polar_5 min).

Example 247

5-(1-Piperidin-4-yl-1H-pyrazol-4-yl)-3-[7-(1H-pyrazol-4-yl)benzothiazol-2-yl]pyridin-2-ylamine dihydrochloride A solution of 4-[6-amino-5-(7-bromobenzothiazol-2-yl)-pyridin-3-yl]-pyrazol-1-ylpiperidine-1-carboxylic acid tert-butyl ester (30 mg, 0.050 mmol), 4-pyrazoleboronic acid (12 mg, 0.11 mmol), potassium carbonate (20 mg, 0.20 mmol) and Pd(dppf)Cl$_2$ (2 mg, 0.01 mmol) in 1,4-dioxane (1.2 mL) and H$_2$O (0.4 mL) was left to stir at 100° C. for 30 min in the microwave reactor. Then, the mixture was passed through PL-Thiol MP SPE resin and the filtrate was concentrated in vacuo. The resulting oil was partitioned between DCM and H$_2$O (3×). The combined organic extracts were treated with brine, dried over anhydrous Na$_2$SO$_4$ and concentrated in vacuo. The Boc-protected intermediate was isolated via prep TLC (5% MeOH in DCM), MS (ES+): m/z=543 [MH$^+$]. The resulting solid was taken up in DCM (1.0 mL) and 1M HCl in ether (1.0 mL) was added. The mixture was left to stir at rt for 1 h. The resulting precipitate was collected by vacuum filtration and washed with DCM, which afforded the title compound as a yellow solid. $^1$H NMR (400 MHz, CD$_3$OD): δ=2.30-2.44 (m, 4H), 3.21-3.29 (m, 2H), 3.56-3.67 (m, 2H), 4.59-4.71 (m, 1H), 7.68 (t, J=7.8 Hz, 1H), 7.79 (d, J=6.8 Hz, 1H), 8.07-8.12 (m, 2H), 8.27 (s, 2H), 8.37 (d, J=2.0 Hz, 1H), 8.42 (s, 1H), 8.85 (d, J=1.8 Hz, 1H), MS (ES+): m/z=443.14 (100) [MH$^+$]. HPLC: $t_R$=1.77 min (ZQ3, nonpolar_5 min).

Example 248

3-[7-(1-Methyl-1H-pyrazol-4-yl)benzothiazol-2-yl]-5-(1-piperidin-4-yl-1H-pyrazol-4-yl)pyridin-2-ylamine dihydrochloride The procedure for 5-(1-piperidin-4-yl-1H-pyrazol-4-yl)-3-[7-(1H-pyrazol-4-yl)benzothiazol-2-yl]pyridin-2-ylamine dihydrochloride was followed. $^1$H NMR (400 MHz, DMSO-d$_6$): δ=2.06-2.34 (m, 4H), 3.05-3.20 (m, 2H), 3.35-3.45 (m, 2H), 3.98 (s, 3H), 4.44-4.60 (m, 1H), 7.62 (t, J=7.8 Hz, 1H), 7.72 (dd, J=7.6, 1.01 Hz, 1H), 8.02 (dd, J=8.0, 1.0 Hz, 1H), 8.08 (d, J=3.5 Hz, 2H), 8.36 (s, 1H) 8.42 (s, 1H) 8.47 (br. s., 1H) 8.53 (d, J=2.0 Hz, 1H). MS (ES+): m/z=457.13 (100) [MH$^+$]. HPLC: $t_R$=1.89 min (ZQ3, nonpolar_5 min).

Example 249

5-(1-Piperidin-4-yl-1H-pyrazol-4-yl)-3-[7-(1H-pyrrol-2-yl)benzothiazol-2-yl]pyridin-2-ylamine dihydrochloride The procedure for 5-(1-piperidin-4-yl-1H-pyrazol-4-yl)-3-[7-(1H-pyrazol-4-yl)benzothiazol-2-yl]pyridin-2-ylamine dihydrochloride was followed. $^1$H NMR (400 MHz, DMSO-d$_6$): δ=1.93-2.07 (m, 2H), 2.08-2.17 (m, 2H), 2.80-2.91 (m, 2H), 3.20-3.28 (m, 2H), 4.30-4.41 (m, 1H), 6.25-6.33 (m, 1H), 6.77-6.84 (m, 1H), 7.00-7.06 (m, 1H), 7.60 (t, J=7.8 Hz, 1H), 7.74 (d, J=7.1 Hz, 1H), 7.91 (br. s., 2H), 7.94 (d, J=8.1 Hz, 1H), 8.00 (s, 1H), 8.27 (d, J=2.3 Hz, 1H), 8.30-8.39 (m, 2H), 8.50 (d, J=2.3 Hz, 1H), 11.64 (br. s., 1H). MS (ES+): m/z=442.19 (100) [MH$^+$]. HPLC: $t_R$=2.34 min (ZQ3, polar_5 min).

Example 250

5-(1-Piperidin-4-yl-1H-pyrazol-4-yl)-3-(7-pyridin-3-ylbenzothiazol-2-yl)pyridin-2-ylamine dihydrochloride The procedure for 5-(1-piperidin-4-yl-1H-pyrazol-4-yl)-3-[7-(1H-pyrazol-4-yl)benzothiazol-2-yl]pyridin-2-ylamine dihydrochloride was followed. $^1$H NMR (400 MHz, DMSO-d$_6$): δ=2.02-2.32 (m, 4H), 3.04-3.16 (m, 2H), 3.45-3.48 [m, 2H], 4.44-4.53 (m, 1H), 7.65-7.70 (m, 2H), 7.71-7.79 (m, 1H), 8.05 (s, 1H), 8.20 (dd, J=8.1, 1.0 Hz, 1H), 8.26 (dt, J=7.8, 1.9 Hz, 1H), 8.33 (br. s., 1H), 8.38 (s, 1H), 8.53 (d, J=2.0 Hz, 1H), 8.59 (br. s., 1H), 8.75 (dd, J=4.8, 1.5 Hz, 1H), 8.82 (br. s., 1H), 9.02 (d, J=1.5 Hz, 1H). MS (ES+): m/z=454.13 (100) [MH$^+$]. HPLC: $t_R$=1.86 min (ZQ3, nonpolar 5 min).

Example 251

5-(1-Piperidin-4-yl-1H-pyrazol-4-yl)-3-[7-(1H-pyrrol-3-yl)benzothiazol-2-yl]pyridin-2-ylamine trifluoroacetate The procedure for 5-(1-piperidin-4-yl-1H-pyrazol-4-yl)-3-[7-(1H-pyrazol-4-yl)benzothiazol-2-yl]pyridin-2-ylamine dihydrochloride was followed, except that TFA in DCM was used for removing the Boc group. $^1$H NMR (400 MHz, CD$_3$OD): δ=2.24-2.43 (m, 4H), 3.19-3.29 (m, 2H), 3.60 (d, J=13.1 Hz, 2H), 4.60 (ddd, J=10.2, 5.3, 5.2 Hz, 1H), 6.66 (q, J=2.5 Hz, 1H), 6.92 (q, J=2.7 Hz, 1H), 7.28-7.36 (m, 1H), 7.55 (t, J=7.8 Hz, 1H), 7.59-7.65 (m, 1H), 7.86-7.93 (m, 1H), 8.00 (s, 1H), 8.19-8.31 (m, 2H), 8.57 (d, J=2.0 Hz, 1H), 10.76 (br. s., 1H). MS (ES+): m/z=442.19 (100) [MH$^+$]. HPLC: $t_R$=2.38 min (ZQ3, polar_5 min).

Example 252

3-(6-Fluorobenzothiazol-2-yl)-5-(1-piperidin-4-yl-1H-pyrazol-4-yl)-pyridin-2-ylamine A solution of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB8) (0.075 g, 0.16 mmol) and 2-chloro-6-fluorobenzothiazole (0.090 g, 0.48 mmol) in 1,4-dioxane (1.7 mL) and H$_2$O (0.6 mL) was charged with potassium carbonate (0.066 g, 0.48 mmol) and (1,1'bis-(diphenylphosphino)-ferrocene) palladium dichloride (0.002 g, 0.003 mmol) under an atmosphere of nitrogen. The mixture was irradiated in the microwave at 100° C., for 30 min. The reaction mixture was partitioned between EtOAc and water and separated. The aqueous layer was extracted with EtOAc (3×) and the combined organic fractions were washed with brine, dried over sodium sulfate, filtered, and concentrated in vacuo. The residue was purified by chromatography on silica gel [eluting 80% EtOAc in hexanes] to afford the Boc-protected product, MS (ES+): m/z=495 [MH$^+$]. This compound was taken up in DCM, charged with 0.25 mL of 1.0 M HCl in ether, and stirred at rt overnight. A solid precipitated out of solution that was filtered off and dried in vacuo to afford the title compound as a yellow solid. $^1$H NMR (400 MHz, DMSO-$d_6$): δ=2.11-2.31 (m, 4H), 3.05-3.18 (m, 2H), 3.41 (d, J=12.8 Hz, 2H), 4.47-4.57 (m, 1H), 7.47 (td, J=9.0, 2.7 Hz, 1H), 8.06 (s, 1H), 8.12-8.19 (m, 2H), 8.36 (br. s., 1H), 8.4 (s, 1H), 8.53 (d, J=2.2 Hz, 1H). MS (ES+): m/z=395.12 [MH$^+$]. HPLC: $t_R$=2.03 min (ZQ2, polar__5 min).

Example 253

3-(6-Chlorobenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2,6-dichloro-1,3-benzothiazole in place of 2-chloro-6-fluorobenzothiazole to afford the title compound as a yellow solid. $^1$H NMR (400 MHz, DMSO-$d_6$): δ=2.10-2.30 (m, 4H), 3.06-3.18 (m, 2H), 3.41 (d, J=13.2 Hz, 2H), 4.52 (ddd, J=14.8, 10.6, 4.2 Hz, 1H), 7.62 (dd, J=8.8, 1.8 Hz, 1H), 8.05 (s, 1H), 8.12 (d, J=8.8 Hz, 1H), 8.31 (br. s., 1H), 8.37 (br. s., 2H), 8.53 (s, 1H). MS (ES+): m/z=411.08 [MH$^+$]. HPLC: $t_R$=2.30 min (ZQ2, polar__5 min).

Example 254

3-(6-Methylbenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2-chloro-6-methyl-1,3-benzothiazole in place of 2-chloro-6-fluorobenzothiazole to afford the title compound as a yellow solid. $^1$H NMR (400 MHz, DMSO-$d_6$): δ=2.10-2.31 (m, 4H), 3.12 (q, J=10.6 Hz, 2H), 3.42 (d, J=12.4 Hz, 2H), 4.47-4.57 (m, 1H), 7.41 (d, J=6.9 Hz, 1H), 7.96-8.02 (m, 2H), 8.05 (s, 1H), 8.31 (br. s., 1H), 8.38 (s, 1H), 8.49 (d, J=2.2 Hz, 1H). MS (ES+): m/z=391.15 [MH$^+$]. HPLC: $t_R$=2.22 min (ZQ2, polar__5 min).

Example 255

3-(6-Methoxybenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2-chloro-6-methoxy-1,3-benzothiazole in place of 2-chloro-6-fluorobenzothiazole to afford the title compound as a yellow solid. $^1$H NMR (400 MHz, DMSO-$d_6$): δ=2.10-2.30 (m, 4H), 3.04-3.17 (m, 2H), 3.41 (d, J=12.8 Hz, 2H), 3.89 (s, 3H), 4.48-4.59 (m, 1H), 7.20 (dd, J=9.1, 2.5 Hz, 1H), 7.78 (d, J=2.5 Hz, 1H), 8.03 (d, J=9.1 Hz, 1H), 8.08 (s, 1H), 8.38-8.45 (m, 2H), 8.50 (d, J=2.0 Hz, 1H). MS (ES+): m/z=407.12 [MH$^+$]. HPLC: $t_R$=2.1$^3$ min (ZQ2, polar__5 min).

Example 256

3-(4-Fluorobenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2-chloro-4-fluoro-1,3-benzothiazole in place of 2-chloro-6-fluorobenzothiazole to afford the title compound as a yellow solid. $^1$H NMR (400 MHz, DMSO-$d_6$): δ=2.11-2.22 (m, 2H), 2.23-2.31 (m, 2H), 3.06-3.18 (m, 2H), 3.42 (d, J=12.1 Hz, 2H), 4.48-4.57 (m, 1H), 7.42-7.49 (m, 1H), 7.50-7.57 (m, 1H), 8.00-8.07 (m, 2H), 8.30 (br. s., 1H), 8.37 (br. s., 1H), 8.54 (s, 1H). MS (ES+): m/z=395.12 [MH$^+$]. HPLC: $t_R$=2.05 min (ZQ2, polar__5 min).

Example 257

3-(4-Methylbenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2-iodo-4-methyl-1,3-benzothiazole in place of 2-chloro-6-fluorobenzothiazole to afford the title compound as a yellow solid. $^1$H NMR (400 MHz, DMSO-$d_6$): δ=2.10-2.31 (m, 4H), 2.74 (s, 3H), 3.05-3.18 (m, 2H), 3.41 (d, J=13.2 Hz, 2H), 4.49-4.57 (m, 1H), 7.41-7.48 (m, 2H), 8.02 (dd, J=6.4, 2.7 Hz, 1H), 8.09 (s, 1H), 8.45 (s, 1H), 8.49 (br. s., 1H), 8.56 (d, J=1.8 Hz, 1H). MS (ES+): m/z=391.14 [MH$^+$]. HPLC: $t_R$=2.11 min (ZQ2, polar__5 min).

Example 258

3-(5-Chlorobenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2,5-dichloro-1,3-benzothiazole in place of 2-chloro-6-fluorobenzothiazole to afford the title compound as a yellow solid. $^1$H NMR (400 MHz, DMSO-$d_6$): δ=2.10-2.22 (m, 2H), 2.22-2.30 (m, 2H), 3.12 (q, J=11.1 Hz, 2H), 3.42 (d, J=12.4 Hz, 2H), 4.47-4.55 (m, 1H), 7.56 (d, J=8.4 Hz, 1H), 8.03 (s, 1H), 8.19-8.24 (m, 2H), 8.26 (br. s., 1H), 8.35 (s, 1H), 8.52 (s, 1H), MS (ES+): m/z=411.09/413.10 (3:1) [MH$^+$]. HPLC: $t_R$=2.18 min (ZQ2, polar__5 min).

2,5-Dichloro-1,3-benzothiazole

To 5-chloro-2-mercaptobenzothiazole (1.5 g, 7.4 mmol) was added sulfuryl chloride (5 mL, excess) with stirring below 5° C. under nitrogen. The resulting suspension was stirred for 3 h at rt, carefully poured onto ice (100 g), and stirred for another 2 h. The white solid that separated out was filtered off, washed repeatedly with cold water, and dried in vacuo to afford the title compound. $^1$H-NMR (CDCl$_3$, 300 MHz): δ=7.95 (s, 1H), 7.70 (d, J=8.4 Hz, 1H), 7.37 (d, J=8.7 Hz, 1H).

5-Chloro-2-mercaptobenzothiazole

A solution of 5-chloro-2-fluoroaniline (2.0 g, 13.7 mmol, 1 eq.) and potassium O-ethyl dithiocarbonate (4.8 g, 30.3 mmol, 2.2 eq) in anhydrous DMF (20 mL) was heated at 100° C. under nitrogen for 4 h. The reaction mixture was cooled to room temp., diluted with water (50 mL), and acidified with 2N HCl with constant stirring at low temperature. Yellowish solid was collected by filtration, and washed with cold water. The wet filter cake was dissolved in ethyl acetate (50 mL), and the solution was dried over sodium sulfate, filtered, and concentrated in vacuo to afford the title compound as yellowish solid. $^1$H-NMR (CDCl$_3$, 300 MHz): δ=7.71 (d, J=8.1 Hz, 1H), 7.34 (d, J=8.1 Hz, 1H), 7.27 (s, 1H).

Example 259

3-(7-Chlorobenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2,7-dichloro-1,3-benzothiazole in place of 2-chloro-6-fluorobenzothiazole to afford the title compound as a yellow solid. $^1$H NMR (400 MHz, DMSO-d$_6$): δ=2.10-2.22 (m, 2H), 2.23-2.31 (m, 2H), 3.12 (q, J=11.1 Hz, 2H), 3.42 (d, J=12.4 Hz, 2H), 4.46-4.56 (m, 1H), 7.60-7.66 (m, 2H), 8.09 (s, 1H), 8.12 (dd, J=6.2, 2.9 Hz, 1H), 8.44 (s, 2H), 8.56 (d, J=1.8 Hz, 1H). MS (ES+): m/z=411.09/413.06 (3:1) [MH$^+$]. HPLC: t$_R$=2.16 min (ZQ2, polar_5 min).

2,7-Dichloro-1,3-benzothiazole

The title compound was prepared from 2,3-dichloroaniline via 7-chloro-2-mercaptobenzothiazole as described for 2,5-dichloro-1,3-benzothiazole.

Example 260

5-(1-Piperidin-4-yl-1H-pyrazol-4-yl)-3-(7-trifluoromethylbenzothiazol-2-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2-chloro-7-trifluoromethyl-1,3-benzothiazole in place of 2-chloro-6-fluoro-1,3-benzothiazole to afford the title compound as a yellow solid. $^1$H NMR (400 MHz, DMSO-d$_6$): δ=2.12-2.31 (m, 4H), 3.05-3.18 (m, 2H), 3.41 (d, J=12.8 Hz, 2H), 4.47-4.57 (m, 1H), 7.83 (t, J=8.0 Hz, 1H), 7.97 (d, J=7.3 Hz, 1H), 8.12 (s, 1H), 8.47 (d, J=8.0 Hz, 1H), 8.49 (s, 1H), 8.57 (s, 1H), 8.60 (d, J=2.2 Hz, 1H). MS (ES+): m/z=445.08 [MH$^+$]. HPLC: t$_R$=2.38 min (ZQ2, polar_5 min).

2-Chloro-7-trifluoromethyl-1,3-benzothiazole

The title compound was prepared from 2-fluoro-3-trifluoromethylaniline via 2-mercapto-7-trifluoromethyl-1,3-benzothiazole as described for 2,5-dichloro-1,3-benzothiazole except that in the first step the reaction mixture was heated to 90° C. for 4 h.

Example 261

5-(1-Piperidin-4-yl-1H-pyrazol-4-yl)-3-(5-trifluoromethylbenzothiazol-2-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2-chloro-5-trifluoromethyl-1,3-benzothiazole in place of 2-chloro-6-fluorobenzothiazole to afford the title compound as a yellow solid. $^1$H NMR (400 MHz, DMSO-d$_6$): δ=2.12-2.30 (m, 4H), 3.04-3.17 (m, 2H), 3.36-3.45 (m, 2H), 4.48-4.58 (m, 1H), 7.84 (dd, J=8.6, 1.2 Hz, 1H), 8.07 (s, 1H), 8.40-8.44 (m, 2H), 8.46 (d, J=8.4 Hz, 1H), 8.54 (s, 1H), 8.57 (d, J=2.2 Hz, 1H). MS (ES+): m/z=445.09 [MH$^+$]. HPLC: t$_R$=2.39 min (ZQ2, polar_5 min).

2-Chloro-5-trifluoromethyl-1,3-benzothiazole

The title compound was prepared from 2-fluoro-5-trifluoromethylaniline via 2-mercapto-5-trifluoromethyl-1,3-benzothiazole as described for 2,5-dichloro-1,3-benzothiazole except that in the first step the reaction mixture was heated to 95° C. for 4 h.

Example 262

5-(1-Piperidin-4-yl-1H-pyrazol-4-yl)-3-(4-trifluoromethylbenzothiazol-2-yl)-pyridin-2-ylamine A mixture of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB8) (75 mg, 0.16 mmol), 2-chloro-4-trifluoromethyl-1,3-benzothiazole (46 mg, 0.19 mmol), potassium carbonate (66 mg, 0.48 mmol), Pd(PPh$_3$)$_4$ (18 mg, 0.016 mmol) in DME (3 mL) and H$_2$O (1 mL) was evacuated and refilled with N$_2$ (3x), then it was heated at 100° C. for 30 min in the microwave reactor. The mixture was diluted with EtOAc (30 mL), washed with brine (10 mL), dried over Na$_2$SO$_4$, filtered, and concentrated in vacuo. The residue was purified by silica gel chromatography (Hex.:EtOAc=30:70→15:85) to give a yellow solid. This material was dissolved in DCM (2 mL) and treated with 1M HCl in diethyl ether (3 mL). The resulting mixture was stirred at room temperature overnight. The title compound was collected by filtration as a yellow solid and washed with DCM. MS (ES+): m/z=445.10 [MH$^+$].

2-Chloro-4-trifluoromethyl-1,3-benzothiazole

The title compound was prepared from 2-fluoro-5-trifluoromethylaniline via 2-mercapto-4-trifluoromethyl-1,3-benzothiazole as described for 2,5-dichloro-1,3-benzothiazole except that in the first step the reaction mixture was heated to 100° C. for 6 h.

Example 263

3-(7-Methylbenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2-chloro-7-methyl-1,3-benzothiazole in place of 2-chloro-6-fluorobenzothiazole to afford the title compound as a yellow solid. $^1$H NMR (400 MHz, DMSO-d$_6$): δ=2.11-2.31 (m, 4H), 2.61 (s, 3H), 3.12 (q, J=11.8 Hz, 2H), 3.42 (d, J=12.8 Hz, 2H), 4.46-4.56 (m, 1H), 7.36 (d, J=7.3 Hz, 1H), 7.52 (t, J=7.7 Hz, 1H), 7.97 (d, J=8.0 Hz, 1H), 8.07 (s, 1H), 8.43 (br. s., 2H), 8.52 (s, 1H). MS (ES+): m/z=391.16 [MH$^+$]. HPLC: t$_R$=2.24 min (ZQ2, polar_5 min).

2-Chloro-7-methyl-1,3-benzothiazole

The title compound was prepared from 2-fluoro-3-methylaniline via 2-mercapto-7-methyl-1,3-benzothiazole as described for 2,5-dichloro-1,3-benzothiazole except that in the first step the reaction mixture was heated to 180° C. for 24 h in a sealed tube.

Example 264

3-(7-Methoxybenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2-chloro-7-methoxy-1,3-benzothiazole in place of 2-chloro-6-fluorobenzothiazole to afford the title compound as a yellow solid. $^1$H NMR (400 MHz, CD$_3$OD): δ=8.80 (d, J=2.0 Hz, 1H), 8.38 (s, 1H), 8.35 (d, J=2.0 Hz, 1H), 8.07 (s, 1H), 7.79 (d, J=8.0 Hz, 1H), 7.59 (m, 1H), 7.13 (d, J=7.6 Hz, 1H), 4.66 (m, 1H), 4.06 (s, 3H), 3.59-3.62 (m, 2H), 2.33-2.39 (m, 4H). MS(ES+): m/z=407.13 [MH$^+$]. HPLC: t$_R$=1.78 min (polar_5 min, ZQ3).

2-Chloro-7-methoxy-1,3-benzothiazole

The title compound was prepared from 2-bromo-3-methoxyaniline via 2-mercapto-7-methoxy-1,3-benzothiazole as described for 2,5-dichloro-1,3-benzothiazole except that in the first step the reaction mixture was heated to 120° C. for 10 h.

Example 265

3-(4-Bromobenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 4-bromo-2-chloro-1,3-benzothiazole in place of 2-chloro-6-fluorobenzothiazole to afford the title compound as a yellow solid. $^1$H NMR (400 MHz, CD$_3$OD): δ=8.81 (s, 1H), 8.44 (s, 1H), 8.41 (s, 1H), 8.11 (d, J=8.0 Hz, 1H), 8.08 (s, 1H), 7.84 (d, J=8.0 Hz, 1H), 7.47 (t, J=8.0 Hz, 1H), 4.68 (m, 1H), 3.59-3.63 (m, 2H), 2.38-2.41 (m, 4H). MS(ES+): m/z=455.01/456.92 [MH$^+$]. HPLC: t$_R$=1.59 min (polar_5 min, ZQ3).

4-Bromo-2-chloro-1,3-benzothiazole

The title compound was prepared from 2,6-dibromoaniline via 4-bromo-2-mercapto-1,3-benzothiazole as described for 2,5-dichloro-1,3-benzothiazole except that in the first step the reaction mixture was heated to 150° C. for 16 h.

Example 266

5-(1-Piperidin-4-yl-1H-pyrazol-4-yl)-3-(6-trifluoromethoxybenzothiazol-2-yl)-pyridin-2-ylamine Following the procedure for 5-(1-piperidin-4-yl-1H-pyrazol-4-yl)-3-(4-trifluoromethylbenzothiazol-2-yl)-pyridin-2-ylamine, but using 2-chloro-6-trifluoromethoxy-1,3-benzothiazole, the title compound was obtained as yellow solid. MS (ES+): m/z=461.08 [MH$^+$].

2-Chloro-6-trifluoromethoxy-1,3-benzothiazole

The title compound was prepared from 2-bromo-4-trifluoromethoxyaniline via 2-mercapto-6-trifluoromethoxy-1,3-benzothiazole as described for 2,5-dichloro-1,3-benzothiazole except that in the first step the reaction mixture was heated to 150° C. for 16 h.

Example 267

2-[2-Amino-5-(1-piperidin-4-yl-1H-pyrazol-4-yl)-pyridin-3-yl]-benzothiazole-5-carbonitrile Following the procedure for 5-(1-piperidin-4-yl-1H-pyrazol-4-yl)-3-(4-trifluoromethylbenzothiazol-2-yl)-pyridin-2-ylamine, but using 2-chloro-1,3-benzothiazole-5-carbonitrile, the title compound was obtained as yellow solid. MS (ES+): m/z=402.13 [MH$^+$].

2-Chloro-1,3-benzothiazole-5-carbonitrile

The title compound was prepared from 3-amino-4-chlorobenzonitrile via 2-mercapto-1,3-benzothiazole-5-carbonitrile as described for 2,5-dichloro-1,3-benzothiazole except that in the first step the reaction mixture was heated to 95° C. for 10 h.

Example 268

2-[2-Amino-5-(1-piperidin-4-yl-1H-pyrazol-4-yl)-pyridin-3-yl]-benzothiazole-6-carbonitrile Following the procedure for 5-(1-piperidin-4-yl-1H-pyrazol-4-yl)-3-(4-trifluoromethylbenzothiazol-2-yl)-pyridin-2-ylamine, but using 2-chloro-1,3-benzothiazole-6-carbonitrile, the title compound was obtained as yellow solid. MS (ES+): m/z=402.13 [MH$^+$].

2-Chloro-1,3-benzothiazole-6-carbonitrile

The title compound was prepared from 4-amino-3-chlorobenzonitrile via 2-mercapto-1,3-benzothiazole-6-carbonitrile as described for 2,5-dichloro-1,3-benzothiazole except that in the first step the reaction mixture was heated to 120° C. for 12 h.

Example 269

3-(7-Fluoro-4-trifluoromethylbenzothiazol-2-yl)-5-(1-piperidin-4-yl-1H-pyrazol-4-yl)-pyridin-2-ylamine To a solution of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB8) (60 mg, 0.127 mmol, 1 eq), 2-chloro-7-fluoro-4-trifluoromethyl-1,3-benzothiazole (42 mg, 0.153 mmol, 1.2 eq), and potassium carbonate (43 mg, 0.317 mmol, 2.5 eq) in 20% aq. dioxane (15 mL) was bubbledN$_2$ gas for 15 min. Catalyst PdCl$_2$dppf (5 mol %) was added to the stirred solution and N$_2$ gas bubbling continued for another 10 min. The reaction mixture was then heated at 80° C. for 2 h. Cooling of the reaction mixture and evaporation of dioxane under reduced pressure yielded a brown residue. It was diluted with water (50 mL) and extracted with ethyl acetate (3×20 mL). The combined organic layers were washed with water (20 mL) and brine (20 mL), dried over sodium sulfate, filtered, and concentrated under reduced pressure to yield a yellowish-green solid. It was purified by column chromatography (50% ethyl acetate in hexane) to afford the BOC-protected title compound as yellowish-green solid; MS(ES+): m/z=563 [MH$^+$]. To a solution of this Boc derivative (40 mg, 0.07 mmol) at 0-5° C. in dry DCM (10 ml) was added 4M HCl in dioxane (0.2 ml) dropwise and stirred the reaction mixture overnight at rt. Removed solvent under reduced pressure to afford the title compound as yellow solid. $^1$H NMR (400 MHz, DMSO-d$_6$): δ=9.06-8.96 (brm, 1H), 8.85-8.73 (brm, 1H), 8.61 (d, J=2.0 Hz, 1H), 8.42 (s, 1H), 8.41 (d, J=2.0 Hz, 1H), 8.17 (very brs, 1H), 8.09 (s, 1H), 8.03 (dd, J=5.2, 8.4 Hz, 1H), 7.59 (t, J=8.4 Hz, 1H), 4.56-4.46 (m$_c$, 1H), 3.41 (brd, J=12.4 Hz, 2H), 3.12 (brq, J=11.4 Hz, 2H), 2.31-2.11 (m, 4H). MS(ES+):

m/z=463.05 (100) [MH⁺], 380.02 (80) [MH⁺-piperidine]. HPLC: $t_R$=2.29 min (polar_5 min, ZQ2).

2-Chloro-7-fluoro-4-trifluoromethyl-1,3-benzothiazole

The title compound was prepared from 2,3-difluoro-6-trifluoromethylaniline via 2-mercapto-7-fluoro-4-trifluoromethyl-1,3-benzothiazole as described for 2,5-dichloro-1,3-benzothiazole except that in the first step the reaction mixture was heated to 90° C. for 4 h.

Example 270

3-(7-Fluorobenzothiazol-2-yl)-5-(1-piperidin-4-yl-1H-pyrazol-4-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 7-fluoro-2-iodo-1,3-benzothiazole and conducting the Suzuki coupling at 50° C. for 1.5 h, the title compound was obtained as a yellow solid. ¹H NMR (400 MHz, CD₃OD): δ=8.84 (d, J=2.0 Hz, 1H), 8.41 (m, 1H), 8.40 (s, 1H), 8.09 (s, 1H), 8.04 (dd, J=0.8, 8.0 Hz, 1H), 7.66 (m, 1H), 7.38 (m, 1H), 4.66 (m, 1H), 3.62 (dt, J=3.2, 13.2, 2H), 3.24-3.28 (m, 2H), 2.36-2.40 (m, 4H). MS(ES+): m/z=395.12 [MH⁺]. HPLC: $t_R$=1.62 min (polar_5 min, ZQ3).

7-Fluoro-2-iodo-1,3-benzothiazole

To a solution of p-TsOH.H₂O (570 mg, 3.0 mmol, 3 eq) in acetonitrile (10 mL) was added 2-amino-7-fluoro-1,3-benzothiazole (168 mg, 1.0 mmol). The resulting suspension was cooled to 10° C., a solution of NaNO₂ (138 mg, 2.0 mmol, 2 eq) and KI (412 mg, 2.5 mmol, 2.5 eq) in 3 mL of water was added, and the reaction mixture was stirred for 4 h. The pH of the reaction mixture was adjusted to 9-10 by addition of saturated aq. NaHCO₃ solution, and the reaction mixture was extracted with ethyl acetate (3×20 mL). The combined extracts were, washed with aqueous sodium thiosulfate solution (30 mL), dried over Na₂SO₄, filtered and concentrated under reduced pressure. The brownish residue was purified by column chromatography (eluted by 1% methanol in DCM) to give the title compound. ¹H-NMR (CDCl₃, 300 MHz): δ=7.71 (dd, J=8.4 & 0.9, 1H), 7.42-7.39 (m, 1H), 7.12 (dt, J=8.1 &1.2, 1H).

2-Amino-7-fluoro-1,3-benzothiazole

A mixture of 7-fluoro-2-methylsulfonyl-1,3-benzothiazole (500 mg, 2.16 mmol) in 10 mL ethanol and 20% ethanolic ammonia (20 mL) was heated at 160° C. in a sealed tube for 12 h. It was cooled to RT, ethanol was removed under reduced pressure, and the brownish residue was purified by column chromatography (5% to 10% methanol in methylene chloride) to afford the title compound. ¹H-NMR (CDCl₃, 300 MHz): δ=7.35 (d, J=7.5 Hz, 1H), 7.33-7.37 (m, 1H), 6.93-6.84 (m, 1H), 5.30 (brs, 2H).

7-Fluoro-2-methanesulfonyl-1,3-benzothiazole

To a well-stirred solution of 7-fluoro-2-methylsulfanyl-1,3-benzothiazole (1.1 g, 5.5 mmol) in acetic acid (15 mL) was added a solution of KMnO₄ (1.74 g, 11 mmol, 2 eq, dissolved in 15 mL water) dropwise, and the reaction mixture was stirred at rt for 30 min. The reaction mixture was extracted with EtOAc (5×25 mL), and the combined organic layers were washed with water (2×20 mL) and brine (10 mL), dried over sodium sulfate, filtered and concentrated under reduced pressure to afford the title compound. ¹H-NMR (CDCl₃, 300 MHz): δ=8.12 (d, J=8.1 Hz, 1H), 7.83-7.28 (m, 1H), 7.04-6.97 (m, 1H), 3.41 (s, 3H).

7-Fluoro-2-methylsulfanyl-1,3-benzothiazole

To a well-stirred solution of 7-fluoro-2-mercaptobenzothiazole (1.0 g, 5.4 mmol) in 10% aq. NaOH (10 mL) was added methyl iodide (2.14 g, 2.8 eq) dropwise, and the reaction mixture was stirred at rt for 30 min. A yellowish solid was collected by filtration, washed with cold water, and dissolved in ethyl acetate (50 mL). The EtOAc solution was dried over sodium sulfate, filtered, and concentrated under reduced pressure to afford the title compound. ¹H-NMR (CDCl₃, 300 MHz): δ=7.66 (d, J=8.1 Hz, 1H), 7.40-7.33 (m, 1H), 7.04-6.97 (m, 1H), 2.80 (s, 3H).

7-Fluoro-2-mercaptobenzothiazole

The title compound was prepared from 2,3-difluoroaniline as described for 5-chloro-2-mercaptobenzothiazole except that in the first step the reaction mixture was heated to 90° C. for 4 h.

Example 271

3-(5-Methoxybenzothiazol-2-yl)-5-(1-piperidin-4-yl-1H-pyrazol-4-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 2-iodo-5-methoxy-1,3-benzothiazole and conducting the Suzuki coupling at 55° C. for 4 h, the title compound was obtained as a yellow solid. ¹H NMR (400 MHz, CD₃OD): δ=8.75 (s, 1H), 8.40 (s, 1H), 8.34 (s, 1H), 8.06 (s, 1H), 7.95 (d, J=8.8 Hz, 1H), 7.69 (d, J=2.4 Hz, 1H), 7.21 (dd, J=2.4, 8.8 Hz, 1H), 4.67 (m, 1H), 3.94 (s, 3H), 3.59-3.62 (m, 2H), 3.25-3.27 (m, 2H), 2.34-2.39 (m, 4H). MS(ES+): m/z=407.13 [MH⁺]. HPLC: $t_R$=1.12 min (polar_5 min, ZQ3).

2-Iodo-5-methoxy-1,3-benzothiazole

The title compound was prepared following the route for 7-fluoro-2-iodo-1,3-benzothiazole from 2,3-difluoroaniline, starting from 2-chloro-5-methoxyaniline and conducting the first step at 150° C. for 16 h.

Example 272

3-(5-Methylbenzothiazol-2-yl)-5-(1-piperidin-4-yl-1H-pyrazol-4-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 2-iodo-5-methyl-1,3-benzothiazole and conducting the Suzuki coupling at 80° C. for 3 h, the title compound was obtained as a yellow solid. ¹H NMR (400 MHz, DMSO-d₆): δ=8.96-8.87 (brm, 1H), 8.75-8.65 (brm, 1H), 8.51 (d, J=2.0 Hz, 1H), 8.40 (s, 1H), 8.37 (brs, 1H), 8.35 (very brs, 1H), 8.06 (d, J=8.0 Hz, 1H), 8.06 (s, 1H), 7.36 (dd, J=8.0, 1.0 Hz, 1H), 4.56-4.48 (m_c, 1H), 3.11 (brq, J=11.0 Hz, 2H), 2.30-2.10 (m, 4H); CH₃ and additional 2H hidden under water peak. MS(ES+): m/z=391.14 (72) [MH+], 308.09 (100) [MH+-piperidine]. HPLC: t_R=2.10 min (polar_5 min, ZQ2).

2-Iodo-5-methyl-1,3-benzothiazole

The title compound was prepared following the route for 7-fluoro-2-iodo-1,3-benzothiazole from 2,3-difluoroaniline, starting from 2-fluoro-5-methylaniline and conducting the first step at 180° C. for 48 h in a sealed tube.

Example 273

3-(7-Bromobenzothiazol-2-yl)-5-(1-piperidin-4-yl-1H-pyrazol-4-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 7-bromo-2-iodo-1,3-benzothiazole and conducting the Suzuki coupling at 60° C. for 4 h, the title compound was obtained as a yellow solid. $^1$H NMR (400 MHz, DMSO-d$_6$): δ=9.20-9.09 (brm, 1H), 9.02-8.90 (brm, 1H), 8.61 (very brs, 1H), 8.60 (s, 2H), 8.52 (s, 1H), 8.18 (d, J=8.0 Hz, 1H), 8.13 (s, 1H), 7.78 (d, J=8.0 Hz, 1H), 7.58 (t, J=8.0 Hz, 1H), 4.57-4.47 (m_c, 1H), 3.40 (brd, J=12.8 Hz, 2H), 3.11 (brq, J=11.2 Hz, 2H), 2.31-2.12 (m, 4H). MS(ES+): m/z=454.98/457.00 (79/83) [MH+], 371.94/373.95 (95/100) [MH+-piperidine]. HPLC: t_R=2.22 min (polar_5 min, ZQ2).

7-Bromo-2-iodo-1,3-benzothiazole

The title compound was prepared following the route for 7-fluoro-2-iodo-1,3-benzothiazole from 2,3-difluoroaniline, starting from 2,3-dibromoaniline (prepared according to *J. Org. Chem.* 1990, 55(9), 2739) and conducting the first step at 95° C. for 4 h.

Example 274

3-(4,5-Difluorobenzothiazol-2-yl)-5-(1-piperidin-4-yl-1H-pyrazol-4-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 2-chloro-4,5-difluoro-1,3-benzothiazole and conducting the Suzuki coupling at 80° C. for 3 h, the title compound was obtained as a yellow solid. MS (ES+): m/z=413.13 [MH+]. HPLC: t_R=2.46 min (ZQ3, polar_5 min).

2-Chloro-4,5-difluoro-1,3-benzothiazole

To a mixture of 2-amino-4,5-difluoro-1,3-benzothiazole (130 mg, 0.70 mmol) and CuSO$_4$ (20 mg) in conc. HCl (20 mL) was added NaNO$_2$ (96 mg, 1.4 mmol, 2 eq, dissolved in 5 mL of water) dropwise at −10° C. over about 15 min. The reaction mixture was stirred for 1 h, poured into a solution of CuCl (67 mg, 0.7 mmol, 1 eq.) in conc. HCl (20 mL), and stirring was continued at ambient temp. for 30 min. The reaction mixture was extracted with diethyl ether (3×30 mL). The combined organic layers were washed with water (10 mL), dilute ammonium hydroxide (10 mL), brine (20 ml), dried over anhydrous Na$_2$SO$_4$, filtered, and concentrated under reduced pressure. The residue was purified by column chromatography on silica gel (eluted by 2% methanol in methylene chloride) to afford the title compound. $^1$H-NMR (CDCl$_3$, 300 MHz): δ=7.20-7.15 (m, 1H), 7.13-7.04 (m, 1H).

2-Amino-4,5-difluoro-1,3-benzothiazole

The title compound was prepared following the route for 2-amino-7-fluoro-1,3-benzothiazole from 2,3-difluoroaniline, starting from 2,3,6-trifluoroaniline and conducting the first step at 100° C. for 4 h.

Example 275

2-[2-Amino-5-(1-piperidin-4-yl-1H-pyrazol-4-yl)-pyridin-3-yl]-benzothiazole-7-carbonitrile Following the procedure for 3-(7-fluoro-4-trifluoromethylbenzothiazol-2-yl)-5-(1-piperidin-4-yl-1H-pyrazol-4-yl)-pyridin-2-ylamine, using 2-iodo-1,3-benzothiazole-7-carbonitrile and conducting the Suzuki coupling at 55° C. for 3 h, the title compound was obtained as a brown solid. $^1$H NMR (400 MHz, DMSO-d$_6$): δ=2.10-2.31 (m, 4H), 3.05-3.18 (m, 2H), 3.37-3.44 (m, 2H), 3.77 (brs, 2H), 4.45-4.54 (m, 1H), 7.51 (brs, 1H), 7.75-7.78 (m, 1H), 8.07 (d, J=7.2 Hz, 1H), 8.10 (s, 1H), 8.44-8.48 (m, 3H), 8.58 (brs, 1H), 8.88 (brs, 1H), 9.10 (brs, 1H). MS(ES+): m/z=402.13 (100) [MH+]. HPLC: t_R=2.06 min (ZQ3, polar_5 min).

2-Iodo-1,3-benzothiazole-7-carbonitrile

The title compound was prepared from 2-methylsulfanyl-1,3-benzothiazole-7-carbonitrile as described for 7-fluoro-2-iodo-1,3-benzothiazole.

2-Methylsulfanyl-1,3-benzothiazole-7-carbonitrile

The title compound was prepared from 7-bromo-2-methylsulfanyl-1,3-benzothiazole by heating with CuCN (1.0 eq.) in DMF at 160° C. for 12 h.

Example 276

3-(5-Bromobenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 5-bromo-2-iodo-1,3-benzothiazole in place of 2-chloro-6-fluorobenzothiazole to afford the title compound as a yellow solid. $^1$H NMR (400 MHz, DMSO-d$_6$): δ=2.11-2.30 (m, 4H), 3.11 (q, J=11.0 Hz, 2H), 3.41 (d, J=12.8 Hz, 2H), 4.47-4.56 (m, 1H), 7.74 (dd, J=8.6, 2.0 Hz, 1H), 8.03-8.08 (m, 2H), 8.34 (br. s., 1H), 8.39 (s, 1H), 8.51 (d, J=1.4 Hz, 1H), 8.54 (d, J=2.2 Hz, 1H). MS (ES+): m/z=455.02/457.00 [MH+]. HPLC: t_R=2.19 min (ZQ2, polar_5 min).

5-Bromo-2-iodo-1,3-benzothiazole

The title compound was obtained following the procedure for 7-fluoro-2-iodo-1,3-benzothiazole, using 2-amino-5-bromo-1,3-benzothiazole.

Example 277

3-(4-Methoxybenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2-chloro-4-methoxy-1,3-benzothiazole in place of 2-chloro-6-fluorobenzothiazole of the title compound as a yellow solid. ¹H NMR (400 MHz, DMSO-$d_6$): δ=2.09-2.30 (m, 4H), 3.05-3.19 (m, 2H), 3.42 (d, J=13.2 Hz, 2H), 4.01 (s, 3H), 4.46-4.56 (m, 1H), 7.14 (d, J=8.0 Hz, 1H), 7.46 (t, J=8.07 Hz, 1H), 7.70 (d, J=8.0 Hz, 1H), 8.03 (s, 1H), 8.25 (br. s., 1H), 8.36 (s, 1H), 8.49 (d, J=2.2 Hz, 1H). MS (ES+): m/z=407.14 [MH⁺]. HPLC: $t_R$=1.93 min (ZQ2, polar_5 min).

2-Chloro-4-methoxy-1,3-benzothiazole

The title compound was obtained following the procedure for 2-chloro-4,5-difluoro-1,3-benzothiazole, using 2-amino-4-methoxy-1,3-benzothiazole.

Example 278

3-(4-Chlorobenzothiazol-2-yl)-5-(1-piperidin-4-yl-1H-pyrazol-4-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2,4-dichlorobenzothiazole in place of 2-chloro-6-fluorobenzothiazole to afford the title compound as a yellow solid. ¹H NMR (400 MHz, DMSO-$d_6$): δ=2.10-2.31 (m, 4H), 3.05-3.19 (m, 2H), 3.33-3.48 (m, 2H), 4.46-4.59 (m, 1H), 7.53 (t, J=7.8 Hz, 1H), 7.71 (d, J=7.3 Hz, 1H), 8.07 (s, 1H), 8.19 (d, J=8.0 Hz, 1H), 8.41 (br. s., 2H), 8.56 (s, 1H). MS (ES+): m/z=411.09/413.08 (3:1) [MH⁺]. HPLC: $t_R$=2.16 min (ZQ2, polar_5 min).

2,4-Dichloro-1,3-benzothiazole

The title compound was obtained following the procedure for 2-chloro-4,5-difluoro-1,3-benzothiazole, using 2-amino-4-chloro-1,3-benzothiazole.

Example 279

5-(1-Piperidin-4-yl-1H-pyrazol-4-yl)-3-(6-trifluoromethylbenzothiazol-2-yl)-pyridin-2-ylamine Same procedure as 3-(6-fluorobenzothiazol-2-yl)-5-(1-piperidin-4-yl-1H-pyrazol-4-yl)-pyridin-2-ylamine except using 2-chloro-6-trifluoromethyl-1,3-benzothiazole in place of 2-chloro-6-fluorobenzothiazole to afford the title compound as a yellow solid. ¹H NMR (400 MHz, DMSO-$d_6$): δ=2.11-2.30 (m, 4H), 3.11 (q, J=10.8 Hz, 2H), 3.41 (d, J=12.4 Hz, 2H), 4.47-4.58 (m, 1H), 7.92 (d, J=8.4 Hz, 1H), 8.08 (s, 1H), 8.32 (d, J=8.4 Hz, 1H), 8.43 (br. s., 2H), 8.58 (br. s., 1H), 8.76 (br. s., 1H). MS (ES+): m/z=445.08 [MH⁺]. HPLC: $t_R$=2.25 min (ZQ2, polar_5 min).

2-Chloro-6-trifluoromethyl-1,3-benzothiazole

The title compound was obtained following the procedure for 2-chloro-4,5-difluoro-1,3-benzothiazole, using 2-amino-6-trifluoromethyl-1,3-benzothiazole.

Example 280

3-(7-Methyl-4-trifluoromethylbenzothiazol-2-yl)-5-(1-piperidin-4-yl-1H-pyrazol-4-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 2-iodo-7-methyl-4-trifluoromethyl-1,3-benzothiazole and conducting the Suzuki coupling at 55° C. for 3 h, the title compound was obtained as a yellow-green solid. ¹H NMR (400 MHz, DMSO-$d_6$): δ=2.10-2.31 (m, 4H), 2.70 (s, 3H), 3.07-3.18 (m, 2H), 3.37-3.44 (m, 2H), 3.54 (brs, 2H), 4.47-4.56 (m, 1H), 7.53 (d, J=9.2 Hz, 1H), 7.88 (d, J=7.6 Hz, 1H), 8.08 (d, J=0.8 Hz, 1H), 8.41-8.46 (m, 2H), 8.57 (d, J=2.4 Hz, 1H), 8.76 (brs, 1H), 8.96 (brs, 1H), MS(ES+): m/z=459.09 (100) [MH⁺]. HPLC: $t_R$=2.32 min (ZQ3, polar_5 min).

2-Iodo-7-methyl-4-trifluoromethyl-1,3-benzothiazole

The title compound was obtained following the procedure for 7-fluoro-2-iodo-1,3-benzothiazole, using 2-amino-7-methyl-4-trifluoromethyl-1,3-benzothiazole.

2-Amino-7-methyl-4-trifluoromethyl-1,3-benzothiazole

A solution of bromine in dichloromethane (3.4 mL, 1.0M in DCM, 1.0 eq) was added dropwise to a solution of (5-methyl-2-trifluoromethylphenyl)-thiourea (800 mg, 3.4 mmol, 1.0 eq) in dry DCM (100 mL) below 30° C. The reaction mixture was heated at reflux for 3 h and cooled to room temp. A precipitate was collected by filtration, then suspended in water (20 mL), and the pH was adjusted to 11 with NH₄OH. The mixture was then extracted with ethyl acetate (3×20 mL), and the combined organic layers were washed with water (30 mL), dried over sodium sulfate, filtered, and concentrated under reduced pressure. The brown residue was purified by column chromatography on silica gel (eluted by 1% methanol in DCM) to afford 2-amino-7-methyl-4-trifluoromethyl-1,3-benzothiozole as white solid. ¹H-NMR (CDCl₃, 300 MHz): δ=7.53 (d, J=8.4, 1H), 7.15 (d, J=8.4, 1H), 5.76 (brs, 2H), 2.59 (s, 3H).

(5-Methyl-2-trifluoromethylphenyl)-thiourea

Benzoyl chloride (880 mg, 6.2 mmol, 1.1 eq) was added dropwise to a solution of ammonium thiocyanate (471 mg, 6.2 mmol, 1.1 eq) in acetone (20 mL). The suspension was heated at reflux, and 2-trifluoromethyl-5-methylaniline (1.0 g, 5.7 mmol, 1.0 eq) was added. The reaction was diluted with acetone (10 mL) and continued to heat under reflux for 1 h. To this mixture, a solution of NaOH (706 mg, 17.6 mmol, 3.1 eq) in water (10 mL) was added and heated at reflux for 1.5 h. The reaction mixture was cooled, and solvents were removed under reduced pressure. The pH was adjusted to 5 with conc. HCl and then to 11 with aqueous NH₄OH to give a precipitate. It was filtered off, washed with water, and dried under vacuum to yield the title compound as white solid. ¹H-NMR (CDCl₃, 300 MHz): δ=7.74 (brs, 1H), 7.67 (d, J=8.1 Hz, 1H), 7.42 (d, J=8.1 Hz, 1H), 6.16 (brs, 2H), 2.75 (s, 3H).

Example 281

5-(1-Piperidin-4-yl-1H-pyrazol-4-yl)-3-(5-trifluoromethoxybenzothiazol-2-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 2-iodo-5-trifluoromethoxy-1,3-benzothiazole and conducting the Suzuki coupling at 50° C. for 2 h, the title compound was obtained as a yellow solid. ¹H NMR (400 MHz, CD₃OD): δ=8.84 (d, J=1.6 Hz, 1H), 8.43 (s, 1H), 8.42 (d, J=2.0 Hz, 1H), 8.24 (d, J=8.4 Hz, 1H), 8.15 (m, 1H), 8.09 (s, 1H), 7.55 (m, 1H), 4.68 (m, 1H), 3.61-3.68 (m, 2H), 3.28-3.30 (m, 2H), 2.35-2.42 (m, 4H). MS(ES+): m/z=461.15 [MH⁺]. HPLC: $t_R$=1.84 min (polar_5 min, ZQ3).

2-Iodo-5-trifluoromethoxy-1,3-benzothiazole

The title compound was obtained following the procedures for the synthesis of 2-iodo-7-methyl-4-trifluoromethyl-1,3-benzothiazole from 2-trifluoromethyl-5-methylaniline, using 3-trifluoromethoxyaniline.

Example 282

3-(7-Chloro-4-trifluoromethylbenzothiazol-2-yl)-5-(1-piperidin-4-yl-1H-pyrazol-4-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 7-chloro-2-iodo-4-trifluoromethyl-1,3-benzothiazole and conducting the Suzuki coupling at 70° C. for 3 h, the title compound was obtained as a yellow-green solid. ¹H NMR (400 MHz, DMSO-d₆): δ=2.14-2.36 (m, 4H), 3.05-3.18 (m, 2H), 3.37-3.44 (m, 2H), 4.01 (brs, 2H), 4.45-4.56 (m, 1H), 7.82 (d, J=8.4 Hz, 1H), 7.99 (d, J=8.4 Hz, 1H), 8.11 (s, 1H), 8.25 (brs, 1H), 8.46 (s, 1H), 8.47 (d, J=2.0 Hz, 1H), 8.62 (d, J=2.4 Hz, 1H), 8.86 (brs, 1H), 9.06 (brs, 1H). MS(ES+): m/z=478.98/481.00 (100/76) [MH⁺]. HPLC: $t_R$=2.37 min (ZQ3, polar_5 min).

7-Chloro-2-iodo-4-trifluoromethyl-1,3-benzothiazole

The title compound was obtained following the procedures for the synthesis of 2-iodo-7-methyl-4-trifluoromethyl-1,3-benzothiazole from 2-trifluoromethyl-5-methylaniline, using 5-chloro-2-trifluoromethylaniline.

Example 283

3-(5-Fluorobenzothiazol-2-yl)-5-(1-piperidin-4-yl-1H-pyrazol-4-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 5-fluoro-2-iodo-1,3-benzothiazole and conducting the Suzuki coupling at 55° C. for 3 h, the title compound was obtained as a yellow solid. ¹H NMR (400 MHz, DMSO-d₆): δ=9.20-9.09 (brm, 1H), 9.04-8.92 (brm, 1H), 8.71 (very brs, 1H), 8.58 (d, J=2.0 Hz, 1H), 8.55 (brs, 1H), 8.47 (s, 1H), 8.28 (dd, J=5.2, 9.0 Hz, 1H), 8.10 (s, 1H), 8.01 (dd, J=2.6, 9.4 Hz, 1H), 7.47 (dt, J=2.4, 9.0 Hz, 1H), 4.58-4.48 (m_c, 1H), 3.40 (brd, J=12.5 Hz, 2H), 3.11 (brq, J=12.0 Hz, 2H), 2.30-2.12 (m, 4H). MS(ES+): m/z=395.09 (73) [MH⁺], 312.05 (100) [MH⁺-piperidine]. HPLC: $t_R$=2.06 min (polar_5 min, ZQ2).

5-Fluoro-2-iodo-1,3-benzothiazole

The title compound was obtained following the procedures for the synthesis of 2-iodo-7-methyl-4-trifluoromethyl-1,3-benzothiazole from 2-trifluoromethyl-5-methylaniline, using 3-fluoroaniline.

Example 284

2-[2-Amino-5-(1-piperidin-4-yl-1H-pyrazol-4-yl)-pyridin-3-yl]-benzothiazole-4-carbonitrile Following the procedure for 3-(7-fluoro-4-trifluoromethylbenzothiazol-2-yl)-5-(1-piperidin-4-yl-1H-pyrazol-4-yl)-pyridin-2-ylamine, using 2-chloro-1,3-benzothiazole-4-carbonitrile and conducting the Suzuki coupling at 80° C. for 2 h, the title compound was obtained as a yellow solid. ¹H NMR (DMSO-d₆, 400 MHz): δ=2.04-2.23 (m, 4H), 3.04 (m, 2H), 3.30 (m, 2H), 4.44 (m_c, 1H), 7.59 (t, J=7.8 Hz, 1H), 7.99 (s, 1H), 8.03 (dd, J=7.6, 1.0 Hz, 1H), 8.34 (s, 1H), 8.49 (dd, J=8.1, 1.0 Hz, 1H), 8.51 (d, J=2.3 Hz, 1H), 8.86 (broad s, 1H), 9.03 (broad s, 1H). MS (ES'): m/z=402.15 [MH⁺]. HPLC: $t_R$=2.28 min (ZQ3, polar_5 min).

2-Chloro-1,3-benzothiazole-4-carbonitrile

The title compound was prepared from 2-amino-1,3-benzothiazole-4-carbonitrile as described for 2-chloro-4,5-difluoro-1,3-benzothiazole.

2-Amino-1,3-benzothiazole-4-carbonitrile

The title compound was prepared from 2-amino-4-bromo-1,3-benzothiazole by heating with CuCN (1.0 eq.) in DMF at 160° C. for 12 h.

2-Amino-4-bromo-1,3-benzothiazole

The title compound was obtained following the procedures for the synthesis of 2-amino-7-methyl-4-trifluoromethyl-1,3-benzothiazole from 2-trifluoromethyl-5-methylaniline, using 2-bromoaniline.

Example 285

5-(1-Piperidin-4-yl-1H-pyrazol-4-yl)-3-(4-trifluoromethoxybenzothiazol-2-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 2-iodo-4-trifluoromethoxy-1,3-benzothiazole and conducting the Suzuki coupling at 50° C. for 12 h, the title compound was obtained as a yellow solid. ¹H NMR (400 MHz, DMSO-d₆): δ=9.12-9.03 (brm, 1H), 8.94-8.82 (brm, 1H), 8.57 (d, J=2.0 Hz, 1H), 8.41 (brs, 2H), 8.34 (very brs, 2H), 8.26 (dd, J=2.2, 6.6 Hz, 1H), 8.07 (s, 1H), 7.66-7.60 (m, 2H), 4.57-4.48 (m_c, 1H), 3.41 (brd, J=12.8 Hz, 2H), 3.11 (brq, J=11.2 Hz, 2H), 2.30-2.12 (m, 4H). MS(ES+): m/z=461.06 (74) [MH⁺], 378.06 (100) [MH⁺-piperidine]. HPLC: $t_R$=2.27 min (polar_5 min, ZQ2).

2-Iodo-4-trifluoromethoxy-1,3-benzothiazole

The title compound was obtained following the procedures for the synthesis of 2-iodo-7-methyl-4-trifluoromethyl-1,3-benzothiazole from 2-trifluoromethyl-5-methylaniline, using 2-trifluoromethoxyaniline.

Example 286

3-(5-Fluoro-4-trifluoromethylbenzothiazol-2-yl)-5-(1-piperidin-4-yl-1H-pyrazol-4-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 5-fluoro-2-iodo-4-trifluoromethyl-1,3-benzothiazole and conducting the Suzuki coupling at 80° C. for 2 h, the title compound was obtained as a yellow solid. ¹H NMR (400 MHz, DMSO-d₆): δ=9.02-8.92 (brm, 1H), 8.80-8.70 (brm, 1H), 8.58 (dd, J=4.8, 9.2 Hz, 1H), 8.57 (d, J=2.0 Hz, 1H), 8.37 (s, 1H), 8.31 (d, J=2.0 Hz, 1H), 8.17 (brs, 1H), 8.05 (s, 1H), 7.64 (dd, J=9.2, 11.2 Hz, 1H), 4.56-4.47 (m$_c$, 1H), 3.40 (brd, J=12.8 Hz, 2H), 3.11 (brq, J=11.4 Hz, 2H), 2.30-2.11 (m, 4H). MS(ES+): m/z=463.07 (95) [MH$^+$], 380.02 (100) [MH$^+$-piperidine]. HPLC: t$_R$=2.28 min (polar__5 min, ZQ2).

5-Fluoro-2-iodo-4-trifluoromethyl-1,3-benzothiazole

The title compound was obtained following the procedure for the synthesis of 2-iodo-7-methyl-4-trifluoromethyl-1,3-benzothiazole from 2-amino-7-methyl-4-trifluoromethyl-1,3-benzothiazole, using 2-amino-5-fluoro-4-trifluoromethyl-1,3-benzothiazole.

Example 287

3-(4-Bromo-6-trifluoromethoxybenzothiazol-2-yl)-5-(1-piperidin-4-yl-1H-pyrazol-4-yl)-pyridin-2-ylamine A mixture of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB8) (75 mg, 0.16 mmol), 4-bromo-2-iodo-6-trifluoromethoxy-1,3-benzothiazole (81 mg, 0.19 mmol), potassium carbonate (66 mg, 0.48 mmol), Pd(PPh$_3$)$_4$ (18 mg, 0.016 mmol) in DME (3 mL) and H$_2$O (1 mL) was evacuated and refilled with N$_2$ (3×), then it was heated at 80° C. for 2 h. The mixture was diluted with EtOAc (30 mL), washed with brine (10 mL), and dried over anhydrous sodium sulfate. The residue was purified by silica gel chromatography (Hex.:EtOAc=30:70→15:85) to give the Boc-protected title compound as a yellow solid, MS (ES+): m/z=639/641 (1/1) [MH$^+$]. This material was dissolved in DCM (1 mL) and treated with 1M HCl in diethyl ether (3 mL, 3 mmol). The resulting mixture was stirred at room temperature overnight. The solid that formed was filtered off, washed with DCM, and dried in vacuo to give the title compound as yellow solid. MS (ES+): m/z=538.98/540.96 (1/1) [MH$^+$].

4-Bromo-2-iodo-6-trifluoromethoxy-1,3-benzothiazole

The title compound was obtained following the procedures for the synthesis of 2-iodo-7-methyl-4-trifluoromethyl-1,3-benzothiazole from 2-trifluoromethyl-5-methylaniline, using 2-bromo-4-trifluoromethoxyaniline.

Example 288

3-[4-(6-Amino-5-benzothiazol-2-ylpyridin-3-yl)-pyrazol-1-yl]-1-piperidin-1-ylpropan-1-one The title compound was prepared according to the procedures described for 3-[4-(6-amino-5-benzothiazol-2-ylpyridin-3-yl)-pyrazol-1-yl]-1-pyrrolidin-1-ylpropan-1-one. $^1$H NMR (400 MHz, CD$_3$OD): δ=1.48-1.56 (m, 4H), 1.60-1.66 (m, 2H), 2.98 (t, J=6.6 Hz, 3.39-3.45 (m, 2H), 3.50-3.56 (m, 2H), 4.49 (t, J=6.6 Hz, 2H), 7.40-7.44 (m, 1H), 7.48-7.53 (m, 1H), 7.80 (s, 1H), 7.95 (t, J=4.0 Hz, 2H), 8.00 (d, J=7.6 Hz, 1H), 8.11 (d, J=2.0 Hz, 1H), 8.27 (d, J=2.0 Hz, 1H). MS (ES$^+$): m/z=433.16 (100) [MH$^+$]. HPLC: t$_R$=3.22 min (ZQ2, polar__5 min).

Example 289

3-[4-(6-Amino-5-benzothiazol-2-ylpyridin-3-yl)-pyrazol-1-yl]-1-(3-hydroxypyrrolidin-1-yl)-propan-1-one The title compound was prepared according to the procedures described for 3-[4-(6-amino-5-benzothiazol-2-ylpyridin-3-yl)-pyrazol-1-yl]-1-pyrrolidin-1-ylpropan-1-one. $^1$H NMR (400 MHz, CD$_3$OD): δ=1.88-2.07 (m, 2H), 2.89-3.01 (m, 2H), 3.34-3.41 (m, 1H), 3.41-3.49 (m, 1H), 3.51-3.58 (m, 2H), 4.34-4.43 (m, J=17.0, 4.3, 4.3, 2.5, 2.2 Hz, 1H), 4.49 (td, J=6.6, 1.6 Hz, 2H), 7.40-7.45 (m, 1H), 7.49-7.53 (m, 1H), 7.84 (s, 1H), 7.96-8.03 (m, 3H), 8.14 (d, J=2.3 Hz, 1H), 8.29 (d, J=2.3 Hz, 1H). MS (ES$^+$): m/z=435.11 (100) [MH$^+$]. HPLC: t$_R$=2.58 min (ZQ3, polar__5 min).

Example 290

3-[4-(6-Amino-5-benzothiazol-2-ylpyridin-3-yl)-pyrazol-1-yl]-1-(4-hydroxypiperidin-1-yl)-propan-1-one The title compound was prepared according to the procedures described for 3-[4-(6-amino-5-benzothiazol-2-ylpyridin-3-yl)-pyrazol-1-yl]-1-pyrrolidin-1-ylpropan-1-one. $^1$H NMR (400 MHz, CD$_3$OD): δ=1.36-1.46 (m, 2H), 1.75-1.85 (m, 2H), 3.01 (td, J=6.6, 3.4 Hz, 2H), 3.10-3.26 (m, 2H), 3.71-3.84 (m, 2H), 3.99-4.07 (m, 1H), 4.48 (t, J=6.7 Hz, 2H), 7.40-7.45 (m, 1H), 7.49-7.53 (m, 1H), 7.84 (s, 1H), 7.96-8.02 (m, 3H), 8.14 (d, J=2.3 Hz, 1H), 8.29 (d, J=2.0 Hz, 1H). MS (ES$^+$): m/z=449.15 (100) [MH$^+$]. HPLC: t$_R$=2.62 min (ZQ3, polar__5 min).

Example 291

3-[4-(6-Amino-5-benzothiazol-2-ylpyridin-3-yl)-pyrazol-1-yl]-1-morpholin-4-ylpropan-1-one The title compound was prepared according to the procedures described for 3-[4-(6-amino-5-benzothiazol-2-ylpyridin-3-yl)-pyrazol-1-yl]-1-pyrrolidin-1-ylpropan-1-one. $^1$H NMR (400 MHz, CD$_3$OD): δ=2.97 (t, J=6.4 Hz, 2H), 3.43-3.48 (m, 2H), 3.54-3.64 (m, 6H), 4.50 (t, J=6.4 Hz, 2H), 7.38-7.43 (m, 1H), 7.47-7.51 (m, 1H), 7.78 (s, 1H), 7.91-7.94 (m, 2H), 7.99 (d, J=7.6 Hz, 1H), 8.08 (d, J=2.3 Hz, 1H), 8.25 (d, J=2.3 Hz, 1H). MS (ES$^+$): m/z=435.15 (100) [MH$^+$]. HPLC: t$_R$=2.81 min (ZQ3, polar__5 min).

Example 292

3-[4-(6-Amino-5-benzothiazol-2-ylpyridin-3-yl)-pyrazol-1-yl]-N-(2-methoxyethyl)-propionamide The title compound was prepared according to the procedures described for 3-[4-(6-amino-5-benzothiazol-2-ylpyridin-3-yl)-pyrazol-1-yl]-1-pyrrolidin-1-ylpropan-1-one. $^1$H NMR (400 MHz, CD$_3$OD): δ=2.77 (t, J=6.6 Hz, 2H), 3.27 (s, 3H), 3.32-3.35 (m, 2H), 3.36-3.39 (m, 2H), 4.46 (t, J=6.6 Hz, 2H), 7.38-7.43 (m, 1H), 7.46-7.51 (m, 1H), 7.76 (s, 1H), 7.85 (s, 1H), 7.93 (d, J=7.3 Hz, 1H), 7.99 (d, J=7.6 Hz, 1H), 8.07 (d, J=2.3 Hz, 1H), 8.24 (d, J=2.3 Hz, 1H). MS (ES$^+$): m/z=423.16 (100) [MH$^+$]. HPLC: t$_R$=2.72 min (ZQ3, polar__5 min).

Example 293

3-[4-(6-Amino-5-benzothiazol-2-ylpyridin-3-yl)-pyrazol-1-yl]-N-(2-hydroxyethyl)-propionamide The title compound was prepared according to the procedures described for 3-[4-(6-amino-5-benzothiazol-2-ylpyridin-3-yl)-pyrazol-1-yl]-1-pyrrolidin-1-ylpropan-1-one. $^1$H NMR (400 MHz, CD$_3$OD): δ=2.79 (t, J=6.7 Hz, 2H), 3.25-3.29 (m, 2H), 3.56 (t, J=5.6 Hz, 2H), 4.48 (t, J=6.6 Hz, 2H), 7.39-7.44 (m, 1H), 7.47-7.53 (m, 1H), 7.78 (s, 1H), 7.89 (s, 1H), 7.95 (d, J=8.1 Hz, 1H), 8.00 (d, J=7.6 Hz, 1H), 8.10 (d, J=2.3 Hz, 1H), 8.26 (d, J=2.3 Hz, 1H). MS (ES$^+$): m/z=409.13 (100) [MH$^+$]. HPLC: t$_R$=2.52 min (ZQ3, polar_5 min).

Example 294

3-[4-(6-Amino-5-benzothiazol-2-ylpyridin-3-yl)-pyrazol-1-yl]-N,N-bis-(2-methoxyethyl)-propionamide The title compound was prepared according to the procedures described for 3-[4-(6-amino-5-benzothiazol-2-ylpyridin-3-yl)-pyrazol-1-yl]-1-pyrrolidin-1-ylpropan-1-one. $^1$H NMR (400 MHz, CD$_3$OD): δ=3.07 (t, J=6.4 Hz, 2H), 3.29 (s, 3H), 3.32 (s, 3H), 3.49 (q, J=4.8 Hz, 4H), 3.53-3.59 (m, 4H), 4.51 (t, J=6.4 Hz, 2H), 7.41-7.46 (m, 1H), 7.52 (td, J=7.6, 1.3 Hz, 1H), 7.81 (s, 1H), 7.92 (s, 1H), 7.96 (d, J=7.3 Hz, 1H), 8.02 (d, J=7.6 Hz, 1H), 8.12 (d, J=2.0 Hz, 1H), 8.28 (d, J=2.3 Hz, 1H). MS (ES$^+$): m/z=481.14 (100) [MH$^+$]. HPLC: t$_R$=3.01 min (ZQ3, polar_5 min).

Example 295

3-[4-(6-Amino-5-benzothiazol-2-ylpyridin-3-yl)-pyrazol-1-yl]-N,N-dimethylpropionamide The title compound was prepared according to the procedures described for 3-[4-(6-amino-5-benzothiazol-2-ylpyridin-3-yl)-pyrazol-1-yl]-1-pyrrolidin-1-ylpropan-1-one. $^1$H NMR (400 MHz, CD$_3$OD): δ=2.93 (s, 3H), 2.97 (t, J=6.7 Hz, 2H), 2.99 (d, J=1.0 Hz, 3H), 4.48 (t, J=6.4 Hz, 2H), 7.41 (t, J=7.6 Hz, 1H), 7.49 (t, J=7.6 Hz, 1H), 7.77 (s, 1H), 7.91-7.95 (m, 2H), 7.99 (d, J=8.3 Hz, 1H), 8.09 (dd, J=2.1, 1.1 Hz, 1H), 8.25 (d, J=1.0 Hz, 1H). MS (ES+): m/z=393.14 (100) [MH$^+$]. HPLC: t$_R$=2.83 min (ZQ3, polar_5 min).

Example 296

3-[4-(6-Amino-5-benzothiazol-2-ylpyridin-3-yl)-pyrazol-1-yl]-N-methylpropionamide The title compound was prepared according to the procedures described for 3-[4-(6-amino-5-benzothiazol-2-ylpyridin-3-yl)-pyrazol-1-yl]-1-pyrrolidin-1-ylpropan-1-one. $^1$H NMR (400 MHz, CD$_3$OD): δ=2.69 (d, J=1.0 Hz, 3H), 2.76 (t, J=6.4 Hz, 2H), 4.43-4.49 (m, 2H), 7.41 (t, J=7.7 Hz, 1H), 7.47-7.53 (m, 1H), 7.79 (s, 1H), 7.90 (s, 1H), 7.95 (d, J=7.8 Hz, 1H), 8.00 (d, J=8.1 Hz, 1H), 8.09-8.12 (m, 1H), 8.24-8.27 (m, 1H). MS (ES$^+$): m/z=379.15 (100) [MH$^+$]. HPLC: t$_R$=2.65 min (ZQ3, polar_5 min).

Example 297

3-[4-(6-Amino-5-benzothiazol-2-ylpyridin-3-yl)-pyrazol-1-yl]-propionamide

The title compound was prepared according to the procedures described for 3-[4-(6-amino-5-benzothiazol-2-ylpyridin-3-yl)-pyrazol-1-yl]-1-pyrrolidin-1-ylpropan-1-one. $^1$H NMR (400 MHz, CD$_3$OD): δ=2.80 (t, J=6.6 Hz, 2H), 4.46 (t, J=6.6 Hz, 2H), 7.39-7.44 (m, 1H), 7.47-7.52 (m, 1H), 7.77 (s, 1H), 7.89 (s, 1H), 7.94 (d, J=8.1 Hz, 1H), 8.00 (d, J=8.1 Hz, 1H), 8.09 (d, J=2.3 Hz, 1H), 8.25 (d, J=2.0 Hz, 1H). MS (ES$^+$): m/z=365.11 (100) [MH$^+$]. HPLC: t$_R$=2.57 min (ZQ3, polar_5 min).

Example 298

5-(1-Piperidin-4-yl-1H-pyrazol-4-yl)-3-(4,5,6,7-tetrahydro-benzothiazol-2-yl)-pyridin-2-ylamine A mixture of 4-{4-[6-amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB8) (30 mg, 0.064 mmol), 2-iodo-4,5,6,7-tetrahydrobenzothiazole (20 mg, 0.077 mmol), potassium carbonate (26 mg, 0.19 mmol), and Pd(PPh$_3$)$_4$ (7.4 mg, 0.0064 mmol) in DME (1.5 mL) and H$_2$O (0.5 mL) was evacuated and refilled with N$_2$ (3×). It was then heated at 100° C. for 30 min in the microwave reactor. The mixture was diluted with EtOAc (30 mL), washed with brine (10 mL), dried over anhydrous sodium sulfate, filtered, and concentrated in vacuo. The residue was purified by silica gel chromatography (Hex.:EtOAc=30:70→15:85) to give a yellow solid. This material was dissolved in DCM (2 mL) and treated with 1M HCl in diethyl ether (3 mL). The resulting mixture was stirred at room temperature for 3 h. The title compound was collected by filtration as a yellow solid, washed with DCM, and dried in vacuo. $^1$H NMR (DMSO-d$_6$, 400 MHz): δ=1.82-1.88 (m, 4H), 2.14-2.23 (m, 4H), 2.81-2.87 (m, 4H), 3.35-3.40 (m, 2H), 4.55 (m$_c$, 1H), 8.09 (s, 1H), 8.44 (d, J=2.0 Hz, 1H), 8.47 (s, 1H), 8.50 (d, J=2.0 Hz, 1H). MS (ES+): m/z=381.17 [MH$^+$].

2-Iodo-4,5,6,7-tetrahydrobenzothiazole

The title compound was obtained following the procedure for 7-fluoro-2-iodo-1,3-benzothiazole, using 4,5,6,7-tetrahydrobenzothiazol-2-ylamine.

Example 299

5-(1-Piperidin-4-yl-1H-pyrazol-4-yl)-3-(5,6,7,8-tetrahydro-4H-cycloheptathiazol-2-yl)-pyridin-2-ylamine Following the procedure for 3-(7-fluoro-4-trifluoromethylbenzothiazol-2-yl)-5-(1-piperidin-4-yl-1H-pyrazol-4-yl)-pyridin-2-ylamine, using 2-iodo-5,6,7,8-tetrahydro-4H-cycloheptathiazole and conducting the Suzuki coupling at 55° C. for 3 h, the title compound was obtained as a yellow solid. MS (ES$^+$): m/z=395.19 [MH$^+$]. HPLC: t$_R$=2.21 min (ZQ3, polar_5 min).

2-Iodo-5,6,7,8-tetrahydro-4H-cycloheptathiazole

The title compound was obtained following the procedure for 7-fluoro-2-iodo-1,3-benzothiazole, using 5,6,7,8-tetrahydro-4H-cycloheptathiazol-2-ylamine.

Example 300

3-(3,4-Dihydro-1H-isoquinolin-2-yl)-5-(1-piperidin-4-yl-1H-pyrazol-4-yl)-pyridin-2-ylamine A mixture of 4-{4-[6-Amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB4) (93.9 mg, 0.200 mmol), 1,2,3,4-tetrahydroisoquinoline (53.3 mg, 0.400 mmol), cupric acetate (36.3 mg, 0.200 mmol), pyridine (32 µL, 0.40 mmol) and DCM (5 mL, 80 mmol) was stirred at rt under an atmosphere of air (Reaction A). Another reaction was set up with the same amount of above reagents, and 4 Å molecular sieves (53 mg, 264 mg/mmol SM) was added (Reaction B). After stirring overnight at rt, the same amount of molecular sieve as in reaction B was added to reaction A. After stirring at rt for 7 h, both reaction mixtures were combined, washed with EDTA solution (2%, 3×30 ml), water (30 ml) and brine (30 ml), dried over MgSO$_4$, filtered, and concentrated in vacuo to give a dark-blue solid. Purification by prep. TLC eluting with 5% MeOH/DCM gave 4-{4-[6-amino-5-(3,4-dihydro-1H-isoquinolin-2-yl)-pyridin-3-yl]-pyrazol-1-yl}-piperidine-1-carboxylic acid tert-butyl ester as brown oil; MS(ES+): m/z=475.12 [MH$^+$]. This brown oil was dissolved in MeOH (10 mL), 1.0 M of HCl in Et$_2$O (10 mL) was added, and the solution was stirred at rt for 3 d. The solvent was removed; the residue was dissolved in DMSO and purified by Gilson HPLC to give the title compound as light-brown oil. $^1$H NMR (400 MHz, DMSO-d$_6$): δ=1.99-2.11 (m, 2H), 2.12-2.19 (m, 2H), 2.89-2.99 (m, 2H), 3.00-3.05 (m, 2H), 3.12-3.18 (m, 2H), 3.26-3.33 (m, 2H), 4.10 (s, 2H), 4.33-4.43 (m, 1H), 5.51 (brs, 2H), 7.13-7.19 (m, 4H), 7.47 (d, J=2.0 Hz, 1H), 7.82 (s, 1H), 7.99 (d, J=2.0 Hz, 1H), 8.13 (s, 1H), 8.30 (brs, 2H). MS(ES+): m/z=375.17 (42) [MH$^+$]. HPLC: t$_R$=1.73 min (ZQ2, polar_5 min).

Example 301

3-(5-Fluoro-3,4-dihydro-1H-isoquinolin-2-yl)-5-(1-piperidin-4-yl-1H-pyrazol-4-yl)-pyridin-2-ylamine 4-{4-[6-Amino-5-(5-fluoro-3,4-dihydro-1H-isoquinolin-2-yl)-pyridin-3-yl]-pyrazol-1-yl}-piperidine-1-carboxylic acid tert-butyl ester (34 mg) was dissolved in MeOH (20 mL), 1.0 M of HCl in Et$_2$O (20 mL) was added, and the mixture was stirred at rt overnight. The solvent was removed in vacuo to give a brown oil. It was purified by Gilson HPLC eluting with H$_2$O/CH$_3$CN/0.1% formic acid mixtures to give the title compound contaminated with the corresponding formamide. This material was dissolved in MeOH (2 ml), aqueous NaOH (10 N, 2 ml) was added, and the solution was stirred at rt overnight. It was then treated with water (5 ml) and extracted with DCM (3×20 ml). The extracts were washed with water (2×20 ml), brine (20 ml), dried over MgSO$_4$, filtered, and concentrated in vacuo, to give the title compound as a beige solid. $^1$H NMR (400 MHz, CD$_3$OD): δ=1.79-1.92 (m, 2H), 1.98-2.06 (m, 2H), 2.63-2.70 (m, 2H), 2.90 (t, J=6.0 Hz, 2H), 3.06-3.14 (m, 2H), 3.18-3.24 (m, 2H), 4.06 (s, 2H), 4.15-4.23 (m, 1H), 6.82 (d, J=8.8 Hz, 1H), 6.85-6.88 (m, 1H), 7.05-7.12 (m, 1H), 7.44 (d, J=2.4 Hz, 1H), 7.66 (d, J=0.8 Hz, 1H), 7.83 (d, J=2.0 Hz, 1H), 7.91 (d, J=0.4 Hz, 1H). MS(ES+): m/z=394.14 (45) [MH$^+$]. HPLC: t$_R$=2.21 min (ZQ2, polar_5 min).

4-{4-[6-Amino-5-(5-fluoro-3,4-dihydro-1H-isoquinolin-2-yl)-pyridin-3-yl]-pyrazol-1-yl}-piperidine-1-carboxylic acid tert-butyl ester A mixture of 4-{4-[6-Amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB4) (170 mg, 0.358 mmol), 5-fluoro-1,2,3,4-tetrahydroisoquinoline (114 mg, 0.716 mmol), cupric acetate (65.7 mg, 0.358 mmol), pyridine (59 µL, 0.72 mmol), 4 Å molecular sieves (95 mg, 264 mg/mmol SM), and DCM (9 mL, 100 mmol) was stirred at rt under an atmosphere of air for 5 d. The mixture was diluted with DCM (50 ml), washed with EDTA solution (2%, 3×50 ml), water (3×50 ml) and brine (50 ml), dried over MgSO$_4$, filtered, and concentrated in vacuo to give a dark black oil that was purified by MDPS to give the title compound as a brown oil. $^1$H NMR (400 MHz, CDCl$_3$): δ=1.48 (s, 9H), 1.87-1.99 (m, 2H), 2.12-2.19 (m, 2H), 2.84-2.98 (m, 2H), 3.00 (t, J=5.6 Hz, 2H), 3.34 (t, J=6.0 Hz, 2H), 4.17 (s, 2H), 4.22-4.36 (m, 3H), 6.90 (d, J=7.2 Hz, 1H), 6.98 (t, J=8.4 Hz, 1H), 7.18-7.24 (m, 1H), 7.50 (d, J=2.0 Hz, 1H), 7.59 (s, 1H), 7.65 (s, 1H), 7.67 (d, J=1.6 Hz, 1H). MS(ES+): m/z=494.38 (100) [MH$^+$]. HPLC: t$_R$=2.84 min (ZQ2, polar_5 min).

Example 302

3-(5-Chloro-3,4-dihydro-1H-isoquinolin-2-yl)-5-(1-piperidin-4-yl-1H-pyrazol-4-yl)-pyridin-2-ylamine 4-{4-[6-Amino-5-(5-chloro-3,4-dihydro-1H-isoquinolin-2-yl)-pyridin-3-yl]-pyrazol-1-yl}-piperidine-1-carboxylic acid tert-butyl ester (26 mg, 0.051 mmol) was dissolved in MeOH (20 mL), 1.0 M of HCl in Et$_2$O (20 mL) was added, and the mixture was stirred at rt overnight. The solvent was removed in vacuo to give the title compound as a brown solid. $^1$H NMR (400 MHz, CD$_3$OD): δ=2.32-2.39 (m, 4H), 3.11 (t, J=6.0 Hz, 2H), 3.22-3.32 (m, 2H), 3.42 (t, J=6.0 Hz, 2H), 3.59 (d, J=13.2 Hz, 2H), 4.27 (s, 2H), 4.58-4.68 (m, 1H), 7.16 (d, J=7.6 Hz, 1H), 7.22 (t, J=8.0 Hz, 1H), 7.32 (d, J=8.0 Hz, 1H), 7.97 (s, 1H), 7.98 (s, 1H), 8.33 (s, 1H). MS(ES+): m/z=409.10/411.08 (46/18) [MH$^+$]. HPLC: t$_R$=2.25 min (ZQ2, polar_5 min).

4-{4-[6-Amino-5-(5-chloro-3,4-dihydro-1H-isoquinolin-2-yl)-pyridin-3-yl]-pyrazol-1-yl}-piperidine-1-carboxylic acid tert-butyl ester A mixture of 4-{4-[6-Amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB4) (245 mg, 0.517 mmol), 5-chloro-1,2,3,4-tetrahydroisoquinoline (175 mg, 1.03 mmol), cupric acetate (94.8 mg, 0.517 mmol), pyridine (84 µL, 1.0 mmol), 4 Å molecular sieves (139 mg, 264 mg/mmol SM), and DCM (9 mL, 100 mmol) was stirred at rt under an atmosphere of air for 3 d. The mixture was diluted with DCM (50 ml), washed with EDTA solution (2%, 3×50 ml), water (3×50 ml) and brine (50 ml), dried over MgSO$_4$, filtered, and concentrated in vacuo to give a dark black oil that was purified by MDPS to give the title compound as a brown solid. $^1$H NMR (400 MHz, CDCl$_3$): δ=1.48 (s, 9H), 1.88-1.99 (m, 2H), 2.12-2.19 (m, 2H), 2.84-2.98 (m, 2H), 3.04 (t, J=6.0 Hz, 2H), 3.36 (t, J=6.0 Hz, 2H), 4.16 (s, 2H), 4.22-4.36 (m, 3H), 7.02 (d, J=7.6 Hz, 1H), 7.19 (t, J=8.0 Hz, 1H), 7.33 (d, J=7.6 Hz, 1H), 7.50 (s, 1H), 7.62 (s, 1H), 7.66 (s, 1H), 7.69 (s, 1H). MS(ES+): m/z=508.77/511.16 (52/20) [MH$^+$]. HPLC: t$_R$=3.00 min (ZQ2, polar_5 min).

Example 303

3-(5,8-Difluoro-3,4-dihydro-1H-isoquinolin-2-yl)-5-(1-piperidin-4-yl-1H-pyrazol-4-yl)-pyridin-2-ylamine 4-{4-[6-Amino-5-(5,8-difluoro-3,4-dihydro-1H-isoquinolin-2-yl)-pyridin-3-yl]-pyrazol-1-yl}-piperidine-1-carboxylic acid tert-butyl ester (26 mg, 0.051 mmol) was dissolved in MeOH (20 mL), 1.0 M of HCl in Et$_2$O (20 mL) was added, and the mixture was stirred at rt overnight. The solvent was removed in vacuo to give the title compound as a brown solid. ¹H NMR (400 MHz, CD₃OD): δ=2.33-2.42 (m, 4H), 3.08 (t, J=5.2 Hz, 2H), 3.23-3.36 (m, 2H), 3.39 (t, J=5.6 Hz, 2H), 3.59 (d, J=12.8 Hz, 2H), 4.24 (s, 2H), 4.62-4.72 (m, 1H), 6.99-7.04 (m, 2H), 7.97 (s, 1H), 8.01 (s, 1H), 8.07 (s, 1H), 8.39 (s, 1H). MS(ES+): m/z=411.08 (42) [MH⁺]. HPLC: $t_R$=2.10 min (ZQ2, polar_5 min).

4-{4-[6-Amino-5-(5,8-difluoro-3,4-dihydro-1H-isoquinolin-2-yl)-pyridin-3-yl]-pyrazol-1-yl}-piperidine-1-carboxylic acid tert-butyl ester A mixture of 4-{4-[6-Amino-5-(4,4,5,5-tetramethyl-[1,3,2]dioxaborolan-2-yl)-pyridin-3-yl]-pyrazol-1-yl}-piperidine-1-carboxylic acid tert-butyl ester (BB4) (245 mg, 0.517 mmol), 5,8-difluoro-1,2,3,4-tetrahydroisoquinoline (175 mg, 1.03 mmol), cupric acetate (94.8 mg, 0.517 mmol), pyridine (84 µL, 1.0 mmol), 4 Å molecular sieves (139 mg, 264 mg/mmol SM), and DCM (9 mL, 100 mmol) was stirred at rt under an atmosphere of air for 3 d. The mixture was diluted with DCM (50 ml), washed with EDTA solution (2%, 3×50 ml), water (3×50 ml) and brine (50 ml), dried over MgSO₄, filtered, and concentrated in vacuo to give a dark black oil that was purified by MDPS to give the title compound as a brown solid. ¹H NMR (400 MHz, CDCl₃): δ=1.48 (s, 9H), 1.88-1.99 (m, 2H), 2.12-2.19 (m, 2H), 2.84-2.98 (m, 2H), 3.00 (t, J=5.6 Hz, 2H), 3.31 (t, J=6.0 Hz, 2H), 4.17 (s, 2H), 4.22-4.36 (m, 3H), 6.92-6.97 (m, 1H), 7.55 (d, J=1.6 Hz, 1H), 7.63 (s, 1H), 7.67 (s, 1H), 7.72 (d, J=1.2 Hz, 1H). MS(ES+): m/z=511.16 (100) [MH⁺]. HPLC: $t_R$=2.93 min (ZQ2, polar_5 min).

Example 304

3-Naphthalen-2-yl-5-(1-piperidin-4-yl-1H-pyrazol-4-yl)-pyridin-2-ylamine trihydrochloride To a solution of 4-[4-(6-amino-5-naphthalen-2-ylpyridin-3-yl)-pyrazol-1-yl]-piperidine-1-carboxylic acid tert-butyl ester (15.2 mg, 0.0324 mmol) in 1,4-dioxane (1.0 mL, 13 mmol) was added HCl (4.0 M solution in 1,4-dioxane; 1.0 mL, 4.0 mmol), and the mixture was stirred at ambient temperature for 2 h. Almost immediately a white solid precipitated. The solid was filtered off, washed with MTBE, and dried in vacuo overnight to give the title compound as off-white solid. ¹H NMR (400 MHz, DMSO-d₆): δ=14.7 (very brs, 1H), 9.32-9.17 (brm, 1H), 9.17-9.02 (brm, 1H), 8.43 (s, 1H), 8.42 (d, J=2.0 Hz, 1H), 8.31 (d, J=2.0 Hz, 1H), 8.12 (s, 1H), 8.11 (d, J=4.8 Hz, 1H), 8.08 (s, 1H), 8.06-8.00 (m_c, 2H), 7.75 (brs, 2H), 7.66-7.59 (m, 3H), 4.53-4.45 (m_c, 1H), 3.36 (brd, J=13.0 Hz, 2H), 3.08 (brq, J=11.2 Hz, 2H), 2.27-2.08 (m, 4H). MS(ES+): m/z=370.19 (37) [MH⁺], 287.12 (100) [MH⁺-piperidine]. HPLC: $t_R$=1.88 min (polar_5 min, ZQ3).

4-[4-(6-Amino-5-naphthalen-2-ylpyridin-3-yl)-pyrazol-1-yl]-piperidine-1-carboxylic acid tert-butyl ester A solution of 2-naphthylboronic acid (43 mg, 0.25 mmol), Pd(PPh₃)₄ (23 mg, 0.020 mmol), and a mixture of 4-[4-(6-amino-5-bromopyridin-3-yl)-pyrazol-1-yl]-piperidine-1-carboxylic acid tert-butyl ester and 4-[4-(2-amino-5-bromopyridin-3-yl)-pyrazol-1-yl]-piperidine-1-carboxylic acid tert-butyl ester (together 92.2 mg, 0.138 mmol) in 1,4-dioxane (3.5 mL, 45 mmol) in a sealable microwave tube was charged with a solution of Cs₂CO₃ (140 mg, 0.44 mmol) in H₂O (0.90 mL, 50 mmol), flushed with nitrogen, sealed and irradiated in the microwave reactor at 105° C. for 60 min. More 2-naphthylboronic acid (11 mg, 0.064 mmol) and Pd(PPh₃)₄ (5.6 mg, 0.0048 mmol) were added, and the solution was heated in the microwave reactor at 105° C. for 30 min. Further 2-naphthylboronic acid (12 mg, 0.070 mmol) and Pd(PPh₃)₄ (4.5 mg, 0.0039 mmol) were added to the solution, which was then heated in the microwave reactor to 105° C. for 30 min. The reaction mixture was diluted with EtOAc, washed with aq. NaHCO₃ solution, water, and brine, dried over MgSO₄, filtered and concentrated in vacuo. The residue was chromatographed on silica gel [10 g/70 mL prepacked cartridge, eluting with DCM→1% MeOH in DCM→2% MeOH in DCM→3% MeOH in DCM]. One obtained a mixture of the title compound and its regioisomer, 4-[4-(2-amino-5-naphthalen-2-ylpyridin-3-yl)-pyrazol-1-yl]-piperidine-1-carboxylic acid tert-butyl ester, as yellow-brown solid. This mixture of regioisomers was separated using the MDPS. ¹H NMR (400 MHz, CDCl₃): δ=8.26 (d, J=2.4 Hz, 1H), 7.99-7.45 (m, 10H), 4.60 (s, 2H), 4.39-4.21 (m, 3H), 2.98-2.85 (brm, 2H), 2.19 (brt, J=13.0 Hz, 2H), 2.05-1.89 (m_c, 2H), 1.48 (s, 9H). MS(ES+): m/z=470.19 (100) [MH⁺]. HPLC: $t_R$=2.85 min (polar_5 min, ZQ3).

4-[4-(2-Amino-5-naphthalen-2-ylpyridin-3-yl)-pyrazol-1-yl]-piperidine-1-carboxylic acid tert-butyl ester ¹H NMR (400 MHz, CDCl₃): δ=8.40 (d, J=2.4 Hz, 1H), 7.99-7.45 (m, 10H), 4.69 (s, 2H), 4.39-4.21 (m, 3H), 2.98-2.85 (brm, 2H), 2.19 (brt, J=13.0 Hz, 2H), 2.05-1.89 (m_c, 2H), 1.49 (s, 9H). MS(ES+): m/z=470.19 (100) [MH⁺]. HPLC: $t_R$=3.00 min (polar_5 min, ZQ3).

4-[4-(6-Amino-5-bromopyridin-3-yl)-pyrazol-1-yl]-piperidine-1-carboxylic acid tert-butyl ester and 4-[4-(2-Amino-5-bromopyridin-3-yl)-pyrazol-1-yl]-piperidine-1-carboxylic acid tert-butyl ester A solution of 2-amino-3,5-dibromopyridine (96.8 mg, 0.384 mmol), 4-[4-(4,4,5,5-tetramethyl-1,3,2-dioxaborolan-2-yl)-pyrazol-1-yl]-piperidine-1-carboxylic acid tert-butyl ester (BB1) (146 mg, 0.388 mmol), and Pd(PPh₃)₄ (35 mg, 0.030 mmol) in 1,4-dioxane (3.2 mL, 41 mmol) was flushed with nitrogen. A solution of Cs₂CO₃ (277 mg, 0.850 mmol) in H₂O (0.80 mL, 44 mmol) was added, and the resulting mixture was flushed again with nitrogen and irradiated in the microwave reactor at 100° C. for 30 min. The reaction was worked up by diluting with EtOAc (≈70 mL), washing with water and brine, and drying over MgSO₄. The extract was filtered and dried in vacuo, giving a brown oil. It was chromatographed on silica gel [10 g/70 mL prepacked cartridge, eluting with DCM→1% MeOH in DCM→2% MeOH in DCM→4% MeOH in DCM]. One obtained a mixture of the regioisomeric title compounds as brown solid. This mixture was used in the next step without separation. 6-Amino isomer: ¹H NMR (400 MHz, CDCl₃): δ=8.14 (d, J=2.0 Hz, 1H), 7.78 (d, J=2.0 Hz, 1H), 7.67 (s, 1H), 7.57 (s, 1H), 4.98 (brs, 2H), 4.36-4.21 (brm, 3H), 2.91 (brt, J=11.2 Hz, 2H), 2.20-2.11 (brm, 2H), 2.01-1.88 (m_c, 2H), 1.48 (s, 9H). MS(ES+): m/z=422.03/423.99 (90/100) [MH⁺]. HPLC: $t_R$=4.18 min (polar_15 min, ZQ3). 2-Amino isomer: ¹H NMR (400 MHz, CDCl3): δ=8.03 (d, J=2.4 Hz, 1H), 7.71 (d, J=0.5 Hz, 1H), 7.64 (d, J=0.5 Hz, 1H), 7.52 (d, J=2.0 Hz, 1H), 4.76 (brs, 2H), 4.36-4.21 (brm, 3H), 2.91 (brt, J=11.2 Hz, 2H), 2.20-2.11 (brm, 2H), 2.01-1.88 (m_c, 2H), 1.48 (s, 9H). MS(ES+): m/z=422.03/424.00 (99/100) [MH⁺]. HPLC: $t_R$=4.58 min (polar_15 min, ZQ3).

The invention claimed is:

1. A compound of Formula I, or a pharmaceutically acceptable salt thereof,

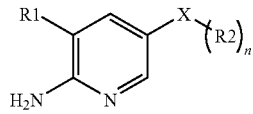

wherein:
- R1 is isoquinolin-3-yl or 1,2,3,4-tetrahydroisoquinolin-2-yl, either of which is optionally substituted with one to four independent R3 groups;
- X is pyrazolyl, pyridyl, thiazolyl, imidazolyl, furyl, thienyl, pyrrolyl, indolyl, indazolyl, or tetrahydropyridyl;
- R2 is H, halogen, CN, alkyl, cycloalkyl, bicycloalkyl, hydroxy, hydroxyalkyl, alkoxy, aryloxy, amino, aminoalkyl, alkylamino, alkylsulfonyl, C(=O)R4, C(=O)OR4, C(=O)NR5R6, NR7C(=O)R4, NR7C(=O)OR4, NR7C(=O)NR5R6, NR7S(=O)$_2$R4, NR7S(=O)R4, aryl, heterocyclyl, heterobicycloalkyl, heterospiroalkyl, heteroaryl, -alkyl-C(=O)R4, -alkyl-C(=O)OR4, -alkyl-C(=O)NR5R6, -alkyl-NR7C(=O)R4, -alkyl-NR7C(=O)OR4, -alkyl-NR7C(=O)NR5R6, -alkyl-NR7SO$_2$R4, -alkyl-NR7SOR4, aryl-alkyl, heterocyclyl-alkyl, or heteroaryl-alkyl, any of which is optionally substituted by one or more independent R3 groups;
- R3 is H, halogen, CN, alkyl, cycloalkyl, alkenyl, alkynyl, hydroxy, hydroxyalkyl, alkoxy, aryloxy, amino, aminoalkyl, alkylamino, alkylsulfonyl, C(=O), C(=S), C(=O)R4, C(=O)OR4, C(=O)NR5R6, NR7C(=O)R4, NR7C(=O)OR4, NR7C(=O)NR5R6, NR7SO$_2$R4, NR7SOR4, aryl, heterocyclyl, heteroaryl, -alkyl-C(=O)R4, -alkyl-C(=O)OR4, -alkyl-C(=O)NR5R6, -alkyl-NR7C(=O)R4, -alkyl-NR7C(=O)OR4, -alkyl-NR7C(=O)NR5R6, -alkyl-NR7SO$_2$R4, -alkyl-NR7SOR4, aryl-alkyl, heterocyclyl-alkyl, or heteroaryl-alkyl, any of which is optionally further substituted by one or more independent R7 groups;
- R4 is alkyl, cycloalkyl, alkenyl, alkynyl, hydroxy, hydroxyalkyl, alkoxy, aryloxy, amino, aminoalkyl, alkylamino, dialkylamino, alkylsulfonyl, aryl, heterocyclyl, heteroaryl, aryl-alkyl, heterocyclyl-alkyl, or heteroaryl-alkyl, any of which is optionally further substituted by one or more independent R7 groups;
- R5 and R6 are each independently H, alkyl, cycloalkyl, or alkoxyalkyl, any of which is optionally substituted by one or more independent R7 groups; or R5 and R6 taken together with the atom that they are attached to form a 4-7 membered saturated or unsaturated heterocycle; wherein said heterocycle is optionally further substituted by one or more independent R7 groups;
- R7 is H, halogen, alkyl, trifluoroalkyl, alkoxy, CN, cycloalkyl, alkoxyalkyl, aryl, hetaryl, or heterocyclyl;
- n is 1.

2. The compound of claim 1, or a pharmaceutically acceptable salt thereof, wherein the compound of Formula I has the Formula Ia

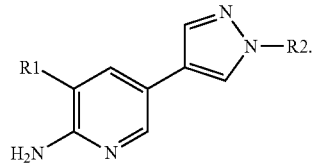

3. The compound of claim 1, or a pharmaceutically acceptable salt thereof, wherein the compound has the Formula Iaa

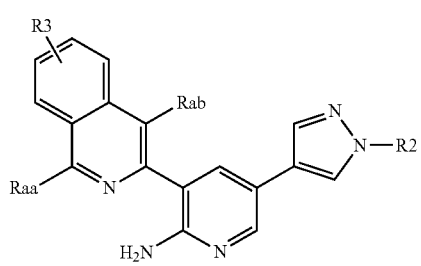

wherein
Raa is H, alkoxy, or alkyl wherein alkoxy or alkyl is optionally further substituted with halogen; and Rab is H or F.

4. The compound of claim 1, or a pharmaceutically acceptable salt thereof, wherein the compound of has the Formula Iac

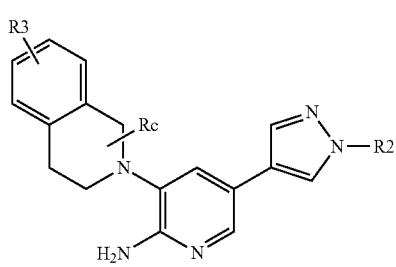

wherein
Rc is H or alkyl wherein alkyl is optionally further substituted with halogen.

5. The compound of claim 1, or a pharmaceutically acceptable salt thereof, wherein R2 is H, alkyl, cycloalkyl, bicycloalkyl, alkylsulfonyl, C(=O)NR5R6, aryl, heterocyclyl, heterobicycloalkyl, heterospiroalkyl, heteroaryl, -alkyl-C(=O)R4, -alkyl-C(=O)OR4, -alkyl-C(=O)NR5R6, -alkyl-NR7C(=O)R4, -alkyl-NR7C(=O)OR4, -alkyl-NR7C(=O)NR5R6, -alkyl-NR7SO$_2$R4, -alkyl-NR7SOR4, aryl-alkyl, heterocyclyl-alkyl, or heteroaryl-alkyl, any of which is optionally further substituted by one or more independent R3 groups.

6. The compound of claim 1, or a pharmaceutically acceptable salt thereof, wherein R2 is H, alkyl, aryl, heterocyclyl, heterobicycloalkyl, heterospiroalkyl, or heteroaryl, any of which is optionally further substituted by one or more independent R3 groups.

7. The compound of claim 1, or a pharmaceutically acceptable salt thereof, wherein R2 is heterocyclyl or heterobicycloalkyl, any of which is optionally further substituted by one or more independent R3 groups.

8. A pharmaceutical composition comprising a compound claim 1, or a pharmaceutically acceptable salt thereof, and a pharmaceutically acceptable carrier.
9. A compound or a pharmaceutically acceptable salt thereof, which is selected from:
| Structure |
|---|
| 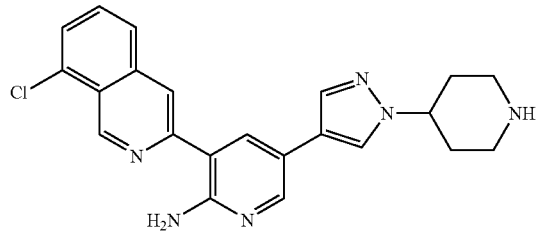 |
| 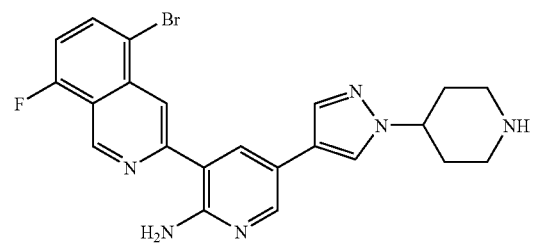 |
| 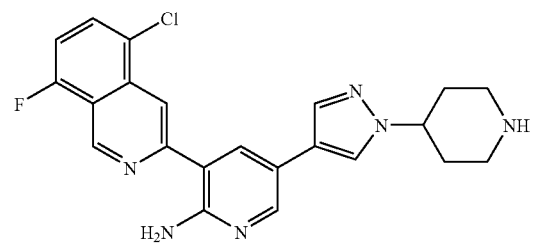 |
| 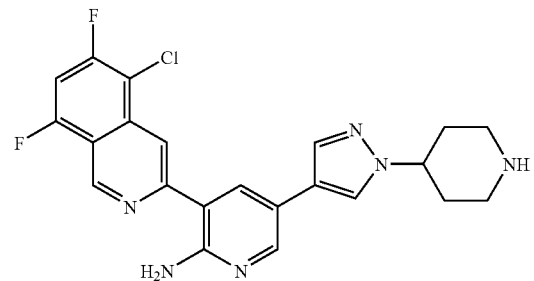 |
| 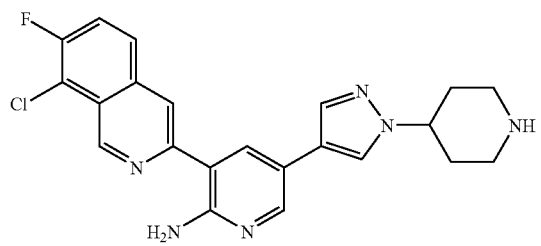 |
-continued
| Structure |
|---|
| 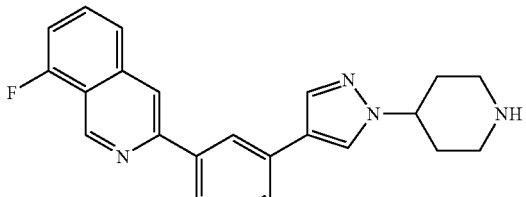 |
| 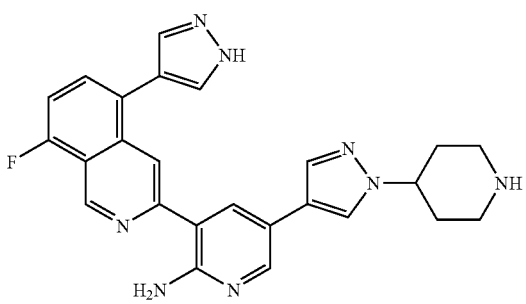 |
| 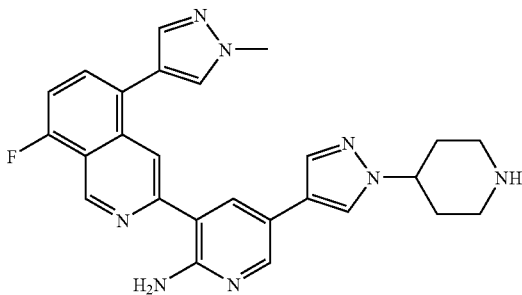 |
| 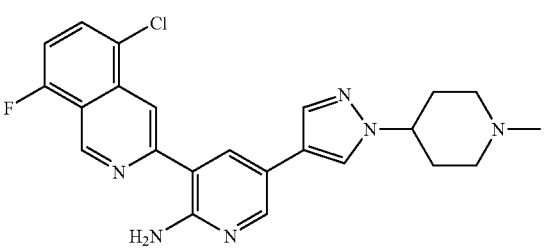 |
| 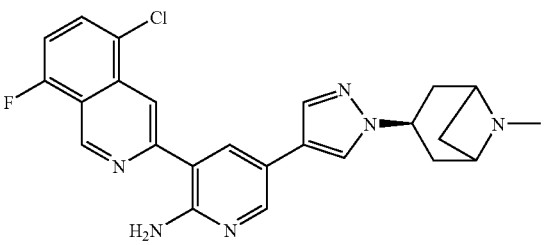 |

| 173 -continued | | 174 -continued |
|---|---|---|
| Structure | | Structure |
| 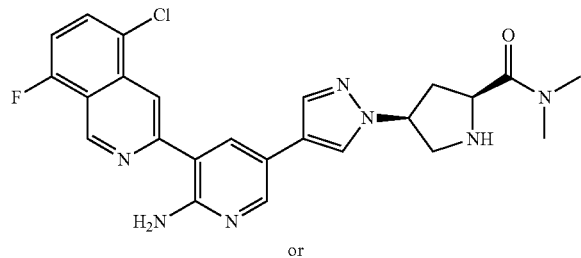 or | | 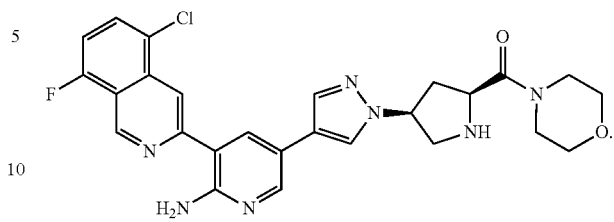 |
* * * * *